(12) United States Patent
Brake et al.

(10) Patent No.: US 9,724,354 B2
(45) Date of Patent: Aug. 8, 2017

(54) COMBINATION OF CATALYTIC MTORC1/2 INHIBITORS AND SELECTIVE INHIBITORS OF AURORA A KINASE

(71) Applicant: Millennium Pharmaceuticals, Inc., Cambridge, MA (US)

(72) Inventors: Rachael L. Brake, Natick, MA (US); Huifeng Niu, Cambridge, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 14/777,888

(22) PCT Filed: Mar. 21, 2014

(86) PCT No.: PCT/US2014/031442
§ 371 (c)(1),
(2) Date: Sep. 17, 2015

(87) PCT Pub. No.: WO2014/153509
PCT Pub. Date: Sep. 25, 2014

(65) Prior Publication Data
US 2016/0271140 A1    Sep. 22, 2016

Related U.S. Application Data

(60) Provisional application No. 61/804,314, filed on Mar. 22, 2013.

(51) Int. Cl.
| | | |
|---|---|---|
| A01N 43/00 | (2006.01) | |
| A61K 31/55 | (2006.01) | |
| A61K 31/519 | (2006.01) | |
| A61K 45/06 | (2006.01) | |

(52) U.S. Cl.
CPC ............ A61K 31/55 (2013.01); A61K 31/519 (2013.01); A61K 45/06 (2013.01)

(58) Field of Classification Search
CPC .................................................. A61K 31/55
USPC ........................................................ 514/215
See application file for complete search history.

(56) References Cited

U.S. PATENT DOCUMENTS

| | | |
|---|---|---|
| 4,099,012 A | 7/1978 | Gschwend |
| 4,469,633 A | 9/1984 | Trybulski |
| 4,481,142 A | 11/1984 | Fryer et al. |
| 5,166,151 A | 11/1992 | Freidinger et al. |
| 5,210,082 A | 5/1993 | Bock et al. |
| 5,593,997 A | 1/1997 | Dow et al. |
| 5,747,487 A | 5/1998 | Albright et al. |
| 6,057,329 A | 5/2000 | Davis et al. |
| 6,277,844 B1 | 8/2001 | Spector et al. |
| 6,390,821 B1 | 5/2002 | Shokat |
| 6,521,417 B1 | 2/2003 | Shokat |
| 6,552,192 B1 | 4/2003 | Hanus et al. |
| 6,624,119 B1 | 9/2003 | Reinhard et al. |
| 6,727,251 B2 | 4/2004 | Bebbington et al. |
| 6,800,633 B2 | 10/2004 | Castelhano et al. |
| 7,026,461 B1 | 4/2006 | Shokat |
| 7,049,116 B2 | 5/2006 | Shokat |
| 7,148,228 B2 | 12/2006 | Kasibhatla et al. |
| 7,271,262 B2 | 9/2007 | La Greca et al. |
| 7,572,784 B2 | 8/2009 | Claiborne et al. |
| 8,026,246 B2 | 9/2011 | Claiborne et al. |
| 8,399,659 B2 | 3/2013 | Claiborne et al. |
| 9,102,678 B2 | 8/2015 | Claiborne et al. |
| 2001/0024833 A1 | 9/2001 | Laborde et al. |
| 2002/0016976 A1 | 2/2002 | Shokat |
| 2002/0156081 A1 | 10/2002 | Hirst et al. |
| 2003/0022885 A1 | 1/2003 | Bebbington et al. |
| 2003/0055068 A1 | 3/2003 | Bebbington et al. |
| 2003/0180924 A1 | 9/2003 | DeSimone |
| 2003/0187001 A1 | 10/2003 | Calderwood et al. |
| 2005/0085472 A1 | 4/2005 | Tanaka et al. |
| 2005/0197340 A1 | 9/2005 | Arora et al. |
| 2006/0074074 A1 | 4/2006 | Ohtsuka et al. |
| 2006/0235031 A1 | 10/2006 | Arnold et al. |
| 2006/0246551 A1 | 11/2006 | Stack et al. |
| 2007/0054915 A1 | 3/2007 | Arora et al. |
| 2007/0072897 A1 | 3/2007 | Mahaney et al. |
| 2007/0099871 A1 | 5/2007 | Davis et al. |
| 2007/0112005 A1 | 5/2007 | Chen et al. |
| 2007/0149521 A1 | 6/2007 | Crew et al. |
| 2007/0185087 A1 | 8/2007 | Claiborne et al. |

(Continued)

FOREIGN PATENT DOCUMENTS

| | | |
|---|---|---|
| CN | 1224424 A | 7/1999 |
| CN | 1278262 A | 12/2000 |

(Continued)

OTHER PUBLICATIONS

Savannah et al. 'Dual Targeting of mTOR and Aurora-A Kinase for the Treatment of Uterine 1-8 Leiomyosarcoma', Clin Cancer Res., 2012, vol. 18, pp. 4633-4645.*
Abdel-Mohsen. Synthesis, Reactions and Antimicrobial Activity of 2-AmiN-4-(8quiNliN1-5-ye-1-(p-tolyl)-pyrrole-3-carbonitrile. Bull. Korean Chem. Soc. 2005;26(5):719-728.
Apsel, et al. Targeted polypharmacology: discovery of dual inhibitors of tyrosine and phosphoiNsitide kinases. Nat Chem Biol. 2008 Nv;4(11):691-9.
Berdnik, D. et al., Drosophila aurora-A is required for centrosome maturation and actin-dependent asymmetirc protein localization during mitosis, Current Biology, 12:640-647 (2002).

(Continued)

Primary Examiner — Nizal Chandrakumar
(74) Attorney, Agent, or Firm — Brenda Herschbach Jarrell; Choate, Hall & Stewart LLP

(57) ABSTRACT

Disclosed are methods for the treatment of proliferative disorders. Disclosed in particular, are methods for treatment of proliferative disorders such as cancer, by administering an mTORC1/2 inhibitor in combination with a selective inhibitor of Aurora A kinase. Preferred MTORC1/2 inhibitors include MLN0128 and the preferred Aurora A kinase inhibitor of the combination is MLN8237.

2 Claims, 5 Drawing Sheets

(56) References Cited

U.S. PATENT DOCUMENTS

| | | |
|---|---|---|
| 2007/0203143 A1 | 8/2007 | Sheppard et al. |
| 2007/0213355 A1 | 9/2007 | Capraro et al. |
| 2007/0224672 A1 | 9/2007 | Leban et al. |
| 2007/0249598 A1 | 10/2007 | Wang et al. |
| 2007/0254883 A1 | 11/2007 | Crew et al. |
| 2007/0293516 A1 | 12/2007 | Knight et al. |
| 2008/0032960 A1 | 2/2008 | Knight et al. |
| 2008/0167292 A1 | 7/2008 | Claiborne et al. |
| 2010/0004235 A1 | 1/2010 | Schirok et al. |
| 2010/0184760 A1 | 7/2010 | Ren et al. |
| 2010/0310651 A1 | 12/2010 | Mittal |
| 2010/0317680 A1 | 12/2010 | Curtin et al. |
| 2011/0312942 A1 | 12/2011 | Claiborne et al. |
| 2011/0312943 A1 | 12/2011 | Claiborne et al. |
| 2012/0010230 A1 | 1/2012 | MacDougall et al. |
| 2015/0166545 A1 | 6/2015 | Claiborne et al. |
| 2016/0185782 A1 | 6/2016 | Claiborne et al. |

FOREIGN PATENT DOCUMENTS

| | | |
|---|---|---|
| CN | 1486310 A | 3/2004 |
| EP | 0014470 A2 | 8/1980 |
| EP | 0273697 A2 | 7/1988 |
| EP | 0773023 A1 | 5/1997 |
| JP | 2001-507349 A | 6/2001 |
| JP | 2003-528141 A | 9/2003 |
| JP | 2004-533999 A | 11/2004 |
| JP | 2005-529163 A | 9/2005 |
| JP | 2007-522217 A | 8/2007 |
| JP | 2009-544617 A | 12/2009 |
| WO | WO-94/17803 A1 | 8/1994 |
| WO | WO-96/31510 A1 | 10/1996 |
| WO | WO-96/40706 A1 | 12/1996 |
| WO | WO-97/15658 A1 | 5/1997 |
| WO | WO-97/19065 A1 | 5/1997 |
| WO | WO-97/32883 A1 | 9/1997 |
| WO | WO-98/14450 A1 | 4/1998 |
| WO | WO-98/28281 A1 | 7/1998 |
| WO | WO-98/58926 A1 | 12/1998 |
| WO | WO-00/42042 A2 | 7/2000 |
| WO | WO-00/67754 A1 | 11/2000 |
| WO | WO-01/10462 A1 | 2/2001 |
| WO | WO-01/19829 A2 | 3/2001 |
| WO | WO-01/72300 A1 | 10/2001 |
| WO | WO-02/22607 A1 | 3/2002 |
| WO | WO-02/066461 A1 | 8/2002 |
| WO | WO-02/068415 A1 | 9/2002 |
| WO | WO-02/072073 A2 | 9/2002 |
| WO | WO-02/076986 A1 | 10/2002 |
| WO | WO-02/094834 A1 | 11/2002 |
| WO | WO-03/000187 A2 | 1/2003 |
| WO | WO-03/013545 A1 | 2/2003 |
| WO | WO-03/103687 A1 | 12/2003 |
| WO | WO-2005/037843 A1 | 4/2005 |
| WO | WO-2005/044181 A2 | 5/2005 |
| WO | WO-2005/047289 A1 | 5/2005 |
| WO | WO-2005/074603 A2 | 8/2005 |
| WO | WO-2005/076987 A2 | 8/2005 |
| WO | WO-2005/085248 A1 | 9/2005 |
| WO | WO-2005/097800 A1 | 10/2005 |
| WO | WO-2005/111039 A2 | 11/2005 |
| WO | WO-2005113556 A1 | 12/2005 |
| WO | WO-2006/050946 A1 | 5/2006 |
| WO | WO-2006/055831 A2 | 5/2006 |
| WO | WO-2006068760 A2 | 6/2006 |
| WO | WO-2006/070198 A1 | 7/2006 |
| WO | WO-2007023115 A2 | 3/2007 |
| WO | WO-2007/0076348 A2 | 7/2007 |
| WO | WO-2007/080601 A1 | 7/2007 |
| WO | WO-2007075554 A2 | 7/2007 |
| WO | WO-2007/0104785 A2 | 9/2007 |
| WO | WO-2007103308 A2 | 9/2007 |
| WO | WO-2007106503 A2 | 9/2007 |
| WO | WO-2007112005 A2 | 10/2007 |
| WO | WO-2007114926 A2 | 10/2007 |
| WO | WO-2007126841 A2 | 11/2007 |
| WO | WO-2007134828 A1 | 11/2007 |
| WO | WO-2008/005266 A2 | 1/2008 |
| WO | WO-2008/011154 A2 | 1/2008 |
| WO | WO-2008/021038 A2 | 2/2008 |
| WO | WO-2008031594 A1 | 3/2008 |
| WO | WO-2008/054808 A2 | 5/2008 |
| WO | WO-2008/063525 A1 | 5/2008 |
| WO | WO-2008083070 A1 | 7/2008 |
| WO | WO-2008/118331 A2 | 10/2008 |
| WO | WO-2008127226 A2 | 10/2008 |
| WO | WO-2009021990 A1 | 2/2009 |
| WO | WO-2009/064802 A2 | 5/2009 |
| WO | WO-2009/070652 A1 | 6/2009 |
| WO | WO-2009088986 A1 | 7/2009 |
| WO | WO-2009088990 A1 | 7/2009 |
| WO | WO-2009114870 A2 | 9/2009 |
| WO | WO-2009114874 A2 | 9/2009 |
| WO | WO-2009/158687 A1 | 12/2009 |
| WO | WO-2010006072 A2 | 1/2010 |
| WO | WO-2010006086 A2 | 1/2010 |
| WO | WO-2010036380 A1 | 4/2010 |
| WO | WO-2010/129816 A2 | 11/2010 |
| WO | WO-2011/014248 A1 | 2/2011 |
| WO | WO-2012/151562 A1 | 11/2012 |

OTHER PUBLICATIONS

Bhat, et al. Pyrazolopyrimidine nucleosides. 12. Synthesis and biological activity of certain pyrazolo[3,4-d]pyrimidine nucleosides related to adeNsine. J Med Chem. Oct. 1981;24(10):1165-72.

Bischoff, J.R. et al., a homologue of Drosophila aurora kinase is oncogenic and amplified in human colorectal cancers, European Molecular Biology Organization, 17:3062-3065 (1998).

Bishop, A.C. et al. "Generation of moNspecific naNmolar tyrosine kinase inhibitors via a chemical genetic approach", Journal of the American Chemical Society, American Chemical Society, Washington, DC, US, vol. 121, N. 4, 1999, pp. 627-31.

Cancer Prevention Overview, http://www.cancer.gov/cancertopics/pdq/prevention/overview/patient, National Cancer Institute, (2009).

Cantor, E.H. et al., Interaction of calcium channel blockers with non-neuronal benzodiazepine binding sites, Proceedings of the National Academy of Sciences, 81:1549-1552 (1984).

Carmena, M. et. al., The Cellular Geography of Aurora Kinases, Nature, 4:842-854 (2003).

Carvajal, R. et al., Aurora kinases: new targets for cancer therapy, Clinical Cancer Research 12(23):6869-6875 (2006).

Cervantes, A. et al., Pharmacokinetic (PK) and pharmacodynamic (PD) results from 2 phase 1 studies of the investigational selective Aurora A Akinase (AAK) inhibitor MLN8237: Exposure-dependent AAK inhibition in human tumors, American Society of Clinical Oncology, 1 (2010).

Cervantes, A. et al., Phase 1 Pharmacokinetic and Pharmacodynamic Study of MLN8237, a Novel, Selective Aurora A Kinase Inhibitor, in Patients with Advanced Solid Tumors, American Society of Clinical Oncology, 1 (2009).

Dees, C.E. et al., Phase 1 study of the investigational drug MLN8237, an oral Aurora A kinase inhibitor, in patients with solid tumors, American Society of Clinical Oncology, 1 (2010).

Development Pipeline Presentations: Abstract Compendium, American Society of Clinical Oncology, (2013).

Ding, S., et al. "A Combinatorial Scaffold Approach Toward Kinase-Directed Heterocycle Libraries", J. Am. Chem. Soc. (2002) 124(8):1594-1596.

Ditchfield, C. et al., Aurora B couples chromosome alignment with anaphase by targeting BubR1, Mad2, and Cenp-E to kinetochores, The Journal of Cell Biology, 161(2):267-280 (2003).

Dutertre, D. et al., On the role of aurora-A in centrosome function, Oncogene, 21:6175-6183 (2002).

Extended European Search Report for EP 14768267.8, dated Oct. 19, 2016, 11 pages.

Falchook, G.S. et al., Food effect study of the investigational Aurora A kinase (AAK) inhibitor MLN8237 (alisertib) in patients with advanced solid tumors, American Society of Clinical Oncology, 1 (2012).

(56) References Cited

OTHER PUBLICATIONS

Farag, et al. Synthesis and reactivity of 2-(benzothiazol-2-y1)-1-bromo-1,2-ethanedione-1-arylhydrazones. Heteroatom Chemistry. 1997; 8(1):45-50.
Feldman, et al. Active-site inhibitors of mTOR target rapamycin-resistant outputs of mTORC1 and mTORC2. PLoS Biol. Feb. 10, 2009;7(2):371-383.
Finch, et al., An Efficient General Route to Furo-, Pyrido- and Thieno-[d][2]benzazepines via Pdo Catalysed Cross Coupling Reactions and Nitrile Ylide Cyclisations, Journal of the Chemical Society Perkin Transactions, 1:1193-1203 (1994).
Friedberg, J.W. et al., Multicenter Phase 2 Trial of alisertib (MLN8237), an Investigational Inhibitor of Aurora a Kinase, in Patients with Aggressive B-cell and T-cell NHL, American Society of Clinical Oncology, 1 (2011).
Gautschi, O. et al., Aurora kinases as anticancer drug targets, Clinical Cancer Research, 14(6):1639-1648 (2008).
Goldberg, S.L. et al., Phase 2 study of MLN8237, an investigational Aurora A Kinase inhibitor in patients with acute myelogenous leukemia or myelodysplastic syndromes, The American Society of Hematology, (2010).
Görgün, G. et al., A Novel Aurora A Kinase Inhibitor MLN8237 Induces Cytotoxicity and Cell Cycle Arrest in Multiple Myeloma, the American Society of Hematology, 3830:1-2 (2009).
Görgün, G. et al., A novel Aurora-A kinase inhibitor MLN8237 induces cytotoxicity and cell-cycle arrest in multiple myeloma, Lymphoid Neoplasia: Blood, 115(25):5202-5213 (2010).
Harrington, E.A. et al., VX-680, a potent and selective small-molecular inhibitor of the Aurora kinases, suppresses tumor growth in vivo, Nature Medicine, 10(3):262-267 (2004).
Hauf, S. et al., The small molecule Hesperadin reveals a role for Aurora B in correcting kinetochore-microtubule attachment and in maintaining the spindle assembly checkpoint, the Journal of Cell Biology, 161(2):281-294 (2003).
Hoar, K. et al., MLN8054, a small-molecule inhibitor of aurora A, causes spindle pole and chromosome congression defects leading to aneuploidy, Molecular and Cellular Biology, 27(12):4513-4525 (2007).
Huck, J.J. et al., Antitumor Activity of the Aurora A Inhibitor MLN8237 Combination with Docetaxel in Xenograft Models of Breast and Prostate Cancer, American Association for Cancer Research, 1 (2009).
International Search Report for PCT/US2005/016445, 4 pages (Dec. 21, 2011).
International Search Report for PCT/US2007/023948, 4 pages (Dec. 21, 2011).
Jones, S.F. et al., Phase I clinical trial of MLN8054, a selective inhibitor of aurora A kinase, Journal of Clinical Oncology, ASCO Annual Meeting Proceedings Part 1, 25(185):3577 (2007).
Kelly, K.R. et al., Results from a phase 1 multicenter trial of alisertib (MLN8237)—an investigational Aurora A kinase inhibitor—in patients with advanced hematologic malignancies, American Society of Clinical Oncology, 1 (2011).
Kollareddy, M. et al., Aurora kinase inhibitors: Progress towards the clinic, Springer: Invest New Drugs, 30:2411-2432 (2012).
Kraybill, B.C. et al. "Inhibitor scaffolds as new allele specific kinase substrates", Journal of the American Chemical Society, American Chemical Society, Washington, DC, US, vol. 124, N. 41, Oct. 16, 2002, pp. 12118-28.
Kreutzberger, et al. 5-Substituierte 4-AmiNpyrimidine durch AmiNmethinylierung von Acetonitrilen. Liebigs Ann. Chem. 1977:537-544.
Lee, et al. All roads lead to mTOR: integrating inflammation and tumor angiogenesis.. Cell Cycle. 2007;6(24):3011-3014.
Liu, L. L. et al., Inhibition of mTOR Pathway Sensitizes Acute Myeloid Leukemia Cells to Aurora Inhibitors by Suppression of Glycolytic Metabolism, Molecular Cancer Research, 11(11): 1326-1336 (2013).

Mahadevan, D. et al., Targeting Aurora Kinase in Aggressive B-Cell Non-Hodgkin's Lymphomas, The American Society of Hematology, 284:1-2 (2009).
Mahedevan, D. et al., Clinical and Laboratory Evaluation of MLN8237, and Investigational Aurora a Kinase (AAK) Inhibitor, for Treatment of Aggressive Non-Hodgkin's Lymphoma, Peripheral T-cell Lymphomas Symposium, (2011).
Majumder, et al. mTOR inhibition reverses Akt-dependent prostate intraepithelial neoplasia through regulation of apoptotic and HIF-1-dependent pathways. Nature Medicine. 2004;10:594-601.
Manfredi, M.G. et al., Antitumor activity in MLN8054, an orally active small-molecule inhibitor of aurora A kinase, Proceedings of the National Academy of Sciences USA, 104(10):4106-4111 (2007).
March, J., Chapter 10: Reactivity, Advanced Organic Chemistry: Reactions, Mechanisms, and Structure, Fourth Edition, pp. 357-362 (1992).
Matulonis, U.A. et al., Gynecologic Oncology, 127(1):63-69 (2012).
Matulonis, U.A. et al., Single-agent activity and safety of teh investigational Aurora A kinase inhibitor MLN8237 in patients with platinum-treated epithelial ovarian, fallopian tube, or primary peritoneal carcinoma, American Society of Clinincal Oncology, 1 (2010).
McMahon, et al. VEGF receptor signaling in tumor angiogenesis. The Oncologist. (2000); 5(suppl 1): 3-10.
Melichar, B. et al., MLN8237 (alisertib), an investigational Aurora A kinase inhibitor, in patients with non-small cell lung cancer, small cell lung cancer, breast cancer, head and neck squamous cell carcinoma, and gastroesophageal cancer: Emerging phase 2 results, American Society of Clinical Oncology, 1 (2012).
Melichar, B. et al., Phase 1/2 study of investigational Aurora A Kinase inhibitor MLN8237 (alisertib): Updated phase 2 results in patients with small lung cancer (SCLC), non-SCLC (NSCLC), breast cancer (BrC), head and neck squamous cell carcinoma (HNSCC), and gastroesophageal cancer (GE), American Society of Clinical Oncology, 1 (2013).
Meraldi, P. et al., Aurora-A overexpression reveals tetraploidization as a major route to centrosome amplification in $p53^{-/-}$cells, the European Molecular Biology Organization Journal, 21(4):483-492 (2002).
Mosse, Y.P. et al., Pediatric Phase 1 Trial and Pharmacokinetic Study of MLN8237, an Oral Selective Small Molecule Inhibitor of Aurora A Kinase: A Children's Oncology Group Phase 1 Consortium Study, American Society of Clinical Oncology, 1 (2010).
Nawrocki, S.T. et al., The Aurora Kinase Inhibitor MLN8237 has Potent Anticancer Activity in CML and Ph+ All Models and Significantly Increases the Efficacy of Nilotinib, Blood, 112:12 (2008).
Niswender, C.M., et al. "Protein Engineering of Protein Kinase a Catalytic Subunits Results in the Acquisition of Nvel Inhibitor Sensitivity", The Journal of Biological Chemistry (2002) 277(32):28916-28922.
Padmanabhan, S. et al., Phase I Study of an investigational Aurora A Kinase inhibitor MLN8237 in patients with advanced hematologic malignancies, American Society of Clinical Oncology, 1 (2010).
Petrie, et al. A Nvel biotinylated adenylate analogue derived from pyrazolo[3,4-d]pyrimidine for labeling DNA probes. Bioconjug Chem. 1991 Nv-Dec;2(6):441-6.
Qi, W, et al., Aurora inhibitor MLN8237 in combination with docetaxel enhances apoptosis and anti-tumor activity in mantle cell lymphoma, Biochem. Pharmacol. 81(7): 881-890 (2011).
Sam, et al. Benzoxazoles: Potent Skeletal Muscle Relaxants. J Pharm Sci. May 1964; 53:538-44.
Sausville, E.A., Aurora kinases dawn as cancer drug targets, Nature Medicine, 10(3):234235 (2004).
Sharma, S. et al., Phase 1 dose-escalation study of the investigational Aurora A Kinase Inhibitor MLN8237 as an enteric-coated tablet formulation in patients with non-hematologic malignancies, American Society of Clinical Oncology, 1 (2011).

(56) References Cited

OTHER PUBLICATIONS

Shionome, Y. et al., Integrity of p53 associated pathways determines induction of apoptosis of tumor cells resistant to Aurora-A kinase inhibitors, PLoS One, 8(1): e55457 (2013).
Solowey, W.E. et al., Peripheral-Acting Benzodiazepines Inhibit the Growth of Human Melanoma Cells and Potentiate the Antiproliferative Activity of Recombinant Human Interferons, the Journal of Interferon Research, 10(3):269-280 (1990).
Stahl, P.H. and Wermuth, C.G., Handbook of Pharmaceutical Salts: Properties, Selection, and Use, pp. 322-323 (2002).
Tanaka, M., et al. "An Unbiased Cell Morphology-Based Screen for New, Biologically Active Small Molecules", PLoS Biology (2005) 3(5):0764-0776.
Third Party Opposition against CR 2014-0544, 7 pages (Apr. 24, 2015). [Spanish].
Vankayalapati, H. et al., Targeting Aurora2 Kinase in Oncogenesis: A Structural Bioinformatics Approach to Target Validation and Rational Drug Design, Molecular Cancer Therapeutics, 2:283-294 (2003).
Venkatakrishnan, K. et al., Clinical pharmacologic considerations for the phase 2/3 dose/regimen of the investigational Aurora A kinase inhibitor MLN8237 (alisertib): Pharmacokinetics, pharmacodynamics, and exposure-safety relationships, American Society of Clinical Oncology, 1 (2012).
Walker, E.H. et al., Structural determinants of phosphoinositide 3-Kinase inhibition by Wortmannin, LY294002, Quercetin, Myricetin, and Staurosporine, Molecular Cell, 6(4) 909-919 (2000).
Wang, J.K.T. et al., Benzodiazepines that bind at peripheral sites inhibit cell proliferation, Proceedings of the National Academy of Sciences, 81:753-756 (1984).
Warner, S.L. et al., Targeting aurora-2 kinase in cancer, Molecular Cancer Therapeutics, 2:589-595 (2003).
Wilder, L., et al. "7-Alkyl- and 7-Cycloalkyl-5-aryl-pyrrolo[2,3-d]pyrimidines-Potent Inhibitors of the Tyrosine Kinase c-Src," Bioorganic & Medicinal Chemistry Letters (2001) 11(6):849-852.
Written Opinion for PCT/US2005/016445, 4 pages (Dec. 21, 2011).
Written Opinion for PCT/US2007/023948, 4 pages (Dec. 21, 2011).
Wu, T.Y. et al., One-pot two-step microwave-assisted reaction in constructing 4,5-disubstituted pyrazolopyrimidines, Organic Letters, 5(20):3587-3590 (2003).
Wymann, M.P. et al., Wortmannin inactivates phosphoinositide 3-kinase by covalent modification of Lys-802, a residue involved in phosphate transfer reaction, Molecular and Cellular Biology,16(4):1722-1734 (1996).
Xia, W. et al., Tumor selective G2/M cell cycle arrest and apoptosis of epithelial and hematological malignancies by BBL22, a benzazepine, Proceedings of the National Academy of Sciences, 97(13):7494-7499 (2000).
Yaguchi, S.I. et al., A novel phospatidylinositol 3-kinase inhibitor, ZSTK474 exerted antitumor activity against human tumor zenografts by oral administration, Proc. Amer. Assoc. Cancer Res., 46 (2005), Abstract 1691.
Zhang, M. et al., Aurora A Kinase Inhibitor MLN8237 in Combination with Docetaxel Induces Synergistic Antitumor Activity in Triple-Negative Breast Cancer Xenograft Models, EORTC, (2010).
Zhou, H. et al., Tumor amplified kinase STK15/BTAK induces centrosome amplification, aneuploidy and transformation, Nature Genetics, 20:189-193 (1998).
Zhou, X. et al., Pharmacokinetics, Pharmacodynamics and Exposure-Pharmacodynamic Relationships of Investigational Drug MLN8237, and Aurora A Kinase Inhibitor in Patients with Advanced Solid Tumors, American Society Clinical Pharmacology Therapeutics, 1-10 (2011).

* cited by examiner

COMBINATION OF CATALYTIC MTORC1/2 INHIBITORS AND SELECTIVE INHIBITORS OF AURORA A KINASE

PRIORITY CLAIM

This application claims priority from U.S. Provisional Patent Application Ser. No. 61/804,314 filed Mar. 22, 2013 which is hereby incorporated by reference in its entirety.

BACKGROUND

In 2008, there were an estimated 12.7 million cases of cancer diagnosed worldwide and about 7.6 million deaths. The global cancer burden is growing at an alarming pace; in 2030 alone, about 21.3 million new cancer cases and 13.1 million cancer deaths are expected to occur, simply due to the growth and aging of the population. Cancer is the second most common cause of death in the US, exceeded only by heart disease, accounting for nearly 1 of every 4 deaths. The National Cancer Institute estimates that approximately 13.7 million Americans with a history of cancer were alive on Jan. 1, 2012. Some of these individuals were cancer free, while others still had evidence of cancer and may have been undergoing treatment. About 1,660,290 new cancer cases are expected to be diagnosed in the US in 2013. In 2013, about 580,350 Americans are expected to die of cancer, almost 1,600 people per day. Although medical advances have improved cancer survival rates, there is a continuing need for new and more effective treatment.

Kinase signaling pathways play a central role in numerous biological processes. Defects in various components of signal transduction pathways have been found to account for a vast number of diseases, including numerous forms of cancer, inflammatory disorders, metabolic disorders, vascular and neuronal diseases (Gaestel et al. Current Medicinal Chemistry (2007) 14:2214-2234). In recent years, kinases that are associated with oncogenic signaling pathways have emerged as important drug targets in cancers.

The cell division cycle, which regulates the transition from quiescence to cell proliferation, also involves various protein kinases that are frequently overexpressed in cancer cells. Because of their important role in the cell division cycle, such cell cycle kinases have also been explored as targets for cancer therapy.

One kinase associated with an oncogenic signaling pathway is the mammalian/mechanistic target of rapamycin (mTOR), which is a serine/threonine protein kinase that regulates cell growth, translational control, angiogenesis and/or cell survival. mTOR is encoded by the FK506 binding protein 12-rapamycin associated protein 1 (FRAP1) gene and is the catalytic subunit of two distinct protein complexes, mTOR complex 1 (mTORC1) and mTOR complex 2 (mTORC2).

mTORC1 function is involved in many growth-related processes such as protein translation, ribosome biogenesis, transcription, autophagy and hypoxic adaptation. mTORC1 is best known as a key regulator of protein translation via its ability to phosphorylate the eukaryotic translation initiation factor 4EBP1, and S6 kinase (Hidalgo, M. *J Clin Onc* (2012) Vol 30, 1).

To date mTORC2 has best been described to regulate two major cell functions, including regulation of Akt and cell cycle-dependent organization of the actin cytoskeleton. mTORC2 phosphorylates Akt on serine 473 (Ser473) in its C-terminal hydrophobic motif, which, in conjunction with PDK1-mediated phosphorylation of threonine 308 (Thr308), confers full activation of Akt (Sarbassov D. D., et al. Science (2005) 307:1098-1101). mTORC2 regulates the actin cytoskeleton through an unclear mechanism which is rapamycin insensitive (Jacinto E., et al. Nat Cell Biol. (2004) 6: 1122-1128). Interestingly, mTORC2 phosphorylates PKC and SGK1 (serum- and glucocorticoid-induced protein kinase 1), and has also been implicated in controlling cell size (Ikenoue T., et al. EMBO J. (2008) 27: 1919-193; Rosner M., et al. Hum Mol Genet., (2009) 18: 3298-3310).

The mTORC1 and mTORC2 complexes are often distinguished by their ability to differentially bind and be inhibited by rapamycin and its analogs (rapalogs), which is in contrast to catalytic inhibitors of mTOR that can equally inhibit mTORC1 and mTORC2. Rapamycin inhibits mTOR by associating with its intracellular receptor FKBP12. The FKBP12-rapamycin complex then binds directly to the FKBP12-Rapamycin Binding (FRB) domain of mTOR enzyme (Jacinto E., et al. Cell (2006) 127: 125-137). As such rapamycin and rapalogs can be considered as allosteric inhibitors regulating the activity of mTORC1 only. Furthermore this regulation can be considered incomplete as the ability of these inhibitors to suppress 4EBP1 phosphorylation (an important downstream effect of mTORC1 inhibition) is considered to be only partial (Hidalgo, M. *J Clin Onc* (2012) Vol 30, 1).

Examples of cell cycle kinases include the Aurora kinases, first identified in yeast (Ipl1), *Xenopus* (Eg2) and *Drosophila* (Aurora). (*Embo J* (1998) 17, 5627-5637; *Genetics* (1993) 135, 677-691; *Cell* (1995) 81, 95-105; *J Cell Sci* (1998) 111(Pt 5), 557-572). In humans, three isoforms of Aurora kinase exist, including Aurora A, Aurora B and Aurora C (Carmena M, Earnshaw W C. *Nat Rev Mol Cell Biol.* (2003) 4:842-54). Aurora A and Aurora B play critical roles in the normal progression of cells through mitosis, whereas Aurora C activity is largely restricted to meiotic cells.

The Aurora A gene (AURKA) localizes to chromosome 20q13.2 which is commonly amplified or overexpressed at a high incidence in a diverse array of tumor types. (*Embo J* (1998) 17, 3052-3065; *Int J Cancer* (2006) 118, 357-363; *J Cell Biol* (2003) 161, 267-280; *Mol Cancer Ther* (2007) 6, 1851-1857; *J Natl Cancer Inst* (2002) 94, 1320-1329). Increased Aurora A gene expression has been correlated to the etiology of cancer and to a worsened prognosis. (*Int J Oncol* (2004) 25, 1631-1639; *Cancer Res* (2007) 67, 10436-10444; *Clin Cancer Res* (2004) 10, 2065-2071; *Clin Cancer Res* (2007) 13, 4098-4104; *Int J Cancer* (2001) 92, 370-373; *Br J Cancer* (2001) 84, 824-831; *J Natl Cancer Inst* (2002) 94, 1320-1329). This concept has been supported in experimental models, demonstrating that Aurora A overexpression leads to oncogenic transformation. (*Cancer Res* (2002) 62, 4115-4122; *Mol Cancer Res* (2009) 7, 678-688; *Oncogene* (2006) 25, 7148-7158; *Cell Res* (2006) 16, 356-366; *Oncogene* (2008) 27, 4305-4314; *Nat Genet* (1998) 20, 189-193). Both in vitro and in vivo studies have demonstrated that Aurora A induces tumorigenesis through genome instability. The potential oncogenic role of Aurora A has led to considerable interest in targeting this kinase for the treatment of cancer.

Previous studies have shown that cell signaling cross-talk between Aurora A and other cellular proteins are essential for fully-transformed phenotypes. The cross-talk between Aurora A and the mTOR signaling pathway represents an example of this. In mouse mammary tumor virus (MMTV)-Aurora A transgenic mice, constitutive phosphorylation of mTOR Ser2448 and Akt Ser473 was discovered in developed mammary tumors (Wang X., et al. *Oncogene* (2006)

25: 7148-7158). Elevated phosphorylation of mTOR Ser2448 and Akt Ser473 in Aurora-A transformed cells suggests that Aurora-A can potentially regulate two mTOR pathways, mTORC1 and mTORC2. More evidence suggests that either or both of mTORC1 and 2 is important for Aurora-A induced transformation since mTOR inhibition can abolish transformed phenotypes induced by Aurora A (Taga M., et al. *Int J Biol Sci* (2009) 19: 444-450). Of note, mammary tumor development can be observed only after long latency in MMTV-Aurora A mice.

Given the importance of the protein kinases involved in signal transduction pathways and the cell division cycle, it would be beneficial if more effective treatment regimens, which target these kinases could be developed. In particular, combined treatment regimens could be helpful for patients suffering from disease conditions including proliferative disorders, autoimmune diseases, inflammatory diseases, fibrotic diseases and kidney diseases, and might potentially even decrease the rate of relapse or overcome the resistance to a particular anticancer agent sometimes seen in these patients.

There is thus a need for new cancer treatment regimens, including combination therapies.

SUMMARY

This invention relates to methods for the treatment of disease conditions including proliferative disorders, autoimmune diseases, inflammatory diseases, fibrotic diseases and kidney diseases. In particular, the invention provides methods for treatment of various disease conditions including proliferative disorders, autoimmune diseases, inflammatory diseases, fibrotic diseases and kidney diseases, by administering an mTORC1/2 inhibitor in combination with a selective inhibitor of Aurora A kinase. The invention also provides pharmaceutical compositions and kits comprising an mTORC1/2 inhibitor in combination with a selective Aurora A kinase inhibitor.

The present invention provides new combination therapies for the treatment of disease conditions including proliferative disorders, autoimmune diseases, inflammatory diseases, fibrotic diseases and kidney diseases. In particular, the present invention provides a method to treat a patient suffering from disease conditions including proliferative disorders, autoimmune diseases, inflammatory diseases, fibrotic diseases and kidney diseases, comprising administering to said patient an mTORC1/2 inhibitor in combination with a selective inhibitor of Aurora A kinase, wherein the amounts of each inhibitor are therapeutically effective when used in combination. The invention also provides an mTORC1/2 inhibitor in combination with a selective inhibitor of Aurora A kinase for use in the manufacture of a medicament for the treatment of disease conditions including proliferative disorders, autoimmune diseases, inflammatory diseases, fibrotic diseases and kidney diseases, wherein the amounts of each inhibitor are therapeutically effective when used in combination. The invention also provides pharmaceutical compositions and kits comprising an mTORC1/2 inhibitor in combination with a selective inhibitor of Aurora A kinase.

While single agent mTORC1/2 inhibitors and single agent selective inhibitors of Aurora A kinase may prove effective in treating a certain number of patients and certain disease conditions including proliferative disorders, autoimmune diseases, inflammatory diseases, fibrotic diseases and kidney diseases, the present inventors have surprisingly discovered that combined therapy with an mTORC1/2 inhibitor and a selective inhibitor of Aurora A kinase offers benefits not achieved with either agent individually.

Without wishing to be bound by theory, the present inventors believe that overexpression of Aurora A is not a strong driving force, and cell transformation by Aurora A requires additional oncogenic events, such as constitutive activation of mTOR/Akt pathway and loss of PTEN tumor suppressor. Therefore, simultaneous inhibition of Aurora A and mTORC1/2 activity may provide enhanced anti tumor potency and provide an improved treatment paradigm for patients that have tumors impacted by both distinct mechanisms.

DETAILED DESCRIPTION

Figure 1:
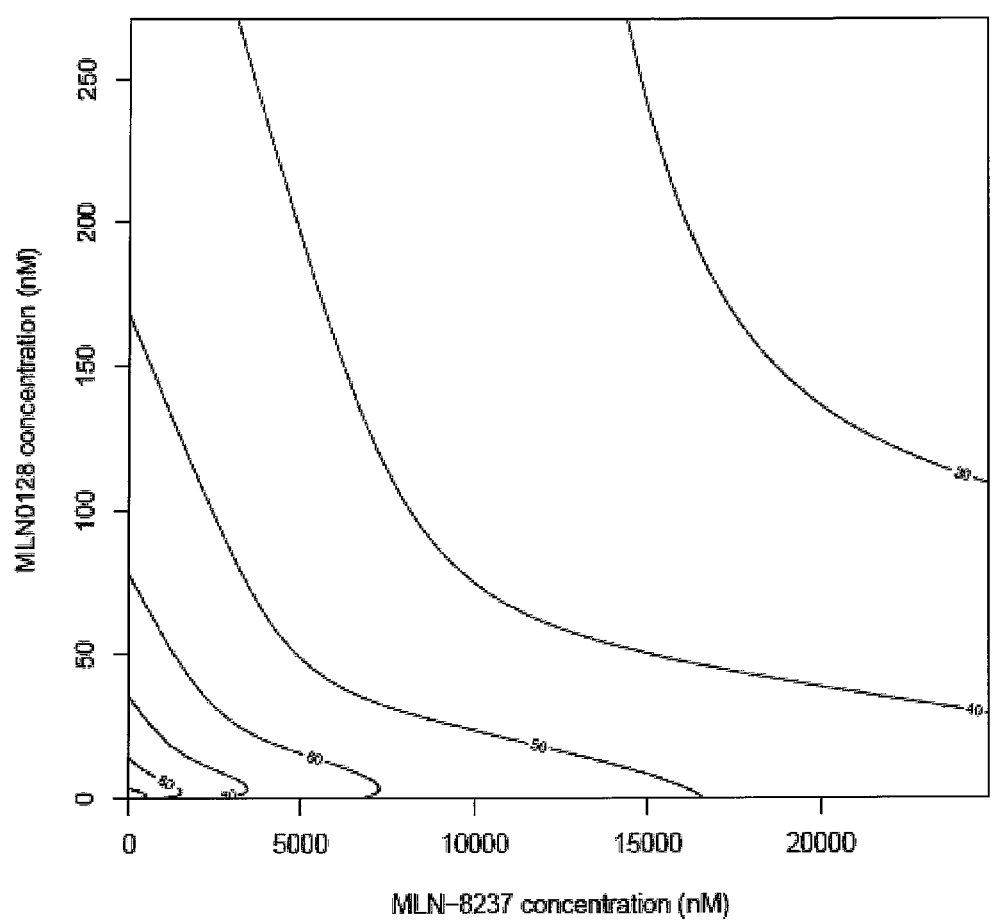
FIG. 1 shows a fitted isobologram for MLN0128 in combination with MLN8237 in the Calu6 lung cancer cell line. The contours range from 90% to 10% viability, with a separation of 10% in viability.

Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. The present invention is not limited by the illustrated ordering of acts or events, as some acts may occur in different orders and/or concurrently with other acts or events. Furthermore, not all illustrated acts or events are required to implement a methodology in accordance with the present invention.

Definitions:

Terms used herein shall be accorded the following defined meanings, unless otherwise indicated.

As used herein, the term "mTOR" refers to the catalytic subunit of two complexes, mTORC1 and mTORC2.

The term "mTOR inhibitor" or "inhibitor of mTOR" is used to signify a compound which is capable of interacting with mTOR and inhibiting its enzymatic activity. Inhibiting mTOR enzymatic activity means reducing the ability of mTOR to phosphorylate a substrate peptide or protein. In various embodiments, such reduction of mTOR activity is at least about 50%, at least about 75%, at least about 90%, at least about 95%, or at least about 99%. In various embodiments, the concentration of mTOR inhibitor required to reduce mTOR enzymatic activity is less than about 1 µM, less than about 500 nM, less than about 100 nM, less than about 50 nM, or less than about 10 nM.

In some embodiments, such inhibition is selective, i.e., the mTOR inhibitor reduces the ability of mTOR to phosphorylate a substrate peptide or protein at a concentration that is lower than the concentration of the inhibitor that is required to produce another, unrelated biological effect, e.g., reduction of the enzymatic activity of a different kinase. In some embodiments, the mTOR inhibitor also reduces the enzymatic activity of another kinase, preferably one that is implicated in cancer.

In some embodiments, the mTOR inhibitor selectively inhibits both mTORC1 and mTORC2 activity relative to one or more type I phosphatidylinositol 3-kinases (PI3-kinase) as ascertained by a cell-based assay or an in vitro kinase assay.

The phrase "an mTORC1/2 inhibitor" when used: herein refers to a catalytic mTOR inhibitor that interacts with and reduces the kinase activity of both mTORC1 and mTORC2 complexes. In some embodiments of the methods of the invention, the mTOR inhibitor binds to and directly inhibits both mTORC1 and mTORC2. For example, the mTOR inhibitor inhibits both mTORC1 and mTORC2 with an IC50 value of about 500 nM or less, 400 nM or less, 300 nM or less, 200 nM or less, 100 nM or less, 50 nM or less, 10 nM or less, or 1 nM or less, as ascertained in an in vitro kinase assay. In another embodiment, the mTOR inhibitor inhibits both mTORC1 and mTORC2 with an IC50 value of about 10 nM or less as ascertained in an in vitro kinase assay, and the mTOR inhibitor is substantially inactive against one or more types I PI3-kinases selected from the group consisting of PI3-kinase α, PI3-kinase β, PI3-kinase γ, and PI3-kinase δ. Alternatively, the mTOR inhibitor inhibits both mTORC1 and mTORC2 with an IC50 value of about 100 nM or less as ascertained in an in vitro kinase assay, and the IC50 value is at least 2, 5 or 10 times less than its IC50 value against all other type I PI3-kinases selected from the group consisting of PI3-kinase α, PI3-kinase β, PI3-kinase γ, and PI3-kinase δ.

As used herein, the term "Aurora A kinase" refers to a serine/threonine kinases involved in mitotic progression. Aurora A kinase is also known as AIK, ARK1, AURA, BTAK, STK6, STK7, STK15, AURORA2, MGC34538, and AURKA. A variety of cellular proteins that play a role in cell division are substrates for phosphorylation by the Aurora A kinase enzyme, including, without limitation, p53, TPX-2, XIEg5 (in *Xenopus*), and D-TACC (in *Drosophila*). The Aurora A kinase enzyme is also itself a substrate for autophosphorylation, e.g., at Thr288. Preferably, the Aurora A kinase is a human Aurora A kinase.

The term "inhibitor of Aurora A kinase" or "Aurora A kinase inhibitor" is used to signify a compound that is capable of interacting with Aurora A kinase and inhibiting its enzymatic activity. Inhibiting Aurora A kinase enzymatic activity means reducing the ability of Aurora A kinase to phosphorylate a substrate peptide or protein. In various embodiments, such reduction of Aurora A kinase activity is at least about 75%, at least about 90%, at least about 95%, or at least about 99%. In various embodiments, the concentration of Aurora A kinase inhibitor required to reduce an Aurora A kinase enzymatic activity is less than about 1 µM, less than about 500 nM, less than about 100 nM, less than about 50 nM, or less than about 10 nM. Preferably, the concentration that is required to inhibit the enzymatic activity of Aurora A kinase is lower than the concentration of the inhibitor that is required to inhibit the enzymatic activity of Aurora B kinase. In various embodiments, the concentration of an Aurora A kinase inhibitor that is required to reduce Aurora A kinase enzymatic activity is at least about 2-fold, at least about 5-fold, at least about 10-fold, at least about 20-fold, at least about 50-fold, at least about 100-fold, at least about 500-fold, or at least about 1000-fold lower than the concentration of the inhibitor that is required to reduce Aurora B kinase enzymatic activity.

Inhibition of Aurora A and inhibition of Aurora B result in markedly different cellular phenotypes. (*Proc. Natl. Acad. Sci.* (2007) 104: 4106; *Mol Cancer Ther* (2009) 8(7), 2046-56; *Chem Biol.* (2008) 15(6) 552-62). For example, inhibition of Aurora A in the absence of Aurora B inhibition results in increased mitotic index as measured by quantifying phosphorylated histone H3 on serine 10 (pHisH3). pHisH3 is a unique substrate of Aurora B in physiological systems (e.g. intact cells). By contrast, inhibition of Aurora B or dual inhibition of Aurora A and Aurora B results in a decrease in pHisH3. Accordingly, as used herein, the term "selective inhibitor of Aurora A kinase" or "selective Aurora A kinase inhibitor" refers to an inhibitor that exhibits an Aurora A kinase inhibitor phenotype at effective antitumor concentrations. In some embodiments, the selective Aurora A kinase inhibitor causes a transient mitotic delay, as measured by quantification of pHisH3, when administered to mice at a dose where the free fraction adjusted concentration ($C_{ave}$) in plasma is equivalent to the free fraction adjusted concentration achieved in plasma in humans at the maximum tolerated dose (MTD). As used herein, "free fraction adjusted concentration" refers to the plasma concentration of free drug (not protein bound).

As used herein, the terms "in combination" or "combination therapy" refer to use of both an mTORC1/2 inhibitor and a selective Aurora A kinase inhibitor in the treatment of the same disease or condition in the same patient. As further described below, unless explicitly specified, the terms "in combination" or "combination therapy" do not restrict the timing of administration of the mTORC1/2 inhibitor and selective Aurora A kinase inhibitor, and thus include both simultaneous and sequential administration of the mTORC1/2 inhibitor and selective Aurora A kinase inhibitor.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%.

As used herein, the term "comprises" means "includes, but is not limited to."

Unless otherwise stated, the connections of compound name moieties are at the rightmost recited moiety. That is, the substituent name starts with a terminal moiety, continues with any linking moieties, and ends with the linking moiety. For example, heteroarylthio $C_{1-4}$ alkyl has a heteroaryl group connected through a thio sulfur to a $C_{1-4}$ alkyl radical that connects to the chemical species bearing the substituent. This condition does not apply where a formula such as, for example "-L-$C_{1-10}$ alkyl-$C_{3-8}$cycloalkyl" is represented. In such case, the terminal group is a $C_{3-8}$cycloalkyl group attached to a linking $C_{1-10}$ alkyl moiety which is attached to an element L, which is itself connected to the chemical species bearing the substituent.

"Acyl" refers to the groups (alkyl)-C(O)—, (aryl)-C(O)—, (heteroaryl)-C(O)—, (heteroalkyl)-C(O)—, and (heterocycloalkyl)-C(O)—, wherein the group is attached to the parent structure through the carbonyl functionality. In some embodiments, it is a $C_1$-$C_{10}$ acyl radical which refers to the total number of chain or ring atoms of the alkyl, aryl, heteroaryl or heterocycloalkyl portion of the acyloxy group plus the carbonyl carbon of acyl, i.e three other ring or chain atoms plus carbonyl. If the R radical is heteroaryl or heterocycloalkyl, the hetero ring or chain atoms contribute to the total number of chain or ring atoms.

The term "aliphatic" or "aliphatic group", as used herein, means a substituted or unsubstituted straight-chain, branched or cyclic $C_{1-12}$ hydrocarbon, which is completely saturated or which contains one or more units of unsaturation, but which is not aromatic. For example, suitable aliphatic groups include substituted or unsubstituted linear, branched or cyclic alkyl, alkenyl, alkynyl groups and hybrids thereof, such as (cycloalkyl)alkyl, (cycloalkenyl) alkyl or (cycloalkyl)alkenyl.

The terms "alkyl", "alkenyl", and "alkynyl", used alone or as part of a larger moiety, refer to a straight and branched chain aliphatic group having from 1 to 12 carbon atoms. Whenever it appears herein, a numerical range such as "1 to 12" refers to each integer in the given range; e.g., "1 to 12 carbon atoms" means that the alkyl group may consist of 1 carbon atom, 2 carbon atoms, 3 carbon atoms, etc., up to and including 12 carbon atoms, although the present definition also covers the occurrence of the term "alkyl" where no numerical range is designated. For purposes of the present invention, the term "alkyl" will be used when the carbon atom attaching the aliphatic group to the rest of the molecule is a saturated carbon atom. However, an alkyl group may include unsaturation at other carbon atoms. Thus, alkyl groups include, without limitation, methyl, ethyl, propyl, isopropyl, allyl, propargyl, n-butyl, iso-butyl, sec-butyl isobutyl, tertiary butyl, pentyl, isopentyl, neopentyl, hexyl, septyl, octyl, nonyl, and decyl.

For purposes of the present invention, the term "alkenyl" will be used when the carbon atom attaching the aliphatic group to the rest of the molecule forms part of a carbon-carbon double bond. Alkenyl groups include, without limitation, vinyl, 1-propenyl, 1-butenyl, 1-pentenyl, and 1-hexenyl.

For purposes of the present invention, the term "alkynyl" will be used when the carbon atom attaching the aliphatic group to the rest of the molecule forms part of a carbon-carbon triple bond. Alkynyl groups include, without limitation, ethynyl, 1-propynyl, 1-butynyl, 1-pentynyl, and 1-hexynyl.

The term "alkylene" refers to a bivalent alkyl group. An "alkylene chain" is a polymethylene group, i.e., —$(CH_2)_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms is replaced with a substituent. Suitable substituents include those described below for a substituted aliphatic group. An alkylene chain also may be substituted at one or more positions with an aliphatic group or a substituted aliphatic group.

The terms "aryl" and "ar-", used alone or as part of a larger moiety, e.g., "aralkyl", "aralkoxy", or "aryloxyalkyl", refer to a $C_6$ to $C_{14}$ aromatic hydrocarbon, comprising one to three rings, each of which is optionally substituted. Preferably, the aryl group is a $C_{6-10}$ aryl group. Aryl groups include, without limitation, phenyl, naphthyl, and anthracenyl. In some embodiments, two adjacent substituents on the aryl ring, taken together with the intervening ring atoms, form an optionally substituted fused 5- to 6-membered aromatic or 4- to 8-membered non-aromatic ring having 0-3 ring heteroatoms selected from the group consisting of O, N, and S. Thus, the term "aryl", as used herein, includes groups in which an aromatic ring is fused to one or more heteroaryl, cycloaliphatic, or heterocyclyl rings, where the radical or point of attachment is on the aromatic ring. Nonlimiting examples of such fused ring systems include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, carbazolyl, acridinyl, phenazinyl, phenothiazinyl, phenoxazinyl, tetrahydroquinolinyl, tetrahydroisoquinolinyl, fluorenyl, indanyl, phenanthridinyl, tetrahydronaphthyl, indolinyl, phenoxazinyl, benzodioxanyl, and benzodioxolyl. An aryl group may be mono-, bi-, tri-, or polycyclic, preferably mono-, bi-, or tricyclic, more preferably mono- or bicyclic. The term "aryl" may be used interchangeably with the terms "aryl group", "aryl moiety", and "aryl ring".

An "aralkyl" or "arylalkyl" group comprises an aryl group covalently attached to an alkyl group, either of which independently is optionally substituted. Preferably, the aralkyl group is $C_{6-10}$ aryl($C_{1-6}$)alkyl, $C_{6-10}$ aryl($C_{1-4}$)alkyl, or $C_{6-10}$ aryl($C_{1-3}$)alkyl, including, without limitation, optionally substituted benzyl, phenethyl, phenpropyl and phenbutyl such as 4-chlorobenzyl, 2,4-dibromobenzyl, 2-methylbenzyl, 2-(3-fluorophenyl)ethyl, 2-(4-methylphenyl)ethyl, 2-(4-(trifluoromethyl)phenyl)ethyl, 2-(2-methoxyphenyl)ethyl, 2-(3-nitrophenyl)ethyl, 2-(2,4-dichlorophenyl)ethyl, 2-(3,5-dimethoxyphenyl)ethyl, 3-phenylpropyl, 3-(3-chlorophenyl)propyl, 3-(2-methylphenyl)propyl, 3-(4-methoxyphenyl)propyl, 3-(4-(trifluoromethyl)phenyl)propyl, 3-(2,4-dichlorophenyl)propyl, 4-phenylbutyl, 4-(4-chlorophenyl)butyl, 4-(2-methylphenyl) butyl, 4-(2,4-dichlorophenyl)butyl, 4-(2-methoxyphenyl) butyl, and 10-phenyldecyl. Either portion of the moiety is unsubstituted or substituted.

The term "$C_{1-10}$alkylaryl" as used herein refers to an alkyl group, as defined above, containing 1 to 10 carbon atoms, branched or unbranched, wherein the aryl group replaces one hydrogen on the alkyl group, for example, 3-phenylpropyl. Either portion of the moiety is unsubstituted or substituted.

"Amino" or "amine" means a nitrogen moiety having two further substituents where, for example, a hydrogen or carbon atom is attached to the nitrogen. For example, representative amino groups include —$NH_2$, —$NHCH_3$, —$N(CH_3)_2$, —NH(($C_{1-10}$)alkyl), —N(($C_{1-10}$)alkyl)$_2$, —NH (aryl), —NH(heteroaryl), —N(aryl)$_2$, —N(heteroaryl)$_2$, and the like. Optionally, the two substituents together with the nitrogen may also form a ring. Unless indicated otherwise, the compounds of the invention containing amino moieties may include protected derivatives thereof. Suitable protecting groups for amino moieties include acetyl, tert-butoxycarbonyl, benzyloxycarbonyl, and the like.

"Amide" or "amido" refers to a chemical moiety with formula —C(O)N(R)$_2$ or —NHC(O)R, where R is selected from the group consisting of hydrogen, alkyl, cycloalkyl, aryl, heteroaryl (bonded through a ring carbon) and heteroalicyclic (bonded through a ring carbon), each of which moiety may itself be optionally substituted. In some embodiments it is a $C_1$-$C_4$ amido or amide radical, which includes the amide carbonyl in the total number of carbons in the radical. The $R^2$ of —N(R)$_2$ of the amide may optionally be taken together with the nitrogen to which it is attached to form a 4-, 5-, 6-, or 7-membered ring. Unless stated otherwise specifically in the specification, an amido group is optionally substituted independently by one or more of the substituents as described herein for alkyl, cycloalkyl, aryl, heteroaryl, or heterocycloalkyl. An amide may be an amino acid or a peptide molecule attached to a compound of Formula (I), thereby forming a prodrug. Any amine, hydroxy, or carboxyl side chain on the compounds described herein can be amidified. The procedures and specific groups to make such amides are known to those of skill in the art and can readily be found in reference sources such as Greene and Wuts, Protective Groups in Organic Synthesis, 3$^{rd}$ Ed., John Wiley & Sons, New York, N.Y., 1999, which is incorporated herein by reference in its entirety.

The term "alkoxy" refers to the group —O-alkyl, including from 1 to 8 carbon atoms of a straight, branched, cyclic configuration and combinations thereof attached to the parent structure through an oxygen. Examples include methoxy, ethoxy, propoxy, isopropoxy, cyclopropyloxy, cyclohexyloxy and the like. "Lower alkoxy" refers to alkoxy groups containing one to six carbons. In some embodiments, $C_1$-$C_4$ alkyl, is an alkyl group which encompasses both straight and branched chain alkyls of from 1 to 4 carbon atoms.

The term "haloalkoxy" refers to an alkoxy group substituted with one or more halo groups, for example chloromethoxy, trifluoromethoxy, difluoromethoxy, perfluoroisobutoxy, and the like.

The term "bicycloalkyl" refers to a structure consisting of two cycloalkyl moieties, unsubstituted or substituted, that have two or more atoms in common. If the cycloalkyl moieties have exactly two atoms in common they are said to be "fused". Examples include, but are not limited to, bicyclo[3.1.0]hexyl, perhydronaphthyl, and the like. If the cycloalkyl moieties have more than two atoms in common they are said to be "bridged". Examples include, but are not limited to, bicyclo[3.2.1]heptyl ("norbornyl"), bicyclo[2.2.2]octyl, and the like. In particular embodiments, "bicycloalkyl," either alone or represented along with another radical, can be a $(C_{4-15})$bicycloalkyl, a $(C_{4-10})$bicycloalkyl, a $(C_{6-10})$bicycloalkyl or a $(C_{8-10})$bicycloalkyl. Alternatively, "bicycloalkyl," either alone or represented along with another radical, can be a $(C_8)$bicycloalkyl, a $(C_9)$bicycloalkyl or a $(C_{10})$bicycloalkyl.

"Bicycloaryl" means a fused, spiro or bridged bicyclic ring assembly wherein at least one of the rings comprising the assembly is aromatic. $(C_X)$bicycloaryl and $(C_{X-Y})$bicycloaryl are typically used where X and Y indicate the number of carbon atoms in the bicyclic ring assembly and directly attached to the ring. In particular embodiments, "bicycloaryl," either alone or represented along with another radical, can be a (a $(C_{4-15})$bicycloaryl, a $(C_{4-10})$bicycloaryl, a $(C_{6-10})$bicycloaryl or a $(C_{8-10})$bicycloaryl. Alternatively, "bicycloalkyl," either alone or represented along with another radical, can be a $(C_8)$bicycloaryl, a $(C_9)$bicycloaryl or a $(C_{10})$bicycloaryl. The term "$C_{1-10}$ alkyl bicycloaryl" refers to a group containing a terminal alkyl group, branched or straight chain and containing 2 to 10 atoms attached to a linking aryl group which is bicyclic, such as for example, 2-(1-naphthyl)-ethyl. Either portion of the moiety is unsubstituted or substituted.

"Carbonyl" means the radical —C(═O)— and/or —C(═O)R, wherein R is hydrogen or a further substituent. It is noted that the carbonyl radical may be further substituted with a variety of substituents to form different carbonyl groups including acids, acid halides, aldehydes, amides, esters, and ketones.

"Carboxy" means the radical —C(═O)—O— and/or —C(═O)—OR, wherein R is hydrogen or a further substituent. It is noted that compounds of the invention containing carboxy moieties may include protected derivatives thereof, i.e., where the oxygen is substituted with a protecting group. Suitable protecting groups for carboxy moieties include benzyl, tert-butyl, and the like.

The term "carboxylalkyl" refers to a terminal carboxyl (—COOH) group attached to branched or straight chain alkyl groups as defined above.

"Cyano" means the radical —CN.

The term "cycloaliphatic", used alone or as part of a larger moiety, refers to a saturated or partially unsaturated cyclic aliphatic ring system having from 3 to about 14 members, wherein the aliphatic ring system is optionally substituted. In some embodiments, the cycloaliphatic is a monocyclic hydrocarbon having 3-8 or 3-6 ring carbon atoms. Nonlimiting examples include cyclopropyl, cyclobutyl, cyclopentyl, cyclopentenyl, cyclohexyl, cyclohexenyl, cycloheptyl, cycloheptenyl, cyclooctyl, cyclooctenyl, and cyclooctadienyl. In some embodiments, the cycloaliphatic is a bridged or fused bicyclic hydrocarbon having 6-12, 6-10, or 6-8 ring carbon atoms, wherein any individual ring in the bicyclic ring system has 3-8 members.

In some embodiments, two adjacent substituents on the cycloaliphatic ring, taken together with the intervening ring atoms, form an optionally substituted fused 5- to 6-membered aromatic or 3- to 8-membered non-aromatic ring having 0-3 ring heteroatoms selected from the group consisting of O, N, and S. Thus, the term "cycloaliphatic" includes aliphatic rings that are fused to one or more aryl, heteroaryl, or heterocyclyl rings. Nonlimiting examples include indanyl, 5,6,7,8-tetrahydroquinoxalinyl, decahydronaphthyl, or tetrahydronaphthyl, where the radical or point of attachment is on the aliphatic ring. The term "cycloaliphatic" may be used interchangeably with the terms "carbocycle", "carbocyclyl", "carbocyclo", or "carbocyclic".

"Cycloalkyl" means a non-aromatic, saturated or partially unsaturated, monocyclic, bicyclic or polycyclic ring assembly that contains only carbon and hydrogen, and may be saturated, or partially unsaturated. $(C_X)$cycloalkyl and $(C_{X-Y})$cycloalkyl are typically used where X and Y indicate the number of carbon atoms in the ring assembly. For example, $(C_{3-10})$cycloalkyl includes cyclopropyl, cyclobutyl, cyclopentyl, cyclohexyl, cyclopentenyl, cyclohexenyl, 2,5-cyclohexadienyl, bicyclo[2.2.2]octyl, adamantan-1-yl, decahydronaphthyl, oxocyclohexyl, dioxocyclohexyl, thiocyclohexyl, 2-oxobicyclo[2.2.1]hept-1-yl, and the like. In particular embodiments, "cycloalkyl," either alone or represented along with another radical, can be a $(C_{3-14})$cycloalkyl, a $(C_{3-10})$cycloalkyl, a $(C_{3-7})$cycloalkyl, a $(C_{8-10})$cycloalkyl or a $(C_{5-7})$cycloalkyl. Alternatively, "cycloalkyl," either alone or represented along with another radical, can be a $(C_5)$cycloalkyl, a $(C_6)$cycloalkyl, a $(C_7)$cycloalkyl, a $(C_8)$cycloalkyl, a $(C_9)$cycloalkyl or a $(C_{10})$cycloalkyl.

The terms "heteroaryl" and "heteroar-", used alone or as part of a larger moiety, e.g., heteroaralkyl, or "heteroaralkoxy", refer to groups having 5 to 14 ring atoms, preferably 5, 6, 9, or 10 ring atoms; having 6, 10, or 14☐ electrons shared in a cyclic array; and having, in addition to carbon atoms, from one to four heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. In some embodiments, two adjacent substituents on the heteroaryl, taken together with the intervening ring atoms, form an optionally substituted fused 5- to 6-membered aromatic or 4- to 8-membered non-aromatic ring having 0-3 ring heteroatoms selected from the group consisting of O, N, and S. Thus, the terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. Additional examples of heteroaryls include, but are not limited to, azepinyl, benzindolyl, 1,3-benzodioxolyl, benzooxazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzoxazolyl, benzopyranyl, benzopyranonyl, benzofuranonyl, benzofurazanyl, benzothiazolyl, benzothienyl (benzothiophenyl), benzothieno[3,2-d]pyrimidinyl, benzotriazolyl, benzo[4,6]imidazo[1,2-a]pyridinyl, carbazolyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzothiophenyl, furazanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, indolinyl, isoindolinyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, pyranyl, pyrazolo[3,4-d]pyrimidinyl, pyrido[3,2-d]pyrimidinyl, pyrido[3,4-d]pyrimidinyl, quinoxalinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, thiapyranyl, triazolyl, tetrazolyl, triazinyl, thieno[2,3-d]pyrimidinyl, thieno[3,2-d]pyrimidinyl, thieno[2,3-c]pyridinyl, and thiophenyl (i.e. thienyl).

A heteroaryl group may be mono-, bi-, tri-, or polycyclic, preferably mono-, bi-, or tricyclic, more preferably mono- or bicyclic. The term "heteroaryl" may be used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle", "heterocyclyl", "heterocyclic radical", and "heterocyclic ring" are used interchangeably and refer to a stable 3- to 7-membered monocyclic, or to a fused 7- to 10-membered or bridged 6- to 10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a heterocyclyl ring having 1-3 heteroatoms selected from oxygen, sulfur or nitrogen, the nitrogen may be N (as in 3,4-dihydro-2H-pyrrolyl), NH (as in pyrrolidinyl) or $^+$NR (as in N-substituted pyrrolidinyl).

A heterocyclic ring can be attached to its pendant group at any heteroatom or carbon atom that results in a stable structure, and any of the ring atoms can be optionally substituted. Examples of such saturated or partially unsaturated heterocyclic radicals include, without limitation, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl.

In some embodiments, two adjacent substituents on a heterocyclic ring, taken together with the intervening ring atoms, for an optionally substituted fused 5- to 6-membered aromatic or 3- to 8-membered non-aromatic ring having 0-3 ring heteroatoms selected from the group consisting of O, N, and S: Thus, the terms "heterocycle", "heterocyclyl", "heterocyclyl ring", "heterocyclic group", "heterocyclic moiety", "heterocycloalkyl" and "heterocyclic radical", are used interchangeably herein, and include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono-, bi-, tri-, or polycyclic, preferably mono-, bi-, or tricyclic, more preferably mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond between ring atoms. The term "partially unsaturated" is intended to encompass rings having multiple sites of unsaturation, but is not intended to include aryl or heteroaryl moieties, as herein defined.

The terms "haloaliphatic", "haloalkyl", "haloalkenyl" and "haloalkoxy" refer to an aliphatic, alkyl, alkenyl or alkoxy group, as the case may be, which is substituted with one or more halogen atoms. Nonlimiting examples include chloromethyl, 2-bromoethyl, 3-iodopropyl, trifluoromethyl, perfluoropropyl, and 8-chlorononyl. As used herein, the term "halogen" or "halo" means F, Cl, Br, or I. The term "fluoroaliphatic" refers to a haloaliphatic wherein the halogen is fluoro.

"Heteroalkyl", "heteroalkenyl" and "heteroalkynyl" include optionally substituted alkyl, alkenyl and alkynyl radicals and which have one or more skeletal chain atoms selected from an atom other than carbon, e.g., oxygen, nitrogen, sulfur, phosphorus or combinations thereof. A numerical range may be given, e.g., $C_1$-$C_4$ heteroalkyl which refers to the chain length in total, which in this example is 4 atoms long. For example, a —$CH_2OCH_2CH_3$ radical is referred to as a "$C_4$" heteroalkyl, which includes the heteroatom center in the atom chain length description. Connection to the rest of the molecule may be through either a heteroatom or a carbon in the heteroalkyl chain. A heteroalkyl group may be substituted with one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, nitro, oxo, thioxo, trimethylsilanyl, —$OR^a$, —$SR^a$, —$OC(O)$—$R^a$, —$N(R^a)_2$, —$C(O)R^a$, —$C(O)OR^a$, —$C(O)N(R^a)_2$, —$N(R^a)C(O)OR^a$, —$N(R^a)C(O)R^a$, —$N(R^a)S(O)_tR^a$ (where t is 1 or 2), —$S(O)_tOR^a$ (where t is 1 or 2), —$S(O)_tN(R^a)_2$ (where t is 1 or 2), or $PO_3(R^a)_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

The term "heteroalkylaryl" refers to a heteroalkyl group as defined above which is attached to an aryl group, and may be attached at a terminal point or through a branched portion of the heteroalkyl, for example, an benzyloxymethyl moiety. Either portion of the moiety is unsubstituted or substituted.

The terms "heteroarylalkyl", "heteroarylalkyl", "heteroaryl-alkyl", "heteroaryl-alkyl", "hetaralkyl" and "heteroaralkyl" are used to describe a group wherein the alkyl chain can be branched or straight chain forming a linking portion of the heteroaralkyl moiety with the terminal heteroaryl portion, as defined above, for example 3-furylmethyl, thenyl, furfuryl, and the like. Either portion of the moiety is unsubstituted or substituted.

The term "heteroalkylheteroaryl" refers likewise to a heteroalkyl group which is attached to a heteroaryl moiety, for example, an ethoxymethylpyridyl group. Either portion of the moiety is unsubstituted or substituted.

The term "heteroalkyl-heterocyclyl" refers to a heteroalkyl group as defined above, which is attached to a heterocyclic group, for example, 4(3-aminopropyl)-N-piperazinyl. Either portion of the moiety is unsubstituted or substituted.

The term "heteroalkyl-$C_{3-8}$cycloalkyl" refers to a heteroalkyl group as defined above, which is attached to a cyclic alkyl containing 3 to 8 carbons, for example, 1-aminobutyl-4-cyclohexyl. Either portion of the moiety is unsubstituted or substituted.

The term "heterobicycloalkyl" refers to a bicycloalkyl structure, which is unsubstituted or substituted, in which at least one carbon atom is replaced with a heteroatom independently selected from oxygen, nitrogen, and sulfur.

The term "heterospiroalkyl" refers to a spiroalkyl structure, which is unsubstituted or substituted, in which at least one carbon atom is replaced with a heteroatom independently selected from oxygen, nitrogen, and sulfur.

"Nitro" means the radical $-NO_2$.

"Hydroxy" means the radical $-OH$.

"Imino" means the radical $-CR(=NR')$ and/or $-C(=NR')-$, wherein R and R' are each independently hydrogen or a further substituent.

The term "oxo" refers to an oxygen that is double bonded to a carbon atom. One in the art understands that an "oxo" requires a second bond from the atom to which the oxo is attached. Accordingly, it is understood that oxo cannot be substituted onto an aryl or heteroaryl ring, unless it forms part of the aromatic system as a tautomer.

The term "substituted", as used herein, means that a hydrogen radical of the designated moiety is replaced with the radical of a specified substituent, provided that the substitution results in a stable or chemically feasible compound. The phrase "one or more substituents", as used herein, refers to a number of substituents that equals from one to the maximum number of substituents possible based on the number of available bonding sites, provided that the above conditions of stability and chemical feasibility are met. Unless otherwise indicated, an optionally substituted group may have a substituent at each substitutable position of the group, and the substituents may be either the same or different.

An aryl (including the aryl moiety in aralkyl, aralkoxy, aryloxyalkyl and the like) or heteroaryl (including the heteroaryl moiety in heteroaralkyl and heteroaralkoxy and the like) group may contain one or more substituents. Examples of suitable substituents on the unsaturated carbon atom of an aryl or heteroaryl group include -halo, $-NO_2$, $-CN$, $-R^*$, $-C(R^*)=C(R^*)_2$, $-C\equiv C-R^*$, $-OR^*$, $-SR°$, $-S(O)R°$, $-SO_2R°$, $-SO_3R°$, $-SO_2N(R^+)_2$, $-N(R^+)_2$, $-NR^+C(O)R^*$, $-NR^+C(O)N(R^+)_2$, $-NR^+CO_2R°$, $-O-CO_2R^*$, $-OC(O)N(R^+)_2$, $-O-C(O)R^*$, $-CO_2R^*$, $-C(O)-C(O)R^*$, $-C(O)R^*$, $-C(O)N(R^+)_2$, $-C(O)N(R^+)C(=NR^+)-N(R^+)_2$, $-N(R^+)C(=NR^+)-N(R^+)-C(O)R^*$, $-C(=NR^+)-N(R^+)_2$, $-C(=NR^+)-OR^*$, $-N(R^+)-N(R^+)_2$, $-N(R^+)C(=NR^+)-N(R^+)_2$, $-NR^+SO_2R°$, $-NR^+SO_2N(R^+)_2$, $-P(O)(R^*)_2$, $-P(O)(OR^*)_2$, $-O-P(O)-OR^*$, and $-P(O)(NR^+)-N(R^+)_2$; or two adjacent substituents, taken together with their intervening atoms, form a 5-6 membered unsaturated or partially unsaturated ring having 0-3 ring atoms selected from the group consisting of N, O, and S.

Each $R^+$, independently, is hydrogen or an optionally substituted aliphatic, aryl, heteroaryl, or heterocyclyl group, or two $R^+$ on the same nitrogen atom, taken together with the nitrogen atom, form a 5-8 membered aromatic or non-aromatic ring having, in addition to the nitrogen atom, 0-2 ring heteroatoms selected from N, O, and S. Each $R^*$ independently is hydrogen or an optionally substituted aliphatic, aryl, heteroaryl, or heterocyclyl group. Each $R°$ is an optionally substituted aliphatic or aryl group.

An aliphatic group or a non-aromatic heterocyclic ring may be substituted with one or more substituents. Examples of suitable substituents on the saturated carbon of an aliphatic group or of a non-aromatic heterocyclic ring include, without limitation, those listed above for the unsaturated carbon of an aryl or heteroaryl group and the following: $=O$, $=S$, $=C(R^*)_2$, $=N-N(R^*)_2$, $=N-OR^*$, $=N-NHC(O)R^*$, $=N-NHCO_2R°$, $=N-NHSO_2R°$, or $=N-R^*$, where each $R^*$ and $R°$ is as defined above.

Suitable substituents on the nitrogen atom of a non-aromatic heterocyclic ring include $-R^*$, $-N(R^*)_2$, $-C(O)R^*$, $-CO_2R^*$, $-C(O)-C(O)R^*$, $-C(O)CH_2C(O)R^*$, $-SO_2R^*$, $-SO_2N(R^*)_2$, $-C(=S)N(R^*)_2$, $-C(=NH)-N(R^*)_2$, and $-NR^*SO_2R^*$; wherein each $R^*$ is as defined above.

Unless otherwise stated, structures depicted herein are meant to include compounds which differ only in the presence of one or more isotopically enriched atoms. For example, compounds having the present structure except for the replacement of a hydrogen atom by a deuterium or tritium, or the replacement of a carbon atom by a $^{13}C$- or $^{14}C$-enriched carbon are within the scope of the invention.

It will be apparent to one skilled in the art that certain compounds described herein may exist in tautomeric forms, all such tautomeric forms of the compounds being within the scope of the invention. Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Exemplary mTORC1/2 Inhibitor Compounds

Any molecule capable of inhibiting the enzymatic activity of mTORC1 and mTORC2 may be used in the methods, pharmaceutical compositions, and kits of the present invention. mTORC1/2 inhibitors can be assayed in vitro or in vivo for their ability to selectively bind to and/or inhibit mTORC1 and mTORC2. In vitro assays include assays to determine selective inhibition of the ability of mTORC1 and mTORC2 to phosphorylate a substrate protein or peptide. Alternate in vitro assays quantitate the ability of the compound to selectively bind to mTORC1 and mTORC2. Selective inhibitor binding may be measured by radiolabelling the inhibitor prior to binding, isolating the inhibitor/mTOR complex and determining the amount of radiolabel bound. Alternatively, selective inhibitor binding may be determined by running a competition experiment in which new inhibitors are incubated with mTOR bound to a known radioligand. The compounds also can be assayed for their ability to affect cellular or physiological functions mediated by mTOR activity. Assays for each of these activities are known in the art.

In some embodiments of the methods of the invention, the mTORC1/2 inhibitor inhibits both mTORC1 and mTORC2 with an IC50 value of about 500 nM or less, 400 nM or less, 300 nM or less, 200 nM or less, 100 nM or less, 50 nM or less, 10 nM or less, or 1 nM or less, as ascertained in an in vitro kinase assay. In another embodiment, the mTORC1/2 inhibitor inhibits both mTORC1 and mTORC2 with an IC50 value of about 10 nM or less as ascertained in an in vitro kinase assay, and the mTORC1/2 inhibitor is substantially inactive against one or more types I PI3-kinases selected from the group consisting of PI3-kinase α, PI3-kinase β, PI3-kinase γ, and PI3-kinase δ. Alternatively, the mTORC1/2 inhibitor inhibits both mTORC1 and mTORC2 with an IC50 value of about 100 nM or less as ascertained in an in vitro kinase assay, and the IC50 value is at least 2, 5 or 10 times less than its IC50 value against all other type I PI3-kinases selected from the group consisting of PI3-kinase α, PI3-kinase β, PI3-kinase γ, and PI3-kinase δ.

In some embodiments, the mTORC1/2 inhibitor is a compound of Formula I:

Formula I or a pharmaceutically acceptable salt thereof, wherein:

$X_1$ is N or C-$E^1$, $X_2$ is N or C, $X_3$ is N or C, $X_4$ is C—$R^9$ or N, $X_5$ is N or C-$E^1$, $X_6$ is C or N, and $X_7$ is C or N; and wherein no more than two nitrogen ring atoms are adjacent;

$R_1$ is H, -L-$C_{1-10}$alkyl, -L-$C_{3-8}$cycloalkyl, -L-$C_{1-10}$alkyl-$C_{3-8}$cycloalkyl, -L-aryl, -L-heteroaryl, -L-$C_{1-10}$alkylaryl, -L-$C_{1-10}$alkylhetaryl, -L-$C_{1-10}$alkylheterocylyl, -L-$C_{2-10}$alkenyl, -L-$C_{2-10}$alkynyl, -L-$C_{2-10}$alkenyl-$C_{3-8}$cycloalkyl, -L-$C_{2-10}$alkynyl-$C_{3-8}$cycloalkyl, -L-heteroalkyl, -L-heteroalkylaryl, -L-heteroalkylheterocyl, -L-heteroalkyl-heterocylyl, -L-heteroalkyl-$C_{3-8}$cycloalkyl, -L-aralkyl, -L-heteroaralkyl, or -L-heterocyclyl, each of which is unsubstituted or is substituted by one or more independent $R^3$;

L is absent, —(C=O)—, —C(=O)O—, —C(=O)N($R^{31}$)—, —S—, —S(O)—, —S(O)$_2$—, —S(O)$_2$N($R^{31}$)—, or —N($R^{31}$)—;

$E^1$ and $E^2$ are independently —($W^1$)$_j$—$R^4$;

$M_1$ is a 5, 6, 7, 8, 9, or -10 membered ring system, wherein the ring system is monocyclic or bicyclic, substituted with $R_5$ and additionally optionally substituted with one or more —($W^2$)$_k$—$R^2$;

each k is 0 or 1;

j in $E^1$ or j in $E^2$, is independently 0 or 1;

$W^1$ is —O—, —N$R^7$—, —S(O)$_{0-2}$—, —C(O)—, —C(O)N($R^7$)—, —N($R^7$)C(O)—, —N($R^7$)S(O)—, —N($R^7$)S(O)$_2$—, —C(O)O—, —CH($R^7$)N(C(O)O$R^8$)—, —CH($R^7$)N(C(O)$R^8$)—, —CH($R^7$)N(SO$_2R^8$)—, —CH($R^7$)N($R^8$)—, —CH($R^7$)C(O)N($R^8$)—, —CH($R^7$)N($R^8$)C(O)—, —CH($R^7$)N($R^8$)S(O)—, or —CH($R^7$)N($R^8$)S(O)$_2$—;

$W^2$ is —O—, —N$R^7$—, —S(O)$_{0-2}$—, —C(O)—, —C(O)N($R^7$)—, —N($R^7$)C(O)—, —N($R^7$)C(O)N($R^8$)—, —N($R^7$)S(O)—, —N($R^7$)S(O)$_2$—, —C(O)O—, —CH($R^7$)N(C(O)O$R^8$)—, —CH($R^7$)N(C(O)$R^8$)—, —CH($R^7$)N(SO$_2R^8$)—, —CH($R^7$)N($R^8$)—, —CH($R^7$)C(O)N($R^8$)—, —CH($R^7$)N($R^8$)C(O)—, —CH($R^7$)N($R^8$)S(O)—, or —CH($R^7$)N($R^8$)S(O)$_2$—;

$R^2$ is hydrogen, halogen, —OH, —$R^{31}$, —CF$_3$, —OCF$_3$, —O$R^{31}$, —N$R^{31}R^{32}$, —N$R^{34}R^{35}$, —C(O)$R^{31}$, —CO$_2R^{31}$, —C(=O)N$R^{31}R^{32}$, —C(=O)N$R^{34}R^{35}$, —NO$_2$, —CN, —S(O)$_{0-2}R^{31}$, —SO$_2$N$R^{31}R^{32}$, —SO$_2$N$R^{34}R^{35}$, —N$R^{31}$C(=O)$R^{32}$, —N$R^{31}$C(=O)O$R^{32}$, —N$R^{31}$C(=O)N$R^{32}R^{33}$, —N$R^{31}$S(O)$_{0-2}R^{32}$, —C(=S)O$R^{31}$, —C(=O)S$R^{31}$, —N$R^{31}$C(=N$R^{32}$)N$R^{33}R^{32}$, —N$R^{31}$C(=N$R^{32}$)O$R^{33}$, —N$R^{31}$C(=N$R^{32}$)S$R^{33}$, —OC(=O)O$R^{33}$, —OC(=O)N$R^{31}R^{32}$, —OC(=O)S$R^{31}$, —SC(=O)O$R^{31}$, —P(O)O$R^{31}$O$R^{32}$, —SC(=O)N$R^{31}R^{32}$, aryl (e.g. bicyclic aryl, unsubstituted aryl, or substituted monocyclic aryl), hetaryl, $C_{1-10}$alkyl, $C_{3-8}$cycloalkyl, $C_{1-10}$alkyl-$C_{3-8}$cycloalkyl, $C_{3-8}$cycloalkyl-$C_{1-10}$alkyl, $C_{3-8}$cycloalkyl-$C_{2-10}$alkenyl, $C_{3-8}$cycloalkyl-$C_{2-10}$alkynyl, $C_{1-10}$alkyl-$C_{2-10}$alkenyl, $C_{1-10}$alkyl-$C_{2-10}$alkynyl, $C_{1-10}$alkylaryl (e.g. $C_{2-10}$alkyl-monocyclic aryl, $C_{1-10}$alkyl-substituted monocyclic aryl, or $C_{1-10}$alkylbicycloaryl), $C_{1-10}$alkylhetaryl, $C_{1-10}$alkylheterocyclyl, $C_{2-10}$alkenyl, $C_{2-10}$alkynyl, $C_{2-10}$alkenyl-$C_{1-10}$alkyl, $C_{2-10}$alkynyl-$C_{1-10}$alkyl, $C_{2-10}$alkenylaryl, $C_{2-10}$alkenylhetaryl, $C_{2-10}$alkenylheteroalkyl, $C_{2-10}$alkenylheterocyclcyl, $C_{2-10}$alkenyl-$C_{3-8}$cycloalkyl, $C_{2-10}$alkynylaryl, $C_{2-10}$alkynylhetaryl, $C_{2-10}$alkynylheteroalkyl, $C_{2-10}$alkynylheterocyclyl, $C_{2-10}$alkynyl-$C_{3-8}$cycloalkenyl, $C_{1-10}$alkoxy $C_{1-10}$alkyl, $C_{1-10}$alkoxy-$C_{2-10}$alkenyl, $C_{1-10}$alkoxy-$C_{2-10}$alkynyl, heterocyclyl, heteroalkyl, heterocyclyl-$C_{1-10}$alkyl, heterocyclyl-$C_{2-10}$alkenyl, heterocyclyl-$C_{2-10}$alkynyl, aryl-$C_{1-10}$ alkyl (e.g. monocyclic aryl-$C_{2-10}$alkyl, substituted monocyclic aryl-$C_{1-10}$alkyl, or bicycloaryl-$C_{1-10}$alkyl), aryl-$C_{2-10}$alkenyl, aryl-$C_{2-10}$alkynyl, aryl-heterocyclyl, hetaryl-$C_{1-10}$alkyl, hetaryl-$C_{2-10}$alkenyl, hetaryl-$C_{2-10}$alkynyl, hetaryl-$C_{3-8}$cycloalkyl, hetaryl-heteroalkyl, or hetaryl-heterocyclyl, wherein each of said bicyclic aryl or heteroaryl moiety is unsubstituted, or wherein each of bicyclic aryl, heteroaryl moiety or monocyclic aryl moiety is substituted with one or more independent alkyl, heteroalkyl, alkenyl, alkynyl, cycloalkyl, heterocycloalkyl, aryl, arylalkyl, heteroaryl, heteroarylalkyl, halo, —OH, —$R^{31}$, —CF$_3$, —OCF$_3$, —O$R^{31}$, —N$R^{31}R^{32}$, —N$R^{34}R^{35}$, —C(O)$R^{31}$, —CO$_2R^{31}$, —C(=O)N$R^{31}R^{32}$, —C(=O)N$R^{34}R^{35}$, —NO$_2$, —CN, —S(O)$_{0-2}R^{31}$, —SO$_2$N$R^{31}R^{32}$, —SO$_2$N$R^{34}R^{35}$, —N$R^{31}$C(=O)$R^{32}$, —N$R^{31}$C(=O)O$R^{32}$, —N$R^{31}$C(=O)N$R^{32}R^{33}$, —N$R^{31}$S(O)$_{0-2}R^{32}$, —C(=S)O$R^{31}$, —C(=O)S$R^{31}$, —N$R^{31}$C(=N$R^{32}$)N$R^{33}R^{32}$, —N$R^{31}$C(=N$R^{32}$)O$R^{33}$, —N$R^{31}$C(=N$R^{32}$)S$R^{33}$, —OC(=O)O$R^{33}$, —OC(=O)N$R^{31}R^{32}$, —OC(=O)S$R^{31}$, —SC(=O)O$R^{31}$, —P(O)O$R^{31}$O$R^{32}$, or —SC(=O)N$R^{31}R^{32}$, and wherein each of said alkyl, cycloalkyl, heterocyclyl, or heteroalkyl moiety is unsubstituted or is substituted with one or more alkyl, heteroalkyl, alkenyl, alkynyl, cycloalkyl, heterocycloalkyl, aryl, arylalkyl, heteroaryl, heteroarylalkyl, halo, —OH, —$R^{31}$, —$CF_3$, —$OCF_3$, —$OR^{31}$, —O-aryl, —$NR^{31}R^{32}$, —$NR^{34}R^{35}$, —$C(O)R^{31}$, —$CO_2R^{31}$, —$C(=O)NR^{34}R^{35}$, or —$C(=O)NR^{31}R^{32}$;

$R^3$ and $R^4$ are independently hydrogen, halogen, —OH, —$R^{31}$, —$CF_3$, —$OCF_3$, —$OR^{31}$, —$NR^{31}R^{32}$, —$NR^{34}R^{35}$, —$C(O)R^{31}$, —$CO_2R^{31}$, —$C(=O)NR^{31}R^{32}$, —$C(=O)NR^{34}R^{35}$, —$NO_2$, —CN, —$S(O)_{0-2}R^{31}$, —$SO_2NR^{31}R^{32}$, —$SO_2NR^{34}R^{35}$, —$NR^{31}C(=O)R^{32}$, —$NR^{31}C(=O)OR^{32}$, —$NR^{31}C(=O)NR^{32}R^{33}$, —$NR^{31}S(O)_{0-2}R^{32}$, —$C(=S)OR^{31}$, —$C(=O)SR^{31}$, —$NR^{31}C(=NR^{32})NR^{33}R^{32}$, —$NR^{31}C(=NR^{32})OR^{33}$, —$NR^{31}C(=NR^{32})SR^{33}$, —$OC(=O)OR^{33}$, —$OC(=O)NR^{31}R^{32}$, —$OC(=O)SR^{31}$, —$SC(=O)OR^{31}$, —$P(O)OR^{31}OR^{32}$, —$SC(=O)NR^{31}R^{32}$, aryl, hetaryl, $C_{1-4}$alkyl, $C_{1-10}$alkyl, $C_{3-8}$cycloalkyl, $C_{1-10}$alkyl-$C_{3-8}$cycloalkyl, $C_{3-8}$cycloalkyl-$C_{1-10}$alkyl, $C_{3-8}$cycloalkyl-$C_{2-10}$alkenyl, $C_{3-8}$cycloalkyl-$C_{2-10}$alkynyl, $C_{1-10}$alkyl-$C_{2-10}$alkenyl, $C_{1-10}$alkyl-$C_{2-10}$alkynyl, $C_{1-10}$alkylaryl, $C_{1-10}$alkylhetaryl, $C_{1-10}$alkylheterocyclyl, $C_{2-10}$alkenyl, $C_{2-10}$alkynyl, $C_{2-10}$alkenyl-$C_{1-10}$alkyl, $C_{2-10}$alkynyl-$C_{1-10}$alkyl, $C_{2-10}$alkenylaryl, $C_{2-10}$alkenylhetaryl, $C_{2-10}$alkenylheteroalkyl, $C_{2-10}$alkenylheterocyclcyl, $C_{2-10}$alkenyl-$C_{3-8}$cycloalkyl, $C_{2-10}$alkynyl-$C_{3-8}$cycloalkyl, $C_{2-10}$alkynylaryl, $C_{2-10}$alkynylhetaryl, $C_{2-10}$alkynylheteroalkyl, $C_{2-10}$alkynylheterocyclyl, $C_{2-10}$alkynyl-$C_{3-8}$cycloalkenyl, $C_{1-10}$alkoxy $C_{1-10}$alkyl, $C_{1-10}$alkoxy-$C_{2-10}$alkenyl, $C_{1-10}$alkoxy-$C_{2-10}$alkynyl, heterocyclyl, heterocyclyl-$C_{1-10}$alkyl, heterocyclyl-$C_{2-10}$alkenyl, heterocyclyl-$C_{2-10}$alkynyl, aryl-$C_{1-10}$alkyl, aryl-$C_{2-10}$alkenyl, aryl-$C_{2-10}$alkynyl, aryl-heterocyclyl, hetaryl-$C_{1-10}$alkyl, hetaryl-$C_{2-10}$alkenyl, hetaryl-$C_{2-10}$alkynyl, hetaryl-$C_{3-8}$cycloalkyl, heteroalkyl, hetaryl-heteroalkyl, or hetaryl-heterocyclyl, wherein each of said aryl or heteroaryl moiety is unsubstituted or is substituted with one or more independent halo, —OH, —$R^{31}$, —$CF_3$, —$OCF_3$, —$OR^{31}$, —$NR^{31}R^{32}$, —$NR^{34}R^{35}$, —$C(O)R^{31}$, —$CO_2R^{31}$, —$C(=O)NR^{31}R^{32}$, —$C(=O)NR^{34}R^{35}$, —$NO_2$, —CN, —$S(O)_{0-2}R^{31}$, —$SO_2NR^{31}R^{32}$, —$SO_2NR^{34}R^{35}$, —$NR^{31}C(=O)R^{32}$, —$NR^{31}C(=O)OR^{32}$, —$NR^{31}C(=O)NR^{32}R^{33}$, —$NR^{31}S(O)_{0-2}R^{32}$, —$C(=S)OR^{31}$, —$C(=O)SR^{31}$, —$NR^{31}C(=NR^{32})NR^{33}R^{32}$, —$NR^{31}C(=NR^{32})OR^{33}$, —$NR^{31}C(=NR^{32})SR^{33}$, —$OC(=O)OR^{33}$, —$OC(=O)NR^{31}R^{32}$, —$OC(=O)SR^{31}$, —$SC(=O)OR^{31}$, —$P(O)OR^{31}OR^{32}$, or —$SC(=O)NR^{31}R^{32}$, and wherein each of said alkyl, cycloalkyl, heterocyclyl, or heteroalkyl moiety is unsubstituted or is substituted with one or more halo, —OH, —$R^{31}$, —$CF_3$, —$OCF_3$, —$OR^{31}$, —O-aryl, —$NR^{31}R^{32}$, —$NR^{34}R^{35}$, —$C(O)R^{31}$, —$CO_2R^{31}$, —$C(=O)NR^{34}R^{35}$, or —$C(=O)NR^{31}R^{32}$;

$R^5$ is hydrogen, halogen, —OH, —$R^{31}$, —$CF_3$, —$OCF_3$, —$OR^{31}$, —$NR^{31}R^{32}$, —$NR^{34}R^{35}$, —$C(O)R^{31}$, —$CO_2R^{31}$, —$C(=O)NR^{31}R^{32}$, —$C(=O)NR^{34}R^{35}$, —$NO_2$, —CN, —$S(O)_{0-2}R^{31}$, —$SO_2NR^{31}R^{32}$, —$SO_2NR^{34}R^{35}$, —$NR^{31}C(=O)R^{32}$, —$R^{31}C(=O)OR^{32}$, —$NR^{31}C(=O)NR^{32}R^{33}$, —$NR^{31}S(O)_{0-2}R^{32}$, —$C(=S)OR^{31}$, —$C(=O)SR^{31}$, —$NR^{31}C(=NR^{32})NR^{33}R^{32}$, —$NR^{31}C(=NR^{32})OR^{33}$, —$NR^{31}C(=NR^{32})SR^{33}$, —$OC(=O)OR^{33}$, —$OC(=O)NR^{31}R^{32}$, —$OC(=O)SR^{31}$, —$SC(=O)OR^{31}$, —$P(O)OR^{31}OR^{32}$, or —$SC(=O)NR^{31}R^{32}$;

each of $R^{31}$, $R^{32}$, and $R^{33}$ is independently H or $C_{1-10}$alkyl, wherein the $C_{1-10}$alkyl is unsubstituted or is substituted with one or more aryl, heteroalkyl, heterocyclyl, or hetaryl group, wherein each of said aryl, heteroalkyl, heterocyclyl, or hetaryl group is unsubstituted or is substituted with one or more halo, —OH, —$C_{1-10}$alkyl, —$CF_3$, —O-aryl, —$OCF_3$, —$OC_{1-10}$alkyl, —$NH_2$, —$N(C_{1-10}$alkyl)($C_{1-10}$alkyl), —$NH(C_{1-10}$alkyl), —NH(aryl), —$NR^{34}R^{35}$, —$C(O)(C_{1-10}$alkyl), —$C(O)(C_{1-10}$alkyl-aryl), —C(O)(aryl), —$CO_2$—$C_{1-10}$alkyl, —$CO_2$—$C_{1-10}$alkylaryl, —$CO_2$-aryl, —$C(=O)N(C_{1-10}$alkyl)($C_{1-10}$alkyl), —$C(=O)NH(C_{1-10}$alkyl), —$C(=O)NR^{34}R^{35}$, —$C(=O)NH_2$, —$OCF_3$, —$O(C_{1-10}$alkyl), —O-aryl, —N(aryl)($C_{1-10}$alkyl), —$NO_2$, —CN, —$S(O)_{0-2}$ $C_{1-10}$alkyl, —$S(O)_{0-2}$ $C_{1-10}$alkylaryl, —$S(O)_{0-2}$ aryl, —$SO_2N$(aryl), —$SO_2$ $N(C_{1-10}$alkyl)($C_{1-10}$alkyl), —$SO_2$ $NH(C_{1-10}$alkyl) or —$SO_2NR^{34}R^{35}$;

$R^{34}$ and $R^{35}$ in —$NR^{34}R^{35}$, —$C(=O)NR^{34}R^{35}$, or —$SO_2NR^{34}R^{35}$, are taken together with the nitrogen atom to which they are attached to form a 3-10 membered saturated or unsaturated ring; wherein said ring is independently unsubstituted or is substituted by one or more —$NR^{31}R^{32}$, hydroxyl, halogen, oxo, aryl, hetaryl, $C_{1-6}$alkyl, or O-aryl, and wherein said 3-10 membered saturated or unsaturated ring independently contains 0, 1, or 2 more heteroatoms in addition to the nitrogen atom;

each of $R^1$ and $R^8$ is independently hydrogen, $C_{1-10}$alkyl, $C_{2-10}$alkenyl, aryl, heteroaryl, heterocyclyl or $C_{3-10}$cycloalkyl, each of which except for hydrogen is unsubstituted or is substituted by one or more independent $R^6$;

$R^6$ is halo, —$OR^{31}$, —SH, —$NH_2$, —$NR^{34}R^{35}$, —$NR^{31}R^{32}$, —$CO_2R^{31}$, —$CO_2$aryl, —$C(=O)NR^{31}R^{32}$, $C(=O)NR^{34}R^{35}$, —$NO_2$, —CN, —$S(O)_{0-2}$ $C_{1-10}$alkyl, —$S(O)_{0-2}$aryl, —$SO_2NR^{34}R^{35}$, —$SO_2NR^{31}R^{32}$, $C_{1-10}$alkyl, $C_{2-10}$alkenyl, $C_{2-10}$alkynyl; aryl-$C_{1-10}$alkyl, aryl-$C_{2-10}$alkenyl, aryl-$C_{2-10}$alkynyl, hetaryl-$C_{1-10}$alkyl, hetaryl-$C_{2-10}$alkenyl, hetaryl-$C_{2-10}$alkynyl, wherein each of said alkyl, alkenyl, alkynyl, aryl, heteroalkyl, heterocyclyl, or hetaryl group is unsubstituted or is substituted with one or more independent halo, cyano, nitro, —$OC_{1-10}$alkyl, $C_{1-10}$alkyl, $C_{2-10}$alkenyl, $C_{2-10}$alkynyl, halo$C_{1-10}$alkyl, halo$C_{2-10}$alkenyl, halo$C_{2-10}$alkynyl, —COOH, —$C(=O)NR^{31}R^{32}$, —$C(=O)NR^{34}R^{35}$, —$SO_2NR^{34}R^{35}$, —$SO_2NR^{31}R^{32}$, —$NR^{31}R^{32}$, or —$NR^{34}R^{35}$; and $R^9$ is H, halo, —$OR^{31}$, —SH, —$NH_2$, —$NR^{34}R^{35}$, —$NR^{31}R^{32}$, —$CO_2R^{31}$, —$CO_2$aryl, —$C(=O)NR^{31}R^{32}$, $C(=O)NR^{34}R^{35}$, —$NO_2$, —CN, —$S(O)_{0-2}$ $C_{1-10}$alkyl, —$S(O)_{0-2}$aryl, —$SO_2NR^{34}R^{35}$, —$SO_2NR^{31}R^{32}$, $C_{1-10}$alkyl, $C_{2-10}$alkenyl, $C_{2-10}$alkynyl; aryl-$C_{1-10}$alkyl, aryl-$C_{2-10}$alkenyl, aryl-$C_{2-10}$alkynyl, hetaryl-$C_{1-10}$alkyl, hetaryl-$C_{2-10}$alkenyl, hetaryl-$C_{2-10}$alkynyl, wherein each of said alkyl, alkenyl, alkynyl, aryl, heteroalkyl, heterocyclyl, or hetaryl group is unsubstituted or is substituted with one or more independent halo, cyano, nitro, —$OC_{1-10}$alkyl, $C_{1-10}$alkyl, $C_{2-10}$alkenyl, $C_{2-10}$alkynyl, halo$C_{1-10}$alkyl, halo$C_{2-10}$alkenyl, halo$C_{2-10}$alkynyl, —COOH, —$C(=O)NR^{31}R^{32}$, —$C(=O)NR^{34}R^{35}$, —$SO_2NR^{34}R^{35}$, —$SO_2NR^{31}R^{32}$, —$NR^{31}R^{32}$, or —$NR^{34}R^{35}$.

$M_1$ is a 5, 6, 7, 8, 9, or -10 membered ring system, wherein the ring system is monocyclic or bicyclic. The monocyclic $M_1$ ring is unsubstituted or substituted with one or more $R^5$ substituents (including 0, 1, 2, 3, 4, or 5 $R^5$ substituents). In some embodiments, the monocyclic $M_1$ ring is aromatic (including phenyl) or heteroaromatic (including but not limited to pyridinyl, pyrrolyl, imidazolyl, thiazolyl, or pyrimidinyl). The monocyclic $M_1$ ring may be a 5 or 6 membered ring (including but not limited to pyridinyl, pyrrolyl, imidazolyl, thiazolyl, or pyrimidinyl). In some embodiments, $M_2$ is a five membered heteroaromatic group with one heteroatom, wherein the heteroatom is N, S, or O. In another embodiment, $M_2$ is a five membered heteroaromatic group with two heteroatoms, wherein the heteroatoms are nitrogen and oxygen or nitrogen and sulfur.

The bicyclic $M_1$ ring is unsubstituted or substituted with one or more $R^5$ substituents (including 0, 1, 2, 3, 4, 5, 6 or 7 $R^5$ substituents). Bicyclic $M_1$ ring is a 7, 8, 9, or 10 membered aromatic or heteroaromatic. Examples of an aromatic bicyclic $M_1$ ring include naphthyl. In other embodiments the bicyclic $M_1$ ring is heteroaromatic and includes but is not limited to benzothiazolyl, quinolinyl, quinazolinyl, benzoxazolyl, and benzoimidazolyl.

In some embodiments, $M_1$ is a moiety having a structure of Formula M1-A or Formula M1-B:

Formula M1-A

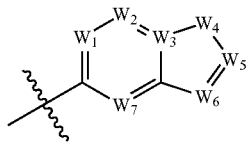

Formula M1-B

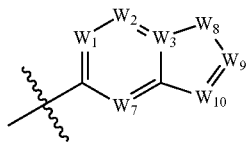

wherein $W_1$, $W_2$, and $W_7$ are independently N or C—$R^5$; $W_4$ and $W_{10}$ are independently N—$R^5$, O, or S; $W_6$ and $W_8$ are independently N or C—$R^5$; $W_5$ and $W_9$ are independently N or C—$R^2$; and $W_3$ is C or N, provided no more than two N and/or N—$R^5$ are adjacent and no two O or S are adjacent.

In some embodiments of the invention, the $M_1$ moiety of Formula M1-A is a moiety of Formula M1-A1, Formula M1-A2, Formula M1-A3, or Formula M1-A4:

Formula M1-A1

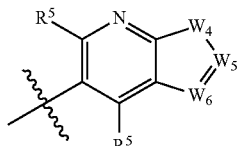

Formula M1-A2

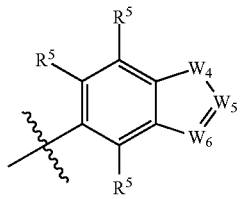

Formula M1-A3

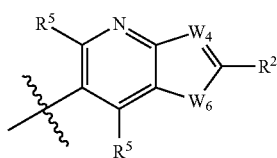

Formula M1-A4

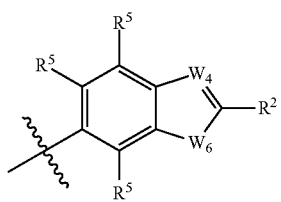

wherein $W_4$ is N—$R^5$, O, or S; $W_6$ is N or C—$R^5$ and $W_5$ is N or C—$R^2$.

Some nonlimiting examples of the $M_1$ moiety of Formula M1-A include:

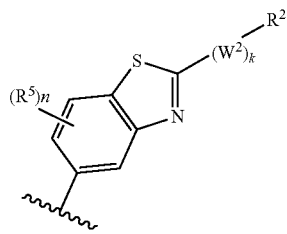

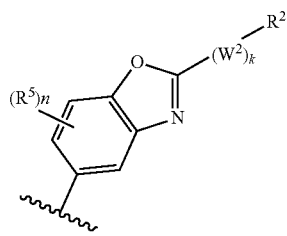

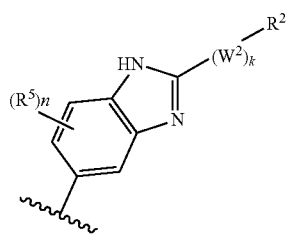

wherein $R^5$ is —$(W^1)_k$—$R^{53}$ or $R^{55}$; each k is independently 0 or 1, n is 0, 1, 2, or 3, and —$(W^1)_k$—$R^{53}$ and $R^{55}$ are as defined above.

In other embodiments of the invention, the $M_1$ moiety of Formula M1-B is a moiety of Formula M1-B1, Formula M1-B2, Formula M1-B3, or Formula M1-B4:

Formula M1-B1

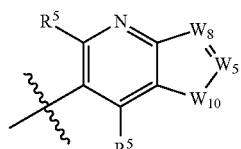

Formula M1-B2

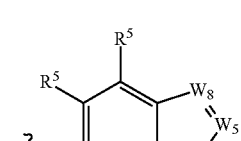

Formula M1-B3

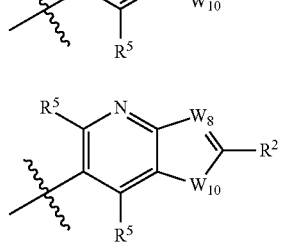

-continued

Formula M1-B4

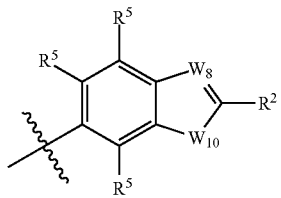

wherein $W_{10}$ is $N-R^5$, O, or S, $W_8$ is N or $C-R^5$, and $W_5$ is N or $C-R^2$.

Some nonlimiting examples of the $M_1$ moiety of Formula M1-B include:

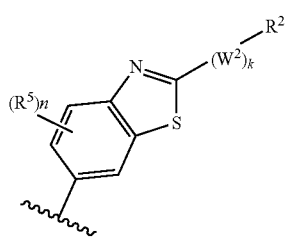

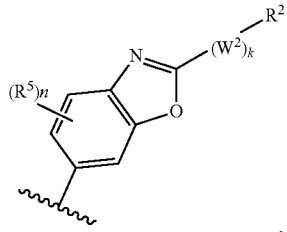

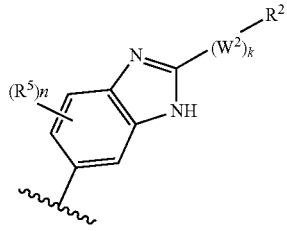

wherein $R'^5$ is $-(W^1)_k-R^{53}$ or $R^{55}$; k is 0 or 1, n is 0, 1, 2, or 3, and $-(W^1)_k-R^{53}$ and $R^{55}$ are as defined above.

In some other embodiments of the invention, the mTORC1/2 inhibitor has the Formula I-A:

Formula I-A

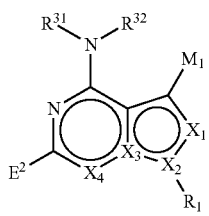

or a pharmaceutically acceptable salt thereof, wherein:
$X_1$ is N or $C-E^1$, $X_2$ is N, $X_3$ is C, and $X_4$ is $C-R^9$ or N; or
$X_1$ is N or $C-E^1$, $X_2$ is C, $X_3$ is N, and $X_4$ is $C-R^9$ or N;
$R_1$ is $-H$, -L-$C_{1-10}$alkyl, -L-$C_{3-8}$cycloalkyl, -L-$C_{1-10}$alkyl-$C_{3-8}$cycloalkyl, -L-aryl, -L-heteroaryl, -L-$C_{1-10}$alkylaryl, -L-$C_{1-10}$alkylheteroaryl, -L-$C_{1-10}$alkylheterocyclyl, -L-$C_{2-10}$alkenyl, -L-$C_{2-10}$alkynyl, -L-$C_{2-10}$alkenyl-$C_{3-8}$cycloalkyl, -L-$C_{2-10}$alkynyl-$C_{3-8}$cycloalkyl, -L-heteroalkyl, -L-heteroalkylaryl, -L-heteroalkylheteroaryl, -L-heteroalkyl-heterocyclyl, -L-heteroalkyl-$C_{3-8}$cycloalkyl, -L-aralkyl, -L-heteroaralkyl, or -L-heterocyclyl, each of which is unsubstituted or is substituted by one or more independent $R^3$;

L is absent, $-(C=O)-$, $-C(=O)O-$, $-C(=O)N(R^{31})-$, $-S-$, $-S(O)-$, $-S(O)_2-$, $-S(O)_2N(R^{31})-$, or $-N(R^{31})-$;

$M_1$ is a moiety having the structure of Formula M1-F1 or M1-F2:

Formula M1-F1

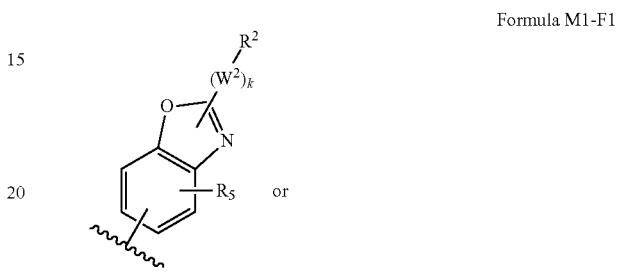

or

Formula M1-F2

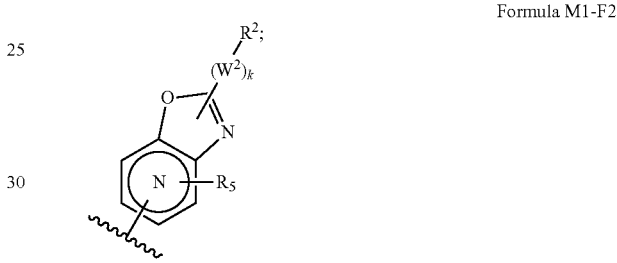

k is 0 or 1;
$E^1$ and $E^2$ are independently $-(W^1)_j-R^4$;
j, in each instance (i.e., in $E^1$ or j in $E^2$), is independently 0 or 1
$W^1$ is $-O-$, $-NR^7-$, $-S(O)_{0-2}-$, $-C(O)-$, $-C(O)N(R^7)-$, $-N(R^7)C(O)-$, $-N(R^7)S(O)-$, $-N(R^7)S(O)_2-$, $-C(O)O-$, $-CH(R^7)N(C(O)OR^8)-$, $-CH(R^7)N(C(O)R^8)-$, $-CH(R^7)N(SO_2R^8)-$, $-CH(R^7)N(R^8)-$, $-CH(R^7)C(O)N(R^8)-$, $-CH(R^7)N(R^8)C(O)-$, $-CH(R^7)N(R^8)S(O)-$, or $-CH(R^7)N(R^8)S(O)_2-$;
$W^2$ is $-O-$, $-NR^7-$, $-S(O)_{0-2}-$, $-C(O)-$, $-C(O)N(R^7)-$, $-N(R^7)C(O)-$, $-N(R^7)C(O)N(R^8)-$, $-N(R^7)S(O)-$, $-N(R^7)S(O)_2-$, $-C(O)O-$, $-CH(R^7)N(C(O)OR^8)-$, $-CH(R^7)N(C(O)R^8)-$, $-CH(R^7)N(SO_2R^8)-$, $-CH(R^7)N(R^8)-$, $-CH(R^7)C(O)N(R^8)-$, $-CH(R^7)N(R^8)C(O)-$, $-CH(R^7)N(R^8)S(O)-$, or $-CH(R^7)N(R^8)S(O)_2-$;

$R^2$ is hydrogen, halogen, $-OH$, $-R^{31}$, $-CF_3$, $-OCF_3$, $-OR^{31}$, $-NR^{31}R^{32}$, $-NR^{34}R^{35}$, $-C(O)R^{31}$, $-CO_2R^{31}$, $-C(=O)NR^{31}R^{32}$, $-C(=O)NR^{34}R^{35}$, $-NO_2$, $-CN$, $-S(O)_{0-2}R^{31}$, $-SO_2NR^{31}R^{32}$, $-SO_2NR^{34}R^{35}$, $-NR^{31}C(=O)R^{32}$, $-NR^{31}C(=O)OR^{32}$, $-NR^{31}C(=O)NR^{32}R^{33}$, $-NR^{31}S(O)_{0-2}R^{32}$, $-C(=S)OR^{31}$, $-C(=O)SR^{31}$, $-NR^{31}C(=NR^{32})NR^{33}R^{32}$, $-NR^{31}C(=NR^{32})OR^{33}$, $-NR^{31}C(=NR^{32})SR^{33}$, $-OC(=O)OR^{33}$, $-OC(=O)NR^{31}R^{32}$, $-OC(=O)SR^{31}$, $-SC(=O)OR^{31}$, $-P(O)OR^{31}OR^{32}$, $-SC(=O)NR^{31}R^{32}$, aryl (e.g. bicyclic aryl, unsubstituted aryl, or substituted monocyclic aryl), heteroaryl, $C_{1-10}$alkyl, $C_{3-8}$cycloalkyl, $C_{1-10}$alkyl-$C_{3-8}$cycloalkyl, $C_{3-8}$cycloalkyl-$C_{1-10}$alkyl, $C_{3-8}$cycloalkyl-$C_{2-10}$alkenyl, $C_{3-8}$cycloalkyl-$C_{2-10}$alkynyl, $C_{1-10}$alkyl-$C_{2-10}$alkenyl, $C_{1-10}$alkyl-$C_{2-10}$alkynyl, $C_{1-10}$alkylaryl (e.g. $C_{2-10}$alkyl-monocyclic aryl, $C_{1-10}$alkyl-substituted monocyclic aryl, or $C_{1-10}$alkylbicycloaryl), $C_{1-10}$alkylheteroaryl, $C_{1-10}$alkylheterocyclyl, $C_{2-10}$alkenyl, $C_{2-10}$alkynyl, $C_{2-10}$alkenyl-$C_{1-10}$alkyl, $C_{2-10}$alkynyl-$C_{1-10}$alkyl, $C_{2-10}$alkenylaryl, $C_{2-10}$alkenylheteroaryl, $C_{2-10}$alkenyl-heteroalkyl, $C_{2-10}$alkenylheterocyclcyl, $C_{2-10}$alkenyl-$C_{3-8}$cycloalkyl, $C_{2-10}$alkynylaryl, $C_{2-10}$alkynylheteroaryl, $C_{2-10}$alkynylheteroalkyl, $C_{2-10}$alkynylheterocyclyl, $C_{2-10}$alkynyl-$C_{3-8}$cycloalkenyl, $C_{1-10}$alkoxy $C_{1-10}$alkyl, $C_{1-10}$alkoxy-$C_{2-10}$alkenyl, $C_{1-10}$alkoxy-$C_{2-10}$alkynyl, heterocyclyl, heteroalkyl, heterocyclyl-$C_{1-10}$alkyl, heterocyclyl-$C_{2-10}$alkenyl, heterocyclyl-$C_{2-10}$alkynyl, aryl-$C_{1-10}$alkyl (e.g. monocyclic aryl-$C_{2-10}$alkyl, substituted monocyclic aryl-$C_{1-10}$alkyl, or bicycloaryl-$C_{1-10}$alkyl), aryl-$C_{2-10}$alkenyl, aryl-$C_{2-10}$alkynyl, aryl-heterocyclyl, heteroaryl-$C_{1-10}$alkyl, heteroaryl-$C_{2-10}$alkenyl, heteroaryl-$C_{2-10}$alkynyl, heteroaryl-$C_{3-8}$cycloalkyl, heteroaryl-heteroalkyl, or heteroaryl-heterocyclyl, wherein each of said bicyclic aryl or heteroaryl moiety is unsubstituted, or wherein each of bicyclic aryl, heteroaryl moiety or monocyclic aryl moiety is substituted with one or more independent alkyl, heteroalkyl, alkenyl, alkynyl, cycloalkyl, heterocycloalkyl, aryl, arylalkyl, heteroaryl, heteroarylalkyl, halo, —OH, —$R^{31}$, —$CF_3$, —$OCF_3$, —$OR^{31}$, —$NR^{31}R^{32}$, —$NR^{34}R^{35}$, —C(O)$R^{31}$, —$CO_2R^{31}$, —C(=O)$NR^{31}R^{32}$, —C(=O)$NR^{34}R^{35}$, —$NO_2$, —CN, —S(O)$_{0-2}R^{31}$, —$SO_2NR^{31}R^{32}$, —$SO_2NR^{34}R^{35}$, —$NR^{31}$C(=O)$R^{32}$, —$NR^{31}$C(=O)$OR^{32}$, —$NR^{31}$C(=O)$NR^{32}R^{33}$, —$NR^{31}$S(O)$_{0-2}R^{32}$, —C(=S)$OR^{31}$, —C(=O)$SR^{31}$, —$NR^{31}$C(=$NR^{32}$)$NR^{33}R^{32}$, —$NR^{31}$C(=$NR^{32}$)$R^{33}$, —$NR^{31}$C(=$NR^{32}$)$SR^{33}$, —OC(=O)$OR^{33}$, —OC(=O)$NR^{31}R^{32}$, —OC(=O)$SR^{31}$, —SC(=O)$OR^{31}$, —P(O)$OR^{31}OR^{32}$, or —SC(=O)$NR^{31}R^{32}$, and wherein each of said alkyl, cycloalkyl, heterocyclyl, or heteroalkyl moiety is unsubstituted or is substituted with one or more alkyl, heteroalkyl, alkenyl, alkynyl, cycloalkyl, heterocycloalkyl, aryl, arylalkyl, heteroaryl, heteroarylalkyl, halo, —OH, —$R^{31}$, —$CF_3$, —$OCF_3$, —$OR^{31}$, —O-aryl, —$NR^{31}R^{32}$, —$NR^{34}R^{35}$, —C(O)$R^{31}$, —$CO_2R^{31}$, —C(=O)$NR^{34}R^{35}$, or —C(=O)$NR^{31}R^{32}$;

$R^3$ and $R^4$ are independently hydrogen, halogen, —OH, —$R^{31}$, —$CF_3$, —$OCF_3$, —$OR^{31}$, —$NR^{31}R^{32}$, —$NR^{34}R^{35}$, —C(O)$R^{31}$, —$CO_2R^{31}$, —C(=O)$NR^{31}R^{32}$, —C(=O)$NR^{34}R^{35}$, —$NO_2$, —CN, —S(O)$_{0-2}R^{31}$, —$SO_2NR^{31}R^{32}$, —$SO_2NR^{34}R^{35}$, —$NR^{31}$C(=O)$R^{32}$, —$NR^{31}$C(=O)$OR^{32}$, —$NR^{31}$C(=O)$NR^{32}R^{33}$, —$NR^{31}$S(O)$_{0-2}R^{32}$, —C(=S)$OR^{31}$, —C(=O)$SR^{31}$, —$NR^{31}$C(=$NR^{32}$)$NR^{33}R^{32}$, —$NR^{31}$C(=$NR^{32}$)$OR^{33}$, —$NR^{31}$C(=$NR^{32}$)$SR^{33}$, —OC(=O)$OR^{33}$, —OC(=O)$NR^{31}R^{32}$, —OC(=O)$SR^{31}$, —SC(=O)$OR^{31}$, —P(O)$OR^{31}OR^{32}$, —SC(=O)$NR^{31}R^{32}$, aryl, heteroaryl, $C_{1-4}$alkyl, $C_{1-10}$alkyl, $C_{3-8}$cycloalkyl, $C_{1-10}$alkyl-$C_{3-8}$cycloalkyl, $C_{3-8}$cycloalkyl-$C_{1-10}$alkyl, $C_{3-8}$cycloalkyl-$C_{2-10}$alkenyl, $C_{3-8}$cycloalkyl-$C_{2-10}$alkynyl, $C_{1-10}$alkyl-$C_{2-10}$alkenyl, $C_{1-10}$alkyl-$C_{2-10}$alkynyl, $C_{1-10}$alkylaryl, $C_{1-10}$alkylheteroaryl, $C_{1-10}$alkylheterocyclyl, $C_{2-10}$alkenyl, $C_{2-10}$alkynyl, $C_{2-10}$alkenyl-$C_{1-10}$alkyl, $C_{2-10}$alkynyl-$C_{1-10}$alkyl, $C_{2-10}$alkenylaryl, $C_{2-10}$alkenylheteroaryl, $C_{2-10}$alkenyl-heteroalkyl, $C_{2-10}$alkenylheterocyclcyl, $C_{2-10}$alkenyl-$C_{3-8}$cycloalkyl, $C_{2-10}$alkynyl-$C_{3-8}$cycloalkyl, $C_{2-10}$alkynylaryl, $C_{2-10}$alkynylheteroaryl, $C_{2-10}$alkynylheteroalkyl, $C_{2-10}$alkynylheterocyclyl, $C_{2-10}$alkynyl-$C_{3-8}$cycloalkyl, $C_{1-10}$alkoxy $C_{1-10}$alkyl, $C_{1-10}$alkoxy-$C_{2-10}$alkenyl, $C_{1-10}$alkoxy-$C_{2-10}$alkynyl, heterocyclyl, heterocyclyl-$C_{1-10}$alkyl, heterocyclyl-$C_{2-10}$alkenyl, heterocyclyl-$C_{2-10}$alkynyl, aryl-$C_{1-10}$alkyl, aryl-$C_{2-10}$alkenyl, aryl-$C_{2-10}$alkynyl, aryl-heterocyclyl, heteroaryl-$C_{1-10}$alkyl, heteroaryl-$C_{2-10}$alkenyl, heteroaryl-$C_{2-10}$alkynyl, heteroaryl-$C_{3-8}$cycloalkyl, heteroalkyl, heteroaryl-heteroalkyl, or heteroaryl-heterocyclyl, wherein each of said aryl or heteroaryl moiety is unsubstituted or is substituted with one or more independent halo, —OH, —$R^{31}$, —$CF_3$, —$OCF_3$, —$OR^{31}$, —$NR^{31}R^{32}$, —$NR^{34}R^{35}$, —C(O)$R^{31}$, —$CO_2R^{31}$, —C(=O)$NR^{31}R^{32}$, —C(=O)$NR^{34}R^{35}$, —$NO_2$, —CN, —S(O)$_{0-2}R^{31}$, —$SO_2NR^{31}R^{32}$, —$SO_2NR^{34}R^{35}$, —$NR^{31}$C(=O)$R^{32}$, —$NR^{31}$C(=O)$OR^{32}$, —$NR^{31}$C(=O)$NR^{32}R^{33}$, —$NR^{31}$S(O)$_{0-2}R^{32}$, —C(=S)$OR^{31}$, —C(=O)$SR^{31}$, —$NR^{31}$C(=$NR^{32}$)$NR^{33}R^{32}$, —$NR^{31}$C(=$NR^{32}$)$OR^{33}$, —$NR^{31}$C(=$NR^{32}$)$SR^{33}$, —OC(=O)$OR^{33}$, —OC(=O)$NR^{31}R^{32}$, —OC(=O)$SR^{31}$, —SC(=O)$OR^{31}$, —P(O)$OR^{31}OR^{32}$, or —SC(=O)$NR^{31}R^{32}$, and wherein each of said alkyl, cycloalkyl, heterocyclyl, or heteroalkyl moiety is unsubstituted or is substituted with one or more halo, —OH, —$R^{31}$, —$CF_3$, —$OCF_3$, —$OR^{31}$, —O-aryl, —$NR^{31}R^{32}$, —$NR^{34}R^{35}$, —C(O)$R^{31}$, —$CO_2R^{31}$, —C(=O)$NR^{34}R^{35}$, or —C(=O)$NR^{31}R^{32}$;

$R^5$ is hydrogen, halogen, —OH, —$R^{31}$, —$CF_3$, —$OCF_3$, —$OR^{31}$, —$NR^{31}R^{32}$, —$NR^{34}R^{35}$, —C(O)$R^{31}$, —$CO_2R^{31}$, —C(=O)$NR^{31}R^{32}$, —C(=O)$NR^{34}R^{35}$, —$NO_2$, —CN, —S(O)$_{0-2}R^{31}$, —$SO_2NR^{31}R^{32}$, —$SO_2NR^{34}R^{35}$, —$NR^{31}$C(=O)$R^{32}$, —$NR^{31}$C(=O)$OR^{32}$, —$NR^{31}$C(=O)$NR^{32}R^{33}$, —$NR^{31}$S(O)$_{0-2}R^{32}$, —C(=S)$OR^{31}$, —C(=O)$SR^{31}$, —$NR^{31}$C(=$NR^{32}$)$NR^{33}R^{32}$, —$NR^{31}$C(=$NR^{32}$)$OR^{33}$, —$NR^{31}$C(=$NR^{32}$)$SR^{33}$, —OC(=O)$OR^{33}$, —OC(=O)$NR^{31}R^{32}$, —OC(=O)$SR^{31}$, —SC(=O)$OR^{31}$, —P(O)$OR^{31}OR^{32}$, or —SC(=O)$NR^{31}R^{32}$;

$R^{31}$, $R^{32}$, and $R^{33}$, in each instance, are independently H or $C_{1-10}$alkyl, wherein the $C_{1-10}$alkyl is unsubstituted or is substituted with one or more aryl, heteroalkyl, heterocyclyl, or heteroaryl group, wherein each of said aryl, heteroalkyl, heterocyclyl, or heteroaryl group is unsubstituted or is substituted with one or more halo, —OH, —$C_{1-10}$alkyl, —$CF_3$, —O-aryl, —$OCF_3$, —$OC_{1-10}$alkyl, —$NH_2$, —N($C_{1-10}$alkyl)($C_{1-10}$alkyl), —NH($C_{1-10}$alkyl), —NH(aryl), —$NR^{34}R^{35}$, —C(O)($C_{1-10}$alkyl), —C(O)($C_{1-10}$alkyl-aryl), —C(O)(aryl), —$CO_2$—$C_{1-10}$alkyl, —$CO_2$—$C_{1-10}$alkylaryl, —$CO_2$-aryl, —C(=O)N($C_{1-10}$alkyl)($C_{1-10}$alkyl), —C(=O)NH($C_{1-10}$alkyl), —C(=O)$NR^{34}R^{35}$, —C(=O)$NH_2$, —$OCF_3$, —O($C_{1-10}$alkyl), —O-aryl, —N(aryl)($C_{1-10}$alkyl), —$NO_2$, —CN, —S(O)$_{0-2}$ $C_{1-10}$alkyl, —S(O)$_{0-2}$ $C_{1-10}$alkylaryl, —S(O)$_{0-2}$ aryl, —$SO_2$N(aryl), —$SO_2$N($C_{1-10}$alkyl)($C_{1-10}$alkyl), —$SO_2$ NH($C_{1-10}$alkyl) or —$SO_2NR^{34}R^{35}$;

$R^{34}$ and $R^{35}$ in —$NR^{34}R^{35}$, —C(=O)$NR^{34}R^{35}$, or —$SO_2NR^{34}R^{35}$, are taken together with the nitrogen atom to which they are attached to form a 3-10 membered saturated or unsaturated ring; wherein said ring is independently unsubstituted or is substituted by one or more —$NR^{31}R^{32}$, hydroxyl, halogen, oxo, aryl, heteroaryl, $C_{1-6}$alkyl, or O-aryl, and wherein said 3-10 membered saturated or unsaturated ring independently contains 0, 1, or 2 more heteroatoms in addition to the nitrogen atom;

$R^7$ and $R^8$ are each independently hydrogen, $C_{1-10}$alkyl, $C_{2-10}$alkenyl, aryl, heteroaryl, heterocyclyl or $C_{3-10}$cycloalkyl, each of which except for hydrogen is unsubstituted or is substituted by one or more independent $R^6$;

$R^6$ is halo, —$OR^{31}$, —SH, —$NH_2$, —$NR^{34}R^{35}$, —$NR^{31}R^{32}$, —$CO_2R^{31}$, —$CO_2$aryl, —C(=O)$NR^{31}R^{32}$, C(=O)$NR^{34}R^{35}$, —$NO_2$, —CN, —S(O)$_{0-2}$ $C_{1-10}$alkyl, —S(O)$_{0-2}$aryl, —$SO_2NR^{34}R^{35}$, —$SO_2NR^{31}R^{32}$, $C_{1-10}$alkyl, $C_{2-10}$alkenyl, $C_{2-10}$alkynyl; aryl-$C_{1-10}$alkyl, aryl-$C_{2-10}$alkenyl, aryl-$C_{2-10}$alkynyl, heteroaryl-$C_{1-10}$alkyl, heteroaryl-$C_{2-10}$alkenyl, heteroaryl-$C_{2-10}$alkynyl, wherein each of said alkyl, alkenyl, alkynyl, aryl, heteroalkyl, heterocyclyl, or heteroaryl group is unsubstituted or is substituted with one or more independent halo, cyano, nitro, —O$C_{1-10}$alkyl, $C_{1-10}$alkyl, $C_{2-10}$alkenyl, $C_{2-10}$alkynyl, halo$C_{1-10}$alkyl, halo$C_{2-10}$alkenyl, halo$C_{2-10}$alkynyl, —COOH, —C(=O)NR$^{31}$R$^{32}$, —C(=O)NR$^{34}$R$^{35}$, —SO$_2$NR$^{34}$R$^{35}$, —SO$_2$ NR$^{31}$R$^{32}$, —NR$^{31}$R$^{32}$, or —NR$^{34}$R$^{35}$; and R$^9$ is H, halo, —OR$^{31}$, —SH, —NH$_2$, —NR$^{34}$R$^{35}$, —NR$^{31}$R$^{32}$, —CO$_2$R$^{31}$, —CO$_2$aryl, —C(=O)NR$^{31}$R$^{32}$, C(=O)NR$^{34}$R$^{35}$, —NO$_2$, —CN, —S(O)$_{0-2}$ $C_{1-10}$alkyl, —SO$_2$NR$^{34}$R$^{35}$, —SO$_2$NR$^{31}$R$^{32}$, —S(O)$_{0-2}$aryl, —SO$_2$NR$^{34}$R$^{35}$, —SO$_2$NR$^{31}$R$^{32}$, $C_{1-10}$alkyl, $C_{2-10}$alkenyl, $C_{2-10}$alkynyl; aryl-$C_{1-10}$alkyl, aryl-$C_{2-10}$alkenyl, aryl-$C_{2-10}$alkynyl, heteroaryl-$C_{1-10}$alkyl, heteroaryl-$C_{2-10}$alkenyl, heteroaryl-$C_{2-10}$alkynyl, wherein each of said alkyl, alkenyl; alkynyl, aryl, heteroalkyl, heterocyclyl, or heteroaryl group is unsubstituted or is substituted with one or more independent halo, cyano, nitro, —O$C_{1-10}$alkyl, $C_{1-10}$alkyl, $C_{2-10}$alkenyl, $C_{2-10}$alkynyl, halo$C_{1-10}$alkyl, halo$C_{2-10}$alkenyl, halo$C_{2-10}$alkynyl, —COOH, —C(=O)NR$^{31}$R$^{32}$, —C(=O)NR$^{34}$R$^{35}$, —SO$_2$NR$^{34}$R$^{35}$, —SO$_2$ NR$^{31}$R$^{32}$, —NR$^{31}$R$^{32}$, or —NR$^{34}$R$^{35}$.

In some embodiments, $X_4$ is C—R$^9$.

In some other embodiments of the invention, the mTORC1/2 inhibitor is as defined above, wherein the compound is of Formula I-B:

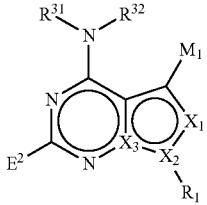

Formula I-B or a pharmaceutically acceptable salt thereof, and wherein the substituents are as defined above.

In various embodiments the compound of Formula I-B or its pharmaceutically acceptable salt thereof, is a compound having the structure of Formula I-B1 or Formula I-B2:

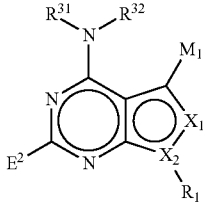

Formula I-B1

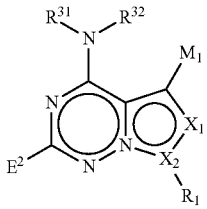

Formula I-B2 or a pharmaceutically acceptable salt thereof.

In various embodiments of Formula I-B1, $X_1$ is N and $X_2$ is N. In other embodiments, $X_1$ is C-E$^1$ and $X_2$ is N. In yet other embodiments, $X_1$ is NH and $X_2$ is C.

In further embodiments, $X_1$ is CH-E$^1$ and $X_2$ is C.

In various embodiments of Formula I-B2, $X_1$ is N and $X_2$ is C. In further embodiments, $X_1$ is C-E$^1$ and $X_2$ is C.

In various embodiments, $X_1$ is C—(W$^1$)$_j$—R$^4$, where j is 0.

In another embodiment, $X_1$ is CH. In yet another embodiment, $X_1$ is C-halogen, where halogen is Cl, F, Br, or I.

In various embodiments of $X_1$, it is C—(W$^1$)$_j$—R$^4$. In various embodiments of $X_1$, j is 1, and W$^1$ is —O—. In various embodiments of $X_1$, j is 1, and W$^1$ is —NR$^7$—. In various embodiments of $X_1$, j is 1, and W$^1$ is —NH—. In various embodiments of $X_1$, j is 1, and W$^1$ is —S(O)$_{0-2}$—. In various embodiments of $X_1$, j is 1, and W$^1$ is —C(O)—. In various embodiments of $X_1$, j is 1, and W$^1$ is —C(O)N(R$^7$)—. In various embodiments of $X_1$, j is 1, and W$^1$ is —N(R$^7$)C(O)—. In various embodiments of $X_1$, j is 1, and W$^1$ is —N(R$^7$)S(O)—. In various embodiments of $X_1$, j is 1, and W$^1$ is —N(R$^7$)S(O)$_2$—. In various embodiments of $X_1$, j is 1, and W$^1$ is —C(O)O—. In various embodiments of $X_1$, j is 1, and W$^1$ is CH(R$^7$)N(C(O)OR$^8$)—. In various embodiments of $X_1$, j is 1, and W$^1$ is —CH(R$^7$)N(C(O)R$^8$)—. In various embodiments of $X_1$, j is 1, and W$^1$ is —CH(R$^7$)N(SO$_2$R)—. In various embodiments of $X_1$, j is 1, and W$^1$ is —CH(R$^7$)N(R$^8$)—. In various embodiments of $X_1$, j is 1, and W$^1$ is —CH(R$^7$)C(O)N(R$^8$)—. In various embodiments of $X_1$, j is 1, and W$^1$ is —CH(R$^7$)N(R$^8$)C(O)—. In various embodiments of $X_1$, j is 1, and W$^1$ is —CH(R$^7$)N(R$^8$)S(O)—. In various embodiments of $X_1$, j is 1, and W$^1$ is —CH(R$^7$)N(R$^8$)S(O)$_2$—.

In another embodiment, $X_1$ is CH$_2$. In yet another embodiment, $X_1$ is CH-halogen, where halogen is Cl, F, Br, or I.

In another embodiment, $X_1$ is N.

In various embodiments, $X_2$ is N. In other embodiments, $X_2$ is C.

In various embodiments, E$^2$ is —(W$^1$)$_j$—R$^4$, where j is 0.

In another embodiment, E$^2$ is CH. In yet another embodiment, E$^2$ is C-halogen, where halogen is Cl, F, Br, or I.

In various embodiments of E$^2$, it is —(W$^1$)$_j$—R$^4$. In various embodiments of E$^2$, j is 1, and W$^1$ is —O—. In various embodiments of E$^2$, j is 1, and W$^1$ is —NR$^7$—. In various embodiments of E$^2$, j is 1, and W$^1$ is —NH—. In various embodiments of E$^2$, j is 1, and W$^1$ is —S(O)$_{0-2}$—. In various embodiments of E$^2$, j is 1, and W$^1$ is —C(O)—. In various embodiments of E$^2$, j is 1, and W$^1$ is —C(O)N(R$^7$)—. In various embodiments of E$^2$, j is 1, and W$^1$ is —N(R$^7$)C(O)—. In various embodiments of E$^2$, j is 1, and W$^1$ is —N(R$^7$)S(O)—. In various embodiments of E$^2$, j is 1, and W$^1$ is —N(R$^7$)S(O)$_2$—. In various embodiments of E$^2$, j is 1, and W$^1$ is —C(O)O—. In various embodiments of E$^2$, j is 1, and W$^1$ is CH(R$^7$)N(C(O)OR$^8$)—. In various embodiments of E$^2$, j is 1, and W$^1$ is —CH(R$^7$)N(C(O)R$^8$)—. In various embodiments of E$^2$, j is 1, and W$^1$ is —CH(R$^7$)N(SO$_2$R$^8$)—. In various embodiments of E$^2$, j is 1, and W$^1$ is —CH(R$^7$)N(R$^8$)—. In various embodiments of E$^2$, j is 1, and W$^1$ is —CH(R$^7$)C(O)N(R$^8$)—. In various embodiments of E$^2$, j is 1, and W$^1$ is —CH(R$^7$)N(R$^8$)C(O)—. In various embodiments of E$^2$, j is 1, and W$^1$ is —CH(R$^7$)N(R$^8$)S(O)—. In various embodiments of E$^2$, j is 1, and W$^1$ is —CH(R$^7$)N(R$^8$)S(O)$_2$—.

In various embodiments when M$_1$ is a moiety of Formula M1-F1, M$_1$ is benzoxazolyl substituted with —(W$_2$)$_k$—R$_2$. In some embodiments, M$_1$ is a benzoxazolyl substituted at the 2-position with —(W$^2$)$_j$—R$^2$. In some embodiments, M$_1$ is either a 5-benzoxazolyl or a 6-benzoxazolyl moiety, optionally substituted at the 2-position with —(W²)ⱼ—R².
Exemplary Formula M1-F1 M₁ moieties include but are not limited to the following:

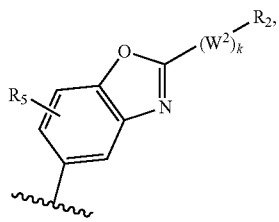

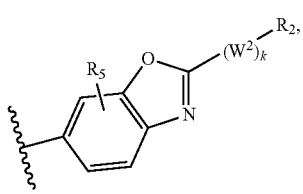

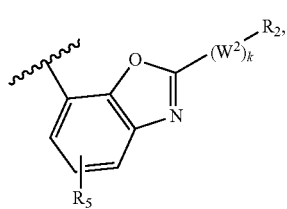

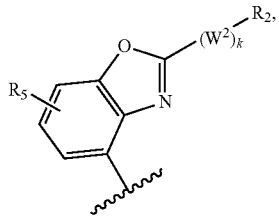

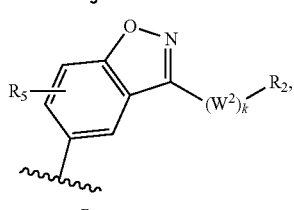

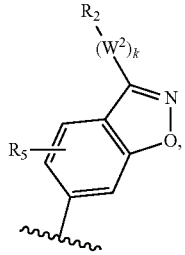

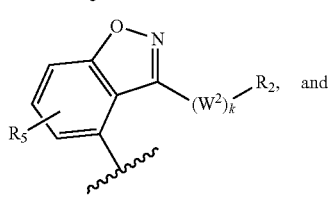

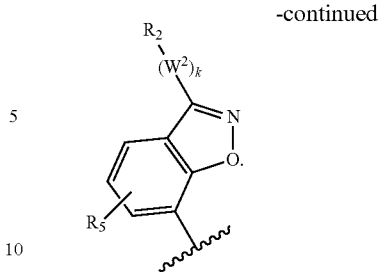

In various embodiments when M₁ is a moiety of Formula M1-F2, Formula M1-F2 is an aza-substituted benzoxazolyl moiety having a structure of one of the following formulae:

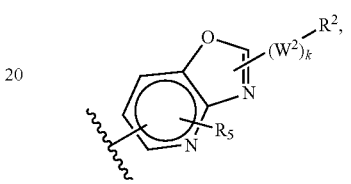

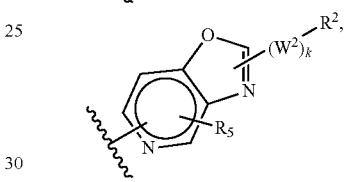

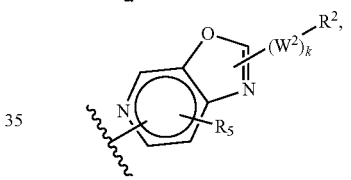

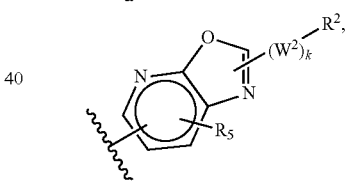

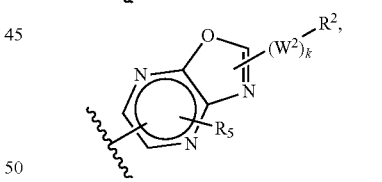

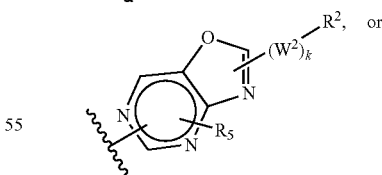

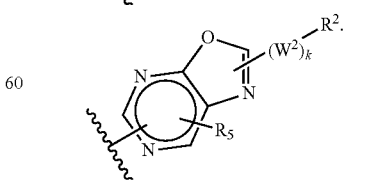

Exemplary Formula M1-F2 M₁ moieties include but are not limited to the following:

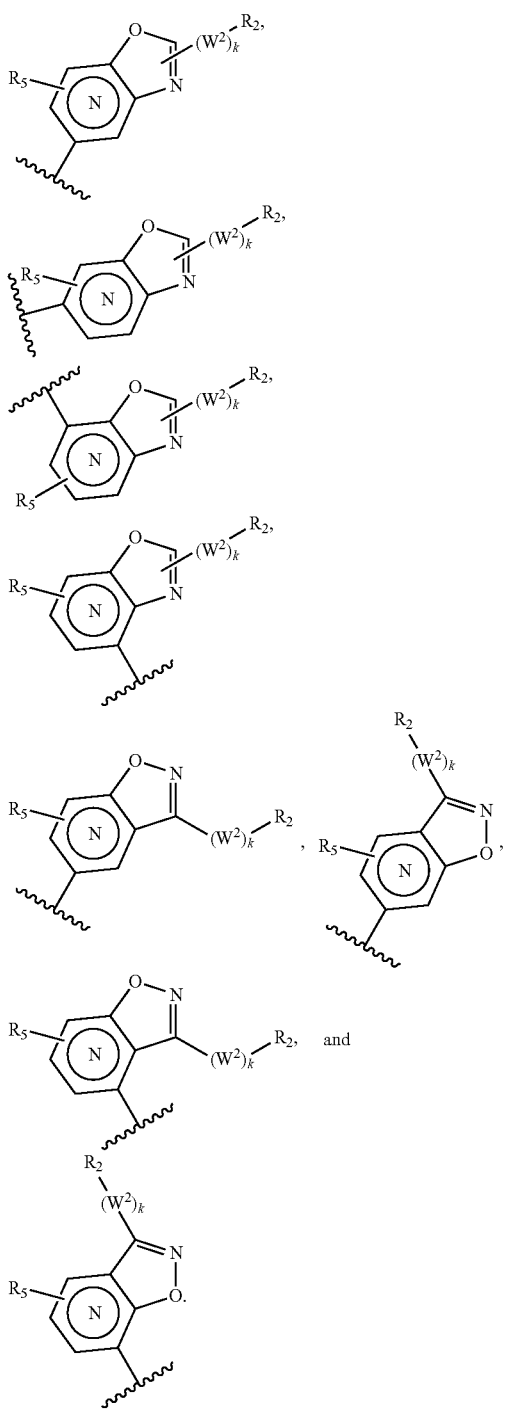

In various embodiments of $M_1$, k is 0. In other embodiments of $M_1$, k is 1, and $W^2$ is selected from one of the following: —O—, —NR$^7$—, —S(O)$_{0-2}$—, —C(O)—, —C(O)N(R$^7$)—, —N(R$^7$)C(O)—, or —N(R$^7$)C(O)N(R$^8$)—. In yet another embodiment of $M_1$, k is 1, and $W^2$ is —N(R$^7$)S(O)—, —N(R$^7$)S(O)$_2$—, —C(O)O—, —CH(R$^7$)N(C(O)OR$^8$)—, —CH(R$^7$)N(C(O)R$^8$)—, or —CH(R$^7$)N(SO$_2$R$^8$)—. In a further embodiment of $M_1$, k is 1, and $W^2$ is —CH(R$^7$)N(R$^8$)—, —CH(R$^7$)C(O)N(R$^8$)—, —CH(R$^7$)N(R$^8$)C(O)—, or —CH(R$^7$)N(R$^8$)S(O)—. In yet another embodiment of $M_1$, k is 1, and $W^2$ is —CH(R$^7$)N(R$^8$)S(O)$_2$—.

In some other embodiments, the mTORC1/2 inhibitor is a compound of Formula I-C or Formula I-D:

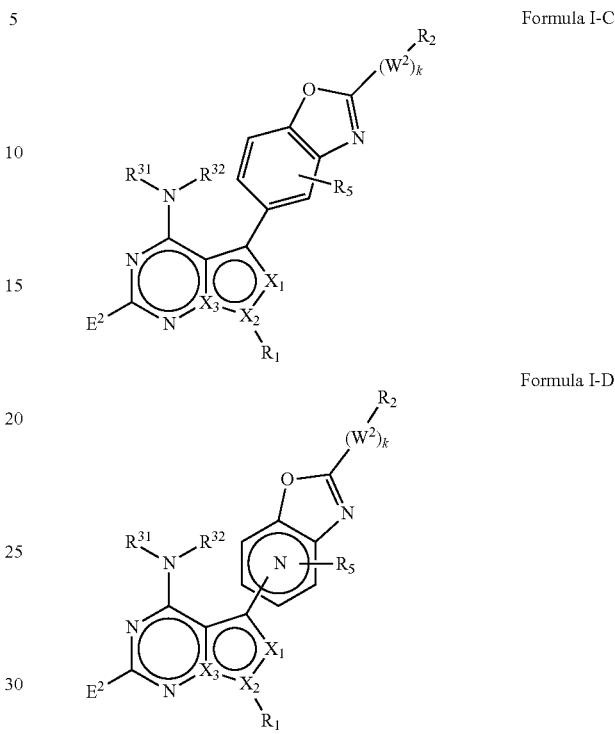

or a pharmaceutically acceptable salt thereof, wherein $X_1$ is N or C-E$^1$, $X_2$ is N, and $X_3$ is C; or $X_1$ is N or C-E$^1$, $X_2$ is C, and $X_3$ is N;

$R_1$ is —H, -L-C$_{1-10}$alkyl, -L-C$_{3-8}$cycloalkyl, -L-C$_{1-10}$alkyl-C$_{3-8}$cycloalkyl, -L-aryl, -L-heteroaryl, -L-C$_{1-10}$alkylaryl, -L-C$_{1-10}$alkylheteroaryl, -L-C$_{1-10}$alkylheterocyclyl, -L-C$_{2-10}$alkenyl, -L-C$_{2-10}$alkynyl, -L-C$_{2-10}$alkenyl-C$_{3-8}$cycloalkyl, -L-C$_{2-10}$alkynyl-C$_{3-8}$cycloalkyl, -L-heteroalkyl, -L-heteroalkylaryl, -L-heteroalkylheteroaryl, -L-heteroalkyl-heterocyclyl, -L-heteroalkyl-C$_{3-8}$cycloalkyl, -L-aralkyl, -L-heteroaralkyl, or -L-heterocyclyl, each of which is unsubstituted or is substituted by one or more independent $R^3$;

L is absent, —(C═O)—, —C(═O)O—, —C(═O)N(R$^{31}$)—, —S—, —S(O)—, —S(O)$_2$—, —S(O)$_2$N(R$^{31}$)—, or —N(R$^{31}$)—;

E$^1$ and E$^2$ are independently —(W$^1$)$_j$—R$^4$;

j in E$^1$ or j in E$^2$, is independently 0 or 1;

$W^1$ is —O—, —NR$^7$—, —S(O)$_{0-2}$—, —C(O)—, —C(O)N(R$^7$)—, —N(R$^7$)C(O)—, —N(R$^7$)S(O)—, —N(R$^7$)S(O)$_2$—, —C(O)O—, —CH(R$^7$)N(C(O)OR$^8$)—, —CH(R$^7$)N(C(O)R$^8$)—, —CH(R$^7$)N(SO$_2$R$^8$)—, —CH(R$^7$)N(R$^8$)—, —CH(R$^7$)C(O)N(R$^8$)—, —CH(R$^7$)N(R$^8$)C(O)—, —CH(R$^7$)N(R$^8$)S(O)—, or —CH(R$^7$)N(R$^8$)S(O)$_2$—;

$W^2$ is —O—, —NR$^7$—, —S(O)$_{0-2}$—, —C(O)—, —C(O)N(R$^7$)—, —N(R$^7$)C(O)—, —N(R$^7$)C(O)N(R$^8$)—, —N(R$^7$)S(O)—, —N(R$^7$)S(O)$_2$—, —C(O)O—, —CH(R$^7$)N(C(O)OR$^8$)—, —CH(R$^7$)N(C(O)R$^8$)—, —CH(R$^7$)N(SO$_2$R$^8$)—, —CH(R$^7$)N(R$^8$)—, —CH(R$^7$)C(O)N(R$^8$)—, —CH(R$^7$)N(R$^8$)C(O)—, —CH(R$^7$)N(R$^8$)S(O)—, or —CH(R$^7$)N(R$^8$)S(O)$_2$—;

k is 0 or 1;

$R^2$ is hydrogen, halogen, —OH, —$R^{31}$, —$CF_3$, —$OCF_3$, —$OR^{31}$, —$NR^{31}R^{32}$, —$NR^{34}R^{35}$, —$C(O)R^{31}$, —$CO_2R^{31}$, —$C(=O)NR^{31}R^{32}$, —$C(=O)NR^{34}R^{35}$, —$NO_2$, —CN, —$S(O)_{0-2}R^{31}$, —$SO_2NR^{31}R^{32}$, —$SO_2NR^{34}R^{35}$, —$NR^{31}C(=O)R^{32}$, —$NR^{31}C(=O)OR^{32}$, —$NR^{31}C(=O)NR^{32}R^{33}$, —$NR^{31}S(O)_{0-2}R^{32}$, —$C(=S)OR^{31}$, —$C(=O)SR^{31}$, —$NR^{31}C(=NR^{32})NR^{33}R^{32}$, —$NR^{31}C(=NR^{32})OR^{33}$, —$NR^{31}C(=NR^{32})SR^{33}$, —$OC(=O)OR^{33}$, —$OC(=O)NR^{31}R^{32}$, —$OC(=O)SR^{31}$, —$SC(=O)OR^{31}$, —$P(O)OR^{31}OR^{32}$, —$SC(=O)NR^{31}R^{32}$, aryl (e.g. bicyclic aryl, unsubstituted aryl, or substituted monocyclic aryl), heteroaryl, $C_{1-10}$alkyl, $C_{3-8}$cycloalkyl, $C_{1-10}$alkyl-$C_{3-8}$cycloalkyl, $C_{3-8}$cycloalkyl-$C_{1-10}$alkyl, $C_{3-8}$cycloalkyl-$C_{2-10}$alkenyl, $C_{3-8}$cycloalkyl-$C_{2-10}$alkynyl, $C_{1-10}$alkyl-$C_{2-10}$alkenyl, $C_{1-10}$alkyl-$C_{2-10}$alkynyl, $C_{1-10}$alkylaryl (e.g. $C_{2-10}$alkyl-monocyclic aryl, $C_{1-10}$alkyl-substituted monocyclic aryl, or $C_{1-10}$alkylbicycloaryl), $C_{1-10}$alkylheteroaryl, $C_{1-10}$alkylheterocyclyl, $C_{2-10}$alkenyl, $C_{2-10}$alkynyl, $C_{2-10}$alkenyl-$C_{1-10}$alkyl, $C_{2-10}$alkynyl-$C_{1-10}$alkyl, $C_{2-10}$alkenylaryl, $C_{2-10}$alkenylheteroaryl, $C_{2-10}$alkenylheteroalkyl, $C_{2-10}$alkenylheterocyclcyl, $C_{2-10}$alkenyl-$C_{3-8}$cycloalkyl, $C_{2-10}$alkynylaryl, $C_{2-10}$alkynylheteroaryl, $C_{2-10}$alkynylheteroalkyl, $C_{2-10}$alkynylheterocyclyl, $C_{2-10}$alkynyl-$C_{3-8}$cycloalkenyl, $C_{1-10}$alkoxy $C_{1-10}$alkyl, $C_{1-10}$alkoxy-$C_{2-10}$alkenyl, $C_{1-10}$alkoxy-$C_{2-10}$alkynyl, heterocyclyl-$C_{1-10}$alkyl, heterocyclyl-$C_{2-10}$alkenyl, heterocyclyl-$C_{2-10}$alkynyl, aryl-$C_{1-10}$alkyl (e.g. monocyclic aryl-$C_{2-10}$alkyl, substituted monocyclic aryl-$C_{1-10}$alkyl, or bicycloaryl-$C_{1-10}$alkyl), aryl-$C_{2-10}$alkenyl, aryl-$C_{2-10}$alkynyl, aryl-heterocyclyl, heteroaryl-$C_{1-10}$alkyl, heteroaryl-$C_{2-10}$alkenyl, heteroaryl-$C_{2-10}$alkynyl, heteroaryl-$C_{3-8}$cycloalkyl, heteroaryl-heteroalkyl, or heteroaryl-heterocyclyl, wherein each of said bicyclic aryl or heteroaryl moiety is unsubstituted, or wherein each of bicyclic aryl, heteroaryl moiety or monocyclic aryl moiety is substituted with one or more independent alkyl, heteroalkyl, alkenyl, alkynyl, cycloalkyl, heterocycloalkyl, aryl, arylalkyl, heteroaryl, heteroarylalkyl, halo, —OH, —$R^{31}$, —$CF_3$, —$OCF_3$, —$OR^{31}$, —$NR^{31}R^{32}$, —$NR^{34}R^{35}$, —$C(O)R^{31}$, —$CO_2R^{31}$, —$C(=O)NR^{31}R^{32}$, —$C(=O)NR^{34}R^{35}$, —$NO_2$, —CN, —$S(O)_{0-2}R^{31}$, —$SO_2NR^{31}R^{32}$, —$SO_2NR^{34}R^{35}$, —$NR^{31}C(=O)R^{32}$, —$NR^{31}C(=O)OR^{32}$, —$NR^{31}C(=O)NR^{32}R^{33}$, —$NR^{31}S(O)_{0-2}R^{32}$, —$C(=S)OR^{31}$, —$C(=O)SR^{31}$, —$NR^{31}C(=NR^{32})NR^{33}R^{32}$, —$NR^{31}C(=NR^{32})OR^{33}$, —$NR^{31}C(=NR^{32})SR^{33}$, —$OC(=O)OR^{33}$, —$OC(=O)NR^{31}R^{32}$, —$OC(=O)SR^{31}$, —$SC(=O)OR^{31}$, —$P(O)OR^{31}OR^{32}$, or —$SC(=O)NR^{31}R^{32}$ s, and wherein each of said alkyl, cycloalkyl, heterocyclyl, or heteroalkyl moiety is unsubstituted or is substituted with one or more alkyl, heteroalkyl, alkenyl, alkynyl, cycloalkyl, heterocycloalkyl, aryl, arylalkyl, heteroaryl, heteroarylalkyl, halo, —OH, —$R^{31}$, —$CF_3$, —$OCF_3$, —$OR^{31}$, —O-aryl, —$NR^{31}R^{32}$, —$NR^{34}R^{35}$, —$C(O)R^{31}$, —$CO_2R^{31}$, —$C(=O)NR^{34}R^{35}$, or —$C(=O)NR^{31}R^{32}$;

$R^3$ and $R^4$ are independently hydrogen, halogen, —OH, —$R^{31}$, —$CF_3$, —$OCF_3$, —$OR^{31}$, —$NR^{31}R^{32}$, —$NR^{34}R^{35}$, —$C(O)R^{31}$, —$CO_2R^{31}$, —$C(=O)NR^{31}R^{32}$, —$C(=O)NR^{34}R^{35}$, —$NO_2$, —CN, —$S(O)_{0-2}R^{31}$, —$SO_2NR^{31}R^{32}$, —$SO_2NR^{34}R^{35}$, —$NR^{31}C(=O)R^{32}$, —$NR^{31}C(=O)OR^{32}$, —$NR^{31}C(=O)NR^{32}R^{33}$, —$NR^{31}S(O)_{0-2}R^{32}$, —$C(=S)OR^{31}$, —$C(=O)SR^{31}$, —$NR^{31}C(=NR^{32})NR^{33}R^{32}$, —$NR^{31}C(=NR^{32})OR^{33}$, —$NR^{31}C(=NR^{32})SR^{33}$, —$OC(=O)OR^{33}$, —$OC(=O)NR^{31}R^{32}$, —$OC(=O)SR^{31}$, —$SC(=O)OR^{31}$, —$P(O)OR^{31}OR^{32}$, —$SC(=O)NR^{31}R^{32}$, aryl, heteroaryl, $C_{1-10}$alkyl, $C_{3-8}$cycloalkyl, $C_{1-10}$alkyl-$C_{3-8}$cycloalkyl, $C_{3-8}$cycloalkyl-$C_{1-10}$alkyl, $C_{3-8}$cycloalkyl-$C_{2-10}$alkenyl, $C_{3-8}$cycloalkyl-$C_{2-10}$alkynyl, $C_{1-10}$alkyl-$C_{2-10}$alkenyl, $C_{1-10}$alkyl-$C_{2-10}$alkynyl, $C_{1-10}$alkylaryl, $C_{1-10}$alkylheteroaryl, $C_{1-10}$alkylheterocyclyl, $C_{2-10}$alkenyl, $C_{2-10}$alkynyl, $C_{2-10}$alkenyl-$C_{1-10}$alkyl, $C_{2-10}$alkynyl-$C_{1-10}$alkyl, $C_{2-10}$alkenylaryl, $C_{2-10}$alkenylheteroaryl, $C_{2-10}$alkenyl-heteroalkyl, $C_{2-10}$alkenylheterocyclcyl, $C_{2-10}$alkenyl-$C_{3-8}$cycloalkyl, $C_{2-10}$alkynylaryl, $C_{2-10}$alkynylheteroaryl, $C_{2-10}$alkynylheteroalkyl, $C_{2-10}$alkynylheterocyclyl, $C_{2-10}$alkynyl-$C_{3-8}$cycloalkenyl, $C_{1-10}$alkoxy $C_{1-10}$alkyl, $C_{1-10}$alkoxy-$C_{2-10}$alkenyl, $C_{1-10}$alkoxy-$C_{2-10}$alkynyl, heterocyclyl-$C_{1-10}$alkyl, heterocyclyl-$C_{2-10}$alkenyl, heterocyclyl-$C_{2-10}$alkynyl, aryl-$C_{1-10}$alkyl, aryl-$C_{2-10}$alkenyl, aryl-$C_{2-10}$alkynyl, aryl-heterocyclyl, heteroaryl-$C_{1-10}$alkyl, heteroaryl-$C_{2-10}$alkenyl, heteroaryl-$C_{2-10}$alkynyl, heteroaryl-$C_{3-8}$cycloalkyl, heteroaryl-heteroalkyl, or heteroaryl-heterocyclyl, wherein each of said aryl or heteroaryl moiety is unsubstituted or is substituted with one or more independent alkyl, heteroalkyl, alkenyl, alkynyl, cycloalkyl, heterocycloalkyl, aryl, arylalkyl, heteroaryl, heteroarylalkyl, halo, —OH, —$R^{31}$, —$CF_3$, —$OCF_3$, —$OR^{31}$, —$NR^{31}R^{32}$, —$NR^{34}R^{35}$, —$C(O)R^{31}$, —$CO_2R^{31}$, —$C(=O)NR^{31}R^{32}$, —$C(=O)NR^{34}R^{35}$, —$NO_2$, —CN, —$S(O)_{0-2}R^{31}$, —$SO_2NR^{31}R^{32}$, —$SO_2NR^{34}R^{35}$, —$NR^{31}C(=O)R^{32}$, —$NR^{31}C(=O)OR^{32}$, —$NR^{31}C(=O)NR^{32}R^{33}$, —$NR^{31}S(O)_{0-2}R^{32}$, —$C(=S)OR^{31}$, —$C(=O)SR^{31}$, —$NR^{31}C(=NR^{32})NR^{33}R^{32}$, —$NR^{31}C(=NR^{32})OR^{33}$, —$NR^{31}C(=NR^{32})SR^{33}$, —$OC(=O)OR^{33}$, —$OC(=O)NR^{31}R^{32}$, —$OC(=O)SR^{31}$, —$SC(=O)OR^{31}$, —$P(O)OR^{31}OR^{32}$, or —$SC(=O)NR^{31}R^{32}$, and wherein each of said alkyl, cycloalkyl, heterocyclyl, or heteroalkyl moiety is unsubstituted or is substituted with one or more alkyl, heteroalkyl, alkenyl, alkynyl, cycloalkyl, heterocycloalkyl, aryl, arylalkyl, heteroaryl, heteroarylalkyl, halo, —OH, —$R^{31}$, —$CF_3$, —$OCF_3$, —$OR^{31}$, —O-aryl, —$NR^{31}R^{32}$, —$NR^{34}R^{35}$, —$C(O)R^{31}$, —$CO_2R^{31}$, $C(=O)NR^{34}R^{35}$, or —$C(=O)NR^{31}R^{32}$;

$R^5$ is hydrogen, halogen, —OH, —$R^{31}$, —$CF_3$, —$OCF_3$, —$OR^{31}$, —$NR^{31}R^{32}$, —$NR^{34}R^{35}$, —$C(O)R^{31}$, —$CO_2R^{31}$, —$C(=O)NR^{31}R^{32}$, —$C(=O)NR^{34}R^{35}$, —$NO_2$, —CN, —$S(O)_{0-2}R^{31}$, —$SO_2NR^{31}R^{32}$, —$SO_2NR^{34}R^{35}$, —$NR^{31}C(=O)R^{32}$, —$NR^{31}C(=O)OR^{32}$, —$NR^{31}C(=O)NR^{32}R^{33}$, —$NR^{31}S(O)_{0-2}R^{32}$, —$C(=S)OR^{31}$, —$C(=O)SR^{31}$, —$NR^{31}C(=NR^{32})NR^{33}R^{32}$, —$NR^{31}C(=NR^{32})OR^{33}$, —$NR^{31}C(=NR^{32})SR^{33}$, —$OC(=O)OR^{33}$, —$OC(=O)NR^{31}R^{32}$, —$OC(=O)SR^{31}$, —$SC(=O)OR^{31}$, —$P(O)OR^{31}OR^{32}$, or —$SC(=O)NR^{31}R^{32}$;

$R^{31}$, $R^{32}$, and $R^{33}$, in each instance, are independently H or $C_{1-10}$alkyl, wherein the $C_{1-10}$alkyl is unsubstituted or is substituted with one or more aryl, heteroalkyl, heterocyclyl, or heteroaryl group, wherein each of said aryl, heteroalkyl, heterocyclyl, or heteroaryl group is unsubstituted or is substituted with one or more halo, —OH, —$C_{1-10}$alkyl, —$CF_3$, —O-aryl, —$OCF_3$, —$OC_{1-10}$alkyl, —$NH_2$, —$N(C_{1-10}$alkyl$)(C_{1-10}$alkyl$)$, —$NH(C_{1-10}$alkyl$)$, —NH(aryl), —$NR^{34}R^{35}$, —$C(O)(C_{1-10}$alkyl$)$, —$C(O)(C_{1-10}$alkyl$)$, —$C(O)(C_{1-10}$alkyl-aryl$)$, —C(O)(aryl), —$CO_2$—$C_{1-10}$alkyl, —$CO_2$—$C_{1-10}$alkylaryl, —$CO_2$-aryl, —$C(=O)N(C_{1-10}$alkyl$)(C_{1-10}$alkyl$)$, —$C(=O)NH(C_{1-10}$alkyl$)$, —$C(=O)NR^{34}R^{35}$, —$C(=O)NH_2$, —$OCF_3$, —$O(C_{1-10}$alkyl$)$, —O-aryl, —N(aryl)$(C_{1-10}$alkyl$)$, —$NO_2$, —CN, —$S(O)_{0-2}$ $C_{1-10}$alkyl, —S(O)$_{0-2}$ C$_{1-10}$alkylaryl, —S(O)$_{0-2}$aryl, —SO$_2$N(aryl), —SO$_2$N(C$_{1-10}$alkyl)(C$_{1-10}$alkyl), —SO$_2$ NH(C$_{1-10}$alkyl) or —SO$_2$NR$^{34}$R$^{35}$;

R$^{34}$ and R$^{35}$ in —NR$^{34}$R$^{35}$, —C(=O)NR$^{34}$R$^{35}$, or —SO$_2$NR$^{34}$R$^{35}$, are taken together with the nitrogen atom to which they are attached to form a 3-10 membered saturated or unsaturated ring; wherein said ring is independently unsubstituted or is substituted by one or more —NR$^{31}$R$^{32}$, hydroxyl, halogen, oxo, aryl, heteroaryl, C$_{1-6}$alkyl, or O-aryl, and wherein said 3-10 membered saturated or unsaturated ring independently contains 0, 1, or 2 more heteroatoms in addition to the nitrogen atom; and R$^7$ and R$^8$ are each independently hydrogen, C$_{1-10}$alkyl, C$_{2-10}$alkenyl, aryl, heteroaryl, heterocyclyl or C$_{3-10}$cycloalkyl, each of which except for hydrogen is unsubstituted or is substituted by one or more independent R$^6$; and R$^6$ is halo, —OR$^{31}$, —SH, NH$_2$, —NR$^{34}$R$^{35}$, —NR$^{31}$R$^{32}$, —CO$_2$R$^{31}$, —CO$_2$aryl, —C(=O)NR$^{31}$R$^{32}$, C(=O) NR$^{34}$R$^{35}$, —NO$_2$, —CN, —S(O)$_{0-2}$ C$_{1-10}$alkyl, —S(O)$_{0-2}$aryl, —SO$_2$NR$^{34}$R$^{35}$, —SO$_2$NR$^{31}$R$^{32}$, C$_{1-10}$alkyl, C$_{2-10}$alkenyl, or C$_{2-10}$alkynyl; or R$^6$ is aryl-C$_{1-10}$alkyl, aryl-C$_{2-10}$alkenyl, aryl-C$_{2-10}$alkynyl, heteroaryl-C$_{1-10}$alkyl, heteroaryl-C$_{2-10}$alkenyl, heteroaryl-C$_{2-10}$alkynyl, each of which is unsubstituted or is substituted with one or more independent halo, cyano, nitro, —OC$_{1-10}$alkyl, C$_{1-10}$alkyl, C$_{2-10}$alkenyl, C$_{2-10}$alkynyl, haloC$_{1-10}$alkyl, haloC$_{2-10}$alkenyl, haloC$_{2-10}$alkynyl, —COOH, —C(=O)NR$^{31}$R$^{32}$, —C(=O) NR$^{34}$R$^{35}$, —SO$_2$NR$^{34}$R$^{35}$, —SO$_2$ NR$^{31}$R$^{32}$, —NR$^{31}$R$^{32}$, or —NR$^{34}$R$^{35}$.

In various embodiments of the compound of Formula I-C, the compound has a structure of Formula I-C1 or Formula I-C2:

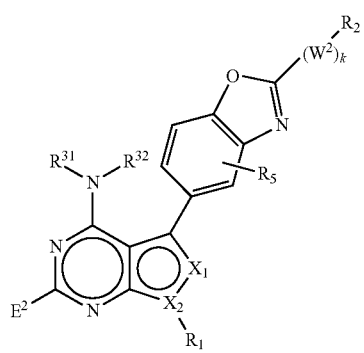

Formula I-C1

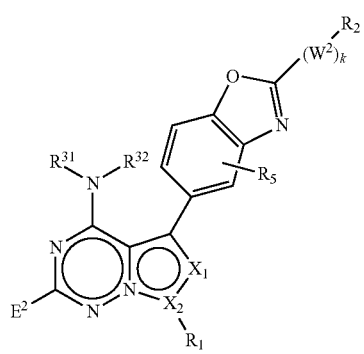

Formula I-C2 or a pharmaceutically acceptable salt thereof.

In some embodiments of Formula I-C1, X$_1$ is N and X$_2$ is N. In other embodiments, X$_1$ is C-E$^1$ and X$_2$ is N. In yet other embodiments, X$_1$ is NH and X$_2$ is C. In further embodiments, X$_1$ is CH-E$^1$ and X$_2$ is C.

In several embodiments of Formula I-C2, X$_1$ is N and X$_2$ is C. In yet other embodiments, X$_1$ is NH and X$_2$ is C. In further embodiments, X$_1$ is CH-E$^1$ and X$_2$ is C.

In various embodiments of the compound of Formula I-D, the compound has a structure of Formula I-D1 or Formula I-D2:

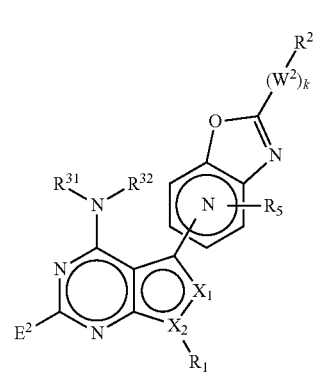

Formula I-D1

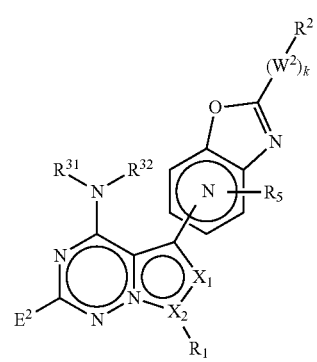

Formula I-D2 or a pharmaceutically acceptable salt thereof.

In some embodiments of Formula I-D1, X$_1$ is N and X$_2$ is N. In other embodiments, X$_1$ is C-E$^1$ and X$_2$ is N. In yet other embodiments, X$_1$ is NH and X$_2$ is C. In further embodiments, X$_1$ is CH-E$^1$ and X$_2$ is C.

In several embodiments of Formula I-D2, X$_1$ is N and X$_2$ is C. In further embodiments, X$_1$ is C-E$^1$ and X$_2$ is C.

In various embodiments, X$_1$ is C—(W$^1$)$_j$—R$^4$, where j is 0.

In another embodiment, X$_1$ is CH. In yet another embodiment, X$_1$ is C-halogen, where halogen is Cl, F, Br, or I.

In various embodiments of X$_1$, it is C—(W$^1$)$_j$—R$^4$. In various embodiments of X$_1$, j is 1, and W$^1$ is —O—. In various embodiments of X$_1$, j is 1, and W$^1$ is —NR$^7$—. In various embodiments of X$_1$, j is 1, and W$^1$ is —NH—. In various embodiments of X$_1$, j is 1, and W$^1$ is —S(O)$_{0-2}$—. In various embodiments of X$_1$, j is 1, and W$^1$ is —C(O)—. In various embodiments of X$_1$, j is 1, and W$^1$ is —C(O)N(R$^7$)—. In various embodiments of X$_1$, j is 1, and W$^1$ is —N(R$^7$)C(O)—. In various embodiments of X$_1$, j is 1, and W$^1$ is —N(R$^7$)S(O)—. In various embodiments of X$_1$, j is 1, and W$^1$ is —N(R$^7$)S(O)$_2$—. In various embodiments of X$_1$, j is 1, and W$^1$ is —C(O)O—. In various embodiments of X$_1$, j is 1, and W$^1$ is CH(R$^7$)N(C(O)OR$^8$)—. In various embodiments of X$_1$, j is 1, and W$^1$ is —CH(R$^7$)N(C(O)R$^8$)—. In various embodiments of X$_1$, j is 1, and W$^1$ is —CH(R$^7$)N(SO$_2$R$^8$)—. In various embodiments of X$_1$, j is 1, and W$^1$ is —CH(R$^7$)N(R$^8$)—. In various embodiments of X$_1$, j is 1, and W$^1$ is —CH(R$^7$)C(O)N(R$^8$)—. In various embodiments of X$_1$, j is 1, and W$^1$ is —CH(R$^7$)N(R$^8$)C(O)—. In various embodiments of X$_1$, j is 1, and W$^1$ is —CH(R$^7$)N(R$^8$)S(O)—. In various embodiments of X$_1$, j is 1, and W$^1$ is —CH(R$^7$)N(R$^8$)S(O)$_2$—.

In various embodiments, X$_1$ is CH—(W$^1$)$_j$—R$^4$, where j is 0.

In another embodiment, X$_1$ is CH$_2$. In yet another embodiment, X$_1$ is CH-halogen, where halogen is Cl, F, Br, or I.

In various embodiments of X$_1$, it is CH—(W$^1$)$_j$—R$^4$. In various embodiments of X$_1$, j is 1, and W$^1$ is —O—. In various embodiments of X$_1$, j is 1, and W$^1$ is —NR$^7$—. In various embodiments of X$_1$, j is 1, and W$^1$ is —NH—. In various embodiments of X$_1$, j is 1, and W$^1$ is —S(O)$_{0-2}$—. In various embodiments of X$_1$, j is 1, and W$^1$ is —C(O)—. In various embodiments of X$_1$, j is 1, and W$^1$ is —C(O)N(R$^7$)—. In various embodiments of X$_1$, j is 1, and W$^1$ is —N(R$^7$)C(O)—. In various embodiments of X$_1$, j is 1, and W$^1$ is —N(R$^7$)S(O)—. In various embodiments of X$_1$, j is 1, and W$^1$ is —N(R$^7$)S(O)$_2$—. In various embodiments of X$_1$, j is 1, and W$^1$ is —C(O)O—. In various embodiments of X$_1$, j is 1, and W$^1$ is CH(R$^7$)N(C(O)OR$^8$)—. In various embodiments of X$_1$, j is 1, and W$^1$ is —CH(R$^7$)N(C(O)R$^8$)—. In various embodiments of X$_1$, j is 1, and W$^1$ is —CH(R$^7$)N(SO$_2$R$^8$)—. In various embodiments of X$_1$, j is 1, and W$^1$ is —CH(R$^7$)N(R$^8$)—. In various embodiments of X$_1$, j is 1, and W$^1$ is —CH(R$^7$)C(O)N(R$^8$)—. In various embodiments of X$_1$, j is 1, and W$^1$ is —CH(R$^7$)N(R$^8$)C(O)—. In various embodiments of X$_1$, j is 1, and W$^1$ is —CH(R$^7$)N(R$^8$)S(O)—. In various embodiments of X$_1$, j is 1, and W$^1$ is —CH(R$^7$)N(R$^8$)S(O)$_2$—.

In another embodiment, X$_1$ is N.

In various embodiments, X$_2$ is N. In other embodiments, X$_2$ is C.

In various embodiments, E$^2$ is —(W$^1$)$_j$—R$^4$, where j is 0.

In another embodiment, E$^2$ is CH. In yet another embodiment, E$^2$ is C-halogen, where halogen is Cl, F, Br, or I.

In various embodiments of E$^2$, it is —(W$^1$)$_j$—R$^4$. In various embodiments of E$^2$, j is 1, and W$^1$ is —O—. In various embodiments of E$^2$, j is 1, and W$^1$ is —NR$^7$—. In various embodiments of E$^2$, j is 1, and W$^1$ is —NH—. In various embodiments of E$^2$, j is 1, and W$^1$ is —S(O)$_{0-2}$—. In various embodiments of E$^2$, j is 1, and W$^1$ is —C(O)—. In various embodiments of E$^2$, j is 1, and W$^1$ is —C(O)N(R$^7$)—. In various embodiments of E$^2$, j is 1, and W$^1$ is —N(R$^7$)C(O)—. In various embodiments of E$^2$, j is 1, and W$^1$ is —N(R$^7$)S(O)—. In various embodiments of E$^2$, j is 1, and W$^1$ is —N(R$^7$)S(O)$_2$—. In various embodiments of E$^2$, j is 1, and W$^1$ is —C(O)O—. In various embodiments of E$^2$, j is 1, and W$^1$ is CH(R$^7$)N(C(O)OR$^8$)—. In various embodiments of E$^2$, j is 1, and W$^1$ is —CH(R$^7$)N(C(O)R$^8$)—. In various embodiments of E$^2$, j is 1, and W$^1$ is —CH(R$^7$)N(SO$_2$R$^8$)—. In various embodiments of E$^2$, j is 1, and W$^1$ is —CH(R$^7$)N(R$^8$)—. In various embodiments of E$^2$, j is 1, and W$^1$ is —CH(R$^7$)C(O)N(R$^8$)—. In various embodiments of E$^2$, j is 1, and W$^1$ is —CH(R$^7$)N(R$^8$)C(O)—. In various embodiments of E$^2$, j is 1, and W$^1$ is —CH(R$^7$)N(R$^8$)S(O)—. In various embodiments of E$^2$, j is 1, and W$^1$ is —CH(R$^7$)N(R$^8$)S(O)$_2$—.

In various embodiments, k is 0. In other embodiments, k is 1 and W$^2$ is —O—. In another embodiment, k is 1 and W$^2$ is —NR$^7$—. In yet another embodiment of, k is 1, and W$^2$ is —S(O)$_{0-2}$—. In another embodiment of, k is 1 and W$^2$ is —C(O)—. In a further embodiment, k is 1 and W$^2$ is —C(O)N(R$^7$)—. In another embodiment, k is 1, and W$^2$ is —N(R$^7$)C(O)—. In another embodiment, k is 1 and W$^2$ is —N(R$^7$)C(O)N(R$^8$)—. In yet another embodiment, k is 1 and W$^2$ is —N(R$^7$)S(O)—. In still yet another embodiment, k is 1 and W$^2$ is —N(R$^7$)S(O)$_2$—. In a further embodiment, k is 1 and W$^2$ is —C(O)O—. In another embodiment, k is 1 and W$^2$ is —CH(R$^7$)N(C(O)OR$^8$)—. In another embodiment, k is 1 and W$^2$ is —CH(R$^7$)N(C(O)R$^8$)—. In another embodiment, k is 1 and W$^2$ is —CH(R$^7$)N(SO$_2$R$^8$)—. In a further embodiment, k is 1 and W$^2$ is —CH(R$^7$)N(R$^8$)—. In another embodiment, k is 1 and W$^2$ is —CH(R$^7$)C(O)N(R$^8$)—. In yet another embodiment, k is 1 and W$^2$ is —CH(R$^7$)N(R$^8$)C(O)—. In another embodiment, k is 1 and W$^2$ is —CH(R$^7$)N(R$^8$)S(O)—. In yet another embodiment, k is 1 and W$^2$ is —CH(R$^7$)N(R$^8$)S(O)$_2$—.

In some other embodiments, the mTORC1/2 inhibitor is a compound of Formula I-E:

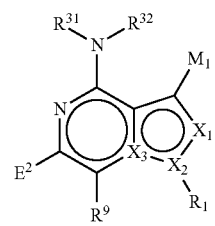

Formula I-E or a pharmaceutically acceptable salt thereof, wherein: X$_1$ is N or C-E$^1$, X$_2$ is N, and X$_3$ is C; or X$_1$ is N or C-E$^1$, X$_2$ is C, and X$_3$ is N;

R$_1$ is —H, -L-C$_{1-10}$alkyl, -L-C$_{3-8}$cycloalkyl, -L-C$_{1-10}$alkyl-C$_{3-8}$cycloalkyl, -L-aryl, -L-heteroaryl, -L-C$_{1-10}$alkylaryl, -L-C$_{1-10}$alkylheteroaryl, -L-C$_{1-10}$alkylheterocyclyl, -L-C$_{2-10}$alkenyl, -L-C$_{2-10}$alkynyl, -L-C$_{2-10}$alkenyl-C$_{3-8}$cycloalkyl, -L-C$_{2-10}$alkynyl-C$_{3-8}$cycloalkyl, -L-heteroalkyl, -L-heteroalkylaryl, -L-heteroalkylheteroaryl, -L-heteroalkyl-heterocyclyl, -L-heteroalkyl-C$_{3-8}$cycloalkyl, -L-aralkyl, -L-heteroaralkyl, or -L-heterocyclyl, each of which is unsubstituted or is substituted by one or more independent R$^3$;

L is absent, —(C=O)—, —C(=O)O—, —C(=O)N(R$^{31}$)—, —S—, —S(O)—, —S(O)$_2$—, —S(O)$_2$N(R$^{31}$)—, or —N(R$^{31}$)—;

M$_1$ is a moiety having the structure of Formula M1-F1 or Formula M1-F2:

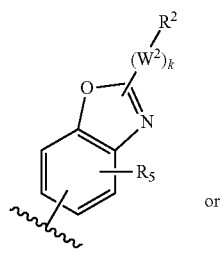

Formula M1-F1 or

-continued

Formula M1-F2

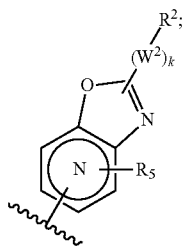

k is 0 or 1;

$E^1$ and $E^2$ are independently $-(W^1)_j-R^4$;

j in $E^1$ or j in $E^2$, is independently 0 or 1;

$W^1$ is $-O-$, $-NR^7-$, $-S(O)_{0-2}-$, $-C(O)-$, $-C(O)N(R^7)-$, $-N(R^7)C(O)-$, $-N(R^7)S(O)-$, $-N(R^7)S(O)_2-$, $-C(O)O-$, $-CH(R^7)N(C(O)OR^8)-$, $-CH(R^7)N(C(O)R^8)-$, $-CH(R^7)N(SO_2R^8)-$, $-CH(R^7)N(R^8)-$, $-CH(R^7)C(O)N(R^8)-$, $-CH(R^7)N(R^8)C(O)-$, $-CH(R^7)N(R^8)S(O)-$, or $-CH(R^7)N(R^8)S(O)_2-$;

$W^2$ is $-O-$, $-NR^7-$, $-S(O)_{0-2}-$, $-C(O)-$, $-C(O)N(R^7)-$, $-N(R^7)C(O)-$, $-N(R^7)C(O)N(R^8)-$, $-N(R^7)S(O)-$, $-N(R^7)S(O)_2-$, $-C(O)O-$, $-CH(R^7)N(C(O)OR^8)-$, $-CH(R^7)N(C(O)R^8)-$, $-CH(R^7)N(SO_2R^8)-$, $-CH(R^7)N(R^8)-$, $-CH(R^7)C(O)N(R^8)-$, $-CH(R^7)N(R^8)C(O)-$, $-CH(R^7)N(R^8)S(O)-$, or $-CH(R^7)N(R^8)S(O)_2-$;

$R^2$ is hydrogen, halogen, $-OH$, $-R^{31}$, $-CF_3$, $-OCF_3$, $-OR^{31}$, $-NR^{31}R^{32}$, $-NR^{34}R^{35}$, $-C(O)R^{31}$, $-CO_2R^{31}$, $-C(=O)NR^{31}R^{32}$, $-C(=O)NR^{34}R^{35}$, $-NO_2$, $-CN$, $-S(O)_{0-2}R^{31}$, $-SO_2NR^{31}R^{32}$, $-SO_2NR^{34}R^{35}$, $-NR^{31}C(=O)R^{32}$, $-NR^{31}C(=O)OR^{32}$, $-NR^{31}C(=O)NR^{32}R^{33}$, $-NR^{31}S(O)_{0-2}R^{32}$, $-C(=S)OR^{31}$, $-C(=O)SR^{31}$, $-NR^{31}C(=NR^{32})NR^{33}R^{32}$, $-NR^{31}C(=NR^{32})OR^{33}$, $-NR^{31}C(=NR^{32})SR^{33}$, $-OC(=O)OR^{33}$, $-OC(=O)NR^{31}R^{32}$, $-OC(=O)SR^{31}$, $-SC(=O)OR^{31}$, $-P(O)OR^{31}OR^{32}$, $-SC(=O)NR^{31}R^{32}$, aryl (e.g. bicyclic aryl, unsubstituted aryl, or substituted monocyclic aryl), heteroaryl, $C_{1-10}$alkyl, $C_{3-8}$cycloalkyl, $C_{1-10}$alkyl-$C_{3-8}$cycloalkyl, $C_{3-8}$cycloalkyl-$C_{1-10}$alkyl, $C_{3-8}$cycloalkyl-$C_{2-10}$alkenyl, $C_{3-8}$cycloalkyl-$C_{2-10}$alkynyl, $C_{1-10}$alkyl-$C_{2-10}$alkenyl, $C_{1-10}$alkyl-$C_{2-10}$alkynyl, $C_{1-10}$alkylaryl (e.g. $C_{2-10}$alkyl-monocyclic aryl, $C_{1-10}$alkyl-substituted monocyclic aryl, or $C_{1-10}$alkylbicycloaryl), $C_{1-10}$alkylheteroaryl, $C_{1-10}$alkylheterocyclyl, $C_{2-10}$alkenyl, $C_{2-10}$alkynyl, $C_{2-10}$alkenyl-$C_{1-10}$alkyl, $C_{2-10}$alkynyl-$C_{1-10}$alkyl, $C_{2-10}$alkenylaryl, $C_{2-10}$alkenylheteroaryl, $C_{2-10}$alkenylheteroalkyl, $C_{2-10}$alkenylheterocyclcyl, $C_{2-10}$alkenyl-$C_{3-8}$cycloalkyl, $C_{2-10}$alkynylaryl, $C_{2-10}$alkynylheteroaryl, $C_{2-10}$alkynylheteroalkyl, $C_{2-10}$alkynylheterocyclyl, $C_{2-10}$alkynyl-$C_{3-8}$cycloalkenyl, $C_{1-10}$alkoxy $C_{1-10}$alkyl, $C_{1-10}$alkoxy-$C_{2-10}$alkenyl, $C_{1-10}$alkoxy-$C_{2-10}$alkynyl, heterocyclyl-$C_{1-10}$alkyl, heterocyclyl-$C_{2-10}$alkenyl, heterocyclyl-$C_{2-10}$alkynyl, aryl-$C_{1-10}$alkyl (e.g. monocyclic aryl-$C_{2-10}$alkyl, substituted monocyclic aryl-$C_{1-10}$alkyl, or bicycloaryl-$C_{1-10}$alkyl), aryl-$C_{2-10}$alkenyl, aryl-$C_{2-10}$alkynyl, aryl-heterocyclyl, heteroaryl-$C_{1-10}$alkyl, heteroaryl-$C_{2-10}$alkenyl, heteroaryl-$C_{2-10}$alkynyl, heteroaryl-$C_{3-8}$cycloalkyl, heteroaryl-heteroalkyl, or heteroaryl-heterocyclyl, wherein each of said bicyclic aryl or heteroaryl moiety is unsubstituted, or wherein each of bicyclic aryl, heteroaryl moiety or monocyclic aryl moiety is substituted with one or more independent alkyl, heteroalkyl, alkenyl, alkynyl, cycloalkyl, heterocycloalkyl, aryl, arylalkyl, heteroaryl, heteroarylalkyl, halo, $-OH$, $-R^{31}$, $-CF_3$, $-OCF_3$, $-OR^{31}$, $-NR^{31}R^{32}$, $-NR^{34}R^{35}$, $-C(O)R^{31}$, $-CO_2R^{31}$, $-C(=O)NR^{31}R^{32}$, $-C(=O)NR^{34}R^{35}$, $-NO_2$, $-CN$, $-S(O)_{0-2}R^{31}$, $-SO_2NR^{31}R^{32}$, $-SO_2NR^{34}R^{35}$, $-NR^{31}C(=O)R^{32}$, $-NR^{31}C(=O)OR^{32}$, $-NR^{31}C(=O)NR^{32}R^{33}$, $-NR^{31}S(O)_{0-2}R^{32}$, $-C(=S)OR^{31}$, $-C(=O)SR^{31}$, $-NR^{31}C(=NR^{32})NR^{33}R^{32}$, $-NR^{31}C(=NR^{32})OR^{33}$, $-NR^{31}C(=NR^{32})SR^{33}$, $-OC(=O)OR^{33}$, $-OC(=O)NR^{31}R^{32}$, $-OC(=O)SR^{31}$, $-SC(=O)OR^{31}$, $-P(O)OR^{31}OR^{32}$, or $-SC(=O)NR^{31}R^{32}$, and wherein each of said alkyl, cycloalkyl, heterocyclyl, or heteroalkyl moiety is unsubstituted or is substituted with one or more alkyl, heteroalkyl, alkenyl, alkynyl, cycloalkyl, heterocycloalkyl, aryl, arylalkyl, heteroaryl, heteroarylalkyl, halo, $-OH$, $-R^{31}$, $-CF_3$, $-OCF_3$, $-OR^{31}$, $-O$-aryl, $-NR^{31}R^{32}$, $-NR^{34}R^{35}$, $-C(O)R^{31}$, $-CO_2R^{31}$, $-C(=O)NR^{34}R^{35}$, or $-C(=O)NR^{31}R^{32}$;

$R^3$ and $R^4$ are independently hydrogen, halogen, $-OH$, $-R^{31}$, $-CF_3$, $-OCF_3$, $-OR^{31}$, $-NR^{31}R^{32}$, $-NR^{34}R^{35}$, $-C(O)R^{31}$, $-CO_2R^{31}$, $-C(=O)NR^{31}R^{32}$, $-C(=O)NR^{34}R^{35}$, $-NO_2$, $-CN$, $-S(O)_{0-2}R^{31}$, $-SO_2NR^{31}R^{32}$, $-SO_2NR^{34}R^{35}$, $-NR^{31}C(=O)R^{32}$, $-NR^{31}C(=O)OR^{32}$, $-NR^{31}C(=O)NR^{32}R^{33}$, $-NR^{31}S(O)_{0-2}R^{32}$, $-C(=S)OR^{31}$, $-C(=O)SR^{31}$, $-NR^{31}C(=NR^{32})NR^{33}R^{32}$, $-NR^{31}C(=NR^{32})OR^{33}$, $-NR^{31}C(=NR^{32})SR^{33}$, $-OC(=O)OR^{33}$, $-OC(=O)NR^{31}R^{32}$, $-OC(=O)SR^{31}$, $-SC(=O)OR^{31}$, $-P(O)OR^{31}OR^{32}$, $-SC(=O)NR^{31}R^{32}$, aryl, heteroaryl, $C_{1-4}$alkyl, $C_{1-10}$alkyl, $C_{3-8}$cycloalkyl, $C_{1-10}$alkyl-$C_{3-8}$cycloalkyl, $C_{3-8}$cycloalkyl-$C_{1-10}$alkyl, $C_{3-8}$cycloalkyl-$C_{2-10}$alkenyl, $C_{3-8}$cycloalkyl-$C_{2-10}$alkynyl, $C_{1-10}$alkyl-$C_{2-10}$alkenyl, $C_{1-10}$alkyl-$C_{2-10}$alkynyl, $C_{1-10}$alkylaryl, $C_{1-10}$alkylheteroaryl, $C_{1-10}$alkylheterocyclyl, $C_{2-10}$alkenyl, $C_{2-10}$alkynyl, $C_{2-10}$alkenyl-$C_{1-10}$alkyl, $C_{2-10}$alkynyl-$C_{1-10}$alkyl, $C_{2-10}$alkenylaryl, $C_{2-10}$alkenylheteroaryl, $C_{2-10}$alkenylheteroalkyl, $C_{2-10}$alkenylheterocyclcyl, $C_{2-10}$alkenyl-$C_{3-8}$cycloalkyl, $C_{2-10}$alkynyl-$C_{3-8}$cycloalkyl, $C_{2-10}$alkynylaryl, $C_{2-10}$alkynylheteroaryl, $C_{2-10}$alkynylheteroalkyl, $C_{2-10}$alkynylheterocyclyl, $C_{2-10}$alkynyl-$C_{3-8}$cycloalkenyl, $C_{1-10}$alkoxy $C_{1-10}$alkyl, $C_{1-10}$alkoxy-$C_{2-10}$alkenyl, $C_{1-10}$alkoxy-$C_{2-10}$alkynyl, heterocyclyl, heterocyclyl-$C_{1-10}$alkyl, heterocyclyl-$C_{2-10}$alkenyl, heterocyclyl-$C_{2-10}$alkynyl, aryl-$C_{1-10}$alkyl, aryl-$C_{2-10}$alkenyl, aryl-$C_{2-10}$alkynyl, aryl-heterocyclyl, heteroaryl-$C_{1-10}$alkyl, heteroaryl-$C_{2-10}$alkenyl, heteroaryl-$C_{2-10}$alkynyl, heteroaryl-$C_{3-8}$cycloalkyl, heteroalkyl, heteroaryl-heteroalkyl, or heteroaryl-heterocyclyl, wherein each of said aryl or heteroaryl moiety is unsubstituted or is substituted with one or more independent halo, $-OH$, $-R^{31}$, $-CF_3$, $-OCF_3$, $-OR^{31}$, $-NR^{31}R^{32}$, $-NR^{34}R^{35}$, $-C(O)R^{31}$, $-CO_2R^{31}$, $-C(=O)NR^{31}R^{32}$, $-C(=O)NR^{34}R^{35}$, $-NO_2$, $-CN$, $-S(O)_{0-2}R^{31}$, $-SO_2NR^{31}R^{32}$, $-SO_2NR^{34}R^{35}$, $-R^{31}C(=O)R^{32}$, $-NR^{31}C(=O)OR^{32}$, $-NR^{31}C(=O)NR^{32}R^{33}$, $-NR^{31}S(O)_{0-2}R^{32}$, $-C(=S)OR^{31}$, $-C(=O)SR^{31}$, $-NR^{31}C(=NR^{32})NR^{33}R^{32}$, $-NR^{31}C(=NR^{32})OR^{33}$, $-NR^{31}C(=NR^{32})SR^{33}$, $-OC(=O)OR^{33}$, $-OC(=O)NR^{31}R^{32}$, $-OC(=O)SR^{31}$, $-SC(=O)OR^{31}$, $-P(O)OR^{31}OR^{32}$, or $-SC(=O)NR^{31}R^{32}$, and wherein each of said alkyl, cycloalkyl, heterocyclyl, or heteroalkyl moiety is unsubstituted or is substituted with one or more halo, $-OH$, $-R^{31}$, $-CF_3$, $-OCF_3$, $-OR^{31}$, $-O$-aryl, $-NR^{31}R^{32}$, $-NR^{34}R^{35}$, $-C(O)R^{31}$, $-CO_2R^{31}$, $-C(=O)NR^{34}R^{35}$, or $-C(=O)NR^{31}R^{32}$;

$R^5$ is hydrogen, halogen, —OH, —$R^{31}$, —$CF_3$, —$OCF_3$, —$OR^{31}$, —$NR^{31}R^{32}$, —$NR^{34}R^{35}$, —$C(O)R^{31}$, —$CO_2R^{31}$, —$C(=O)NR^{31}R^{32}$, —$C(=O)NR^{34}R^{35}$, —$NO_2$, —$CN$, —$S(O)_{0-2}R^{31}$, —$SO_2NR^{31}R^{32}$, —$SO_2NR^{34}R^{35}$, —$NR^{31}C(=O)R^{32}$, —$NR^{31}C(=O)$ $OR^{32}$, —$NR^{31}C(=O)NR^{32}R^{33}$, —$NR^{31}S(O)_{0-2}R^{32}$, —$C(=S)OR^{31}$, —$C(=O)SR^{31}$, —$NR^{31}C(=NR^{32})$ $NR^{33}R^{32}$, —$NR^{31}C(=NR^{32})OR^{33}$, —$NR^{31}C(=NR^{32})$ $SR^{33}$, —$OC(=O)OR^{33}$, —$OC(=O)NR^{31}R^{32}$, —$OC(=O)SR^{31}$, —$SC(=O)OR^{31}$, —$P(O)OR^{31}OR^{32}$, or —$SC(=O)NR^{31}R^{32}$;

$R^{31}$, $R^{32}$, and $R^{33}$, in each instance, are independently H or $C_{1-10}$alkyl, wherein the $C_{1-10}$alkyl is unsubstituted or is substituted with one or more aryl, heteroalkyl, heterocyclyl, or heteroaryl group wherein each of said aryl, heteroalkyl, heterocyclyl, or heteroaryl group is unsubstituted or is substituted with one or more halo, —OH, —$C_{1-10}$alkyl, —$CF_3$, —O-aryl, —$OCF_3$, —$OC_{1-10}$alkyl, —$NH_2$, —$N(C_{1-10}$alkyl$)(C_{1-10}$alkyl$)$, —$NH(C_{1-10}$alkyl$)$, —$NH(aryl)$, —$NR^{34}R^{35}$, —$C(O)(C_{1-10}$alkyl$)$, —$C(O)$ $(C_{1-10}$alkyl-aryl$)$, —$C(O)(aryl)$, —$CO_2$—$C_{1-10}$alkyl, —$CO_2$—$C_{1-10}$alkylaryl, —$CO_2$-aryl, —$C(=O)N(C_{1-10}$ alkyl$)(C_{1-10}$alkyl$)$, —$C(=O)NH(C_{1-10}$alkyl$)$, —$C(=O)$ $NR^{34}R^{35}$, —$C(=O)NH_2$, —$OCF_3$, —$O(C_{1-10}$alkyl$)$, —O-aryl, —$N(aryl)(C_{1-10}$alkyl$)$, —$NO_2$, —$CN$, —$S(O)_{0-2}$ $C_{1-10}$alkyl, —$S(O)_{0-2}$ $C_{1-10}$alkylaryl, —$S(O)_{0-2}$aryl, —$SO_2N(aryl)$, —$SO_2N(C_{1-10}$alkyl$)$ $(C_{1-10}$alkyl$)$, —$SO_2$ $NH(C_{1-10}$alkyl$)$ or —$SO_2NR^{34}R^{35}$;

$R^{34}$ and $R^{35}$ in —$NR^{34}R^{35}$, —$C(=O)NR^{34}R^{35}$, or —$SO_2NR^{34}R^{35}$, are taken together with the nitrogen atom to which they are attached to form a 3-10 membered saturated or unsaturated ring; wherein said ring is independently unsubstituted or is substituted by one or more —$NR^{31}R^{32}$, hydroxyl, halogen, oxo, aryl, heteroaryl, $C_{1-6}$alkyl, or O-aryl, and wherein said 3-10 membered saturated or unsaturated ring independently contains 0, 1, or 2 more heteroatoms in addition to the nitrogen atom;

$R^7$ and $R^8$ are each independently hydrogen, $C_{1-10}$alkyl, $C_{2-10}$alkenyl, aryl, heteroaryl, heterocyclyl or $C_{3-10}$cycloalkyl, each of which except for hydrogen is unsubstituted or is substituted by one or more independent $R^6$;

$R^6$ is halo, —$OR^{31}$, —$SH$, —$NH_2$, —$NR^{34}R^{35}$, —$NR^{31}R^{32}$, —$CO_2R^{31}$, —$CO_2$aryl, —$C(=O)NR^{31}R^{32}$, $C(=O)NR^{34}R^{35}$, —$NO_2$, —$CN$, —$S(O)_{0-2}$ $C_{1-10}$alkyl, —$S(O)_{0-2}$aryl, —$SO_2NR^{34}R^{35}$, —$SO_2NR^{31}R^{32}$, $C_{1-10}$alkyl, $C_{2-10}$alkenyl, $C_{2-10}$alkynyl; aryl-$C_{1-10}$alkyl, aryl-$C_{2-10}$alkenyl, aryl-$C_{2-10}$alkynyl, heteroaryl-$C_{1-10}$alkyl, heteroaryl-$C_{2-10}$alkenyl, heteroaryl-$C_{2-10}$alkynyl, wherein each of said alkyl, alkenyl, alkynyl, aryl, heteroalkyl, heterocyclyl, or heteroaryl group is unsubstituted or is substituted with one or more independent halo, cyano, nitro, —$OC_{1-10}$alkyl, $C_{1-10}$alkyl, $C_{2-10}$alkenyl, $C_{2-10}$alkynyl, halo$C_{1-10}$alkyl, halo$C_{2-10}$alkenyl, halo$C_{2-10}$alkynyl, —COOH, —$C(=O)NR^{31}R^{32}$, —$C(=O)NR^{34}R^{35}$, —$SO_2NR^{34}R^{35}$, —$SO_2$ $NR^{31}R^{32}$, —$NR^{31}R^{32}$, or —$NR^{34}R^{35}$; and $R^9$ is H, halo, —$OR^{31}$, —$SH$, —$NH_2$, —$NR^{34}R^{35}$, —$NR^{31}R^{32}$, —$CO_2R^{31}$, —$CO_2$aryl, —$C(=O)NR^{31}R^{32}$, $C(=O)NR^{34}R^{35}$, —$NO_2$, —$CN$, —$S(O)_{0-2}$ $C_{1-10}$alkyl, —$S(O)_{0-2}$aryl, —$SO_2NR^{34}R^{35}$, —$SO_2NR^{31}R^{32}$, $C_{1-10}$alkyl, $C_{2-10}$alkenyl, $C_{2-10}$alkynyl; aryl-$C_{1-10}$alkyl, aryl-$C_{2-10}$alkenyl, aryl-$C_{2-10}$alkynyl, heteroaryl-$C_{1-10}$alkyl, heteroaryl-$C_{2-10}$alkenyl, heteroaryl-$C_{2-10}$alkynyl, wherein each of said alkyl, alkenyl, alkynyl, aryl, heteroalkyl, heterocyclyl, or heteroaryl group is unsubstituted or is substituted with one or more independent halo, cyano, nitro, —$OC_{1-10}$alkyl, $C_{1-10}$alkyl, $C_{2-10}$alkenyl, $C_{2-10}$alkynyl, halo$C_{1-10}$alkyl, halo$C_{2-10}$alkenyl, halo$C_{2-10}$alkynyl, —COOH, —$C(=O)NR^{31}R^{32}$, —$C(=O)NR^{34}R^{35}$, —$SO_2NR^{34}R^{35}$, —$SO_2$ $NR^{31}R^{32}$, —$NR^{31}R^{32}$, or —$NR^{34}R^{35}$.

In various embodiments of the compound of Formula I-E, the compound has a structure of Formula I-E1 or Formula I-E2:

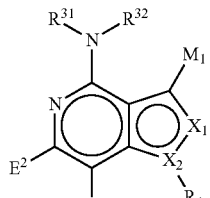

Formula I-E1

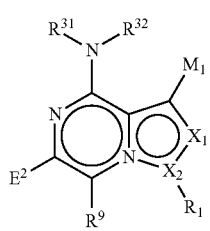

Formula I-E2 or a pharmaceutically acceptable salt thereof.

In some embodiments of Formula I-E1, $X_1$ is N and $X_2$ is N. In other embodiments, $X_1$ is C-$E^1$ and $X_2$ is N. In yet other embodiments, $X_1$ is NH and $X_2$ is C. In further embodiments, $X_1$ is CH-$E^1$ and $X_2$ is C.

In several embodiments of Formula I-E2, $X_1$ is N and $X_2$ is C. In further embodiments, $X_1$ is C-$E^1$ and $X_2$ is C.

In various embodiments, $X_1$ is C—$(W^1)_j$—$R^4$, where j is 0.

In another embodiment, $X_1$ is CH. In yet another embodiment, $X_1$ is C-halogen, where halogen is Cl, F, Br, or I.

In various embodiments of $X_1$, it is C—$(W^1)_j$—$R^4$. In various embodiments of $X_1$, j is 1, and $W^1$ is —O—. In various embodiments of $X_1$, j is 1, and $W^1$ is —$NR^7$—. In various embodiments of $X_1$, j is 1, and $W^1$ is —NH—. In various embodiments of $X_1$, j is 1, and $W^1$ is —$S(O)_{0-2}$—. In various embodiments of $X_1$, j is 1, and $W^1$ is —C(O)—. In various embodiments of $X_1$, j is 1, and $W^1$ is —C(O)N $(R^7)$—. In various embodiments of $X_1$, j is 1, and $W^1$ is —N($R^7$)C(O)—. In various embodiments of $X_1$, j is 1, and $W^1$ is —N($R^7$)S(O)—. In various embodiments of $X_1$, j is 1, and $W^1$ is —N($R^7$)S(O)$_2$—. In various embodiments of $X_1$, j is 1, and $W^1$ is —C(O)O—. In various embodiments of $X_1$, j is 1, and $W^1$ is CH($R^7$)N(C(O)O$R^8$)—. In various embodiments of $X_1$, j is 1, and $W^1$ is —CH($R^7$)N(C(O)$R^8$)—. In various embodiments of $X_1$, j is 1, and $W^1$ is —CH($R^7$)N $(SO_2R^8)$—. In various embodiments of $X_1$, j is 1, and $W^1$ is —CH($R^7$)N($R^8$)—. In various embodiments of $X_1$, j is 1, and $W^1$ is —CH($R^7$)C(O)N($R^8$)—. In various embodiments of $X_1$, j is 1, and $W^1$ is —CH($R^7$)N($R^8$)C(O)—. In various embodiments of $X_1$, j is 1, and $W^1$ is —CH($R^7$)N($R^8$)S (O)—. In various embodiments of $X_1$, j is 1, and $W^1$ is —CH($R^7$)N($R^8$)S(O)$_2$—.

In another embodiment, $X_1$ is N.

In various embodiments, $X_2$ is N. In other embodiments, $X_2$ is C.

In various embodiments, $E^2$ is —$(W^1)_j$—$R^4$, where j is 0.

In another embodiment, $E^2$ is CH. In yet another embodiment, $E^2$ is C-halogen, where halogen is Cl, F, Br, or I.

In various embodiments of $E^2$, it is $-(W^1)_j-R^4$. In various embodiments of $E^2$, j is 1, and $W^1$ is $-O-$. In various embodiments of $E^2$, j is 1, and $W^1$ is $-NR^7-$. In various embodiments of $E^2$, j is 1, and $W^1$ is $-NH-$. In various embodiments of $E^2$, j is 1, and $W^1$ is $-S(O)_{0-2}-$. In various embodiments of $E^2$, j is 1, and $W^1$ is $-C(O)-$. In various embodiments of $E^2$, j is 1, and $W^1$ is $-C(O)N(R^7)-$. In various embodiments of $E^2$, j is 1, and $W^1$ is $-N(R^7)C(O)-$. In various embodiments of $E^2$, j is 1, and $W^1$ is $-N(R^7)S(O)-$. In various embodiments of $E^2$, j is 1, and $W^1$ is $-N(R^7)S(O)_2-$. In various embodiments of $E^2$, j is 1, and $W^1$ is $-C(O)O-$. In various embodiments of $E^2$, j is 1, and $W^1$ is $CH(R^7)N(C(O)OR^8)-$. In various embodiments of $E^2$, j is 1, and $W^1$ is $-CH(R^7)N(C(O)R^8)-$. In various embodiments of $E^2$, j is 1, and $W^1$ is $-CH(R^7)N(SO_2R^8)-$. In various embodiments of $E^2$, j is 1, and $W^1$ is $-CH(R^7)N(R^8)-$. In various embodiments of $E^2$, j is 1, and $W^1$ is $-CH(R^7)C(O)N(R^8)-$. In various embodiments of $E^2$, j is 1, and $W^1$ is $-CH(R^7)N(R^8)C(O)-$. In various embodiments of $E^2$, j is 1, and $W^1$ is $-CH(R^7)N(R^8)S(O)-$. In various embodiments of $E^2$, j is 1, and $W^1$ is $-CH(R^7)N(R^8)S(O)_2-$.

In various embodiments when $M_1$ is a moiety of Formula I-E1, $M_1$ is benzoxazolyl substituted with $-(W_2)_k-R_2$. In some embodiments, $M_1$ is a benzoxazolyl moiety, substituted at the 2-position with $-(W_2)_k-R_2$. In some embodiments, $M_1$ is either a 5-benzoxazolyl or a 6-benzoxazolyl moiety, optionally substituted with $-(W_2)_k-R_2$. Exemplary Formula I-E1 $M_1$ moieties include but are not limited to the following:

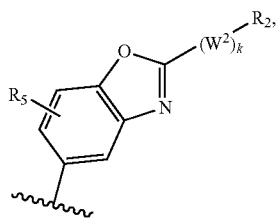

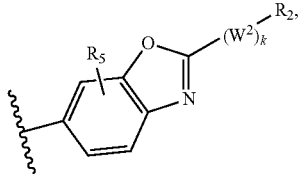

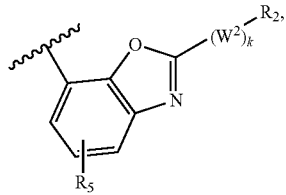

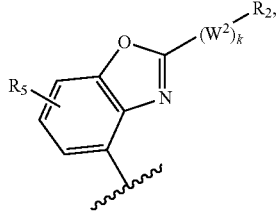

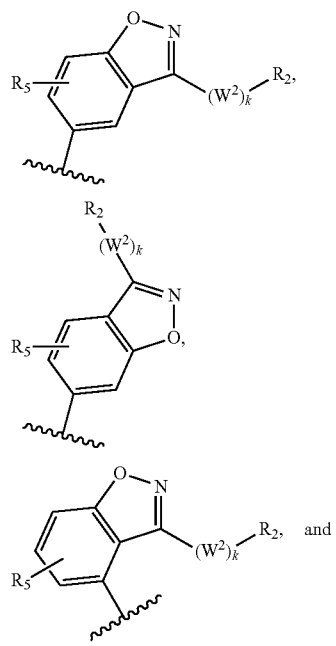

In various embodiments when $M_1$ is a moiety of Formula I-E2, Formula I-E2 is an aza-substituted benzoxazolyl moiety having a structure of one of the following formulae:

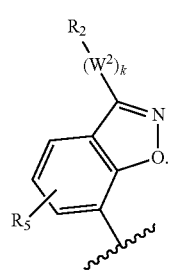

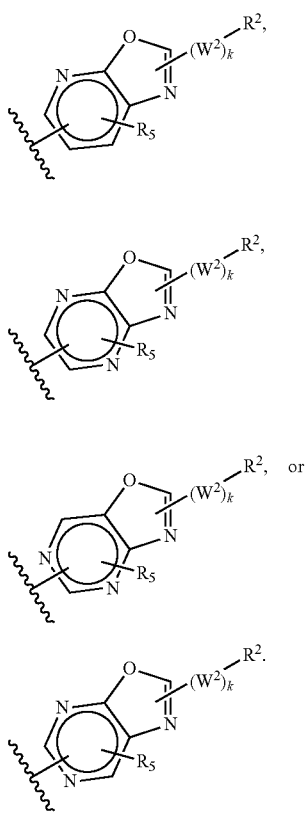

Exemplary Formula I-E2 M₁ moieties include but are not limited to the following:

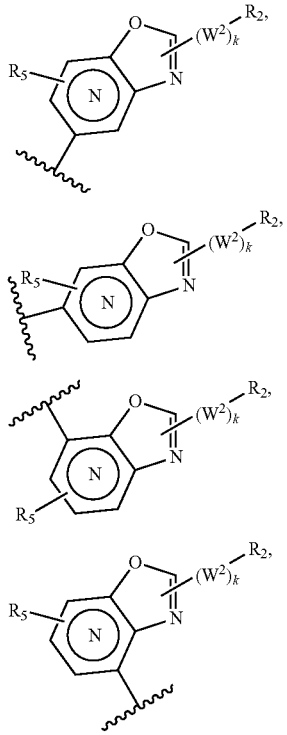

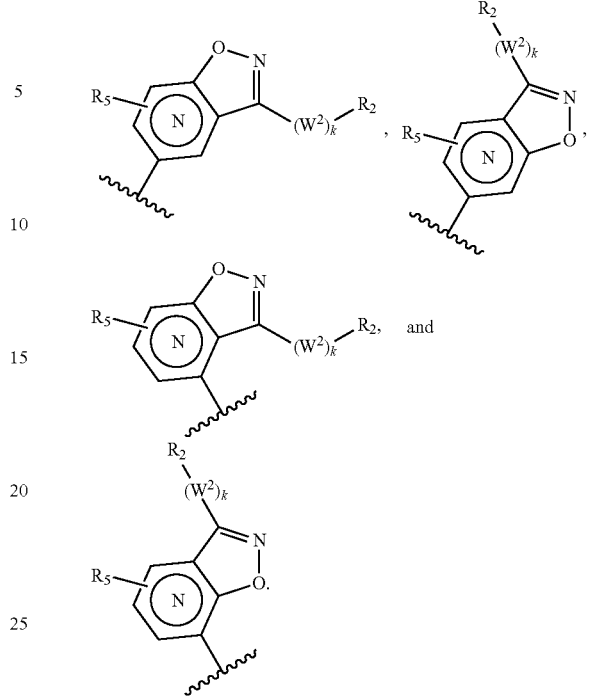

In various embodiments of M₁, k is 0. In other embodiments of M₁, k is 1 and W² is —O—. In another embodiment of M₁, k is 1 and W² is —NR⁷—. In yet another embodiment of M₁, k is 1 and W² is —S(O)₀₋₂—. In another embodiment of M₁, k is 1 and W² is —C(O)—. In a further embodiment of M₁, k is 1 and W² is —C(O)N(R⁷)—. In another embodiment of M₁, k is 1 and W² is —N(R⁷)C(O)—. In another embodiment, k is 1 and W² is —N(R⁷)C(O)N(R⁸)—. In yet another embodiment of M₁, k is 1 and W² is —N(R⁷)S(O)—. In still yet another embodiment of M₁, k is 1 and W² is —N(R⁷)S(O)₂—. In a further embodiment of M₁, k is 1 and W² is —C(O)O—. In another embodiment of M₁, k is 1 and W² is —CH(R⁷)N(C(O)OR⁸)—. In another embodiment of M₁, k is 1 and W² is —CH(R⁷)N(C(O)R⁸)—. In another embodiment of M₁, k is 1 and W² is —CH(R⁷)N(SO₂R⁸)—. In a further embodiment of M₁, k is 1 and W² is —CH(R⁷)N(R⁸)—. In another embodiment of M₁, k is 1 and W² is —CH(R⁷)C(O)N(R⁸)—. In yet another embodiment of M₁, k is 1 and W² is —CH(R⁷)N(R⁸)C(O)—. In another embodiment of M₁, k is 1 and W² is —CH(R⁷)N(R⁸)S(O)—. In yet another embodiment of M₁, k is 1 and W² is —CH(R⁷)N(R⁸)S(O)₂—.

Additional embodiments of compounds of Formula I, including I-A, I-B, I-C, I-D, I-E and others are described below.

In various embodiments of compounds of Formula I, L is absent. In another embodiment, L is —(C=O)—. In another embodiment; L is C(=O)O—. In a further embodiment, L is —C(=O) NR³¹—. In yet another embodiment, L is —S—. In one embodiment, L is —S(O)—. In another embodiment, L is —S(O)₂—. In yet another embodiment, L is —S(O)₂NR³¹—. In another embodiment, L is —NR³¹—.

In various embodiments of compounds of Formula I, R₁ is -L-C₁₋₁₀alkyl, which is unsubstituted. In another embodiment, R₁ is -L-C₁₋₁₀alkyl, which is substituted by one or more independent R³. In yet another embodiment, R₁ is -L-unsubstituted C₁₋₁₀alkyl, where L is absent. In another embodiment, $R_1$ is -L-$C_{1-10}$alkyl, which is substituted by one or more independent $R^3$, and L is absent.

In various embodiments of compounds of Formula I, $R_1$ is -L-$C_{3-8}$cycloalkyl, which is unsubstituted. In another embodiment, $R_1$ is L-$C_{3-8}$cycloalkyl, which is substituted by one or more independent $R^3$. In yet another embodiment, $R_1$ is -L-$C_{3-8}$cycloalkyl, which is unsubstituted, and L is absent. In a further embodiment, $R_1$ is -L-$C_{3-8}$cycloalkyl which is substituted by one or more independent $R^3$, and L is absent.

In various embodiments of compounds of Formula I, $R_1$ is H.

In various embodiments of compounds of Formula I, $R_1$ is -L-aryl, which is unsubstituted. In another embodiment, $R_1$ is -L-aryl, which is substituted by one or more independent $R^3$. In another embodiment, $R_1$ is -L-aryl which is unsubstituted, and L is absent. In yet another embodiment, $R_1$ is -L-aryl, which is substituted by one or more independent $R^3$, and L is absent.

In various embodiments of compounds of Formula I, $R_1$ is -L-heteroaryl, which is unsubstituted. In another embodiment, $R_1$ is -L-heteroaryl, which is substituted by one or more independent $R^3$. In a further embodiment, $R_1$ is -L-heteroaryl which is unsubstituted and L is absent. In yet another embodiment, $R_1$ is -L-heteroaryl, which is substituted by one or more independent $R^3$, and L is absent.

In various embodiments of compounds of Formula I, $R_1$ is -L-$C_{1-10}$alkyl-$C_{3-8}$cycloalkyl, which is unsubstituted. In another embodiment, $R_1$ is -L-$C_{1-10}$alkyl-$C_{3-8}$cycloalkyl, which is substituted by one or more independent $R^3$. In a further embodiment, $R_1$ is -L-$C_{1-10}$alkyl-$C_{3-8}$cycloalkyl which is unsubstituted and L is absent. In yet another embodiment, $R_1$ is -L-$C_{1-10}$alkyl-$C_{3-8}$cycloalkyl, which is substituted by one or more independent $R^3$, and L is absent.

In various embodiments of compounds of Formula I, $R_1$ is -L-$C_{1-10}$alkylaryl, which is unsubstituted. In another embodiment, $R_1$ is -L-$C_{1-10}$alkylaryl, which is substituted by one or more independent $R^3$. In a further embodiment, $R_1$ is -L-$C_{1-10}$alkylaryl which is unsubstituted and L is absent. In yet another embodiment, $R_1$ is -L-$C_{1-10}$alkylaryl, which is substituted by one or more independent $R^3$, where L is absent.

In various embodiments of compounds of Formula I, $R_1$ is -L-$C_{1-10}$alkylheteroaryl, which is unsubstituted. In another embodiment, $R_1$ is -L-$C_{1-10}$alkylheteroaryl, which is substituted by one or more independent $R^3$. In a further embodiment, $R_1$ is -L-$C_{1-10}$alkylheteroaryl which is unsubstituted and L is absent. In yet another embodiment, $R_1$ is -L-$C_{1-10}$alkylheteroaryl, which is substituted by one or more independent $R^3$, where L is absent.

In various embodiments of compounds of Formula I, $R_1$ is -L-$C_{1-10}$alkylheterocyclyl, which is unsubstituted. In another embodiment, $R_1$ is -L-$C_{1-10}$alkylheterocyclyl, which is substituted by one or more independent $R^3$. In a further embodiment, $R_1$ is -L-$C_{1-10}$alkylheterocyclyl which is unsubstituted and L is absent. In yet another embodiment, $R_1$ is -L-$C_{1-10}$alkylheterocyclyl, which is substituted by one or more independent $R^3$, where L is absent.

In various embodiments of compounds of Formula I, $R_1$ is -L-$C_{2-10}$alkenyl, which is unsubstituted. In another embodiment, $R_1$ is -L-$C_{2-10}$alkenyl which is substituted by one or more independent $R^3$. In a further embodiment, $R_1$ is -L-$C_{2-10}$alkenyl which is unsubstituted and L is absent. In yet another embodiment, $R_1$ is -L-$C_{2-10}$alkenyl, which is substituted by one or more independent $R^3$, where L is absent.

In various embodiments of compounds of Formula I, $R_1$ is -L-$C_{2-10}$alkynyl, which is unsubstituted. In another embodiment, $R_1$ is -L-$C_{2-10}$alkynyl which is substituted by one or more independent $R^3$. In a further embodiment, $R_1$ is -L-$C_{2-10}$alkynyl which is unsubstituted and L is absent. In yet another embodiment, $R_1$ is -L-$C_{2-10}$alkynyl, which is substituted by one or more independent $R^3$, where L is absent.

In various embodiments of compounds of Formula I, $R_1$ is -L-$C_{2-10}$alkenyl-$C_{3-8}$cycloalkyl, which is unsubstituted. In another embodiment, $R_1$ is -L-$C_{2-10}$alkenyl-$C_{3-8}$cycloalkyl which is substituted by one or more independent $R^3$. In a further embodiment, $R_1$ is -L-$C_{2-10}$alkenyl-$C_{3-8}$cycloalkyl which is unsubstituted and L is absent. In yet another embodiment, $R_1$ is -L-$C_{2-10}$alkenyl-$C_{3-8}$cycloalkyl, which is substituted by one or more independent $R^3$, where L is absent.

In various embodiments of compounds of Formula I, $R_1$ is -L-$C_{2-10}$alkynyl-$C_{3-8}$cycloalkyl, which is unsubstituted. In another embodiment, $R_1$ is -L-$C_{2-10}$alkynyl-$C_{3-8}$cycloalkyl which is substituted by one or more independent $R^3$. In a further embodiment, $R_1$ is -L-$C_{2-10}$alkynyl-$C_{3-8}$cycloalkyl which is unsubstituted and L is absent. In yet another embodiment, $R_1$ is -L-$C_{2-10}$alkynyl-$C_{3-8}$cycloalkyl, which is substituted by one or more independent $R^3$, where L is absent.

In various embodiments of compounds of Formula I, $R_1$ is -L-$C_{2-10}$alkynyl-$C_{3-8}$cycloalkyl, which is unsubstituted. In another embodiment, $R_1$ is -L-$C_{2-10}$alkynyl-$C_{3-8}$cycloalkyl which is substituted by one or more independent $R^3$. In a further embodiment, $R_1$ is -L-$C_{2-10}$alkynyl-$C_{3-8}$cycloalkyl which is unsubstituted and L is absent. In yet another embodiment, $R_1$ is -L-$C_{2-10}$alkynyl-$C_{3-8}$cycloalkyl, which is substituted by one or more independent $R^3$, where L is absent.

In various embodiments of compounds of Formula I, $R_1$ is -L-heteroalkyl, which is unsubstituted. In another embodiment, $R_1$ is -L-heteroalkyl which is substituted by one or more independent $R^3$. In a further embodiment, $R_1$ is -L-heteroalkyl which is unsubstituted and L is absent. In yet another embodiment, $R_1$ is -L-heteroalkyl, which is substituted by one or more independent $R^3$, where L is absent.

In various embodiments of compounds of Formula I, $R_1$ is -L-heteroalkylaryl, which is unsubstituted. In another embodiment, $R_1$ is -L-heteroalkylaryl which is substituted by one or more independent $R^3$. In a further embodiment, $R_1$ is -L-heteroalkylaryl which is unsubstituted and L is absent. In yet another embodiment, $R_1$ is -L-heteroalkylaryl, which is substituted by one or more independent $R^3$, where L is absent.

In various embodiments of compounds of Formula I, $R_1$ is -L-heteroalkylheteroaryl, which is unsubstituted. In another embodiment, $R_1$ is -L-heteroalkylheteroaryl, which is substituted by one or more independent $R^3$. In a further embodiment, $R_1$ is -L-heteroalkylheteroaryl which is unsubstituted and L is absent. In yet another embodiment, $R_1$ is -L-heteroalkylheteroaryl, which is substituted by one or more independent $R^3$, where L is absent.

In various embodiments of compounds of Formula, $R_1$ is -L-heteroalkyl-heterocyclyl, which is unsubstituted. In another embodiment, $R_1$ is -L-heteroalkyl-heterocyclyl, which is substituted by one or more independent $R^3$. In a further embodiment, $R_1$ is -L-heteroalkyl-heterocyclyl which is unsubstituted, and L is absent. In yet another embodiment, $R_1$ is -L-heteroalkyl-heterocyclyl, which is substituted by one or more independent $R^3$, where L is absent.

In various embodiments of compounds of Formula I, $R_1$ is -L-heteroalkyl-$C_{3-8}$cycloalkyl, which is unsubstituted. In another embodiment, $R_1$ is -L-heteroalkyl-$C_{3-8}$cycloalkyl, which is substituted by one or more independent $R^3$. In a further embodiment, $R_1$ is -L-heteroalkyl-$C_{3-8}$cycloalkyl which is unsubstituted and L is absent. In yet another embodiment, $R_1$ is -L-heteroalkyl-$C_{3-8}$cycloalkyl, which is substituted by one or more independent $R^3$, where L is absent.

In various embodiments of compounds of Formula I, $R_1$ is -L-aralkyl, which is unsubstituted. In another embodiment, $R_1$ is -L-aralkyl, which is substituted by one or more independent $R^3$. In a further embodiment, $R_1$ is -L-aralkyl which is unsubstituted. In yet another embodiment, $R_1$ is -L-aralkyl, which is substituted by one or more independent $R^3$, where L is absent.

In various embodiments of compounds of Formula I, $R_1$ is -L-heteroaralkyl, which is unsubstituted. In another embodiment, $R_1$ is -L-heteroaralkyl, which is substituted by one or more independent $R^3$. In a further embodiment, $R_1$ is -L-heteroaralkyl which is unsubstituted and L is absent. In yet another embodiment, $R_1$ is -L-heteroaralkyl, which is substituted by one or more independent $R^3$, where L is absent.

In various embodiments of compounds of Formula I, $R_1$ is -L-heterocyclyl, which is unsubstituted. In another embodiment, $R_1$ is -L-heterocyclyl, which is substituted by one or more independent $R^3$. In a further embodiment, $R_1$ is -L-heterocyclyl which is unsubstituted and L is absent. In yet another embodiment, $R_1$ is -L-heterocyclyl, which is substituted by one or more independent $R^3$, where L is absent.

In various embodiments of compounds of Formula I, $R_1$ is a substituent as shown below:

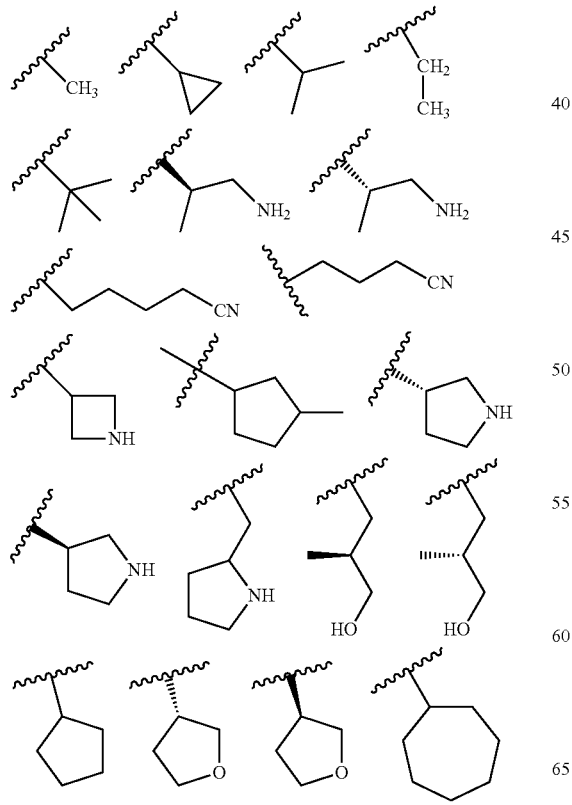

-continued

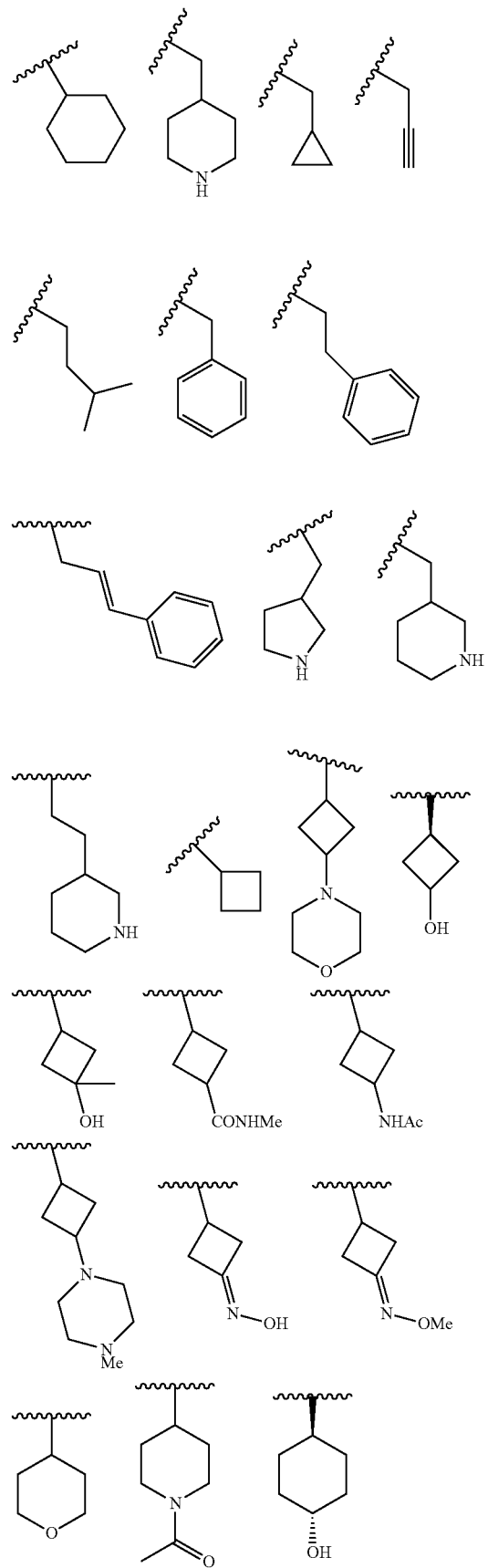

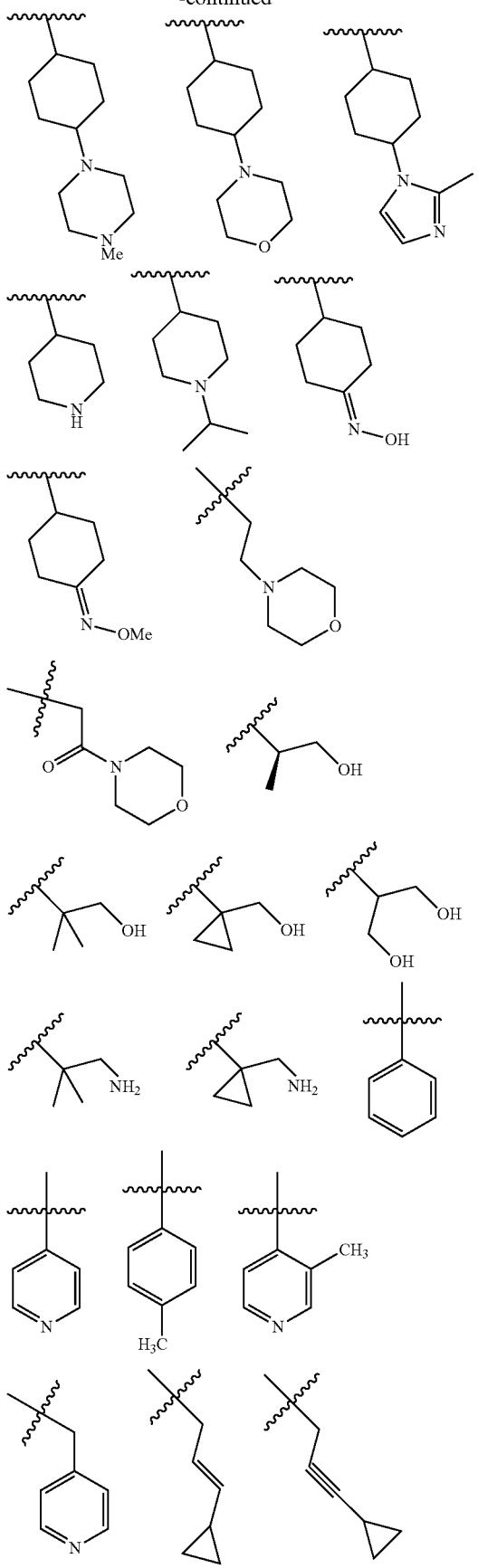
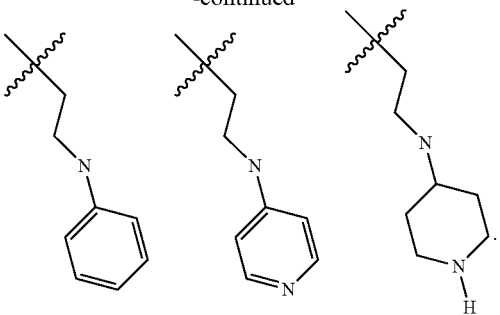

In various embodiments of compounds of Formula I, $R^2$ is hydrogen. In another embodiment, $R^2$ is halogen. In another embodiment, $R^2$ is —OH. In another embodiment, $R^2$ is —$R^{31}$. In another embodiment, $R^2$ is —$CF_3$. In another embodiment, $R^2$ is —$OCF_3$. In another embodiment, $R^2$ is —$OR^{31}$. In another embodiment, $R^2$ is —$NR^{31}R^{32}$. In another embodiment, $R^2$ is —$NR^{34}R^{35}$. In another embodiment, $R^2$ is —$C(O)R^{31}$. In another embodiment, $R^2$ is —$CO_2R^{31}$. In another embodiment, $R^2$ is —$C(=O)NR^{31}R^{32}$. In another embodiment, $R^2$ is —$C(=O)NR^{34}R^{35}$. In another embodiment, $R^2$ is —$NO_2$. In another embodiment, $R^2$ is —CN. In another embodiment, $R^2$ is —$S(O)_{0-2}R^3$. In another embodiment, $R^2$ is —$SO_2NR^{31}R^{32}$. In another embodiment, $R^2$ is —$SO_2NR^{34}R^{35}$. In another embodiment, $R^2$ is —$NR^{31}C(=O)R^{32}$. In another embodiment, $R^2$ is —$NR^{31}C(=O)OR^{32}$. In another embodiment, $R^2$ is —$NR^{31}C(=O)NR^{32}R^{33}$. In another embodiment, $R^2$ is —$NR^{31}S(O)_{0-2}R^{32}$. In another embodiment, $R^2$ is —$C(=S)OR^{31}$. In another embodiment, $R^2$ is —$C(=O)SR^{31}$. In another embodiment, $R^2$ is —$NR^{31}C(=NR^{32})NR^{33}R^{32}$. In another embodiment, $R^2$ is —$NR^{31}C(=NR^{32})OR^{33}$. In another embodiment, $R^2$ is —$NR^{31}C(=NR^{32})SR^{33}$. In another embodiment, $R^2$ is —$OC(=O)OR^{33}$. In another embodiment, $R^2$ is —$OC(=O)NR^{31}R^{32}$. In another embodiment, $R^2$ is —$OC(=O)SR^{31}$. In another embodiment, $R^2$ is —$SC(=O)OR^{31}$. In another embodiment, $R^2$ is —$P(O)OR^{31}OR^{32}$. In another embodiment, $R^2$ is —$SC(=O)NR^{31}R^{32}$. In another embodiment, $R^2$ is monocyclic aryl. In another embodiment, $R^2$ is bicyclic aryl. In another embodiment, $R^2$ is substituted monocyclic aryl. In another embodiment, $R^2$ is heteroaryl. In another embodiment, $R^2$ is $C_{1-4}$alkyl. In another embodiment, $R^2$ is $C_{1-10}$alkyl. In another embodiment, $R^2$ is $C_{3-8}$cycloalkyl. In another embodiment, $R^2$ is $C_{3-8}$cycloalkyl-$C_{1-10}$alkyl. In another embodiment, $R^2$ is $C_{1-10}$alkyl-$C_{3-8}$cycloalkyl. In another embodiment, $R^2$ is $C_{1-10}$alkyl-monocyclic aryl. In another embodiment, $R^2$ is $C_{2-10}$alkyl-monocyclic aryl. In another embodiment, $R^2$ is monocyclic aryl-$C_{2-10}$alkyl. In another embodiment, $R^2$ is $C_{1-10}$alkyl-bicyclicaryl. In another embodiment, $R^2$ is bicyclicaryl-$C_{1-10}$alkyl. In another embodiment, $R^2$ is —$C_{1-10}$alkylheteroaryl. In another embodiment, $R^2$ is —$C_{1-10}$alkylheterocyclyl. In another embodiment, $R^2$ is —$C_{2-10}$alkenyl. In another embodiment, $R^2$ is —$C_{2-10}$alkynyl. In another embodiment, $R^2$ is $C_{2-10}$alkenylaryl. In another embodiment, $R^2$ is $C_{2-10}$alkenylheteroaryl. In another embodiment, $R^2$ is $C_{2-10}$alkenylheteroalkyl. In another embodiment, $R^2$ is $C_{2-10}$alkenylheterocyclyl. In another embodiment, $R^2$ is —$C_{2-10}$alkynylaryl. In another embodiment, $R^2$ is —$C_{2-10}$alkynylheteroaryl. In another embodiment, $R^2$ is —$C_{2-10}$alkynylheteroalkyl. In another embodiment, $R^2$ is —$C_{2-10}$alkynylheterocyclyl. In another embodiment, $R^2$ is —$C_{2-10}$alkynyl$C_{3-8}$cycloalkyl. In another embodiment, $R^2$ is —$C_{2-10}$alkynyl$C_{3-8}$cycloalkenyl. In another embodiment, $R^2$ is —$C_{1-10}$alkoxy-$C_{1-10}$alkyl. In another embodiment, $R^2$ is —$C_{1-10}$alkoxy-$C_{2-10}$alkenyl. In another embodiment, $R^2$ is —$C_{1-10}$alkoxy-$C_{2-10}$alkynyl. In another embodiment, $R^2$ is -heterocyclyl $C_{1-10}$alkyl. In another embodiment, $R^2$ is heterocyclyl$C_{2-10}$alkenyl. In another embodiment, $R^2$ is heterocyclyl$C_{2-10}$alkynyl. In another embodiment, $R^2$ is aryl-$C_{2-10}$alkyl. In another embodiment, $R^2$ is aryl-$C_{1-10}$alkyl. In another embodiment, $R^2$ is aryl-$C_{2-10}$alkenyl. In another embodiment, $R^2$ is aryl-$C_{2-10}$alkynyl. In another embodiment, $R^2$ is aryl-heterocyclyl. In another embodiment, $R^2$ is heteroaryl-$C_{1-10}$alkyl. In another embodiment, $R^2$ is heteroaryl-$C_{2-10}$alkenyl. In another embodiment, $R^2$ is heteroaryl-$C_{2-10}$alkynyl. In another embodiment, $R^2$ is heteroaryl-$C_{3-8}$cycloalkyl. In another embodiment, $R^2$ is heteroaryl-heteroalkyl. In another embodiment, $R^2$ is heteroaryl-heterocyclyl.

In various embodiments of compounds of Formula I, $R^3$ is hydrogen. In another embodiment, $R^3$ is halogen. In another embodiment, $R^3$ is —OH. In another embodiment, $R^3$ is —$R^{31}$. In another embodiment, $R^3$ is —$CF_3$. In another embodiment, $R^3$ is —$OCF_3$. In another embodiment, $R^3$ is —$OR^{31}$. In another embodiment, $R^3$ is —$NR^{31}R^{32}$. In another embodiment, $R^3$ is —$NR^{34}R^{35}$. In another embodiment, $R^3$ is —$C(O)R^{31}$. In another embodiment, $R^3$ is —$CO_2R^{31}$. In another embodiment, $R^3$ is —$C(=O)NR^{31}R^{32}$. In another embodiment, $R^3$ is —$C(=O)NR^{34}R^{35}$. In another embodiment, $R^3$ is —$NO_2$. In another embodiment, $R^3$ is —CN. In another embodiment, $R^3$ is —$S(O)_{0-2}R^3$. In another embodiment, $R^3$ is —$SO_2NR^{31}R^{32}$. In another embodiment, $R^3$ is —$SO_2NR^{34}R^{35}$. In another embodiment, $R^3$ is —$NR^{31}C(=O)R^{32}$. In another embodiment, $R^3$ is —$NR^{31}C(=O)OR^{32}$. In another embodiment, $R^3$ is —$NR^{31}C(=O)NR^{32}R^{33}$. In another embodiment, $R^3$ is —$NR^{31}S(O)_{0-2}R^{32}$. In another embodiment, $R^3$ is —$C(=S)OR^{31}$. In another embodiment, $R^3$ is —$C(=O)SR^{31}$. In another embodiment, $R^3$ is —$NR^{31}C(=NR^{32})NR^{33}R^{32}$. In another embodiment, $R^3$ is —$NR^{31}C(=NR^{32})OR^{33}$. In another embodiment, $R^3$ is —$NR^{31}C(=NR^{32})SR^{33}$. In another embodiment, $R^3$ is —$OC(=OO)OR^{33}$. In another embodiment, $R^3$ is —$OC(=O)NR^{31}R^{32}$. In another embodiment, $R^3$ is —$OC(=O)SR^{31}$. In another embodiment, $R^3$ is —$SC(=O)OR^{31}$. In another embodiment, $R^3$ is —$P(O)OR^{31}OR^{32}$. In another embodiment, $R^3$ is —$SC(=O)NR^{31}R^{32}$. In another embodiment, $R^3$ is aryl. In another embodiment, $R^2$ is heteroaryl. In another embodiment, $R^3$ is $C_{1-4}$alkyl. In another embodiment, $R^3$ is $C_{1-10}$alkyl. In another embodiment, $R^3$ is $C_{3-8}$cycloalkyl. In another embodiment, $R^3$ is $C_{3-8}$cycloalkyl-$C_{1-10}$alkyl. In another embodiment, $R^3$ is —$C_{1-10}$alkyl-$C_{3-8}$cycloalkyl. In another embodiment, $R^3$ is $C_{2-10}$alkyl-monocyclic aryl. In another embodiment, $R^3$ is monocyclic aryl-$C_{2-10}$alkyl. In another embodiment, $R^3$ is $C_{1-10}$alkyl-bicyclicaryl. In another embodiment, $R^3$ is bicyclicaryl-$C_{1-10}$alkyl. In another embodiment, $R^3$ is $C_{1-10}$alkylheteroaryl. In another embodiment, $R^3$ is $C_{1-10}$alkylheterocyclyl. In another embodiment, $R^3$ is $C_{2-10}$alkenyl. In another embodiment, $R^3$ is $C_{2-10}$alkynyl. In another embodiment, $R^3$ is $C_{2-10}$alkenylaryl. In another embodiment, $R^3$ is $C_{2-10}$alkenylheteroaryl. In another embodiment, $R^3$ is $C_{2-10}$alkenylheteroalkyl. In another embodiment, $R^3$ is $C_{2-10}$alkenylheterocyclyl. In another embodiment, $R^3$ is —$C_{2-10}$alkynylaryl. In another embodiment, $R^3$ is —$C_{2-10}$alkynylheteroaryl. In another embodiment, $R^3$ is —$C_{2-10}$alkynylheteroalkyl. In another embodiment, $R^3$ is —$C_{2-10}$alkynylheterocyclyl. In another embodiment, $R^3$ is —$C_{2-10}$alkynyl$C_{3-8}$cycloalkyl. In another embodiment, $R^3$ is $C_{2-10}$alkynyl$C_{3-8}$cycloalkenyl. In another embodiment, $R^3$ is —$C_{1-10}$alkoxy-$C_{1-10}$alkyl. In another embodiment, $R^3$ is $C_{1-10}$alkoxy-$C_{2-10}$alkenyl. In another embodiment, $R^3$ is —$C_{1-10}$alkoxy-$C_{2-10}$alkynyl. In another embodiment, $R^3$ is heterocyclyl-$C_{1-10}$alkyl. In another embodiment, $R^3$ is -heterocyclyl$C_{2-10}$alkenyl. In another embodiment, $R^3$ is heterocyclyl-$C_{2-10}$alkynyl. In another embodiment, $R^3$ is aryl-$C_{1-10}$alkyl. In another embodiment, $R^3$ is aryl-$C_{2-10}$alkenyl. In another embodiment, $R^3$ is aryl-$C_{2-10}$alkynyl. In another embodiment, $R^3$ is aryl-heterocyclyl. In another embodiment, $R^3$ is heteroaryl-$C_{1-10}$alkyl. In another embodiment, $R^3$ is heteroaryl-$C_{2-10}$alkenyl. In another embodiment, $R^3$ is heteroaryl-$C_{2-10}$alkynyl. In another embodiment, $R^3$ is heteroaryl-$C_{3-8}$cycloalkyl. In another embodiment, $R^3$ is heteroaryl-heteroalkyl. In another embodiment, $R^3$ is heteroaryl-heterocyclyl.

In various embodiments of compounds of Formula I, $R^4$ is hydrogen. In another embodiment, $R^4$ is halogen. In another embodiment, $R^4$ is —OH. In another embodiment, $R^4$ is —$R^{31}$. In another embodiment, $R^4$ is —$CF_3$. In another embodiment, $R^4$ is —$OCF_3$. In another embodiment, $R^4$ is —$OR^{31}$. In another embodiment, $R^4$ is —$NR^{31}R^{32}$. In another embodiment, $R^4$ is —$NR^{34}R^{35}$. In another embodiment, $R^4$ is —$C(O)R^{31}$. In another embodiment, $R^4$ is —$CO_2R^{31}$. In another embodiment, $R^4$ is —$C(=O)NR^{31}R^{32}$. In another embodiment, $R^4$ is —$C(=O)NR^{34}R^{35}$. In another embodiment, $R^4$ is —$NO_2$. In another embodiment, $R^4$ is —CN. In another embodiment, $R^4$ is —$S(O)_{0-2}R^3$. In another embodiment, $R^4$ is —$SO_2NR^{31}R^{32}$. In another embodiment, $R^4$ is —$SO_2NR^{34}R^{35}$. In another embodiment, $R^4$ is —$NR^{31}C(=O)R^{32}$. In another embodiment, $R^4$ is —$NR^{31}C(=O)OR^{32}$. In another embodiment, $R^4$ is —$NR^{31}C(=O)NR^{32}R^{33}$. In another embodiment, $R^4$ is —$NR^{31}S(O)_{0-2}R^{32}$. In another embodiment, $R^4$ is —$C(=S)OR^{31}$. In another embodiment, $R^4$ is —$C(=O)SR^{31}$. In another embodiment, $R^4$ is —$NR^{31}C(=NR^{32})NR^{33}R^{32}$. In another embodiment, $R^4$ is —$NR^{31}C(=NR^{32})OR^{33}$. In another embodiment, $R^4$ is —$NR^{31}C(=NR^{32})SR^{33}$. In another embodiment, $R^4$ is —$OC(=O)OR^{33}$. In another embodiment, $R^4$ is —$OC(=O)NR^{31}R^{32}$. In another embodiment, $R^4$ is —$OC(=O)SR^{31}$. In another embodiment, $R^4$ is —$SC(=O)OR^{31}$. In another embodiment, $R^4$ is —$P(O)OR^{31}OR^{32}$. In another embodiment, $R^4$ is —$SC(=O)NR^{31}R^{32}$. In another embodiment, $R^4$ is aryl. In another embodiment, $R^4$ is heteroaryl. In another embodiment, $R^4$ is $C_{1-4}$alkyl. In another embodiment, $R^4$ is $C_{1-10}$alkyl. In another embodiment, $R^4$ is $C_{3-8}$cycloalkyl. In another embodiment, $R^4$ is $C_{1-10}$alkyl-$C_{3-8}$cycloalkyl. In another embodiment, $R^4$ is $C_{1-10}$alkylaryl. In another embodiment, $R^4$ is $C_{1-10}$alkylheteroaryl. In another embodiment, $R^4$ is $C_{1-10}$alkylheterocyclyl. In another embodiment, $R^4$ is $C_{2-10}$alkenyl. In another embodiment, $R^4$ is $C_{2-10}$alkynyl. In another embodiment, $R^4$ is $C_{2-10}$alkynyl-$C_{3-8}$cycloalkyl. $R^4$ is $C_{2-10}$alkenyl-$C_{3-8}$cycloalkyl. In another embodiment, $R^4$ is $C_{2-10}$alkenylaryl. In another embodiment, $R^4$ is $C_{2-10}$alkenyl-heteroaryl. In another embodiment, $R^4$ is $C_{2-10}$alkenyl-heteroalkyl. In another embodiment, $R^4$ is $C_{2-10}$alkenylheterocyclcyl. In another embodiment, $R^4$ is —$C_{2-10}$alkynylaryl. In another embodiment, $R^4$ is $C_{2-10}$alkynylheteroaryl. In another embodiment, $R^4$ is $C_{2-10}$alkynylheteroalkyl. In another embodiment, $R^4$ is $C_{2-10}$alkynylheterocyclyl. In another embodiment, $R^4$ is $C_{2-10}$alkynyl$C_{3-8}$cycloalkyl. In another embodiment, $R^4$ is heterocyclyl$C_{1-10}$alkyl. In another embodiment, $R^4$ is heterocyclyl-$C_{2-10}$alkenyl. In another embodiment, $R^4$ is heterocyclyl-$C_{2-10}$alkynyl. In another embodiment, $R^4$ is aryl-$C_{1-10}$alkyl. In another embodiment, $R^4$ is aryl-$C_{2-10}$alkenyl. In another embodiment, $R^4$ is aryl-$C_{2-10}$alkynyl. In another embodiment, $R^4$ is aryl-heterocyclyl. In another embodiment, $R^4$ is heteroaryl-$C_{1-10}$alkyl. In another embodiment, $R^4$ is heteroaryl-$C_{2-10}$alkenyl. In another embodiment, $R^4$ is heteroaryl-$C_{2-10}$alkynyl. In another embodiment, $R^4$ is $C_{3-8}$cycloalkyl-$C_{1-10}$alkyl. In another embodiment, $R^4$ is $C_{3-8}$cycloalkyl-$C_{2-10}$alkenyl. In another embodiment, $R^4$ is $C_{3-8}$cycloalkyl-$C_{2-10}$alkynyl.

In various embodiments of compounds of Formula I, $R^5$ is hydrogen. In another embodiment, $R^5$ is halogen. In another embodiment, $R^5$ is —OH. In another embodiment, $R^5$ is —$R^{31}$. In another embodiment, $R^5$ is —$CF_3$. In another embodiment, $R^5$ is —$OCF_3$. In another embodiment, $R^5$ is —$OR^{31}$. In another embodiment, $R^5$ is —$NR^{31}R^{32}$. In another embodiment, $R^5$ is —$NR^{34}R^{35}$. In another embodiment, $R^5$ is —$C(O)R^{31}$. In another embodiment, $R^5$ is —$CO_2R^{31}$. In another embodiment, $R^5$ is —$C(=O)NR^{31}R^{32}$. In another embodiment, $R^5$ is —$C(=O)NR^{34}R^{35}$. In another embodiment, $R^5$ is —$NO_2$. In another embodiment, $R^5$ is —CN. In another embodiment, $R^5$ is —$S(O)_{0-2}R^{31}$. In another embodiment, $R^5$ is —$SO_2NR^{31}R^{32}$. In another embodiment, $R^5$ is —$SO_2NR^{34}R^{35}$. In another embodiment, $R^5$ is —$NR^{31}C(=O)R^{32}$. In another embodiment, $R^5$ is —$NR^{31}C(=O)OR^{32}$. In another embodiment, $R^5$ is —$NR^{31}C(=O)NR^{32}R^{33}$. In another embodiment, $R^5$ is —$NR^{31}S(O)_{0-2}R^{32}$. In another embodiment, $R^5$ is —$C(=S)OR^{31}$. In another embodiment, $R^5$ is —$C(=O)SR^{31}$. In another embodiment, $R^5$ is —$NR^{31}C(=NR^{32})NR^{33}R^{32}$. In another embodiment, $R^5$ is —$NR^{31}C(=NR^{32})OR^{33}$. In another embodiment, $R^5$ is —$NR^{31}C(=NR^{32})SR^{33}$. In another embodiment, $R^5$ is —$OC(=O)OR^{33}$. In another embodiment, $R^5$ is —$OC(=O)NR^{31}R^{32}$. In another embodiment, $R^5$ is —$OC(=O)SR^{31}$. In another embodiment, $R^5$ is —$SC(=O)OR^{31}$. In another embodiment, $R^5$ is —$P(O)OR^{31}OR^{32}$. In another embodiment, $R^5$ is or —$SC(=O)NR^{31}R^{32}$.

In various embodiments of compounds of Formula I, $R^7$ is hydrogen. In another embodiment, $R^7$ is unsubstituted $C_{1-10}$alkyl. In another embodiment, $R^7$ is unsubstituted $C_{2-10}$alkenyl. In another embodiment, $R^7$ is unsubstituted aryl. In another embodiment, $R^7$ is unsubstituted heteroaryl. In another embodiment, $R^7$ is unsubstituted heterocyclyl. In another embodiment, $R^7$ is unsubstituted $C_{3-10}$cycloalkyl. In another embodiment, $R^7$ is $C_{1-10}$alkyl substituted by one or more independent $R^6$. In another embodiment, $R^7$ is $C_{2-10}$alkenyl substituted by one or more independent $R^6$. In another embodiment, $R^7$ is aryl substituted by one or more independent $R^6$. In another embodiment, $R^7$ is heteroaryl substituted by one or more independent $R^6$. In another embodiment, $R^7$ is heterocyclyl substituted by one or more independent $R^6$. In another embodiment, $R^7$ is $C_{3-10}$cycloalkyl substituted by one or more independent $R^6$.

In various embodiments of compounds of Formula I, $R^8$ is hydrogen. In another embodiment, $R^8$ is unsubstituted $C_{1-10}$alkyl. In another embodiment, $R^8$ is unsubstituted $C_{2-10}$alkenyl. In another embodiment, $R^8$ is unsubstituted aryl. In another embodiment, $R^8$ is unsubstituted heteroaryl. In another embodiment, $R^8$ is unsubstituted heterocyclyl. In another embodiment, $R^8$ is unsubstituted $C_{3-10}$cycloalkyl. In another embodiment, $R^8$ is $C_{1-10}$alkyl substituted by one or more independent $R^6$. In another embodiment, $R^8$ is $C_{2-10}$alkenyl substituted by one or more independent $R^6$. In another embodiment, $R^8$ is aryl substituted by one or more independent $R^6$. In another embodiment, $R^8$ is heteroaryl substituted by one or more independent $R^6$. In another embodiment, $R^8$ is heterocyclyl substituted by one or more independent $R^6$. In another embodiment, $R^8$ is $C_{3-10}$cycloalkyl substituted by one or more independent $R^6$.

In various embodiments of compounds of Formula I, $R^6$ is halo. In another embodiment, $R^6$ is —$OR^{31}$. In another embodiment, $R^6$ is —SH. In another embodiment, $R^6$ is $NH_2$. In another embodiment, $R^6$ is —$NR^{34}R^{35}$. In another embodiment, $R^6$ is —$NR^{31}R^{32}$. In another embodiment, $R^6$ is —$CO_2R^{31}$. In another embodiment, $R^6$ is —$CO_2$aryl. In another embodiment, $R^6$ is —$C(=O)NR^{31}R^{32}$. In another embodiment, $R^6$ is $C(=O)$ $NR^{34}R^{35}$. In another embodiment, $R^6$ is —$NO_2$. In another embodiment, $R^6$ is —CN. In another embodiment, $R^6$ is —$S(O)_{0-2}$ $C_{1-10}$alkyl. In another embodiment, $R^6$ is —$S(O)_{0-2}$aryl. In another embodiment, $R^6$ is —$SO_2NR^{34}R^{35}$. In another embodiment, $R^6$ is —$SO_2NR^{31}R^{32}$. In another embodiment, $R^6$ is $C_{1-10}$alkyl. In another embodiment, $R^6$ is $C_{2-10}$alkenyl. In another embodiment, $R^6$ is $C_{2-10}$alkynyl. In another embodiment, $R^6$ is unsubstituted aryl-$C_{1-10}$alkyl. In another embodiment, $R^6$ is unsubstituted aryl-$C_{2-10}$alkenyl. In another embodiment, $R^6$ is unsubstituted aryl-$C_{2-10}$alkynyl. In another embodiment, $R^6$ is unsubstituted heteroaryl-$C_{1-10}$alkyl. In another embodiment, $R^6$ is unsubstituted heteroaryl-$C_{2-10}$alkenyl. In another embodiment, $R^6$ is aryl-$C_{1-10}$alkyl, aryl-$C_{2-10}$alkenyl, aryl-$C_{2-10}$alkynyl, heteroaryl-$C_{1-10}$alkyl, or heteroaryl-$C_{2-10}$alkenyl substituted by one or more independent halo. In another embodiment, $R^6$ is aryl-$C_{1-10}$alkyl, aryl-$C_{2-10}$alkenyl, aryl-$C_{2-10}$alkynyl, heteroaryl-$C_{1-10}$alkyl, or heteroaryl-$C_{2-10}$alkenyl substituted by one or more independent cyano. In another embodiment, $R^6$ is aryl-$C_{1-10}$alkyl, aryl-$C_{2-10}$alkenyl, aryl-$C_{2-10}$alkynyl, heteroaryl-$C_{1-10}$alkyl, or heteroaryl-$C_{2-10}$alkenyl substituted by one or more independent nitro. In another embodiment, $R^6$ is aryl-$C_{1-10}$alkyl, aryl-$C_{2-10}$alkenyl, aryl-$C_{2-10}$alkynyl, heteroaryl-$C_{1-10}$alkyl, or heteroaryl-$C_{2-10}$alkenyl substituted by one or more independent —$OC_{1-10}$alkyl. In another embodiment, $R^6$ is aryl-$C_{1-10}$alkyl, aryl-$C_{2-10}$alkenyl, aryl-$C_{2-10}$alkynyl, heteroaryl-$C_{1-10}$alkyl, or heteroaryl-$C_{2-10}$alkenyl substituted by one or more independent —$C_{1-10}$alkyl. In another embodiment, $R^6$ is aryl-$C_{1-10}$alkyl, aryl-$C_{2-10}$alkenyl, aryl-$C_{2-10}$alkynyl, heteroaryl-$C_{1-10}$alkyl, or heteroaryl-$C_{2-10}$alkenyl substituted by one or more independent —$C_{2-10}$alkenyl. In another embodiment, $R^6$ is aryl-$C_{1-10}$alkyl, aryl-$C_{2-10}$alkenyl, aryl-$C_{2-10}$alkynyl, heteroaryl-$C_{1-10}$alkyl, or heteroaryl-$C_{2-10}$alkenyl substituted by one or more independent —$C_{2-10}$alkynyl. In another embodiment, $R^6$ is aryl-$C_{1-10}$alkyl, aryl-$C_{2-10}$alkenyl, aryl-$C_{2-10}$alkynyl, heteroaryl-$C_{1-10}$alkyl, or heteroaryl-$C_{2-10}$alkenyl substituted by one or more independent -(halo)$C_{1-10}$alkyl. In another embodiment, $R^6$ is aryl-$C_{1-10}$alkyl, aryl-$C_{2-10}$alkenyl, aryl-$C_{2-10}$alkynyl, heteroaryl-$C_{1-10}$alkyl, or heteroaryl-$C_{2-10}$alkenyl substituted by one or more independent -(halo)$C_{2-10}$alkenyl. In another embodiment, $R^6$ is aryl-$C_{1-10}$alkyl, aryl-$C_{2-10}$alkenyl, aryl-$C_{2-10}$alkynyl, heteroaryl-$C_{1-10}$alkyl, or heteroaryl-$C_{2-10}$alkenyl substituted by one or more independent -(halo) $C_{2-10}$alkynyl. In another embodiment, $R^6$ is aryl-$C_{1-10}$alkyl, aryl-$C_{2-10}$alkenyl, aryl-$C_{2-10}$alkynyl, heteroaryl-$C_{1-10}$alkyl, or heteroaryl-$C_{2-10}$alkenyl substituted by one or more independent —COOH. In another embodiment, $R^6$ is aryl-$C_{1-10}$alkyl, aryl-$C_{2-10}$alkenyl, aryl-$C_{2-10}$alkynyl, heteroaryl-$C_{1-10}$alkyl, or heteroaryl-$C_{2-10}$alkenyl substituted by one or more independent —$C(=O)NR^{31}R^{32}$. In another embodiment, $R^6$ is aryl-$C_{1-10}$alkyl, aryl-$C_{2-10}$alkenyl, aryl-$C_{2-10}$alkynyl, heteroaryl-$C_{1-10}$alkyl, or heteroaryl-$C_{2-10}$alkenyl substituted by one or more independent —$C(=O)$ $NR^{34}R^{35}$. In another embodiment, $R^6$ is aryl-$C_{1-10}$alkyl, aryl-$C_{2-10}$alkenyl, aryl-$C_{2-10}$alkynyl, heteroaryl-$C_{1-10}$alkyl, or heteroaryl-$C_{2-10}$alkenyl substituted by one or more independent —SO$_2$NR$^{34}$R$^{35}$. In another embodiment, R$^6$ is aryl-C$_{1-10}$alkyl, aryl-C$_{2-10}$alkenyl, aryl-C$_{2-10}$alkynyl, heteroaryl-C$_{1-10}$alkyl, or heteroaryl-C$_{2-10}$alkenyl substituted by one or more independent —SO$_2$NR$^{31}$R$^{32}$. In another embodiment, R$^6$ is aryl-C$_{1-10}$alkyl, aryl-C$_{2-10}$alkenyl, aryl-C$_{2-10}$alkynyl, heteroaryl-C$_{1-10}$alkyl, or heteroaryl-C$_{2-10}$alkenyl substituted by one or more independent —NR$^{31}$R$^{32}$. In another embodiment, R$^6$ is aryl-C$_{1-10}$alkyl, aryl-C$_{2-10}$alkenyl, aryl-C$_{2-10}$alkynyl, heteroaryl-C$_{1-10}$alkyl, or heteroaryl-C$_{2-10}$alkenyl substituted by one or more independent —NR$^{34}$R$^{35}$.

In various embodiments of compounds of Formula I, R$^9$ is H. In another embodiment, R$^9$ is halo. In another embodiment, R$^9$ is —OR$^{31}$. In another embodiment, R$^9$ is —SH. In another embodiment, R$^9$ is NH$_2$. In another embodiment, R$^9$ is —NR$^{34}$R$^{35}$. In another embodiment, R$^9$ is —NR$^{31}$R$^{32}$. In another embodiment, R$^9$ is —CO$_2$R$^{31}$. In another embodiment, R$^9$ is —CO$_2$aryl. In another embodiment, R$^9$ is —C(=O)NR$^{31}$R$^{32}$. In another embodiment, R$^9$ is C(=O)NR$^{34}$R$^{35}$. In another embodiment, R$^9$ is —NO$_2$. In another embodiment, R$^9$ is —CN. In another embodiment, R$^9$ is —S(O)$_{0-2}$ C$_{1-10}$alkyl. In another embodiment, R$^9$ is —S(O)$_{0-2}$aryl. In another embodiment, R$^9$ is —SO$_2$NR$^{34}$R$^{35}$. In another embodiment, R$^9$ is —SO$_2$NR$^{31}$R$^{32}$. In another embodiment, R$^9$ is C$_{1-10}$alkyl. In another embodiment, R$^9$ is C$_{2-10}$alkenyl. In another embodiment, R$^9$ is C$_{2-10}$alkynyl. In another embodiment, R$^9$ is unsubstituted aryl-C$_{1-10}$alkyl. In another embodiment, R$^9$ is unsubstituted aryl-C$_{2-10}$alkenyl. In another embodiment, R$^9$ is unsubstituted aryl-C$_{2-10}$alkynyl. In another embodiment, R$^9$ is unsubstituted heteroaryl-C$_{1-10}$alkyl. In another embodiment, R$^9$ is unsubstituted heteroaryl-C$_{2-10}$alkenyl. In another embodiment, R$^9$ is aryl-C$_{1-10}$alkyl, aryl-C$_{2-10}$alkenyl, aryl-C$_{2-10}$alkynyl, heteroaryl-C$_{1-10}$alkyl, or heteroaryl-C$_{2-10}$alkenyl substituted by one or more independent halo. In another embodiment, R$^9$ is aryl-C$_{1-10}$alkyl, aryl-C$_{2-10}$alkenyl, aryl-C$_{2-10}$alkynyl, heteroaryl-C$_{1-10}$alkyl, or heteroaryl-C$_{2-10}$alkenyl substituted by one or more independent cyano. In another embodiment, R$^9$ is aryl-C$_{1-10}$alkyl, aryl-C$_{2-10}$alkenyl, aryl-C$_{2-10}$alkynyl, heteroaryl-C$_{1-10}$alkyl, or heteroaryl-C$_{2-10}$alkenyl substituted by one or more independent nitro.

In various embodiments of compounds of Formula I, R$^{31}$ is H. In some embodiments, R$^{31}$ is unsubstituted C$_{1-10}$alkyl. In some embodiments, R$^{31}$ is substituted C$_{1-10}$alkyl. In some embodiments, R$^{31}$ is C$_{1-10}$alkyl substituted with one or more aryl. In some embodiments, R$^{31}$ is C$_{1-10}$alkyl substituted with one or more heteroalkyl. In some embodiments, R$^{31}$ is C$_{1-10}$alkyl substituted with one or more heterocyclyl. In some embodiments, R$^{31}$ is C$_{1-10}$alkyl substituted with one or more heteroaryl.

In various embodiments of compounds of Formula I, R$^{32}$ is H. In some embodiments, R$^{32}$ is unsubstituted C$_{1-10}$alkyl. In some embodiments, R$^{32}$ is substituted C$_{1-10}$alkyl. In some embodiments, R$^{32}$ is C$_{1-10}$alkyl substituted with one or more aryl. In some embodiments, R$^{32}$ is C$_{1-10}$alkyl substituted with one or more heteroalkyl. In some embodiments, R$^{32}$ is C$_{1-10}$alkyl substituted with one or more heterocyclyl. In some embodiments, R$^{32}$ is C$_{1-10}$alkyl substituted with one or more heteroaryl.

In various embodiments of compounds of Formula I, R$^{33}$ is unsubstituted C$_{1-10}$alkyl. In some embodiments, R$^{33}$ is substituted C$_{1-10}$alkyl. In some embodiments, R$^{33}$ is C$_{1-10}$alkyl substituted with one or more aryl. In some embodiments, R$^{33}$ is C$_{1-10}$alkyl substituted with one or more heteroalkyl. In some embodiments, R$^{33}$ is C$_{1-10}$alkyl substituted with one or more heterocyclyl. In some embodiments, R$^{33}$ is C$_{1-10}$alkyl substituted with one or more heteroaryl.

In various embodiments of compounds of Formula I, R$^{34}$ and R$^{35}$ in —NR$^{34}$R$^{35}$, —C(=O)NR$^{34}$R$^{35}$, or —SO$_2$NR$^{34}$R$^{35}$, are taken together with the nitrogen atom to which they are attached to form a 3-10 membered saturated or unsaturated ring; wherein said ring is independently unsubstituted or is substituted by one or more —NR$^{31}$R$^{32}$, hydroxyl, halogen, oxo, aryl, heteroaryl, C$_{1-6}$alkyl, or O-aryl, and wherein said 3-10 membered saturated or unsaturated ring independently contains 0, 1, or 2 more heteroatoms in addition to the nitrogen.

In some embodiments, the R$^{34}$ and R$^{35}$ in —NR$^{34}$R$^{35}$, —C(=O)NR$^{34}$R$^{35}$, or —SO$_2$NR$^{34}$R$^{35}$, are taken together with the nitrogen atom to which they are attached to form:

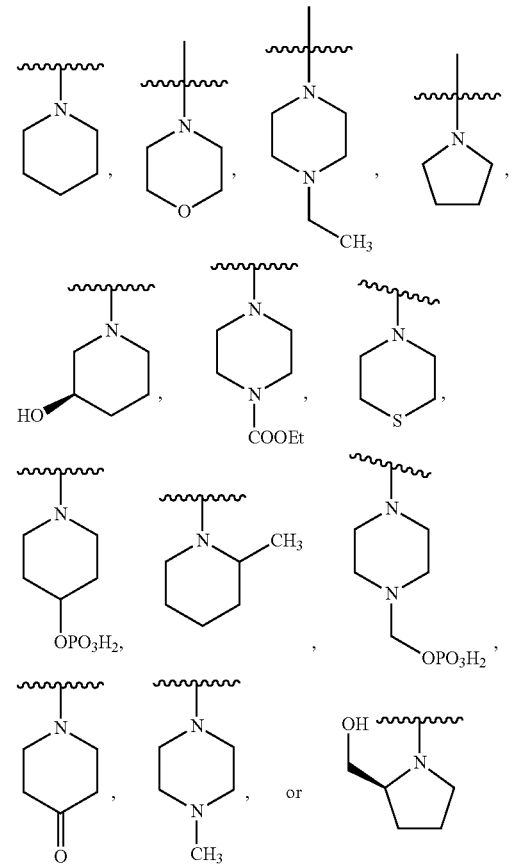

In another embodiment, X$_1$ is C—NH$_2$.

In various embodiments, X$_1$ is C—NH—R$^4$, where —NH—R$^4$ is:

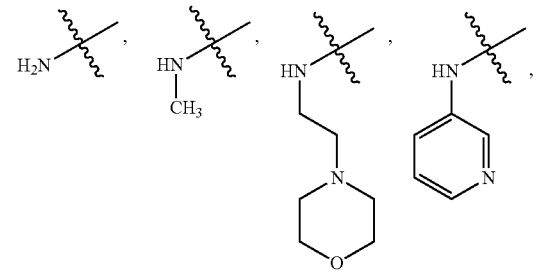

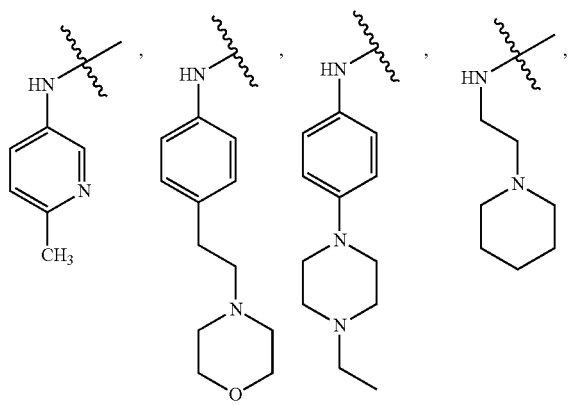

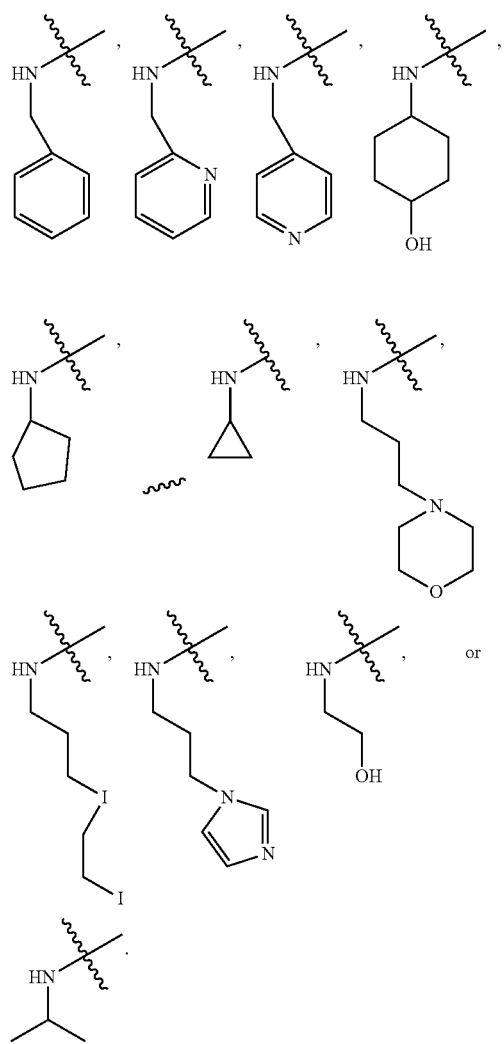

In one embodiment, the invention provides an inhibitor of Formula I-C1 where $R^5$ is H. In another embodiment, the invention provides an inhibitor of Formula I-C2 where $R^5$ is H.

In some embodiments of the invention, the mTORC1/2 inhibitor is a compound of Formula I-C1a:

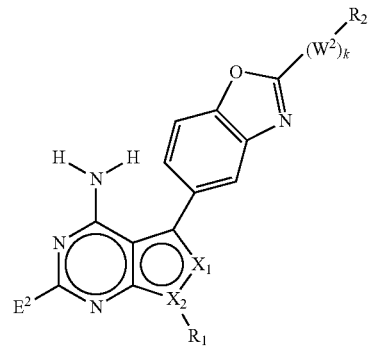

Formula I-C1a or a pharmaceutically acceptable salt thereof wherein:
$E^2$ is —H;
$X_1$ and $X_2$ are N;
$R_1$ is -L-$C_{1-10}$alkyl, -L-$C_{3-8}$cycloalkyl, -L-$C_{1-10}$alkylheterocyclyl, or -L-heterocyclyl, each of which is unsubstituted or is substituted by one or more independent $R^3$;
L is absent, —(C=O)—, —C(=O)O—, —C(=O)N($R^{31}$)—, —S—, —S(O)—, —S(O)$_2$—, —S(O)$_2$N($R^{31}$)—, or —N($R^{31}$)—;
$R^3$ is hydrogen, —OH, —O$R^{31}$, —N$R^{31}R^{32}$, —C(O)$R^{31}$, —C(=O)N$R^{31}R^{32}$, —C(=O)N$R^{34}R^{35}$, aryl, heteroaryl, $C_{1-4}$alkyl, $C_{1-10}$alkyl, $C_{3-8}$cycloalkyl, or heterocyclyl, wherein each of said aryl or heteroaryl moiety is unsubstituted or is substituted with one or more independent alkyl, heteroalkyl, alkenyl, alkynyl, cycloalkyl, heterocycloalkyl, aryl, arylalkyl, heteroaryl, heteroarylalkyl, halo, —OH, —$R^{31}$, —CF$_3$, —OCF$_3$, —O$R^{31}$, —N$R^{31}R^{32}$, —N$R^{34}R^{35}$, —C(O)$R^{31}$, —CO$_2R^{31}$, —C(=O)N$R^{31}R^{32}$, —C(=O)N$R^{34}R^{35}$, —NO$_2$, —CN, —S(O)$_{0-2}R^{31}$, —SO$_2$N$R^{31}R^{32}$, —SO$_2$N$R^{34}R^{35}$, —N$R^{31}$C(=O)$R^{32}$, —N$R^{31}$C(=O)O$R^{32}$, —N$R^{31}$C(=O)N$R^{32}R^{33}$, —N$R^{31}$S(O)$_{0-2}R^{32}$, —C(=S)O$R^{31}$, —C(=O)S$R^{31}$, —N$R^{31}$C(=N$R^{32}$)N$R^{33}R^{32}$, —N$R^{31}$C(=N$R^{32}$)O$R^{33}$, —N$R^{31}$C(=N$R^{32}$)S$R^{33}$, —OC(=O)O$R^{33}$, —OC(=O)N$R^{31}R^{32}$, —OC(=O)S$R^{31}$, —SC(=O)O$R^{31}$, —P(O)O$R^{31}$O$R^{32}$, or —SC(=O)N$R^{31}R^{32}$, and wherein each of said alkyl, cycloalkyl, or heterocyclyl moiety is unsubstituted or is substituted with one or more alkyl, heteroalkyl, alkenyl, alkynyl, cycloalkyl, heterocycloalkyl, aryl, arylalkyl, heteroaryl, heteroarylalkyl, halo, —OH, —$R^{31}$, —CF$_3$, —OCF$_3$, —O$R^{31}$, —O-aryl, —N$R^{31}R^{32}$, —N$R^{34}R^{35}$, —C(O)$R^{31}$, —CO$_2R^{31}$, —C(=O)N$R^{34}R^{35}$, or —C(=O)N$R^{31}R^{32}$;
—($W^2$)$_k$— is —NH—, —N(H)C(O)— or —N(H)S(O)$_2$—;
$R^2$ is hydrogen, halogen, —O$R^{31}$, —N$R^{31}R^{32}$, —N$R^{34}R^{35}$, —C(O)$R^{31}$, —CO$_2R^{31}$, —C(=O)N$R^{31}R^{32}$, —C(=O)N$R^{34}R^{35}$, —S(O)$_{0-2}R^{31}$, —SO$_2$N$R^{31}R^{32}$, —SO$_2$N$R^{34}R^{35}$, bicyclic aryl, substituted monocyclic aryl, heteroaryl, $C_{1-10}$alkyl, $C_{3-8}$cycloalkyl, $C_{1-10}$alkyl-$C_{3-8}$cycloalkyl, $C_{3-8}$cycloalkyl-$C_{1-10}$alkyl, $C_{3-8}$cycloalkyl-$C_{2-10}$alkenyl, $C_{3-8}$cycloalkyl-$C_{2-10}$alkynyl, $C_{2-10}$alkyl-monocyclic aryl, monocyclic aryl-$C_{2-10}$alkyl, $C_{1-10}$alkylbicycloaryl, bicycloaryl-$C_{1-10}$alkyl, substituted $C_{1-10}$alkylaryl, substituted aryl-$C_{1-10}$alkyl, $C_{1-10}$alkylheteroaryl, $C_{1-10}$alkylheterocyclyl, $C_{2-10}$alkenyl, $C_{2-10}$alkynyl, $C_{2-10}$alkenylaryl, $C_{2-10}$alkenylheteroaryl, $C_{2-10}$alkenylheteroalkyl, $C_{2-10}$alkenylheterocyclcyl, $C_{2-10}$alkynylaryl, $C_{2-10}$alkynylheteroaryl, $C_{2-10}$alkynylheteroalkyl, $C_{2-10}$alkynylheterocyclyl, $C_{2-10}$alkenyl-$C_{3-8}$cycloalkyl, $C_{2-10}$alkynyl-$C_{3-8}$cycloalkenyl, $C_{1-10}$alkoxy $C_{1-10}$alkyl, $C_{1-10}$alkoxy$C_{2-10}$alkenyl, $C_{1-10}$alkoxy$C_{2-10}$alkynyl, heterocyclyl, heterocyclyl $C_{1-10}$alkyl, heterocyclyl$C_{2-10}$alkenyl, heterocyclyl-$C_{2-10}$alkynyl, aryl-$C_{2-10}$alkenyl, aryl-$C_{2-10}$alkynyl, aryl-heterocyclyl, heteroaryl-$C_{1-10}$alkyl, heteroaryl-$C_{2-10}$alkenyl, heteroaryl-$C_{2-10}$alkynyl, heteroaryl-$C_{3-8}$cycloalkyl, heteroaryl-heteroalkyl, or heteroaryl-heterocyclyl, wherein each of said bicyclic aryl or heteroaryl moiety is unsubstituted, or wherein each of bicyclic aryl, heteroaryl moiety or monocyclic aryl moiety is substituted with one or more independent halo, —OH, —$R^{31}$, —$CF_3$, —$OCF_3$, —$OR^{31}$, —$NR^{31}R^{32}$, —$NR^{34}R^{35}$, —$C(O)R^{31}$, —$CO_2R^{31}$, —$C(=O)NR^{31}R^{32}$, —$C(=O)NR^{34}R^{35}$, —$NO_2$, —CN, —$S(O)_{0-2}R^{31}$, —$SO_2NR^{31}R^{32}$, —$SO_2NR^{34}R^{35}$, —$NR^{31}C(=O)R^{32}$, —$NR^{31}C(=O)OR^{32}$, —$NR^{31}C(=O)NR^{32}R^{33}$, —$NR^{31}S(O)_{0-2}R^{32}$, —$C(=S)OR^{31}$, —$C(=O)SR^{31}$, —$NR^{31}C(=NR^{32})NR^{33}R^{32}$, —$NR^{31}C(=NR^{32})OR^{33}$, —$NR^{31}C(=NR^{32})SR^{33}$, —$OC(=O)OR^{33}$, —$OC(=O)NR^{31}R^{32}$, —$OC(=O)SR^{31}$, —$SC(=O)OR^{31}$, —$P(O)OR^{31}OR^{32}$, or —$SC(=O)NR^{31}R^{32}$, and wherein each of said alkyl, cycloalkyl, heterocyclyl, or heteroalkyl moiety is unsubstituted or is substituted with one or more halo, —OH, —$R^{31}$, —$CF_3$, —$OCF_3$, —$OR^{31}$, —O-aryl, —$NR^{31}R^{32}$, —$NR^{34}R^{35}$, —$C(O)R^{31}$, —$CO_2R^{31}$, —$C(=O)NR^{34}R^{35}$, or —$C(=O)NR^{31}R^{32}$;

$R^{31}$, $R^{32}$, and $R^{33}$, in each instance, are independently H or $C_{1-10}$alkyl, wherein the $C_{1-10}$alkyl is unsubstituted; and $R^{34}$ and $R^{35}$ in —$NR^{34}R^{35}$, —$C(=O)NR^{34}R^{35}$, or —$SO_2NR^{34}R^{35}$, are taken together with the nitrogen atom to which they are attached to form a 3-10 membered saturated or unsaturated ring; wherein said ring is independently unsubstituted or is substituted by one or more —$NR^{31}R^{32}$, hydroxyl, halogen, oxo, aryl, heteroaryl, $C_{1-6}$alkyl, or O-aryl, and wherein said 3-10 membered saturated or unsaturated ring independently contains 0, 1, or 2 more heteroatoms in addition to the nitrogen.

In another aspect, the mTORC1/2 inhibitor of Formula I-C1 is a compound of Formula I-C1a:

Formula I-C1a

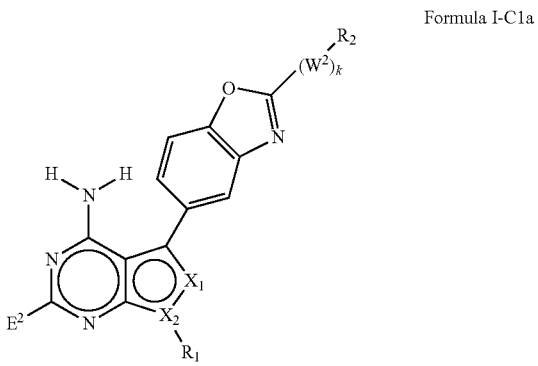

or a pharmaceutically acceptable salt thereof, wherein: $E^2$ is —H; $X_1$ is CH and $X_2$ is N;

$R_1$ is -L-$C_{1-10}$alkyl, -L-$C_{3-8}$cycloalkyl, -L-$C_{1-10}$alkylheterocyclyl, or -L-heterocyclyl, each of which is unsubstituted or is substituted by one or more independent $R^3$;

L is absent, —(C=O)—, —C(=O)O—, —C(=O)N($R^{31}$)—, —S—, —S(O)—, —$S(O)_2$—, —$S(O)_2$N($R^{31}$)—, or —N($R^{31}$)—;

$R^3$ is hydrogen, —OH, —$OR^{31}$, —$NR^{31}R^{32}$, —$C(O)R^{31}$, —$C(=O)NR^{31}R^{32}$, —$C(=O)NR^{34}R^{35}$, aryl, heteroaryl, $C_{1-4}$alkyl, $C_{1-10}$alkyl, $C_{3-8}$cycloalkyl, or heterocyclyl, wherein each of said aryl or heteroaryl moiety is unsubstituted or is substituted with one or more independent alkyl, heteroalkyl, alkenyl, alkynyl, cycloalkyl, heterocycloalkyl, aryl, arylalkyl, heteroaryl, heteroarylalkyl, halo, —OH, —$R^{31}$, —$CF_3$, —$OCF_3$, —$OR^{31}$, —$NR^{31}R^{32}$, —$NR^{34}R^{35}$, —$C(O)R^{31}$, —$CO_2R^{31}$, —$C(=O)NR^{31}R^{32}$, —$C(=O)NR^{34}R^{35}$, —$NO_2$, —CN, —$S(O)_{0-2}R^{31}$, —$SO_2NR^{31}R^{32}$, —$SO_2NR^{34}R^{35}$, —$NR^{31}C(=O)R^{32}$, —$NR^{31}C(=O)OR^{32}$, —$NR^{31}C(=O)NR^{32}R^{33}$, —$NR^{31}S(O)_{0-2}R^{32}$, —$C(=S)OR^{31}$, —$C(=O)SR^{31}$, —$NR^{31}C(=NR^{32})NR^{33}R^{32}$, —$NR^{31}C(=NR^{32})OR^{33}$, —$NR^{31}C(=NR^{32})SR^{33}$, —$OC(=O)OR^{33}$, —$OC(=O)NR^{31}R^{32}$, —$OC(=O)SR^{31}$, —$SC(=O)OR^{31}$, —$P(O)OR^{31}OR^{32}$, or —$SC(=O)NR^{31}R^{32}$, and wherein each of said alkyl, cycloalkyl, or heterocyclyl moiety is unsubstituted or is substituted with one or more alkyl, heteroalkyl, alkenyl, alkynyl, cycloalkyl, heterocycloalkyl, aryl, arylalkyl, heteroaryl, heteroarylalkyl, halo, —OH, —$R^{31}$, —$CF_3$, —$OCF_3$, —$OR^{31}$, —O-aryl, —$NR^{31}R^{32}$, —$NR^{34}R^{35}$, —$C(O)R^{31}$, —$CO_2R^{31}$, —$C(=O)NR^{34}R^{35}$, or —$C(=O)NR^{31}R^{32}$;

—$(W^2)_k$— is —NH—, —N(H)C(O)— or —$N(H)S(O)_2$—;

$R^2$ is hydrogen, halogen, —$OR^{31}$, —$NR^{31}R^{32}$, —$NR^{34}R^{35}$, —$C(O)R^{31}$, —$CO_2R^{31}$, —$C(=O)NR^{31}R^{32}$, —$C(=O)NR^{34}R^{35}$, —$S(O)_{0-2}R^{31}$, —$S_2NR^{31}R^{32}$, —$SO_2NR^{34}R^{35}$, bicyclic aryl, substituted monocyclic aryl, heteroaryl, $C_{1-10}$alkyl, $C_{3-8}$cycloalkyl, $C_{1-10}$alkyl-$C_{3-8}$cycloalkyl, $C_{3-8}$cycloalkyl-$C_{1-10}$alkyl, $C_{2-10}$alkyl-monocyclic aryl, monocyclic aryl-$C_{2-10}$alkyl, $C_{1-10}$alkylbicycloaryl, bicycloaryl-$C_{1-10}$alkyl, substituted $C_{1-10}$alkylaryl, substituted aryl-$C_{1-10}$alkyl, $C_{1-10}$alkylheteroaryl, $C_{1-10}$alkylheterocyclyl, $C_{2-10}$alkenyl, $C_{2-10}$alkynyl, heterocyclyl, heterocyclyl $C_{1-10}$alkyl, heterocyclyl-$C_{2-10}$alkenyl, heterocyclyl-$C_{2-10}$alkynyl, aryl-heterocyclyl, heteroaryl-$C_{1-10}$alkyl, heteroaryl-heteroalkyl, or heteroaryl-heterocyclyl, wherein each of said bicyclic aryl or heteroaryl moiety is unsubstituted, or wherein each of bicyclic aryl, heteroaryl moiety or monocyclic aryl moiety is substituted with one or more independent halo, —OH, —$R^{31}$, —$CF_3$, —$OCF_3$, —$OR^{31}$, —$R^{31}R^{32}$, —$NR^{34}R^{35}$, —$C(O)R^{31}$, —$CO_2R^{31}$, —$C(=O)NR^{31}R^{32}$, —$C(=O)NR^{34}R^{35}$, —$NO_2$, —CN, —$S(O)_{0-2}R^{31}$, —$SO_2NR^{31}R^{32}$, —$SO_2NR^{34}R^{35}$, —$NR^{31}C(=O)R^{32}$, —$NR^{31}C(=O)OR^{32}$, —$NR^{31}C(=O)NR^{32}R_{33}$, —$R^{31}S(O)_{0-2}R^{32}$, —$C(=S)OR^{31}$, —$C(=O)SR^{31}$, —$NR^{31}C(=NR^{32})NR^{33}R^{32}$, —$NR^{31}C(=NR^{32})OR^{33}$, —$NR^{31}C(=NR^{32})SR^{33}$, —$OC(=O)OR^{33}$, —$OC(=O)NR^{31}R^{32}$, —$OC(=O)SR^{31}$, —$SC(=O)OR^{31}$, —$P(O)OR^{31}OR^{32}$, or —$SC(=O)NR^{31}R^{32}$, and wherein each of said alkyl, cycloalkyl, heterocyclyl, or heteroalkyl moiety is unsubstituted or is substituted with one or more halo, —OH, —$R^{31}$, —$CF_3$, —$OCF_3$, —$OR^{31}$, —O-aryl, —$NR^{31}R^{32}$, —$NR^{34}R^{35}$, —$C(O)R^{31}$, —$CO_2R^{31}$, —$C(=O)NR^{34}R^{35}$, or —$C(=O)NR^{31}R^{32}$;

$R^{31}$, $R^{32}$, and $R^{33}$, in each instance, are independently H or $C_{1-10}$alkyl, wherein the $C_{1-10}$alkyl is unsubstituted; and $R^{34}$ and $R^{35}$ in —$NR^{34}R^{35}$, —$C(=O)NR^{34}R^{35}$, or —$SO_2NR^{34}R^{35}$, are taken together with the nitrogen atom to which they are attached to form a 3-10 membered saturated or unsaturated ring; wherein said ring is independently unsubstituted or is substituted by one or more —$NR^{31}R^{32}$, hydroxyl, halogen, oxo, aryl, heteroaryl, $C_{1-6}$alkyl, or O-aryl, and wherein said 3-10 membered saturated or unsaturated ring independently contains 0, 1, or 2 more heteroatoms in addition to the nitrogen.

In some other embodiments, the mTORC1/2 inhibitor is a compound of Formula I-A:

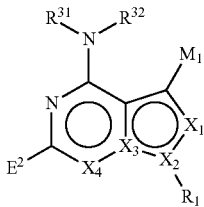

Formula I-A or a pharmaceutically acceptable salt thereof, wherein:
$X_1$ is N or C-$E^1$, $X_2$ is N, $X_3$ is C, and $X_4$ is C—$R^9$ or N; or
$X_1$ is N or C-$E^1$, $X_2$ is C, $X_3$ is N, and $X_4$ is C—$R^9$ or N;
$R_1$ is —H, -L-$C_{1-10}$alkyl, -L-$C_{3-8}$cycloalkyl, -L-$C_{1-10}$alkyl-$C_{3-8}$cycloalkyl, -L-aryl, -L-heteroaryl, -L-$C_{1-10}$alkylaryl, -L-$C_{1-10}$alkylheteroaryl, -L-$C_{1-10}$alkylheterocyclyl, -L-$C_{2-10}$alkenyl, -L-$C_{2-10}$alkynyl, -L-$C_{2-10}$alkenyl-$C_{3-8}$cycloalkyl, -L-$C_{2-10}$alkynyl-$C_{3-8}$cycloalkyl, -L-heteroalkyl, -L-heteroalkylaryl, -L-heteroalkylheteroaryl, -L-heteroalkyl-heterocyclyl, -L-heteroalkyl-$C_{3-8}$cycloalkyl, -L-aralkyl, -L-heteroaralkyl, or -L-heterocyclyl, each of which is unsubstituted or is substituted by one or more independent $R^3$;
L is absent, —(C=O)—, —C(=O)O—, —C(=O)N($R^{31}$)—, —S—, —S(O)—, —S(O)$_2$—, —S(O)$_2$N($R^{31}$)—, or —N($R^{31}$)—;
$M_1$ is benzothiazolyl substituted with —($W^2$)$_k$—$R^2$;
k is 0 or 1;
$E^1$ and $E^2$ are independently —($W^1$)$_j$—$R^4$;
j, in each instance (i.e., in $E^1$ or j in $E^2$), is independently 0 or 1
$W^1$ is —O—, —N$R^7$—, —S(O)$_{0-2}$—, —C(O)—, —C(O)N($R^7$)—, —N($R^7$)C(O)—, —N($R^7$)S(O)—, —N($R^7$)S(O)$_2$—, —C(O)O—, —CH($R^7$)N(C(O)O$R^8$)—, —CH($R^7$)N(C(O)$R^8$)—, —CH($R^7$)N(SO$_2R^8$)—, —CH($R^7$)N($R^8$)—, —CH($R^7$)C(O)N($R^8$)—, —CH($R^7$)N($R^8$)C(O)—, —CH($R^7$)N($R^8$)S(O)—, or —CH($R^7$)N($R^8$)S(O)$_2$—;
$W^2$ is —O—, —N$R^7$—, —S(O)$_{0-2}$—, —C(O)—, —C(O)N($R^7$)—, —N($R^7$)C(O)—, —N($R^7$)C(O)N($R^8$)—, —N($R^7$)S(O)—, —N($R^7$)S(O)$_2$—, —C(O)O—, —CH($R^7$)N(C(O)O$R^8$)—, —CH($R^7$)N(C(O)$R^8$)—, —CH($R^7$)N(SO$_2R^8$)—, —CH($R^7$)N($R^8$)—, —CH($R^7$)C(O)N($R^8$)—, —CH($R^7$)N($R^8$)C(O)—, —CH($R^7$)N($R^8$)S(O)—, or —CH($R^7$)N($R^8$)S(O)$_2$—;
$R^2$ is hydrogen, halogen, —OH, —$R^{31}$, —CF$_3$, —OCF$_3$, —O$R^{31}$, —N$R^{31}R^{32}$, —N$R^{34}R^{35}$, —C(O)$R^{31}$, —CO$_2R^{31}$, —C(=O)N$R^{31}R^{32}$, —C(=O)N$R^{34}R^{35}$, —NO$_2$, —CN, —S(O)$_{0-2}R^{31}$, —SO$_2$N$R^{31}R^{32}$, —SO$_2$N$R^{34}R^{35}$, —N$R^{31}$C(=O)$R^{32}$, —N$R^{31}$C(=O)O$R^{32}$, —N$R^{31}$C(=O)N$R^{32}R^{33}$ N$R^{31}$S(O)$_{0-2}R^{32}$, —C(=S)O$R^{31}$, —C(=O)S$R^{31}$, —N$R^{31}$C(=N$R^{32}$)N$R^{33}R^{32}$, —N$R^{31}$C(=N$R^{32}$)O$R^{33}$, —N$R^{31}$C(=N$R^{32}$)S$R^{33}$, —OC(=O)O$R^{33}$, —OC(=O)N$R^{31}R^{32}$, —OC(=O)S$R^{31}$, —SC(=O)O$R^{31}$, —P(O)O$R^{31}$O$R^{32}$, —SC(=O)N$R^{31}R^{32}$, aryl (e.g. bicyclic aryl, unsubstituted aryl, or substituted monocyclic aryl), heteroaryl, $C_{1-10}$alkyl, $C_{3-8}$cycloalkyl, $C_{1-10}$alkyl-$C_{3-8}$cycloalkyl, $C_{3-8}$cycloalkyl-$C_{1-10}$alkyl, $C_{3-8}$cycloalkyl-$C_{2-10}$alkenyl, $C_{3-8}$cycloalkyl-$C_{2-10}$alkynyl, $C_{1-10}$alkyl-$C_{2-10}$alkenyl, $C_{1-10}$alkyl-$C_{2-10}$alkynyl, $C_{1-10}$alkylaryl (e.g. $C_{2-10}$alkyl-monocyclic aryl, $C_{1-10}$alkyl-substituted monocyclic aryl, or $C_{1-10}$alkylbicycloaryl), $C_{1-10}$alkylheteroaryl, $C_{1-10}$alkylheterocyclyl, $C_{2-10}$alkenyl, $C_{2-10}$alkynyl, $C_{2-10}$alkenyl-$C_{1-10}$alkyl, $C_{2-10}$alkynyl-$C_{1-10}$alkyl, $C_{2-10}$alkenylaryl, $C_{2-10}$alkenylheteroaryl, $C_{2-10}$alkenyl-heteroalkyl, $C_{2-10}$alkenylheterocyclyl, $C_{2-10}$alkenyl-$C_{3-8}$cycloalkyl, $C_{2-10}$alkynylaryl, $C_{2-10}$alkynylheteroaryl, $C_{2-10}$alkynylheteroalkyl, $C_{2-10}$alkynylheterocyclyl, $C_{2-10}$alkynyl-$C_{3-8}$cycloalkenyl, $C_{1-10}$alkoxy $C_{1-10}$alkyl, $C_{1-10}$alkoxy-$C_{2-10}$alkenyl, $C_{1-10}$alkoxy-$C_{2-10}$alkynyl, heterocyclyl, heteroalkyl, heterocyclyl-$C_{1-10}$alkyl, heterocyclyl-$C_{2-10}$alkenyl, heterocyclyl-$C_{2-10}$alkynyl, aryl-$C_{1-10}$alkyl (e.g. monocyclic aryl-$C_{2-10}$alkyl, substituted monocyclic aryl-$C_{1-10}$alkyl, or bicycloaryl-$C_{1-10}$alkyl), aryl-$C_{2-10}$alkenyl, aryl-$C_{2-10}$alkynyl, aryl-heterocyclyl, heteroaryl-$C_{1-10}$alkyl, heteroaryl-$C_{2-10}$alkenyl, heteroaryl-$C_{2-10}$alkynyl, heteroaryl-$C_{3-8}$cycloalkyl, heteroaryl-heteroalkyl, or heteroaryl-heterocyclyl, wherein each of said bicyclic aryl or heteroaryl moiety is unsubstituted, or wherein each of bicyclic aryl, heteroaryl moiety or monocyclic aryl moiety is substituted with one or more independent alkyl, heteroalkyl, alkenyl, alkynyl, cycloalkyl, heterocycloalkyl, aryl, arylalkyl, heteroaryl, heteroarylalkyl, halo, —OH, —$R^{31}$, —CF$_3$, —OCF$_3$, —O$R^{31}$, —N$R^{31}R^{32}$, —N$R^{34}R^{35}$, —C(O)$R^{31}$, —CO$_2R^{31}$, —C(=O)N$R^{31}R^{32}$, —C(=O)N$R^{34}R^{35}$, —NO$_2$, —CN, —S(O)$_{0-2}R^{31}$, —SO$_2$N$R^{31}R^{32}$, —SO$_2$N$R^{34}R^{35}$, —N$R^{31}$C(=O)$R^{32}$, —N$R^{31}$C(=O)O$R^{32}$, —N$R^{31}$C(=O)N$R^{32}R^{32}R^{33}$, —N$R^{31}$S(O)$_{0-2}R^{32}$, —C(=S)O$R^{31}$, —C(=O)S$R^{31}$, —N$R^{31}$C(=N$R^{32}$)N$R^{33}R^{32}$, —N$R^{31}$C(=N$R^{32}$)$R^{33}$, —N$R^{31}$C(=N$R^{32}$)S$R^{33}$, —OC(=O)O$R^{33}$, —OC(=O)N$R^{31}R^{32}$, —OC(=O)S$R^{31}$, —SC(=O)O$R^{31}$, —P(O)O$R^{31}$O$R^{32}$, or —SC(=O)N$R^{31}R^{32}$, and wherein each of said alkyl, cycloalkyl, heterocyclyl, or heteroalkyl moiety is unsubstituted or is substituted with one or more alkyl, heteroalkyl, alkenyl, alkynyl, cycloalkyl, heterocycloalkyl, aryl, arylalkyl, heteroaryl, heteroarylalkyl, halo, —OH, —$R^{31}$, —CF$_3$, —OCF$_3$, —O$R^{31}$, —O-aryl, —N$R^{31}R^{32}$, —N$R^{34}R^{35}$, —C(O)$R^{31}$, —CO$_2R^{31}$, —C(=O)N$R^{34}R^{35}$, or —C(=O)N$R^{31}R^{32}$;
$R^3$ and $R^4$ are independently hydrogen, halogen, —OH, —$R^{31}$, —CF$_3$, —OCF$_3$, —O$R^{31}$, —N$R^{31}R^{32}$, —N$R^{34}R^{35}$, —C(O)$R^{31}$, —CO$_2R^{31}$, —C(=O)N$R^{31}R^{32}$, —C(=O)N$R^{34}R^{35}$, —NO$_2$, —CN, —S(O)$_{0-2}R^{31}$, —SO$_2$N$R^{31}R^{32}$, —SO$_2$N$R^{34}R^{35}$, —N$R^{31}$C(=O)$R^{32}$, —N$R^{31}$C(=O)O$R^{32}$, —N$R^{31}$C(=O)N$R^{32}R^{33}$, —N$R^{31}$S(O)$_{0-2}R^{32}$, —C(=S)O$R^{31}$, —C(=O)S$R^{31}$, —N$R^{31}$C(=N$R^{32}$)N$R^{33}R^{32}$, —N$R^{31}$C(=N$R^{32}$)O$R^{33}$, —N$R^{31}$C(=N$R^{32}$)S$R^{33}$, —OC(=O)O$R^{33}$, —OC(=O)N$R^{31}R^{32}$, —OC(=O)S$R^{31}$, —SC(=O)O$R^{31}$, —P(O)O$R^{31}$O$R^{32}$, —SC(=O)N$R^{31}R^{32}$, aryl, heteroaryl, $C_{1-4}$alkyl, $C_{1-10}$alkyl, $C_{3-8}$cycloalkyl, $C_{1-10}$alkyl-$C_{3-8}$cycloalkyl, $C_{3-8}$cycloalkyl-$C_{1-10}$alkyl, $C_{3-8}$cycloalkyl-$C_{2-10}$alkenyl, $C_{3-8}$cycloalkyl-$C_{2-10}$alkynyl, $C_{1-10}$alkyl-$C_{2-10}$alkenyl, $C_{1-10}$alkyl-$C_{2-10}$alkynyl, $C_{1-10}$alkylaryl, $C_{1-10}$alkylheteroaryl, $C_{1-10}$alkylheterocyclyl, $C_{2-10}$alkenyl, $C_{2-10}$alkynyl, $C_{2-10}$alkenyl-$C_{1-10}$alkyl, $C_{2-10}$alkynyl-$C_{1-10}$alkyl, $C_{2-10}$alkenylaryl, $C_{2-10}$alkenylheteroaryl, $C_{2-10}$alkenyl-heteroalkyl, $C_{2-10}$alkenylheterocyclyl, $C_{2-10}$alkenyl-$C_{3-8}$cycloalkyl, $C_{2-10}$alkynyl-$C_{3-8}$cycloalkyl, $C_{2-10}$alkynylaryl, $C_{2-10}$alkynylheteroaryl, $C_{2-10}$alkynylheteroalkyl, $C_{2-10}$alkynylheterocyclyl, $C_{2-10}$alkynyl-$C_{3-8}$cycloalkenyl, $C_{1-10}$alkoxy $C_{1-10}$alkyl, $C_{1-10}$alkoxy-$C_{2-10}$alkenyl, $C_{1-10}$alkoxy-$C_{2-10}$alkynyl, heterocyclyl, heterocyclyl-$C_{1-10}$alkyl, heterocyclyl-$C_{2-10}$alkenyl, heterocyclyl-$C_{2-10}$alkynyl, aryl-$C_{1-10}$alkyl, aryl-$C_{2-10}$alkenyl, aryl-$C_{2-10}$alkynyl, aryl-heterocyclyl, heteroaryl-$C_{1-10}$alkyl, heteroaryl-$C_{2-10}$alkenyl, heteroaryl-$C_{2-10}$alkynyl, heteroaryl-$C_{3-8}$cycloalkyl, heteroalkyl, heteroaryl-heteroalkyl, or heteroaryl-heterocyclyl, wherein each of said aryl or heteroaryl moiety is unsubstituted or is substituted with one or more independent halo, —OH, —$R^{31}$, —$CF_3$, —$OCF_3$, —$OR^{31}$, —$NR^{31}R^{32}$, —$NR^{34}R^{35}$, —$C(O)R^{31}$, —$CO_2R^{31}$, —$C(=O)NR^{31}R^{32}$, —$C(=O)NR^{34}R^{35}$, —$NO_2$, —CN, —$S(O)_{0-2}R^{31}$, —$SO_2NR^{31}R^{32}$, —$SO_2NR^{34}R^{35}$, —$NR^{31}C(=O)R^{32}$, —$NR^{31}C(=O)OR^{32}$, —$NR^{31}C(=O)NR^{32}R^{33}$, —$NR^{31}S(O)_{0-2}R^{32}$, —$C(=S)OR^{31}$, —$C(=O)SR^{31}$, —$NR^{31}C(=NR^{32})NR^{33}R^{32}$, —$NR^{31}C(=NR^{32})OR^{33}$, —$NR^{31}C(=NR^{32})SR^{33}$, —$OC(=O)OR^{33}$, —$OC(=O)NR^{31}R^{32}$, —$OC(=O)SR^{31}$, —$SC(=O)OR^{31}$, —$P(O)OR^{31}OR^{32}$, or —$SC(=O)NR^{31}R^{32}$, and wherein each of said alkyl, cycloalkyl, heterocyclyl, or heteroalkyl moiety is unsubstituted or is substituted with one or more halo, —OH, —$R^{31}$, —$CF_3$, —$OCF_3$, —$OR^{31}$, —O-aryl, —$NR^{31}R^{32}$, —$NR^{34}R^{35}$, —$C(O)R^{31}$, —$CO_2R^{31}$, —$C(=O)NR^{34}R^{35}$, or —$C(=O)NR^{31}R^{32}$;

$R^5$ is hydrogen, halogen, —OH, —$R^{31}$, —$CF_3$, —$OCF_3$, —$OR^{31}$, —$NR^{31}R^{32}$, —$NR^{34}R^{35}$, —$C(O)R^{31}$, —$CO_2R^{31}$, —$C(=O)NR^{31}R^{32}$, —$C(=O)NR^{34}R^{35}$, —$NO_2$, —CN, —$S(O)_{0-2}R^{31}$, —$SO_2NR^{31}R^{32}$, —$SO_2NR^{34}R^{35}$, —$NR^{31}C(=O)R^{32}$, —$NR^{31}C(=O)OR^{32}$, —$NR^{31}C(=O)NR^{32}R^{33}$, —$NR^{31}S(O)_{0-2}R^{32}$, —$C(=S)OR^{31}$, —$C(=O)SR^{31}$, —$NR^{31}C(=NR^{32})NR^{33}R^{32}$, —$NR^{31}C(=NR^{32})OR^{33}$, —$NR^{31}C(=NR^{32})SR^{33}$, —$OC(=O)OR^{33}$, —$OC(=O)NR^{31}R^{32}$, —$OC(=O)SR^{31}$, —$SC(=O)OR^{31}$, —$P(O)OR^{31}OR^{32}$, or —$SC(=O)NR^{31}R^{32}$;

$R^{31}$, $R^{32}$, and $R^{33}$, in each instance, are independently H or $C_{1-10}$alkyl, wherein the $C_{1-10}$alkyl is unsubstituted or is substituted with one or more aryl, heteroalkyl, heterocyclyl, or heteroaryl group, wherein each of said aryl, heteroalkyl, heterocyclyl, or heteroaryl group is unsubstituted or is substituted with one or more halo, —OH, —$C_{1-10}$alkyl, —$CF_3$, —O-aryl, —$OCF_3$, —$OC_{1-10}$alkyl, —$NH_2$, —$N(C_{1-10}$alkyl$)(C_{1-10}$alkyl$)$, —$NH(C_{1-10}$alkyl$)$, —NH(aryl), —$NR^{34}R^{35}$, —$C(O)(C_{1-10}$alkyl$)$, —$C(O)(C_{1-10}$alkyl-aryl$)$, —$C(O)(aryl)$, —$CO_2$—$C_{1-10}$alkyl, —$CO_2$—$C_{1-10}$alkylaryl, —$CO_2$-aryl, —$C(=O)N(C_{1-10}$alkyl$)(C_{1-10}$alkyl$)$, —$C(=O)NH(C_{1-10}$alkyl$)$, —$C(=O)NR^{34}R^{35}$, —$C(=O)NH_2$, —$OCF_3$, —O($C_{1-10}$alkyl$)$, —O-aryl, —N(aryl)($C_{1-10}$alkyl$)$, —$NO_2$, —CN, —$S(O)_{0-2}$ $C_{1-10}$alkyl, —$S(O)_{0-2}$ $C_{1-10}$alkylaryl, —$S(O)_{0-2}$aryl, —$SO_2N(aryl)$, —$SO_2N(C_{1-10}$alkyl$)(C_{1-10}$alkyl$)$, —$SO_2$ $NH(C_{1-10}$alkyl$)$ or —$SO_2NR^{34}R^{35}$;

$R^{34}$ and $R^{35}$ in —$NR^{34}R^{35}$, —$C(=O)NR^{34}R^{35}$, or —$SO_2NR^{34}R^{35}$, are taken together with the nitrogen atom to which they are attached to form a 3-10 membered saturated or unsaturated ring; wherein said ring is independently unsubstituted or is substituted by one or more —$NR^{31}R^{32}$, hydroxyl, halogen, oxo, aryl, heteroaryl, $C_{1-6}$alkyl, or O-aryl, and wherein said 3-10 membered saturated or unsaturated ring independently contains 0, 1, or 2 more heteroatoms in addition to the nitrogen atom;

$R^7$ and $R^8$ are each independently hydrogen, $C_{1-10}$alkyl, $C_{2-10}$alkenyl, aryl, heteroaryl, heterocyclyl or $C_{3-10}$cycloalkyl, each of which except for hydrogen is unsubstituted or is substituted by one or more independent $R^6$;

$R^6$ is halo, —$OR^{31}$, —SH, —$NH_2$, —$NR^{34}R^{35}$, —$NR^{31}R^{32}$, —$CO_2R^{31}$, —$CO_2$aryl, —$C(=O)NR^{31}R^{32}$, $C(=O)NR^{34}R^{35}$, —$NO_2$, —CN, —$S(O)_{0-2}$ $C_{1-10}$alkyl, —$S(O)_{0-2}$aryl, —$SO_2NR^{34}R^{35}$, —$SO_2NR^{31}R^{32}$, $C_{1-10}$alkyl, $C_{2-10}$alkenyl, $C_{2-10}$alkynyl; aryl-$C_{1-10}$alkyl, aryl-$C_{2-10}$alkenyl, aryl-$C_{2-10}$alkynyl, heteroaryl-$C_{1-10}$alkyl, heteroaryl-$C_{2-10}$alkenyl, heteroaryl-$C_{2-10}$alkynyl, wherein each of said alkyl, alkenyl, alkynyl, aryl, heteroalkyl, heterocyclyl, or heteroaryl group is unsubstituted or is substituted with one or more independent halo, cyano, nitro, —$OC_{1-10}$alkyl, $C_{1-10}$alkyl, $C_{2-10}$alkenyl, $C_{2-10}$alkynyl, halo$C_{1-10}$alkyl, halo$C_{2-10}$alkenyl, halo $C_{2-10}$alkynyl, —COOH, —$C(=O)NR^{31}R^{32}$, —$C(=O)NR^{34}R^{35}$, —$SO_2NR^{34}R^{35}$, —$SO_2$ $NR^{31}R^{32}$, —$NR^{31}R^{32}$, or —$NR^{34}R^{35}$; and $R^9$ is H, halo, —$OR^{31}$, —SH, —$NH_2$, —$NR^{34}R^{35}$, —$NR^{31}R^{32}$, —$CO_2R^{31}$, —$CO_2R^{31}$, —$CO_2R^{31}$, —$CO_2$aryl, —$C(=O)NR^{31}R^{32}$, $C(=O)NR^{34}R^{35}$, —$NO_2$, —CN, —$S(O)_{0-2}$ $C_{1-10}$alkyl, —$S(O)_{0-2}$aryl, —$SO_2NR^{34}R^{35}$, —$SO_2NR^{31}R^{32}$, $C_{1-10}$alkyl, $C_{2-10}$alkenyl, $C_{2-10}$alkynyl; aryl-$C_{1-10}$alkyl, aryl-$C_{2-10}$alkenyl, aryl-$C_{2-10}$alkynyl, heteroaryl-$C_{1-10}$alkyl, heteroaryl-$C_{2-10}$alkenyl, heteroaryl-$C_{2-10}$alkynyl, wherein each of said alkyl, alkenyl, alkynyl, aryl, heteroalkyl, heterocyclyl, or heteroaryl group is unsubstituted or is substituted with one or more independent halo, cyano, nitro, —$OC_{1-10}$alkyl, $C_{1-10}$alkyl, $C_{2-10}$alkenyl, $C_{2-10}$alkynyl, halo$C_{1-10}$alkyl, halo$C_{2-10}$alkenyl, halo$C_{2-10}$alkynyl, —COOH, —$C(=O)NR^{31}R^{32}$, —$C(=O)NR^{34}R^{35}$, —$SO_2NR^{34}R^{35}$, —$SO_2$ $NR^{31}R^{32}$, —$NR^{31}R^{32}$, or —$NR^{34}R^{35}$.

In some embodiments, $X_4$ is C—$R^9$.

In some other embodiments of the invention, the mTORC1/2 inhibitor as defined above is a compound of Formula I-B:

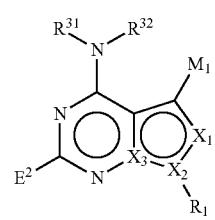

Formula I-B or a pharmaceutically acceptable salt thereof, wherein the substituents are as defined above.

In various embodiments the compound of Formula I-B or its pharmaceutically acceptable salt thereof, is an inhibitor having the structure of Formula I-B1 or Formula I-B2:

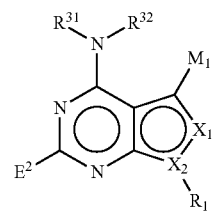

Formula I-B1

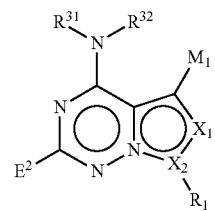

Formula I-B2 or a pharmaceutically acceptable salt thereof.

In various embodiments of Formula I-B1, $X_1$ is N and $X_2$ is N. In other embodiments, $X_1$ is C-$E^1$ and $X_2$ is N. In yet other embodiments, $X_1$ is NH and $X_2$ is C. In further embodiments, $X_1$ is CH-$E^1$ and $X_2$ is C.

In various embodiments of Formula I-B2, $X_1$ is N and $X_2$ is C. In further embodiments, $X_1$ is C-$E^1$ and $X_2$ is C.

In various embodiments, $X_1$ is C—$(W^1)_j$—$R^4$, where j is 0.

In another embodiment, $X_1$ is CH. In yet another embodiment, $X_1$ is C-halogen, where halogen is Cl, F, Br, or I.

In various embodiments of $X_1$, it is C—$(W^1)_j$—$R^4$. In various embodiments of $X_1$, j is 1, and $W^1$ is —O—. In various embodiments of $X_1$, j is 1, and $W^1$ is —N$R^7$—. In various embodiments of $X_1$, j is 1, and $W^1$ is —NH—. In various embodiments of $X_1$, j is 1, and $W^1$ is —S(O)$_{0-2}$—. In various embodiments of $X_1$, j is 1, and $W^1$ is —C(O)—. In various embodiments of $X_1$, j is 1, and $W^1$ is —C(O)N($R^7$)—. In various embodiments of $X_1$, j is 1, and $W^1$ is —N($R^7$)C(O)—. In various embodiments of $X_1$, j is 1, and $W^1$ is —N($R^7$)S(O)—. In various embodiments of $X_1$, j is 1, and $W^1$ is —N($R^7$)S(O)$_2$—. In various embodiments of $X_1$, j is 1, and $W^1$ is —C(O)O—. In various embodiments of $X_1$, j is 1, and $W^1$ is CH($R^7$)N(C(O)O$R^8$)—. In various embodiments of $X_1$, j is 1, and $W^1$ is —CH($R^7$)N(C(O)$R^8$)—. In various embodiments of $X_1$, j is 1, and $W^1$ is —CH($R^7$)N(SO$_2R^8$)—. In various embodiments of $X_1$, j is 1, and $W^1$ is —CH($R^7$)N($R^8$)—. In various embodiments of $X_1$, j is 1, and $W^1$ is —CH($R^7$)C(O)N($R^8$)—. In various embodiments of $X_1$, j is 1, and $W^1$ is —CH($R^7$)N($R^8$)C(O)—. In various embodiments of $X_1$, j is 1, and $W^1$ is —CH($R^7$)N($R^8$)S(O)—. In various embodiments of $X_1$, j is 1, and $W^1$ is —CH($R^7$)N($R^8$)S(O)$_2$—.

In another embodiment, $X_1$ is CH$_2$. In yet another embodiment, $X_1$ is CH-halogen, where halogen is Cl, F, Br, or I.

In another embodiment, $X_1$ is N.

In various embodiments, $X_2$ is N. In other embodiments, $X_2$ is C.

In various embodiments, $E^2$ is —$(W^1)_j$—$R^4$, where j is 0.

In another embodiment, $E^2$ is CH. In yet another embodiment, $E^2$ is C-halogen, where halogen is Cl, F, Br, or I.

In various embodiments of $E^2$, it is —$(W^1)_j$—$R^4$. In various embodiments of $E^2$, j is 1, and $W^1$ is —O—. In various embodiments of $E^2$, j is 1, and $W^1$ is —N$R^7$—. In various embodiments of $E^2$, j is 1, and $W^1$ is —NH—. In various embodiments of $E^2$, j is 1, and $W^1$ is —S(O)$_{0-2}$—. In various embodiments of $E^2$, j is 1, and $W^1$ is —C(O)—. In various embodiments of $E^2$, j is 1, and $W^1$ is —C(O)N($R^7$)—. In various embodiments of $E^2$, j is 1, and $W^1$ is —N($R^7$)C(O)—. In various embodiments of $E^2$, j is 1, and $W^1$ is —N($R^7$)S(O)—. In various embodiments of $E^2$, j is 1, and $W^1$ is —N($R^7$)S(O)$_2$—. In various embodiments of $E^2$, j is 1, and $W^1$ is —C(O)O—. In various embodiments of $E^2$, j is 1, and $W^1$ is CH($R^7$)N(C(O)O$R^8$)—. In various embodiments of $E^2$, j is 1, and $W^1$ is —CH($R^7$)N(C(O)$R^8$)—. In various embodiments of $E^2$, j is 1, and $W^1$ is —CH($R^7$)N(SO$_2R^8$)—. In various embodiments of $E^2$, j is 1, and $W^1$ is —CH($R^7$)N($R^8$)—. In various embodiments of $E^2$, j is 1, and $W^1$ is —CH($R^7$)C(O)N($R^8$)—. In various embodiments of $E^2$, j is 1, and $W^1$ is —CH($R^7$)N($R^8$)C(O)—. In various embodiments of $E^2$, j is 1, and $W^1$ is —CH($R^7$)N($R^8$)S(O)—.

In various embodiments of $E^2$, j is 1, and $W^1$ is —CH($R^7$)N($R^8$)S(O)$_2$—.

In various embodiments of Formula I-A, I-B, I-B1 and I-B2, $M_1$ is:

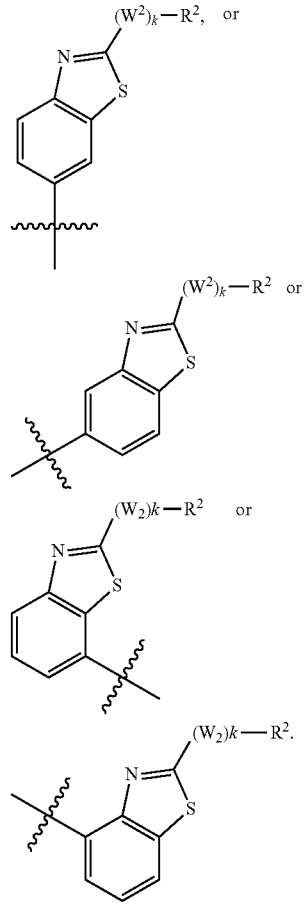

In some embodiments of the invention, $M_1$ is benzothiazolyl substituted with —$(W^2)_k$—$R^2$. $W^2$ can be —O—, —S(O)$_{0-2}$— (including but not limited to —S—, —S(O)—, and —S(O)$_2$—), —C(O)—, or —C(O)O—. In other embodiments, $W^1$ is —N$R^6$— or —CH($R^6$)N($R^7$)—, wherein $R^6$ and $R^7$ are each independently hydrogen, unsubstituted or substituted $C_1$-$C_{10}$alkyl (which includes but is not limited to —CH$_3$, —CH$_2$CH$_3$, n-propyl, isopropyl, n-butyl, tert-butyl, sec-butyl, pentyl, hexyl, and heptyl), unsubstituted or substituted $C_2$-$C_{10}$alkenyl (including but not limited to alkenyl such as, for example, vinyl, allyl, 1-methyl propen-1-yl, butenyl, or pentenyl). Additionally when $W^2$ is —N$R^6$— or —CH($R^6$)N($R^7$)—, $R^6$ and $R^7$ are each independently unsubstituted or substituted aryl (including phenyl and naphthtyl). In yet other embodiments, when $W^2$ is —N$R^6$— or —CH($R^6$)N($R^7$)—, $R^6$ and $R^7$ are each independently heteroaryl, wherein the heteroaryl is unsubstituted or substituted. $R^6$ and $R^7$ heteroaryl is monocyclic heteroaryl, and includes but is not limited to imidazolyl, pyrrolyl, oxazolyl, thiazolyl, and pyridinyl. In some other embodiments, when $W^2$ is —N$R^6$— or —CH($R^6$)N($R^7$)—, $R^6$ and $R^7$ are each independently unsubstituted or substituted heterocyclyl (which includes but is not limited to pyrrolidinyl, tetrahydrofuranyl, piperidinyl, tetrahydropyranyl, thiazolidinyl, imidazolidinyl, morpholinyl, and piperazinyl) or unsubstituted or substituted $C_{3-8}$cycloalkyl (including but not limited to cyclopropyl, cyclobutyl, and cyclopentyl). Non limiting exemplary $W^2$ include —NH—, —N(cyclopropyl), and —N(4-N-piperidinyl).

For example, exemplary mTORC1/2 inhibitors of the invention have the Formulas:
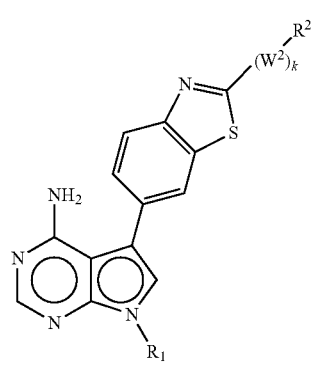
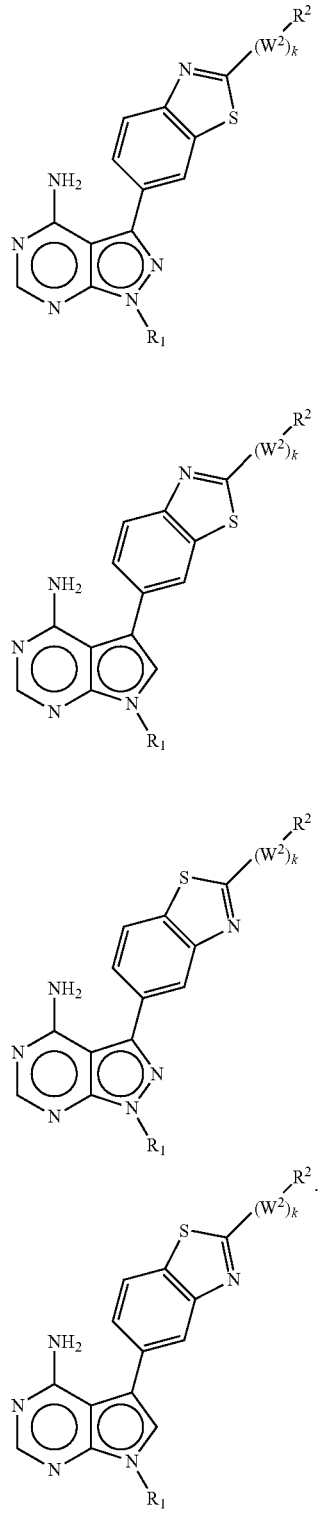
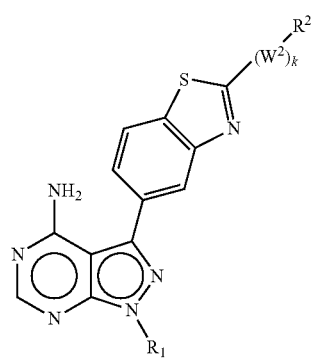
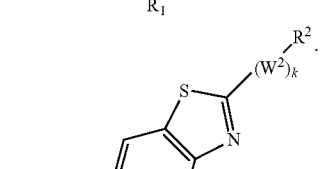
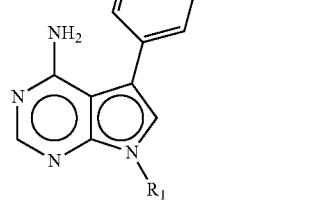
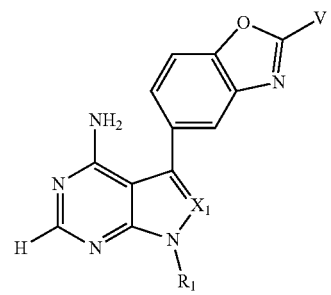
Subclass 1a
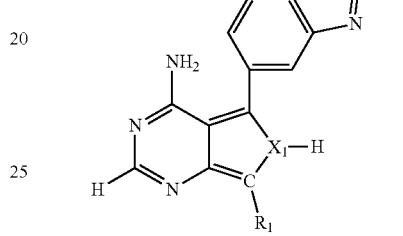
Subclass 1b
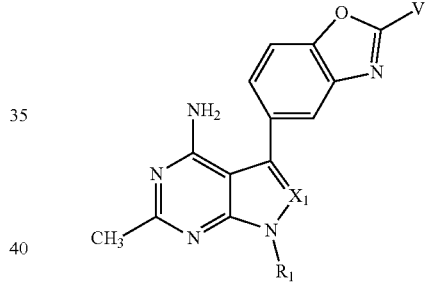
Subclass 2a
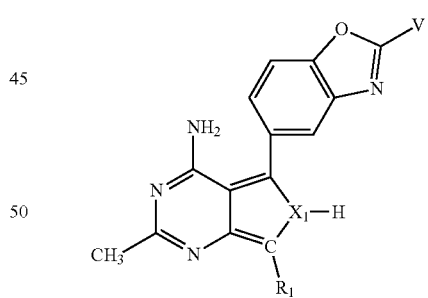
Subclass 2b
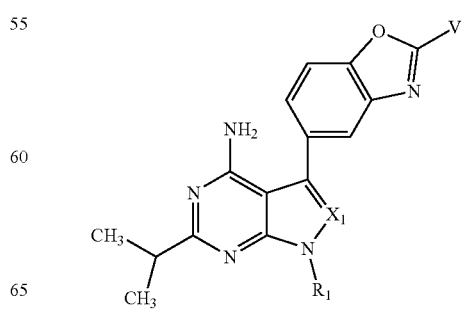
Subclass 3a
Some illustrative mTORC1/2 inhibitor compounds are described below. The mTORC1/2 inhibitor compounds that may be used in the present invention are not limited in any way to the compounds illustrated herein.

Subclass 3b
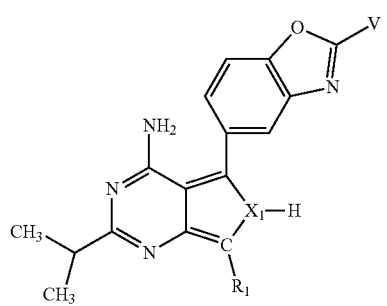
Subclass 4a
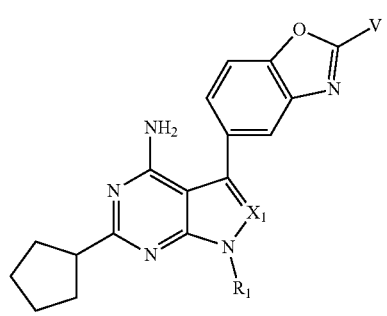
Subclass 4b
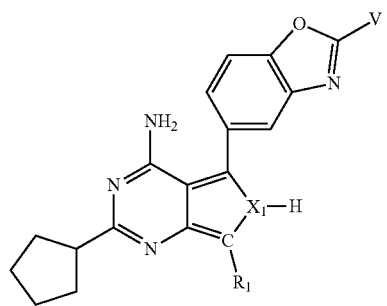
Subclass 5a
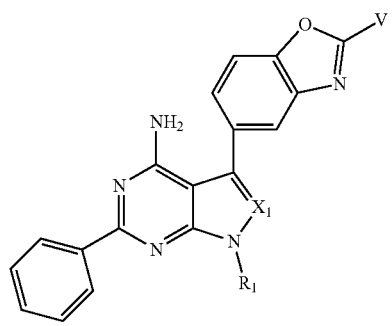
Subclass 5b
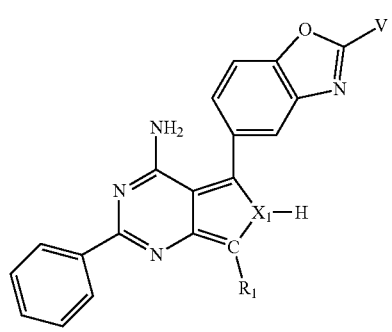
Subclass 6a
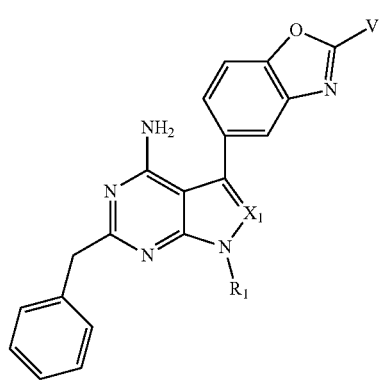
Subclass 6b
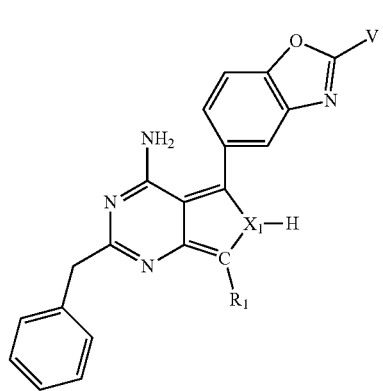
Subclass 7a
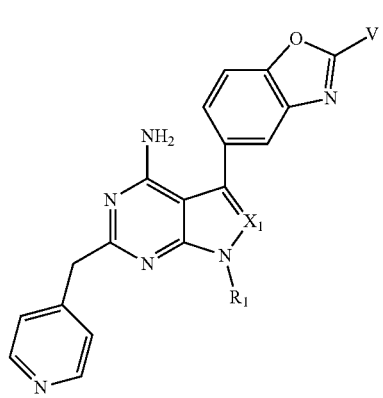
Subclass 7b
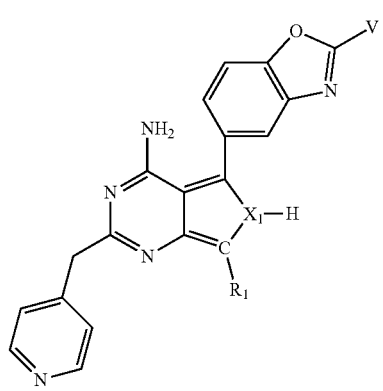

Subclass 8a
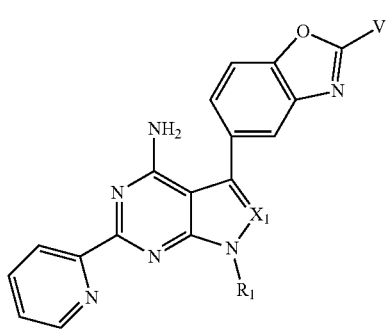
Subclass 8b
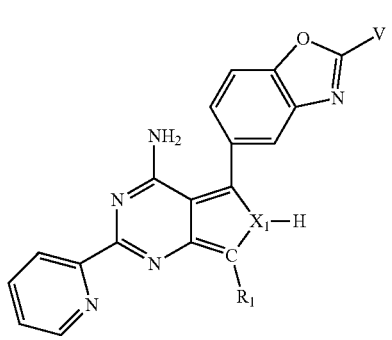
Subclass 9a
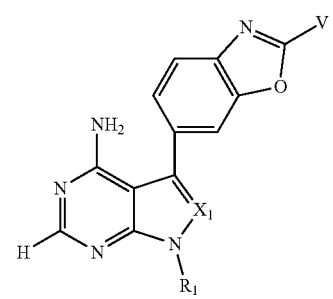
Subclass 9b
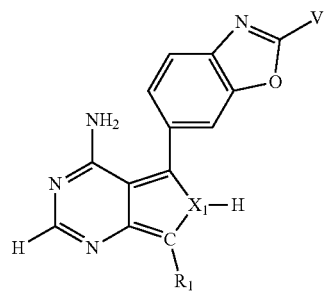
Subclass 10a
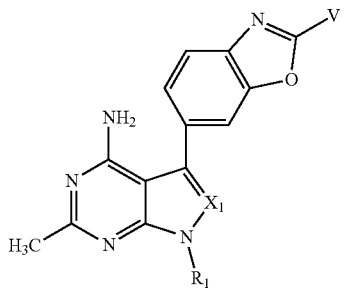
Subclass 10b
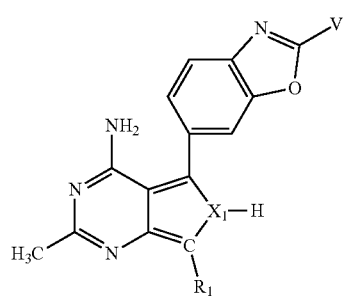
Subclass 11a
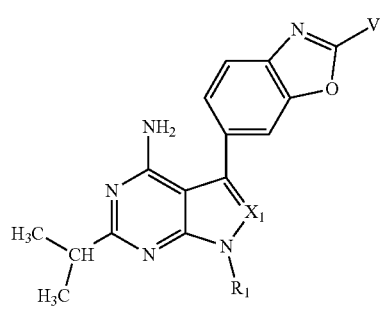
Subclass 11b
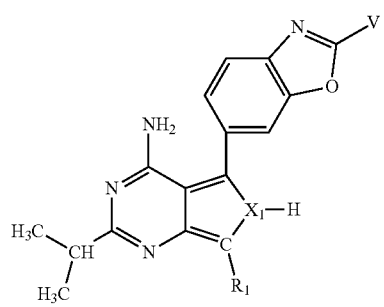
Subclass 12a
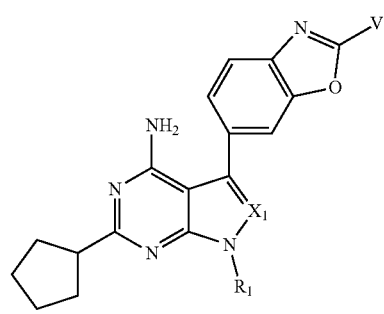
Subclass 12b
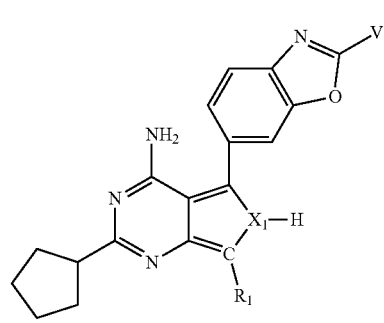

Subclass 13a
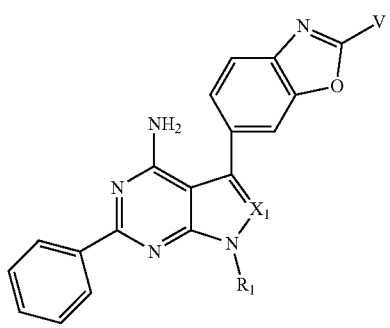
Subclass 13b
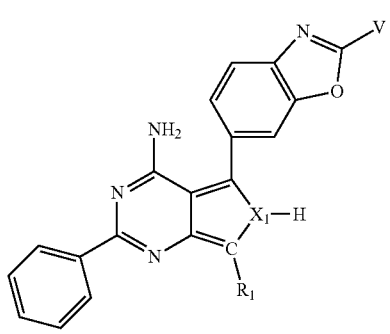
Subclass 14a
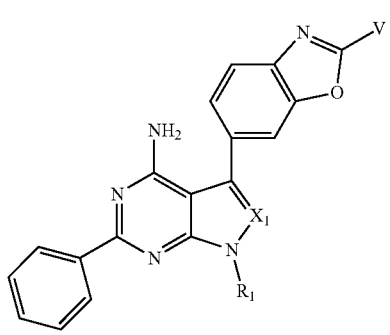
Subclass 14b
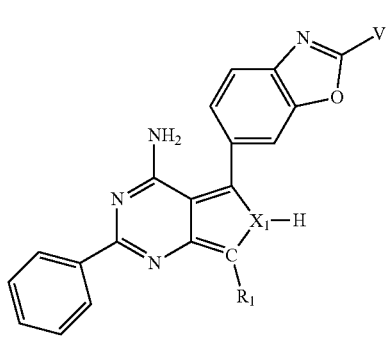
Subclass 15a
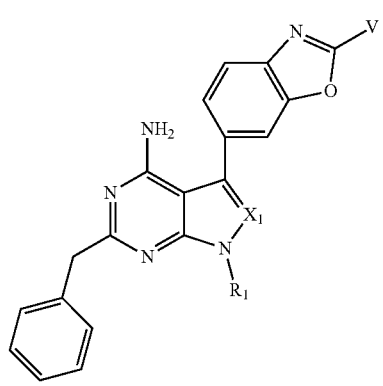
Subclass 15b
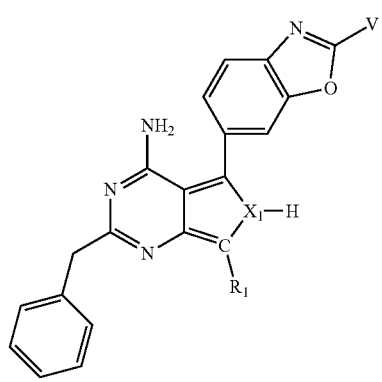
Subclass 16a
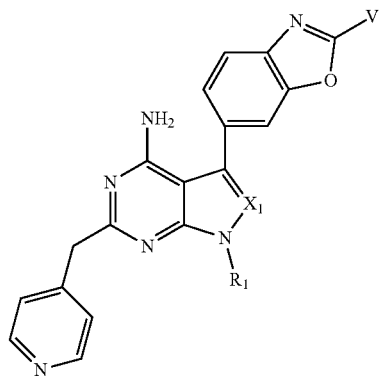
Subclass 16b
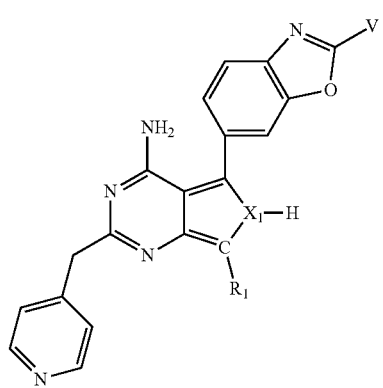
Illustrative compounds of the invention include those of subclass 1a, 1b, 2a, 2b, 3a, 3b, 4a, 4b, 5a, 5b, 6a, 6b, 7a, 7b, 8a, 8b, 9a, 9b, 10a, 10b, 11a, 11b, 12a, 12b, 13a, 13b, 14a, 14b, 15a, 15b, 16a, or 16b, where the substituents $R_1$, $X_1$, and V are as described below.

In other embodiments, when R₁ is H, CH₃, Et, iPr, cyclobutyl, cyclopentyl, phenyl, pyridin-2-yl, N-methylaminocyclohex-4-yl, N-methylpiperidin-4-yl, N-methylaminocyclobut-3-yl, tert-butyl, 1-cyano-but-4-yl, 1-cyano-prop-3-yl, 3-azetidinyl,
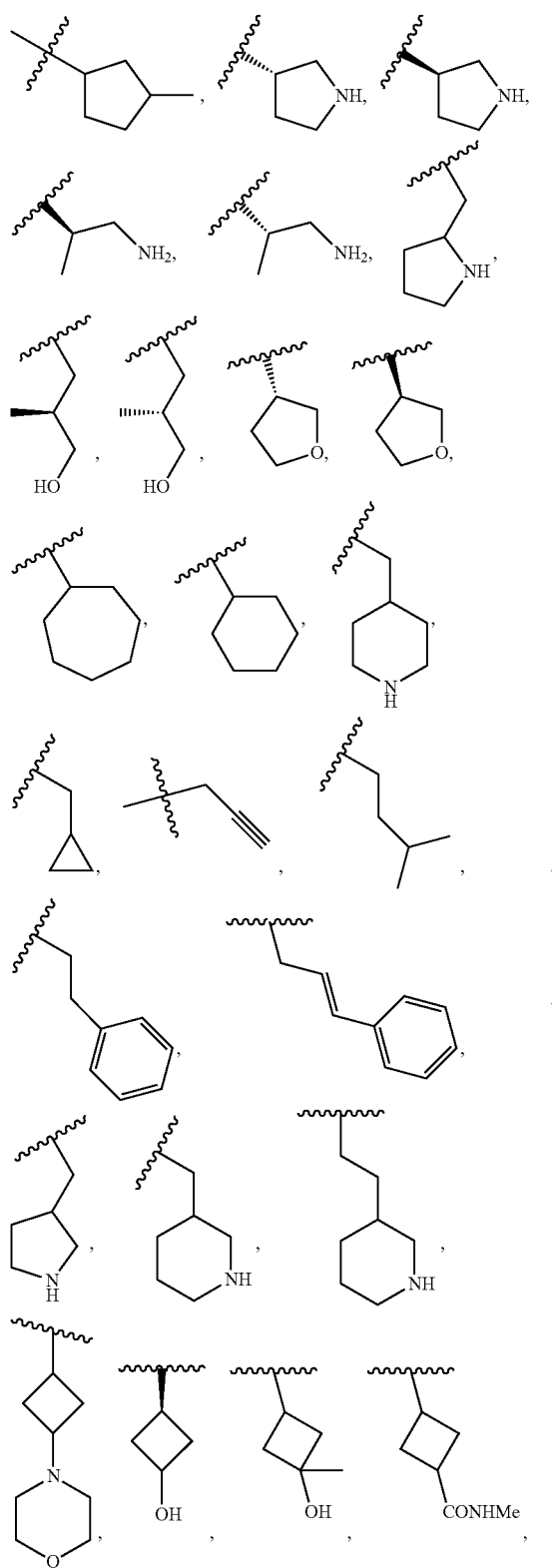
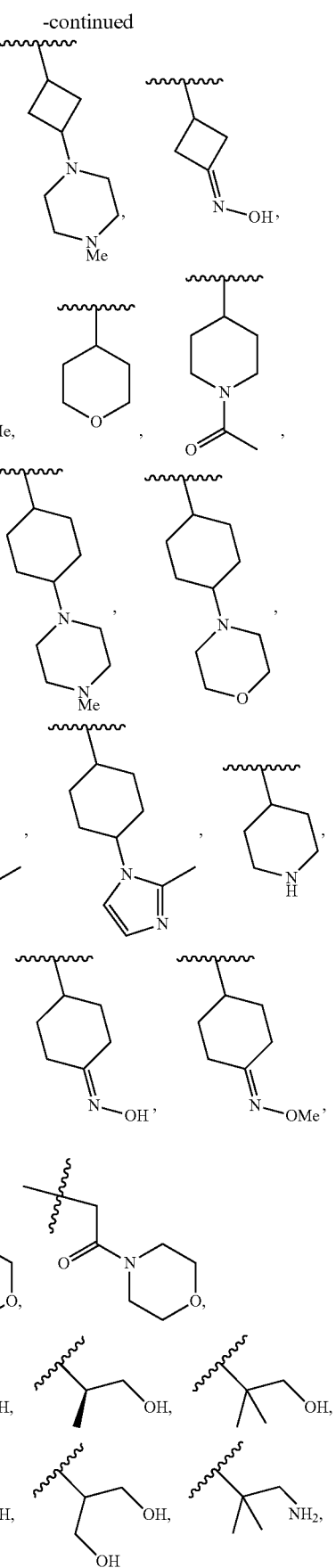
-continued

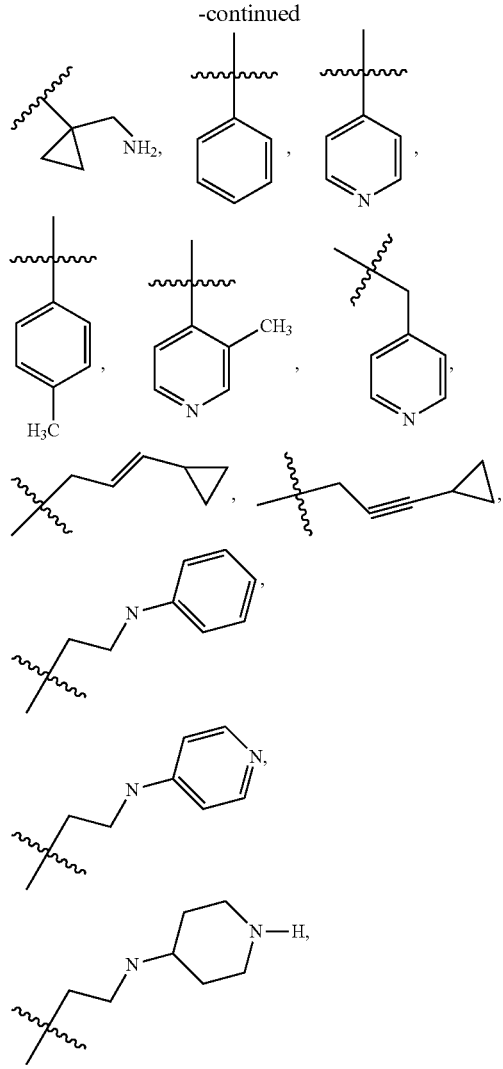

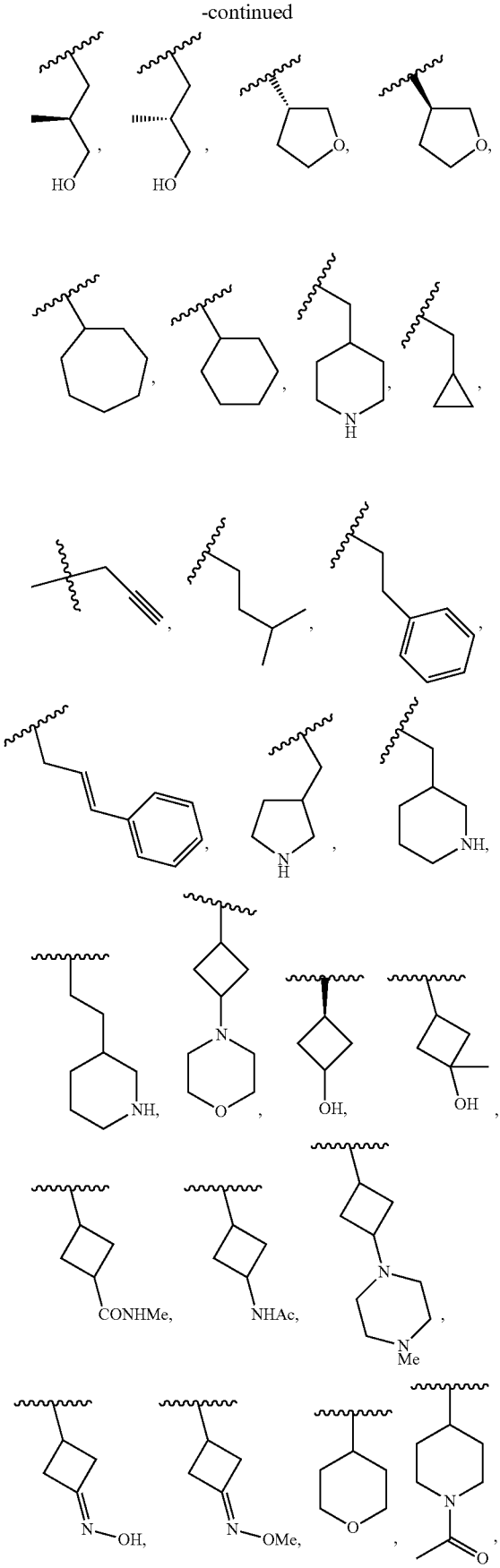

and $X_1$ is N, V is phenylamino, benzyl, phenyl, NHMe, $NH_2$, NHEt, NHCOH, NHCOMe, NHCOEt, NHCOiPr, NHCOOMe, CONHMe, or $NHSO_2Me$. In one embodiment, $R_1$ is iPr, $X_1$ is N, and V is $NH_2$. In another embodiment, $R_1$ is iPr, $X_1$ is N, and V is NHCOMe.

In other embodiments, when $R_1$ is H, $CH_3$, Et, iPr, cyclobutyl, cyclopentyl, phenyl, pyridin-2-yl, N-methylaminocyclohex-4-yl, N-methylpiperidin-4-yl, N-methylaminocyclobut-3-yl, tert-butyl, 1-cyano-but-4-yl, 1-cyano-prop-3-yl, 3-azetidinyl,

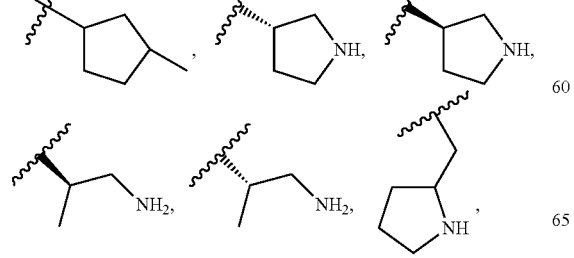

-continued

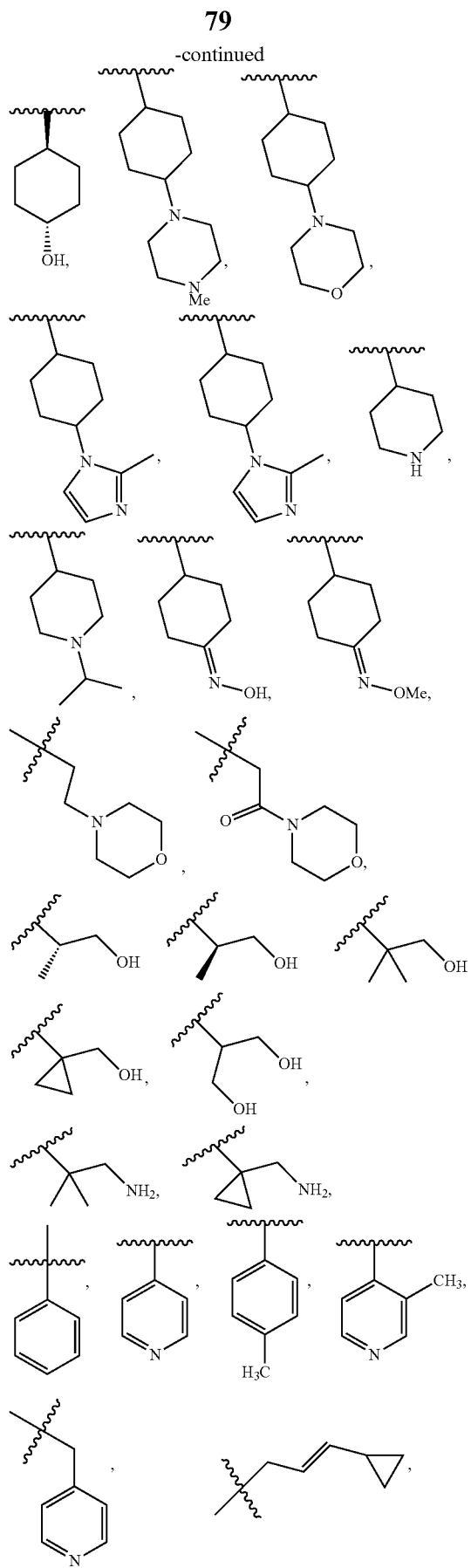

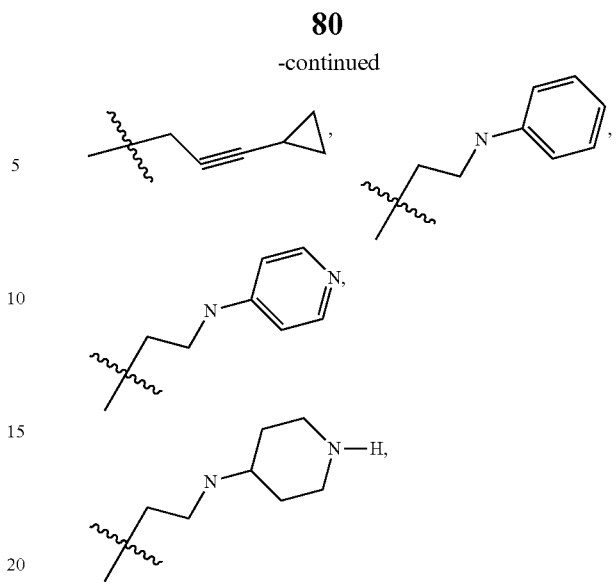

and $X_1$ is N, and V is cyclopropanecarboxamido, cyclopropylamino, morpholinoethylamino, hydroxyethylamino, or N-morpholino. In other embodiments, when $R_1$ is iPr and $X_1$ is N, V is cyclopropanecarboxamido, cyclopropylamino, morpholinoethylamino, hydroxyethylamino, or N-morpholino.

In the noted embodiments above, pyridin-2-yl is

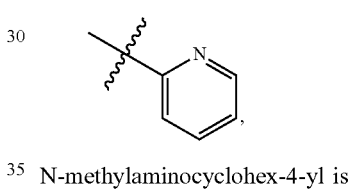

N-methylaminocyclohex-4-yl is

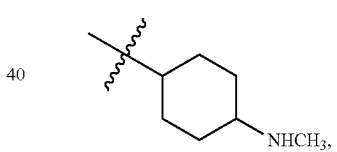

N-methylpiperidin-4-yl is

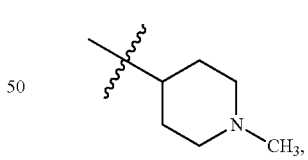

and N-methylaminocyclobut-3-yl is

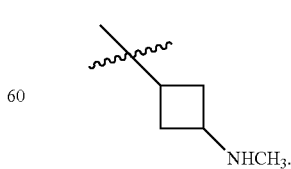

Illustrative compounds of the invention include those of subclass 1a, 1b, 2a, 2b, 3a, 3b, 4a, 4b, 5a, 5b, 6a, 6b, 7a, 7b, 8a, 8b, 9a, 9b, 10a, 10b, 11a, 11b, 12a, 12b, 13a, 13b, 14a, 14b, 15a, 15b, 16a, or 16b, where the substituents $R_1$, $X_1$, and V are as described below. In other embodiments, when $R_1$ is iPr and $X_1$ is N, V is cyclopropanecarboxamido, cyclopropylamino, morpholinoethylamino, hydroxyethylamino, or N-morpholino.

TABLE 1

Several illustrative mTORC1/2 inhibitor compounds

| Compound number | Structure |
|---|---|
| 1 | *structure* |
| 2 | *structure* |
| 3 | *structure* |
| 4 | *structure* |
| 5 | *structure* |
| 6 | *structure* |
| 7 | *structure* |

TABLE 1-continued

Several illustrative mTORC1/2 inhibitor compounds

| Compound number | Structure |
|---|---|
| 8 | 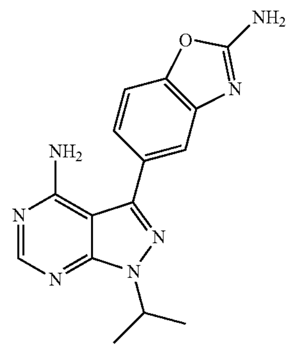 [SMILES: CC(C)n1nc(-c2ccc3oc(N)nc3c2)c2c(N)ncnc21] |
| 9 | 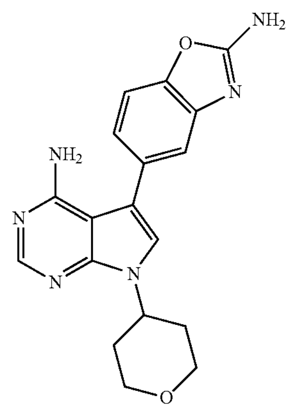 [SMILES: Nc1nc2cc(-c3cn(C4CCOCC4)c4ncnc(N)c34)ccc2o1] |
| 10 | 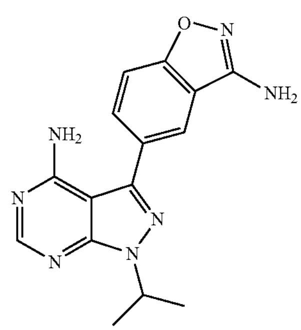 [SMILES: CC(C)n1nc(-c2ccc3onc(N)c3c2)c2c(N)ncnc21] |
| 11 | 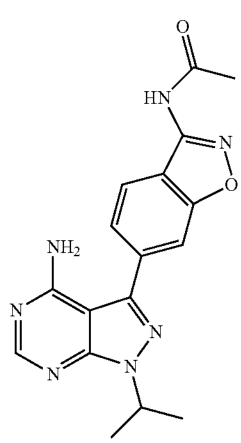 [SMILES: CC(=O)Nc1noc2cc(-c3nn(C(C)C)c4ncnc(N)c34)ccc12] |
| 12 | |
| 13 | |
| 14 | |
| 15 | |

TABLE 1-continued
Several illustrative mTORC1/2 inhibitor compounds
| Compound number | Structure |
|---|---|
| 16 | 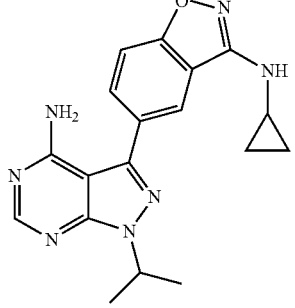 |
| 17 | 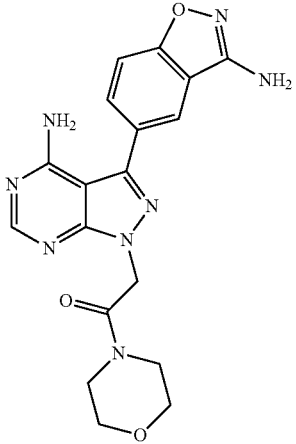 |
| 18 | 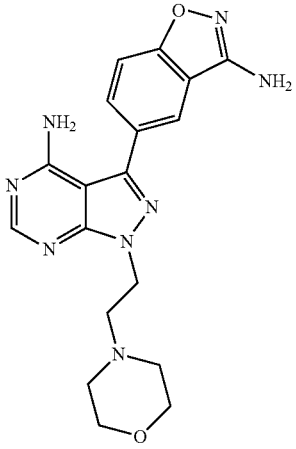 |
| 19 | 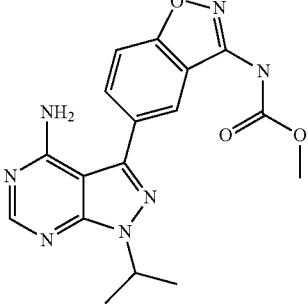 |
| 20 | 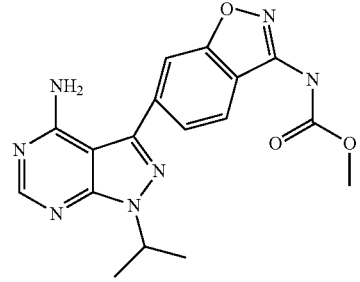 |
| 21 | 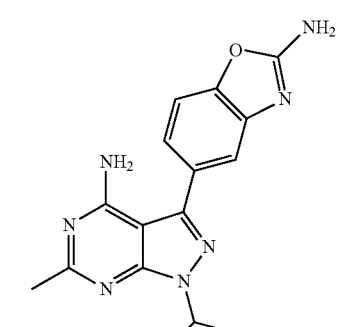 |
| 22 | 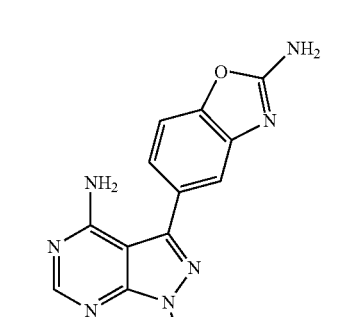 |
| 23 | 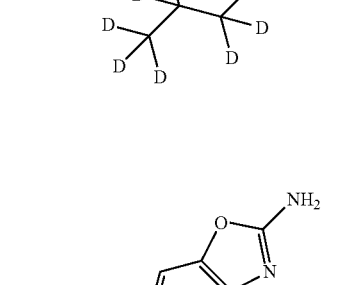 |

TABLE 1-continued

Several illustrative mTORC1/2 inhibitor compounds

| Compound number | Structure |
|---|---|
| 24 | (chemical structure) |
| 25 | (chemical structure) |
| 26 | (chemical structure) |
| 27 | (chemical structure) |
| 16 | (chemical structure) |
| 17 | (chemical structure) |
| 18 | (chemical structure) |

In other embodiments, the present invention provides the following compounds:

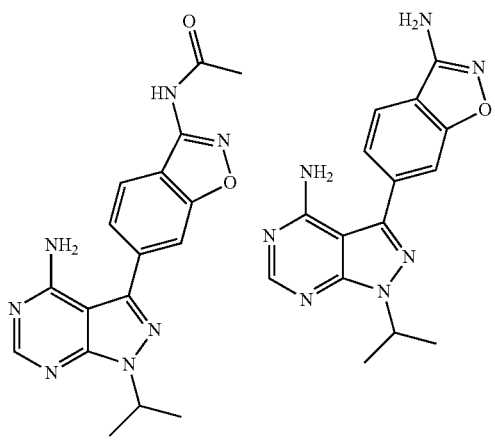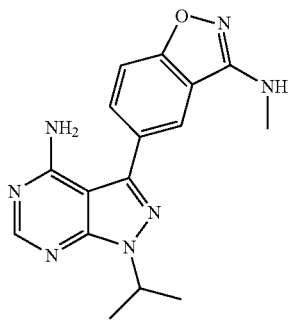 [SMILES: CNc1noc2ccc(-c3nn(C(C)C)c4ncnc(N)c34)cc12]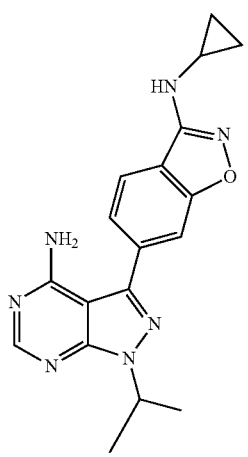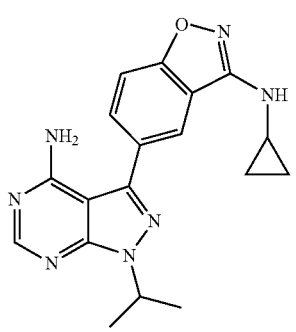 [SMILES: CC(C)n1nc(-c2ccc3onc(NC4CC4)c3c2)c2c(N)ncnc21]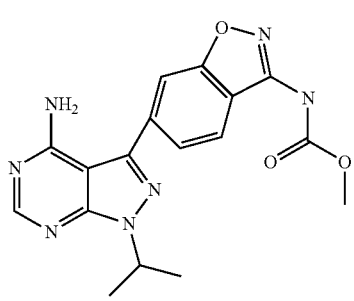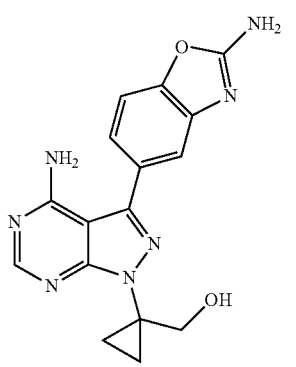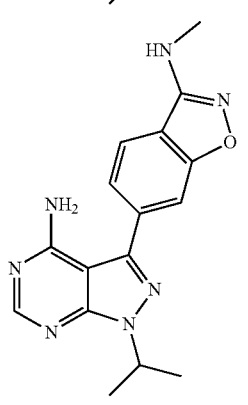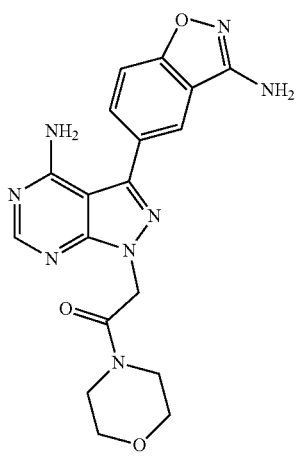

91
-continued
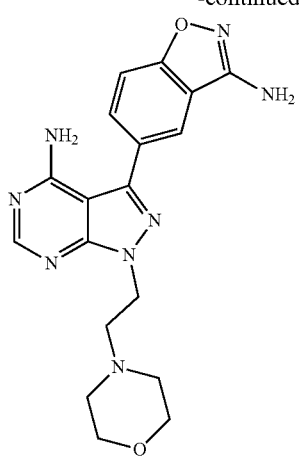
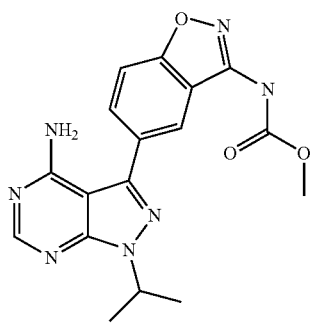 [SMILES: COC(=O)Nc1noc2ccc(-c3nn(C(C)C)c4ncnc(N)c34)cc12]
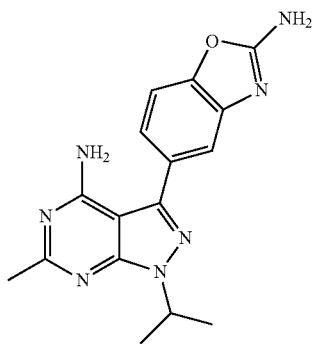 [SMILES: Cc1nc(N)c2c(-c3ccc4oc(N)nc4c3)nn(C(C)C)c2n1]
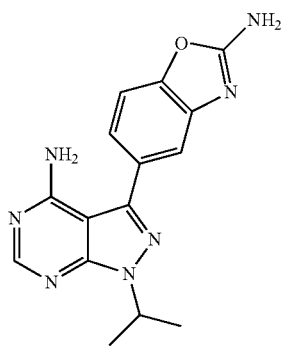
92
-continued
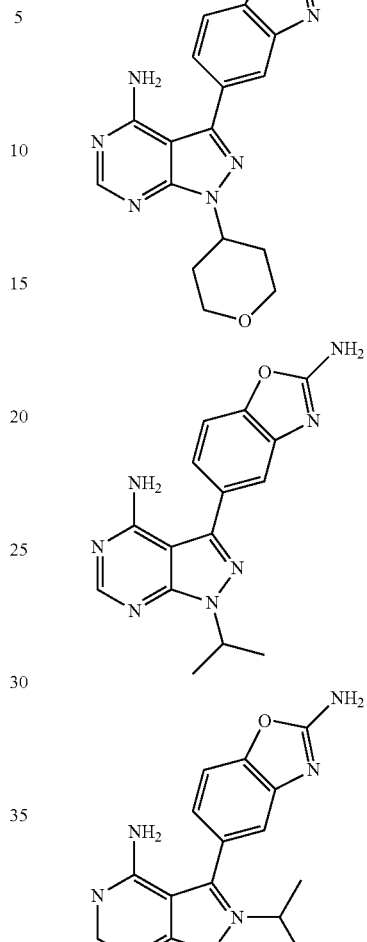
Additional compounds which are mTORC1/2 inhibitors are shown in Table 2.
TABLE 2
| mTORC1/2 inhibitors | |
| --- | --- |
| Compound number | Structure |
| 28 | |

TABLE 2-continued mTORC1/2 inhibitors

| Compound number | Structure |
|---|---|
| 29 | 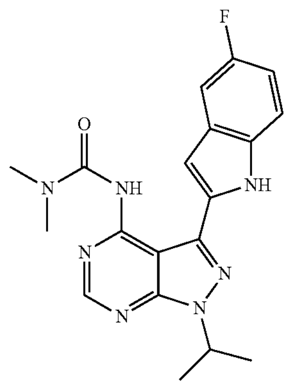 [SMILES: CC(C)n1nc(-c2cc3cc(F)ccc3[nH]2)c2c(NC(=O)N(C)C)ncnc21] |
| 30 | 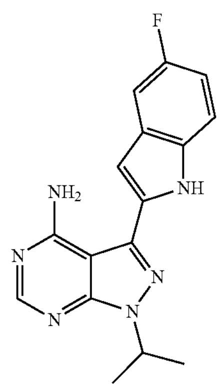 [SMILES: CC(C)n1nc(-c2cc3cc(F)ccc3[nH]2)c2c(N)ncnc21] |
| 31 | 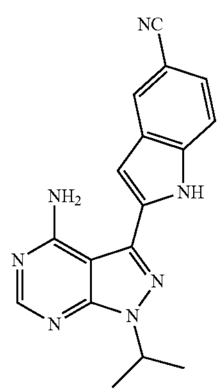 [SMILES: CC(C)n1nc(-c2cc3cc(C#N)ccc3[nH]2)c2c(N)ncnc21] |
| 32 | 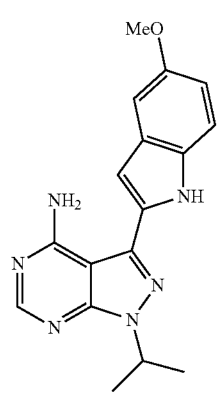 [SMILES: COc1ccc2[nH]c(-c3nn(C(C)C)c4ncnc(N)c34)cc2c1] |
| 33 | |
| 34 | |
| 35 | |
| 36 | |

TABLE 2-continued mTORC1/2 inhibitors

| Compound number | Structure |
|---|---|
| 37 | 4-amino-3-(7-methoxy-1H-indol-2-yl)-1-isopropyl-1H-pyrazolo[3,4-d]pyrimidine |
| 38 | 4-amino-3-(7-hydroxy-1H-indol-2-yl)-1-isopropyl-1H-pyrazolo[3,4-d]pyrimidine |
| 39 | 4-amino-1-cyclopentyl-3-(5-hydroxy-1H-indol-2-yl)-1H-pyrazolo[3,4-d]pyrimidine |
| 40 | 4-amino-3-(7-chloro-5-methoxy-1H-indol-2-yl)-1-isopropyl-1H-pyrazolo[3,4-d]pyrimidine |
| 41 | 4-amino-3-(7-fluoro-5-methoxy-1H-indol-2-yl)-1-isopropyl-1H-pyrazolo[3,4-d]pyrimidine |
| 42 | 4-amino-3-(7-chloro-5-hydroxy-1H-indol-2-yl)-1-isopropyl-1H-pyrazolo[3,4-d]pyrimidine |
| 43 | 4-amino-3-(7-fluoro-5-hydroxy-1H-indol-2-yl)-1-isopropyl-1H-pyrazolo[3,4-d]pyrimidine |
| 44 | 4-amino-3-(6-chloro-1H-indol-2-yl)-1-isopropyl-1H-pyrazolo[3,4-d]pyrimidine |

TABLE 2-continued mTORC1/2 inhibitors

| Compound number | Structure |
|---|---|
| 45 | (structure) |
| 46 | (structure) |
| 47 | (structure) |
| 48 | (structure) |
| 49 | (structure) |
| 50 | (structure) |
| 51 | (structure) |
| 52 | (structure) |

TABLE 2-continued
mTORC1/2 inhibitors
| Compound number | Structure |
|---|---|
| 53 | 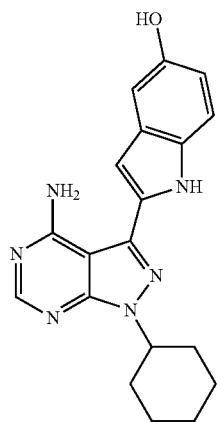 [SMILES: Nc1ncnc2c1c(-c1cc3cc(O)ccc3[nH]1)nn2C1CCCCC1] |
| 54 | 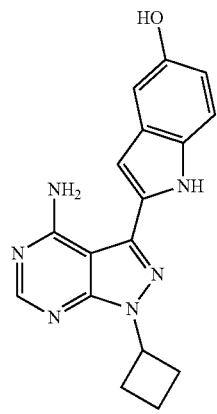 [SMILES: Nc1ncnc2c1c(-c1cc3cc(O)ccc3[nH]1)nn2C1CCC1] |
| 55 | 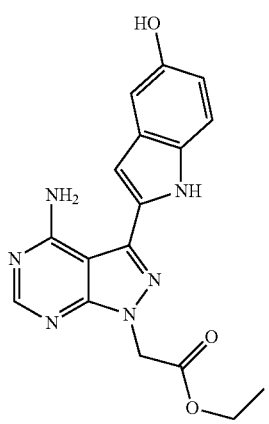 [SMILES: CCOC(=O)Cn1nc(-c2cc3cc(O)ccc3[nH]2)c2c(N)ncnc21] |
| 56 | 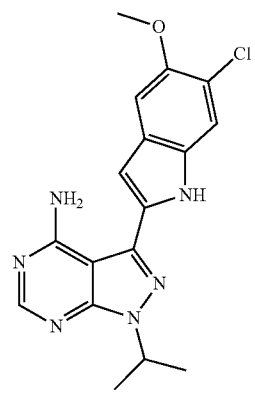 [SMILES: COc1cc2cc(-c3nn(C(C)C)c4ncnc(N)c34)[nH]c2cc1Cl] |
| 57 | 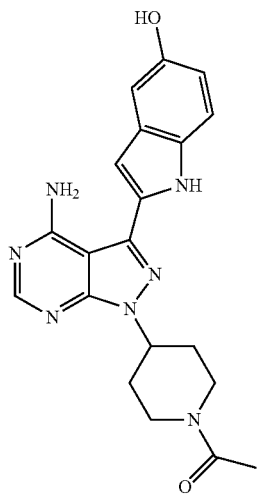 [SMILES: CC(=O)N1CCC(n2nc(-c3cc4cc(O)ccc4[nH]3)c3c(N)ncnc32)CC1] |
| 58 | 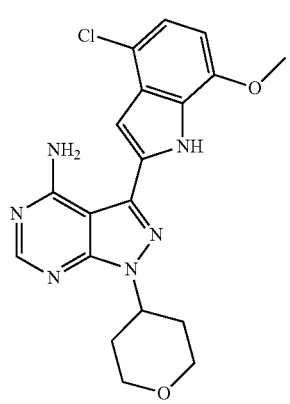 [SMILES: COc1ccc(Cl)c2cc(-c3nn(C4CCOCC4)c4ncnc(N)c34)[nH]c12] |

TABLE 2-continued mTORC1/2 inhibitors

| Compound number | Structure |
|---|---|
| 59 | *4-amino-3-(7-hydroxy-1H-indol-2-yl)-1-(tetrahydro-2H-pyran-4-yl)-1H-pyrazolo[3,4-d]pyrimidine* |
| 60 | *4-amino-3-(7-methoxy-1H-indol-2-yl)-1-(tetrahydro-2H-pyran-4-yl)-1H-pyrazolo[3,4-d]pyrimidine* |
| 61 | *4-amino-3-(7-hydroxy-1H-indol-2-yl)-1-(1-isopropylpiperidin-4-yl)-1H-pyrazolo[3,4-d]pyrimidine* |
| 62 | *1-(4-(4-amino-3-(6-hydroxy-1H-indol-2-yl)-1H-pyrazolo[3,4-d]pyrimidin-1-yl)piperidin-1-yl)ethanone* |
| 63 | *(4-(4-amino-3-(5-hydroxy-1H-indol-2-yl)-1H-pyrazolo[3,4-d]pyrimidin-1-yl)piperidin-1-yl)(cyclopropyl)methanone* |
| 64 | *4-amino-3-(6-chloro-5-hydroxy-1H-indol-2-yl)-1-isopropyl-1H-pyrazolo[3,4-d]pyrimidine* |

TABLE 2-continued mTORC1/2 inhibitors

| Compound number | Structure |
|---|---|
| 65 | (5-hydroxy-1H-indol-2-yl pyrazolo[3,4-d]pyrimidin-4-amine with N1-(2-morpholinoethyl) substituent) |
| 66 | (5-hydroxy-1H-indol-2-yl pyrazolo[3,4-d]pyrimidin-4-amine with N1-(2-morpholino-2-oxoethyl) substituent) |
| 67 | (5-hydroxy-1H-indol-2-yl pyrazolo[3,4-d]pyrimidin-4-amine with N1-(N-methylcarbamoylmethyl) substituent) |
| 68 | (7-hydroxy-1H-indol-2-yl pyrazolo[3,4-d]pyrimidin-4-amine with N1-cyclopentyl substituent) |
| 69 | (4-hydroxy-1H-indol-2-yl pyrazolo[3,4-d]pyrimidin-4-amine with N1-isopropyl substituent) |
| 70 | (5-hydroxy-1H-indol-2-yl pyrazolo[3,4-d]pyrimidin-4-amine with N1-(pyridin-3-ylmethyl) substituent) |
| 71 | (4-chloro-7-hydroxy-1H-indol-2-yl pyrazolo[3,4-d]pyrimidin-4-amine with N1-isopropyl substituent) |

TABLE 2-continued mTORC1/2 inhibitors

| Compound number | Structure |
|---|---|
| 72 | 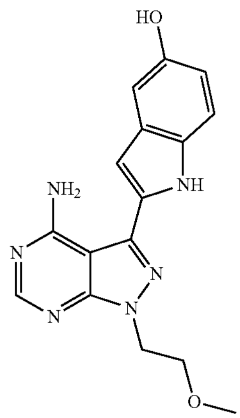 [SMILES: COCCn1nc(-c2cc3cc(O)ccc3[nH]2)c2c(N)ncnc21] |
| 73 | 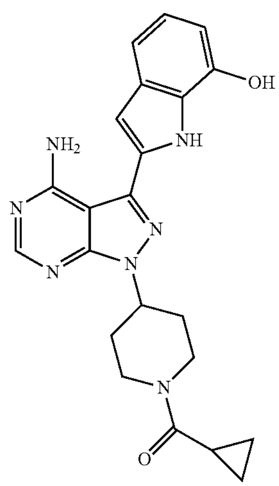 [SMILES: Nc1ncnc2c1c(-c1cc3cccc(O)c3[nH]1)nn2C1CCN(C(=O)C2CC2)CC1] |
| 74 | 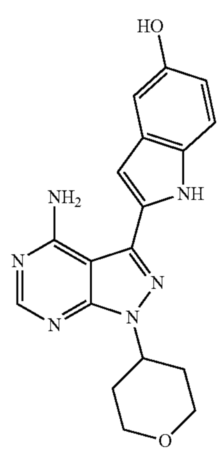 [SMILES: Nc1ncnc2c1c(-c1cc3cc(O)ccc3[nH]1)nn2C1CCOCC1] |
| 75 | |
| 76 | |
| 77 | |

TABLE 2-continued mTORC1/2 inhibitors

| Compound number | Structure |
|---|---|
| 78 | 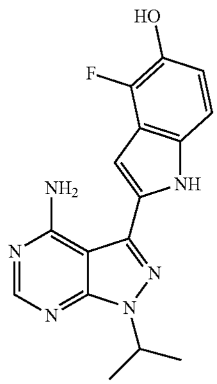 [SMILES: CC(C)n1nc(-c2cc3c(F)c(O)ccc3[nH]2)c2c(N)ncnc21] |
| 79 | 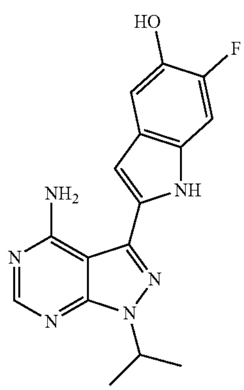 [SMILES: CC(C)n1nc(-c2cc3cc(O)c(F)cc3[nH]2)c2c(N)ncnc21] |
| 80 | 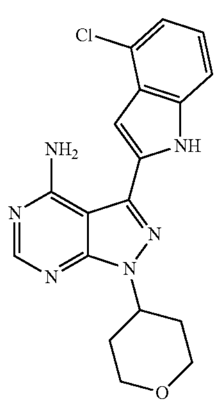 [SMILES: Nc1ncnc2c1c(-c1cc3c(Cl)cccc3[nH]1)nn2C1CCOCC1] |
| 81 | |
| 82 | |
| 83 | |

TABLE 2-continued mTORC1/2 inhibitors

| Compound number | Structure |
|---|---|
| 84 | (structure) |
| 85 | (structure) |
| 86 | (structure) |
| 87 | (structure) |
| 88 | (structure) |
| 89 | (structure) |

TABLE 2-continued
mTORC1/2 inhibitors
| Compound number | Structure |
|---|---|
| 90 | 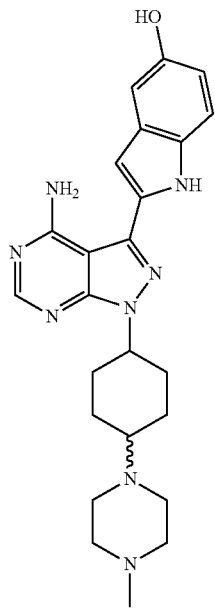 [SMILES: CN1CCN(C2CCC(n3nc(-c4cc5cc(O)ccc5[nH]4)c4c(N)ncnc43)CC2)CC1] |
| 91 | 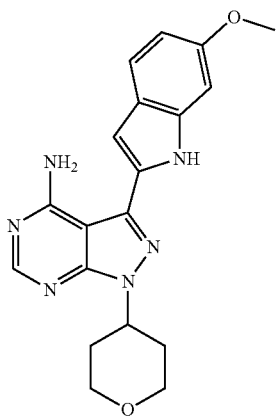 [SMILES: COc1ccc2cc(-c3nn(C4CCOCC4)c4ncnc(N)c34)[nH]c2c1] |
| 92 | 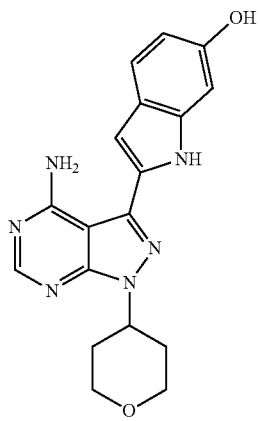 [SMILES: Nc1ncnc2c1c(-c1cc3ccc(O)cc3[nH]1)nn2C1CCOCC1] |
| 93 | 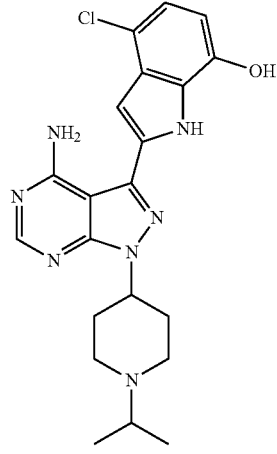 [SMILES: CC(C)N1CCC(n2nc(-c3cc4c(Cl)ccc(O)c4[nH]3)c3c(N)ncnc32)CC1] |
| 94 | 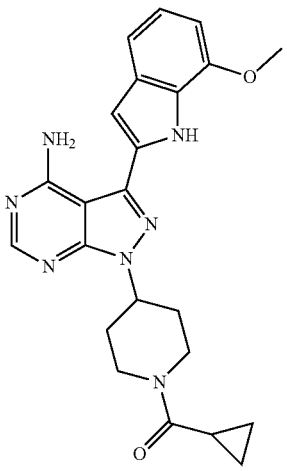 [SMILES: COc1cccc2cc(-c3nn(C4CCN(C(=O)C5CC5)CC4)c4ncnc(N)c34)[nH]c12] |
| 95 | 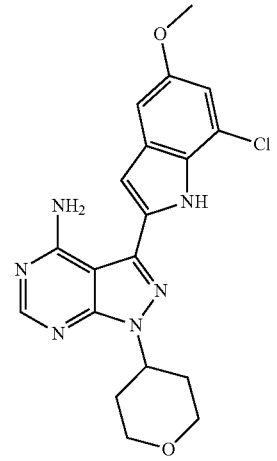 [SMILES: COc1cc(Cl)c2[nH]c(-c3nn(C4CCOCC4)c4ncnc(N)c34)cc2c1] |

TABLE 2-continued mTORC1/2 inhibitors

| Compound number | Structure |
|---|---|
| 96 | *(structure)* |
| 97 | *(structure)* |
| 98 | *(structure)* |

| mTORC1/2 inhibitor | Structure |
|---|---|
| OSI027 | *(structure)* |
| AZD8055 | *(structure)* |

In other embodiments, the mTORC1/2 inhibitor is CC223 (Celgene), OSI027 (OSI Pharmaceuticals), DS3078 (Daiichi), AZD8055 (Astra Zeneca), or AZD2014 (Astra Zeneca).

Structures of exemplary mTORC1/2 inhibitors are shown below:

In some embodiments, the mTORC1/2 inhibitor is a compound as described in U.S. Pat. No. 7,651,687 or 7,585,868; or as described International Patent Applications WO 2007/079164, WO 2007/061737, WO 2007/106503, WO 2007/134828 or WO2011/025889 which are hereby incorporated by reference in their entirety. Compounds of Formulas I, I-A, I-B, I-B1, I-B2, I-C, I-D, I-C1, I-C2, I-D1, I-D2, I-E, I-E1, I-E2, I-C1a are known in the art and can be prepared by the methods of the above referenced patents and patent applications. In one embodiment, the mTORC1/2 inhibitor is 3-(2-amino-1,3-benzoxazol-5-yl)-1-(propan-2-yl)-1H-pyrazolo[3,4-d]pyrimidin-4-amine (MLN0128), or a pharmaceutically acceptable salt thereof.

Exemplary Aurora A Kinase Inhibitor Compounds

Any molecule capable of selectively inhibiting the enzymatic activity of Aurora A kinase may be used in the methods, pharmaceutical compositions, and kits of the present invention. Aurora A kinase inhibitors can be assayed in vitro or in vivo for their ability to selectively bind to and/or inhibit an Aurora A kinase. In vitro assays include assays to determine selective inhibition of the ability of an Aurora A kinase to phosphorylate a substrate protein or peptide. Alternate in vitro assays quantitate the ability of the compound to selectively bind to an Aurora A kinase. Selective inhibitor binding may be measured by radiolabelling the inhibitor prior to binding, isolating the inhibitor/Aurora A kinase complex and determining the amount of radiolabel bound. Alternatively, selective inhibitor binding may be determined by running a competition experiment in which new inhibitors are incubated with Aurora A kinase bound to a known radioligand. The compounds also can be assayed for their ability to affect cellular or physiological functions mediated by Aurora A kinase activity. In order to assess selectivity for Aurora A kinase over Aurora B kinase, inhibitors can also be assayed in vitro and in vivo for their ability to selectively bind to and/or inhibit an Aurora B kinase, using assays analogous to those described above for Aurora A kinase. Inhibitors can be assayed in vitro and in vivo for their ability to inhibit Aurora A kinase in the absence of Aurora B kinase inhibition, by immunofluorescent detection of pHisH3. (*Proc. Natl. Acad. Sci.* (2007) 104, 4106). Assays for each of these activities are known in the art.

In some embodiments the selective Aurora A kinase inhibitor is a small molecular weight compound. In particular, selective inhibitors of Aurora A kinase include the compounds described herein, as well as compounds disclosed in, for example, US Publication No. 2008/0045501, U.S. Pat. No. 7,572,784, WO 05/111039, WO 08/021038, U.S. Pat. No. 7,718,648, WO 08/063525, US Publication No. 2008/0167292, U.S. Pat. No. 8,026,246, WO 10/134965, US Publication No. 2010/0310651, WO 11/014248, US Publication No. 2011/0039826, and US Publication No. 2011/0245234, each of which is hereby incorporated by reference in its entirety, as well as the compounds sodium 4-{[9-chloro-7-(2-fluoro-6-methoxyphenyl)-5H-pyrimido[5,4-d][2]benzazepin-2-yl]amino}-2-methoxybenzoate, ENMD-2076 (EntreMed), and MK-5108 (Vertex/Merck). Also suitable for use in the methods, pharmaceutical compositions, and kits of the invention are solvated and hydrated forms of any of these compounds. Also suitable for use in the methods, pharmaceutical compositions, and kits of the invention are pharmaceutically acceptable salts of any of the compounds, and solvated and hydrated forms of such salts. These selective Aurora A kinase inhibitors can be prepared in a number of ways well known to one skilled in the art of organic synthesis, including, but not limited to, the methods of synthesis described in detail in the references referred to herein.

In some embodiments, the selective Aurora A kinase inhibitor is a compound represented by formula (III):

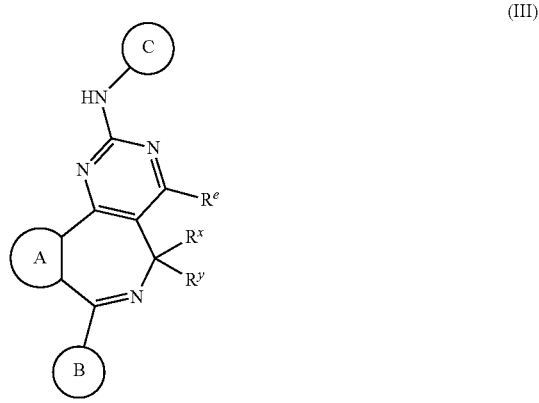

(III)

or a pharmaceutically acceptable salt thereof;
wherein:
Ring A is a substituted or unsubstituted 5- or 6-membered aryl, heteroaryl, cycloaliphatic, or heterocyclyl ring;
Ring B is a substituted or unsubstituted aryl, heteroaryl, cycloaliphatic, or heterocyclyl ring;
Ring C is a substituted or unsubstituted aryl, heteroaryl, heterocyclyl, or cycloaliphatic ring;
$R^e$ is hydrogen, $-OR^5$, $-N(R^4)_2$, $-SR^5$, or a $C_{1-3}$ aliphatic optionally substituted with $R^3$ or $R^7$;

each of $R^x$ and $R^y$ independently is hydrogen, fluoro, or an optionally substituted $C_{1-6}$ aliphatic; or $R^x$ and $R^y$, taken together with the carbon atom to which they are attached, form an optionally substituted 3- to 6-membered cycloaliphatic ring;
each $R^3$ independently is selected from the group consisting of -halo, $-OH$, $-O(C_{1-3}$ alkyl), $-CN$, $-N(R^4)_2$, $-C(O)(C_{1-3}$alkyl), $-CO_2H$, $-CO_2(C_{1-3}$ alkyl), $-C(O)NH_2$, and $-C(O)NH(C_{1-3}$ alkyl);
each $R^4$ independently is hydrogen or an optionally substituted aliphatic, aryl, heteroaryl, or heterocyclyl group; or two $R^4$ on the same nitrogen atom, taken together with the nitrogen atom, form an optionally substituted 5- to 6-membered heteroaryl or 4- to 8-membered heterocyclyl ring having, in addition to the nitrogen atom, 0-2 ring heteroatoms selected from N, O, and S;
each $R^5$ independently is hydrogen or an optionally substituted aliphatic, aryl, heteroaryl, or heterocyclyl group; and
each $R^7$ independently is an optionally substituted aryl, heterocyclyl, or heteroaryl group.

Ring A is a substituted or unsubstituted 5- or 6-membered aryl, heteroaryl, cycloaliphatic, or heterocyclyl ring. Examples of Ring A include furano, dihydrofurano, thieno, dihydrothieno, cyclopenteno, cyclohexeno, 2H-pyrrolo, pyrrolo, pyrrolino, pyrrolidino, oxazolo, thiazolo, imidazolo, imidazolino, imidazolidino, pyrazolo, pyrazolino, pyrazolidino, isoxazolo, isothiazolo, oxadiazolo, triazolo, thiadiazolo, 2H-pyrano, 4H-pyrano, benzo, pyridino, piperidino, dioxano, morpholino, dithiano, thiomorpholino, pyridazino, pyrimidino, pyrazino, piperazino, and triazino, any of which groups may be substituted or unsubstituted. Preferred values for Ring A include, without limitation, substituted or unsubstituted rings selected from the group consisting of furano, thieno, pyrrolo, oxazolo, thiazolo, imidazolo, pyrazolo, isoxazolo, isothiazolo, triazolo, benzo, pyridino, pyridazino, pyrimidino, and pyrazino.

Ring A may be substituted or unsubstituted. In some embodiments, each substitutable saturated ring carbon atom in Ring A is unsubstituted or is substituted with $=O$, $=S$, $=C(R^5)_2$, $=N-N(R^4)_2$, $=N-OR^5$, $=N-NHC(O)R^5$, $=N-NHCO_2R^6$, $=N-NHSO_2R^6$, $=N-R^5$ or $-R^b$, where $R^b$, $R^4$, $R^5$, and $R^6$ are as defined below. Each substitutable unsaturated ring carbon atom in Ring A is unsubstituted or substituted with $-R^b$. Each substitutable ring nitrogen atom in Ring A is unsubstituted or is substituted with $-R^{9b}$, and one ring nitrogen atom in Ring A optionally is oxidized. Each $R^{9b}$ independently is $-C(O)R^5$, $-C(O)N(R^4)_2$, $-CO_2R^6$, $-SO_2R^6$, $-SO_2N(R^4)_2$, or a $C_{1-4}$ aliphatic optionally substituted with $R^3$ or $R^7$.

Each $R^b$ independently is $R^{2b}$, an optionally substituted aliphatic, or an optionally substituted aryl, heterocyclyl, or heteroaryl group; or two adjacent $R^b$, taken together with the intervening ring atoms, form an optionally substituted fused 4- to 8-membered aromatic or non-aromatic ring having 0-3 ring heteroatoms selected from the group consisting of O, N, and S.

Each $R^{2b}$ independently
is -halo, $-NO_2$, $-CN$, $-C(R^5)=C(R^5)_2$, $-C(R^5)=C(R^5)(R^{10})$, $-C\equiv C-R^5$, $-C\equiv C-R^{10}$, $-OR^5$, $-SR^6$, $-S(O)R^6$, $-SO_2R^6$, $-SO_2N(R^4)_2$, $-N(R^4)_2$, $-NR^4C(O)R^5$, $-NR^4C(O)N(R^4)_2$, $-NR^4CO_2R^6$, $-O-CO_2R^5$, $-OC(O)N(R^4)_2$, $-O-C(O)R^5$, $-CO_2R^5$, $-C(O)-C(O)R^5$, $-C(O)R^5$, $-C(O)N(R^4)_2$, $-C(=NR^4)-N(R^4)_2$, $-C(=NR^4)-OR^5$, $-N(R^4)-N(R^4)_2$, $N(R^4)C(=NR^4)-N(R^4)_2$, $-N(R^4)SO_2R^6$, $-N(R^4)SO_2N(R^4)_2$, $-P(O)(R^5)_2$, or —P(O)(OR$^5$)$_2$, where the variables R$^4$, R$^5$, and R$^7$ have the values described above; each R$^6$ independently is an optionally substituted aliphatic or aryl group; and each R$^{10}$ independently is —CO$_2$R$^5$ or —C(O)N(R$^4$)$_2$.

In some embodiments, Ring A is substituted by 0-2 substituents R$^b$. In some such embodiments, each R$^b$ independently is C$_{1-3}$ aliphatic or R$^{2b}$, and each R$^{2b}$ independently is selected from the group consisting of -halo, —NO$_2$, —C(R$^5$)═C(R$^5$)$_2$, —C≡C—R$^5$, —OR$^5$, and —N(R$^4$)$_2$. In some embodiments, each R$^b$ independently is selected from the group consisting of -halo, C$_{1-3}$ aliphatic, C$_{1-3}$ fluoroaliphatic, and —OR$^5$, where R$^5$ is hydrogen or C$_{1-3}$ aliphatic. In certain preferred embodiments, Ring A is substituted with 0, 1, or 2 substituents, preferably 0 or 1 substituents, independently selected from the group consisting of chloro, fluoro, bromo, methyl, trifluoromethyl, and methoxy.

In some embodiments, Ring B is a substituted or unsubstituted mono- or bicyclic aryl or heteroaryl ring selected from the group consisting of furanyl, thienyl, pyrrolyl, oxazolyl, thiazolyl, imidazolyl, pyrazolyl, isoxazolyl, isothiazolyl, oxadiazolyl, triazolyl, thiadiazolyl, phenyl, pyridyl, pyridazinyl, pyrimidinyl, pyrazinyl, triazinyl, indolizinyl, indolyl, isoindolyl, indazolyl, benzo[b]furanyl, benzo[b]thienyl, benzimidazolyl, benzthiazolyl, benzoxazolyl, purinyl, quinolyl, isoquinolyl, cinnolinyl, phthalazinyl, quinazolinyl, quinoxalinyl, naphthyridinyl, and pteridinyl.

Each substitutable saturated ring carbon atom in Ring B is unsubstituted or is substituted with ═O, ═S, ═C(R$^5$)$_2$, ═N—N(R$^4$)$_2$, ═N—OR$^5$, ═N—NHC(O)R$^5$, ═N—NHCO$_2$R$^6$, ═N—NHSO$_2$R$^6$, ═N—R$^5$ or —R$^c$. Each substitutable unsaturated ring carbon atom in Ring B is unsubstituted or substituted with —R$^c$. Each substitutable ring nitrogen atom in Ring B is unsubstituted or is substituted with —R$^{9c}$, and one ring nitrogen atom in Ring B optionally is oxidized. Each R$^{9c}$ independently is —C(O)R$^5$, —C(O)N(R$^4$)$_2$, —CO$_2$R$^6$, —SO$_2$R$^6$, —SO$_2$N(R$^4$)$_2$, or a C$_{1-4}$ aliphatic optionally substituted with R$^3$ or R$^7$. Ring B may be unsubstituted or may be substituted on any one or more of its component rings, wherein the substituents may be the same or different. In some embodiments, Ring B is substituted with 0-2 independently selected R$^c$ and 0-3 independently selected R$^{2c}$ or C$_{1-6}$ aliphatic groups. The variables R$^3$, R$^4$, R$^5$, R$^6$, and R$^7$ are as defined above for Ring A, and R$^c$ and R$^{2c}$ are defined below.

Each R$^c$ independently is R$^{2c}$, an optionally substituted C$_{1-6}$ aliphatic, or an optionally substituted aryl, heteroaryl, or heterocyclyl group.

Each R$^{2c}$ independently is -halo, —NO$_2$, —CN, —C(R$^5$)═C(R$^5$)$_2$, —C(R$^5$)═C(R$^5$)$_2$(R$^{10}$), —C≡C—R$^5$, —C≡C—R$^{10}$, —OR$^5$, —SR$^6$, —S(O)R$^6$, —SO$_2$R$^6$, —SO$_2$N(R$^4$)$_2$, —N(R$^4$)$_2$, —NR$^4$C(O)R$^5$, —NR$^4$C(O)N(R$^4$)$_2$, —NR$^4$CO$_2$R$^6$, —O—CO$_2$R$^5$, —OC(O)N(R$^4$)$_2$, —O—C(O)R$^5$, —C O$_2$R$^5$, —C(O)—C(O)R$^5$, —C(O)R$^5$, —C(O)N(R$^4$)$_2$, —C(═NR$^4$)—N(R$^4$)$_2$, —C(═NR$^4$)—OR$^5$, —N(R$^4$)—N(R$^4$)$_2$, —N(R$^4$)C(═NR$^4$)—N(R$^4$)$_2$, —N(R$^4$)SO$_2$R$^6$, —N(R$^4$)SO$_2$N(R$^4$)$_2$, —P(O)(R$^5$)$_2$, or —P(O)(OR$^5$)$_2$.

In some embodiments, Ring B is a monocyclic 5- or 6-membered aryl or heteroaryl ring, substituted with 0-2 independently selected R and 0-2 independently selected R$^{2c}$ or C$_{1-6}$ aliphatic groups. In certain such embodiments, Ring B is a substituted or unsubstituted phenyl or pyridyl ring.

In some embodiments, Ring B is substituted with 0-2 substituents R$^c$. In some such embodiments, each R$^c$ independently is C$_{1-3}$ aliphatic or R$^{2c}$, and each R$^{2c}$ independently is selected from the group consisting of -halo, —NO$_2$, —C(R$^5$)═C(R$^5$)$_2$, —C≡C—R$^5$, —OR$^5$, and —N(R$^4$)$_2$. In some embodiments, each R$^c$ independently is selected from the group consisting of -halo, C$_{1-3}$ aliphatic, C$_{1-3}$haloaliphatic, and —OR$^5$, where R$^5$ is hydrogen or C$_{1-3}$ aliphatic. In certain preferred embodiments, Ring B is substituted with 0, 1, or 2 substituents, independently selected from the group consisting of chloro, fluoro, bromo, methyl, trifluoromethyl, and methoxy.

Each substitutable saturated ring carbon atom in Ring C is unsubstituted or is substituted with ═O, ═S, ═C(R$^5$)$_2$, ═N—N(R$^4$)$_2$, ═N—OR$^5$, ═N—NHC(O)R$^5$, ═N—NHCO$_2$R$^6$, ═N—NHSO$_2$R$^6$, ═N—R$^5$ or —R$^d$. Each substitutable unsaturated ring carbon atom in Ring C is unsubstituted or substituted with —R$^d$. Each substitutable ring nitrogen atom in Ring C is unsubstituted or is substituted with —R$^{9d}$, and one ring nitrogen atom in Ring C optionally is oxidized. Each R$^{9d}$ independently is —C(O)R$^5$, —C(O)N(R$^4$)$_2$, —CO$_2$R$^6$, —SO$_2$R$^6$, —SO$_2$N(R$^4$)$_2$, or a C$_{1-4}$ aliphatic optionally substituted with R$^3$ or R$^7$. Ring C may be unsubstituted or may be substituted on any one or more of its component rings, wherein the substituents may be the same or different. In some embodiments, Ring C is substituted with 0-2 independently selected R$^d$ and 0-3 independently selected R$^{2d}$ or C$_{1-6}$ aliphatic groups. The variables R$^3$, R$^4$, R$^5$, R$^6$, and R$^7$ are as described above for Rings A and B. The variables R$^d$ and R$^{2d}$ are described below.

Each R$^d$ independently is R$^{2d}$, an optionally substituted aliphatic, or an optionally substituted aryl, heteroaryl, or heterocyclyl group.

Each R$^{2d}$ independently is -halo, —NO$_2$, —CN, —C(R$^5$)═C(R$^5$)$_2$, —C(R$^5$)═C(R$^5$)$_2$(R$^{10}$), —C≡C—R$^5$, —C≡C—R$^{10}$, —OR$^5$, —SR$^6$, —S(O)R$^6$, —SO$_2$R$^6$, —SO$_2$N(R$^4$)$_2$, —N(R$^4$)$_2$, —NR$^4$C(O)R$^5$, —NR$^4$C(O)N(R$^4$)$_2$, —NR$^4$CO$_2$R$^6$, —O—CO$_2$R$^5$, —OC(O)N(R$^4$)$_2$, —O—C(O)R$^5$, —CO$_2$R$^5$, —C(O)—C(O)R$^5$, —C(O)R$^5$, —C(O)N(R$^4$)$_2$, —C(═NR$^4$)—N(R$^4$)$_2$, —C(═NR$^4$)—OR$^5$, —N(R$^4$)—N(R$^4$)$_2$, —N(R$^4$)C(═NR$^4$)—N(R$^4$)$_2$, —N(R$^4$)SO$_2$R$^6$, —N(R$^4$)SO$_2$N(R$^4$)$_2$, —P(O)(R$^5$)$_2$, or —P(O)(OR$^5$)$_2$. Additionally, R$^{2d}$ can be —SO$_3$R$^5$, —C(O)N(R$^4$)C(═NR$^4$)—N(R$^4$)$_2$ or —N(R$^4$)C(═NR$^4$)—N(R$^4$)—C(O)R$^5$.

In some embodiments, Ring C is a monocyclic 5- or 6-membered aryl or heteroaryl ring, which is substituted with 0-2 independently selected substituents R$^d$ and 0-2 independently selected R$^{2d}$ or C$_{1-6}$ aliphatic groups. In some such embodiments, Ring C is an optionally substituted heteroaryl ring selected from the group consisting of pyridyl, pyrimidinyl, pyrazinyl, pyridazinyl, imidazolyl, pyrazolyl, and oxazolyl. In some other embodiments, Ring C is a substituted or unsubstituted phenyl ring. In some embodiments, Ring C is a monocyclic 5- or 6-membered aryl or heteroaryl ring, which is substituted with 0, 1, or 2 substituents R$^d$, as defined above.

In some other embodiments, Ring C is a monocyclic 5- or 6-membered heterocyclyl or cycloaliphatic ring, which is substituted with 0-2 independently selected substituents R$^d$ and 0-2 independently selected R$^{2d}$ or C$_{1-6}$ aliphatic groups.

In some embodiments, the selective Aurora A kinase inhibitor is a compound represented by formula (IV):

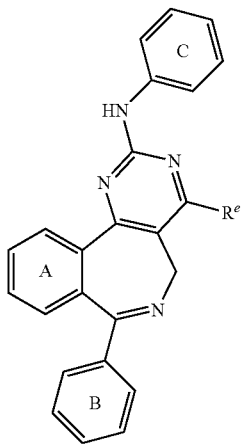

(IV)

or a pharmaceutically acceptable salt thereof;
wherein:
$R^e$ is hydrogen or a $C_{1-3}$ aliphatic optionally substituted with $R^3$ or $R^7$;
Ring A is substituted with 0-3 $R^b$;
  each $R^b$ independently is selected from the group consisting of $C_{1-6}$ aliphatic, $R^{2b}$, $R^{7b}$, -$T^1$-$R^{2b}$, and -$T^1$-$R^{7b}$;
  each $R^{2b}$ independently is -halo, —$NO_2$, —CN, —C($R^5$)=C($R^5$)$_2$, —C≡C—$R^5$, —$OR^5$, —$SR^6$, —S(O)$R^6$, —$SO_2R^6$, —$SO_2N(R^4)_2$, —N($R^4$)$_2$, —$NR^4$C(O)$R^5$, —$NR^4$C(O)N($R^4$)$_2$, —$NR^4CO_2R^6$, —O—$CO_2R^5$, —OC(O)N($R^4$)$_2$, —O—C(O)$R^5$, —$CO_2R^5$, —C(O)—C(O)$R^5$, —C(O)$R^5$, —C(O)N($R^4$)$_2$, —C(=$NR^4$)—N($R^4$)$_2$, —C(=$NR^4$)—$OR^5$, —N($R^4$)—N($R^4$)$_2$, —N($R^4$)C(=$NR^4$)—N($R^4$)$_2$, —N($R^4$)$SO_2R^6$, —N($R^4$)$SO_2$N($R^4$)$_2$, —P(O)($R^5$)$_2$, or —P(O)($OR^5$)$_2$;
  each $R^{7b}$ independently is an optionally substituted aryl, heterocyclyl, or heteroaryl group;
Ring B is substituted with 0-2 independently selected $R^c$ and 0-2 independently selected $R^{2c}$ or $C_{1-6}$ aliphatic groups;
  each $R^c$ independently is selected from the group consisting of $C_{1-6}$ aliphatic, $R^{2c}$, $R^{7c}$, -$T^1$-$R^{2c}$, and -$T^1$-$R^{7c}$;
  each $R^{2c}$ independently is -halo, —$NO_2$, —CN, —C($R^5$)=C($R^5$)$_2$, —C≡C—$R^5$, —$OR^5$, —$SR^6$, —S(O)$R^6$, —$SO_2R^6$, —$SO_2N(R^4)_2$, —N($R^4$)$_2$, —$NR^4$C(O)$R^5$, —$NR^4$C(O)N($R^4$)$_2$, —$NR^4CO_2R^6$, —O—$CO_2R^5$, —OC(O)N($R^4$)$_2$, —O—C(O)$R^5$, —$CO_2R^5$, —C(O)—C(O)$R^5$, —C(O)$R^5$, —C(O)N($R^4$)$_2$, —C(=$NR^4$)—N($R^4$)$_2$, —C(=$NR^4$)—$OR^5$, —N($R^4$)—N($R^4$)$_2$, —N($R^4$)C(=$NR^4$)—N($R^4$)$_2$, —N($R^4$)$SO_2R^6$, —N($R^4$)$SO_2$N($R^4$)$_2$, —P(O)($R^5$)$_2$, or —P(O)($OR^5$)$_2$;
  each $R^{7c}$ independently is an optionally substituted aryl, heterocyclyl, or heteroaryl group;
$T^1$ is a $C_{1-6}$ alkylene chain optionally substituted with $R^3$ or $R^{3b}$, wherein $T^1$ or a portion thereof optionally forms part of a 3- to 7-membered ring;
Ring C is substituted with 0-2 independently selected $R^d$ and 0-3 independently selected $R^{2d}$ or $C_{1-6}$ aliphatic groups;
  each $R^d$ independently is selected from the group consisting of $C_{1-6}$ aliphatic, $R^{2d}$, $R^{7d}$, -$T^2$-$R^{2d}$, -$T^2$-$R^{7d}$, —V-$T^3$-$R^{2d}$, and —V-$T^3$-$R^{7d}$;
$T^2$ is a $C_{1-6}$ alkylene chain optionally substituted with $R^3$ or $R^{3b}$, wherein the alkylene chain optionally is interrupted by —C($R^5$)=C($R^5$)—, —C≡C—, —O—, —S—, —S(O)—, —S(O)$_2$—, —$SO_2$N($R^4$)—, —N($R^4$)—, —N($R^4$)C(O)—, —$NR^4$C(O)N($R^4$)—, —N($R^4$)$CO_2$—, —C(O)N($R^4$)—, —C(O)—, —C(O)—C(O)—, —$CO_2$—, —OC(O)—, —OC(O)O—, —OC(O)N($R^4$)—, —N($R^4$)—N($R^4$)—, —N($R^4$)$SO_2$—, or —$SO_2$N($R^4$)—, and wherein $T^2$ or a portion thereof optionally forms part of a 3-7 membered ring;
$T^3$ is a $C_{1-6}$ alkylene chain optionally substituted with $R^3$ or $R^{3b}$, wherein the alkylene chain optionally is interrupted by —C($R^5$)=C($R^5$)—, —C≡C—, —O—, —S—, —S(O)—, —S(O)$_2$—, —$SO_2$N($R^4$)—, —N($R^4$)—, —N($R^4$)C(O)—, —$NR^4$C(O)N($R^4$)—, —N($R^4$)$CO_2$—, —C(O)N($R^4$)—, —C(O)—, —C(O)—C(O)—, —$CO_2$—, —OC(O)—, —OC(O)O—, —OC(O)N($R^4$)—, —N($R^4$)—N($R^4$)—, —N($R^4$)$SO_2$—, or —$SO_2$N($R^4$)—, and wherein $T^3$ or a portion thereof optionally forms part of a 3-7 membered ring;
V is —C($R^5$)=C($R^5$)—, —C≡C—, —O—, —S—, —S(O)—, —S(O)$_2$—, —$SO_2$N($R^4$)—, —N($R^4$)—, —N($R^4$)C(O)—, —$NR^4$C(O)N($R^4$)—, —N($R^4$)$CO_2$—, —C(O)N($R^4$)—, —C(O)—, —C(O)—C(O)—, —$CO_2$—, —OC(O)—, —OC(O)O—, —OC(O)N($R^4$)—, —C($NR^4$)=N—, —C($OR^5$)=N—, —N($R^4$)—N($R^4$)—, —N($R^4$)$SO_2$—, —N($R^4$)$SO_2$N($R^4$)—, —P(O)($R^5$)—, —P(O)($OR^5$)—O—, —P(O)—O—, or —P(O)($NR^5$)—N($R^5$)—;
$R^{2d}$ is -halo, —$NO_2$, —CN, —C($R^5$)=C($R^5$)$_2$, —C≡C—$R^5$, —$OR^5$, —$SR^6$, —S(O)$R^6$, —$SO_2R^6$, —$SO_2N(R^4)_2$, —N($R^4$)$_2$, —$NR^4$C(O)$R^5$, —$NR^4$C(O)N($R^4$)$_2$, —$NR^4CO_2R^6$, —O—$CO_2R^5$, —OC(O)N($R^4$)$_2$, —O—C(O)$R^5$, —$CO_2R^5$, —C(O)—C(O)$R^5$, —C(O)$R^5$, —C(O)N($R^4$)$_2$, —C(=$NR^4$)—N($R^4$)$_2$, —C(=$NR^4$)—$OR^5$, —N($R^4$)—N($R^4$)$_2$, —N($R^4$)C(=$NR^4$)—N($R^4$)$_2$, —N($R^4$)$SO_2R^6$, —N($R^4$)$SO_2$N($R^4$)$_2$, —P(O)($R^5$)$_2$, or —P(O)($OR^5$)$_2$; and
each $R^{7d}$ independently is an optionally substituted aryl, heterocyclyl, or heteroaryl group.
each $R^3$ independently is selected from the group consisting of -halo, —OH, —O($C_{1-3}$ alkyl), —CN, —N($R^4$)$_2$, —C(O)($C_{1-3}$ alkyl), —$CO_2$H, —$CO_2$($C_{1-3}$ alkyl), —C(O)$NH_2$, and —C(O)NH($C_{1-3}$ alkyl);
each $R^{3b}$ independently is a $C_{1-3}$ aliphatic optionally substituted with $R^3$ or $R^7$, or two substituents $R^{3b}$ on the same carbon atom, taken together with the carbon atom to which they are attached, form a 3- to 6-membered carbocyclic ring;
each $R^4$ independently is hydrogen or an optionally substituted aliphatic, aryl, heteroaryl, or heterocyclyl group; or two $R^4$ on the same nitrogen atom, taken together with the nitrogen atom, form an optionally substituted 5- to 8-membered heteroaryl or heterocyclyl ring having, in addition to the nitrogen atom, 0-2 ring heteroatoms selected from N, O, and S;

each $R^5$ independently is hydrogen or an optionally substituted aliphatic, aryl, heteroaryl, or heterocyclyl group;

each $R^6$ independently is an optionally substituted aliphatic or aryl group; and each $R^7$ independently is an optionally substituted aryl, heterocyclyl, or heteroaryl group.

Table 3 provides the chemical names for specific examples of compounds of formula (IV).

TABLE 3

Examples of Compounds of Formula (IV)

| | |
|---|---|
| IV-1 | 4-[9-Chloro-7-(2-fluoro-phenyl)-5H-benzo[c]pyrimido[4,5-e]azepin-2-ylamino]-N-(2-methylamino-ethyl)-benzamide |
| IV-2 | N-(2-Amino-ethyl)-4-[9-chloro-7-(2-fluoro-phenyl)-5H-benzo[c]pyrimido-[4,5-e]azepin-2-ylamino]-N-methyl-benzamide |
| IV-3 | 4-[9-Chloro-7-(2-fluoro-phenyl)-5H-benzo[c]pyrimido[4,5-e]azepin-2-ylamino]-N-methyl-N-(2-methylamino-ethyl)-benzamide |
| IV-4 | 4-[9-Chloro-7-(2-fluoro-phenyl)-5H-benzo[c]pyrimido[4,5-e]azepin-2-ylamino]-N-(2-dimethylamino-ethyl)-benzamide |
| IV-5 | 4-[9-Chloro-7-(2-fluoro-phenyl)-5H-benzo[c]pyrimido[4,5-e]azepin-2-ylamino]-N-(2-dimethylamino-ethyl)-N-methyl-benzamide |
| IV-6 | 4-[9-Chloro-7-(2-fluoro-phenyl)-5H-benzo[c]pyrimido[4,5-e]azepin-2-ylamino]-N-(3-dimethylamino-propyl)-benzamide |
| IV-7 | 4-[9-Chloro-7-(2-fluoro-phenyl)-5H-benzo[c]pyrimido[4,5-e]azepin-2-ylamino]-N-(3-dimethylamino-propyl)-N-methyl-benzamide |
| IV-8 | {4-[9-Chloro-7-(2-fluoro-phenyl)-5H-benzo[c]pyrimido[4,5-e]azepin-2-ylamino]-phenyl}-piperazin-1-yl-methanone |
| IV-9 | {4-[9-Chloro-7-(2-fluoro-phenyl)-5H-benzo[c]pyrimido[4,5-e]azepin-2-ylamino]-phenyl}-(4-methyl-piperazin-1-yl)-methanone |
| IV-10 | {4-[9-Chloro-7-(2-chloro-phenyl)-5H-benzo[c]pyrimido[4,5-e]azepin-2-ylamino]-phenyl}-(4-methyl-piperazin-1-yl)-methanone |
| IV-11 | [4-(9-Chloro-7-o-tolyl-5H-benzo[c]pyrimido[4,5-e]azepin-2-ylamino)-phenyl]-(4-methyl-piperazin-1-yl)-methanone |
| IV-12 | {4-[9-Chloro-7-(2-methoxy-phenyl)-5H-benzo[c]pyrimido[4,5-e]azepin-2-ylamino]-phenyl}-(4-methyl-piperazin-1-yl)-methanone |
| IV-13 | {4-[9-Chloro-7-(4-fluoro-phenyl)-5H-benzo[c]pyrimido[4,5-e]azepin-2-ylamino]-phenyl}-(4-methyl-piperazin-1-yl)-methanone |
| IV-14 | {4-[7-(2-Fluoro-phenyl)-9-methyl-5H-benzo[c]pyrimido[4,5-e]azepin-2-ylamino]-phenyl}-(4-methyl-piperazin-1-yl)-methanone |
| IV-15 | 2-{3-[9-Chloro-7-(2-fluoro-phenyl)-5H-benzo[c]pyrimido[4,5-e]azepin-2-ylamino]-phenyl}-1-(4-methyl-piperazin-1-yl)-ethanone |
| IV-16 | 4-[9-Chloro-7-(2-fluoro-phenyl)-5H-benzo[c]pyrimido[4,5-e]azepin-2-ylamino]-N-piperidin-4-yl-benzamide |
| IV-17 | (4-Amino-piperidin-1-yl)-{4-[9-chloro-7-(2-fluoro-phenyl)-5H-benzo[c]pyrimido[4,5-e]azepin-2-ylamino]-phenyl}-methanone |
| IV-18 | {4-[9-Chloro-7-(2-fluoro-phenyl)-5H-benzo[c]pyrimido[4,5-e]azepin-2-ylamino]-phenyl}-(4-dimethylamino-piperidin-1-yl)-methanone |
| IV-19 | 4-[9-Chloro-7-(2-fluoro-phenyl)-5H-benzo[c]pyrimido[4,5-e]azepin-2-ylamino]-N-[3-(4-methyl-piperazin-1-yl)-propyl]-benzamide |
| IV-20 | 4-[9-Chloro-7-(2-chloro-phenyl)-5H-benzo[c]pyrimido[4,5-e]azepin-2-ylamino]-N-[3-(4-methyl-piperazin-1-yl)-propyl]-benzamide |
| IV-21 | 4-(9-Chloro-7-o-tolyl-5H-benzo[c]pyrimido[4,5-e]azepin-2-ylamino)-N-[3-(4-methyl-piperazin-1-yl)-propyl]-benzamide |
| IV-22 | 4-[9-Chloro-7-(2-methoxy-phenyl)-5H-benzo[c]pyrimido[4,5-e]azepin-2-ylamino]-N-[3-(4-methyl-piperazin-1-yl)-propyl]-benzamide |
| IV-23 | 4-[9-Chloro-7-(4-fluoro-phenyl)-5H-benzo[c]pyrimido[4,5-e]azepin-2-ylamino]-N-[3-(4-methyl-piperazin-1-yl)-propyl]-benzamide |
| IV-24 | 4-[7-(2-Fluoro-phenyl)-9-methyl-5H-benzo[c]pyrimido[4,5-e]azepin-2-ylamino]-N-[3-(4-methyl-piperazin-1-yl)-propyl]-benzamide |
| IV-25 | 2-{3-[9-Chloro-7-(2-fluoro-phenyl)-5H-benzo[c]pyrimido[4,5-e]azepin-2-ylamino]-phenyl}-N-[3-(4-methyl-piperazin-1-yl)-propyl]-acetamide |
| IV-26 | {4-[9-Chloro-7-(2-fluoro-phenyl)-5H-benzo[c]pyrimido[4,5-e]azepin-2-ylamino]-phenyl}-morpholin-4-yl-methanone |
| IV-27 | 4-[9-Chloro-7-(2-fluoro-phenyl)-5H-benzo[c]pyrimido[4,5-e]azepin-2-ylamino]-N,N-bis-(2-hydroxy-ethyl)-benzamide |
| IV-28 | {4-[9-Chloro-7-(2-chloro-phenyl)-5H-benzo[c]pyrimido[4,5-e]azepin-2-ylamino]-phenyl}-morpholin-4-yl-methanone |
| IV-29 | 4-[9-Chloro-7-(2-fluoro-phenyl)-5H-benzo[c]pyrimido[4,5-e]azepin-2-ylamino]-N-(2-morpholin-4-yl-ethyl)-benzamide |
| IV-30 | 4-[9-Chloro-7-(2-chloro-phenyl)-5H-benzo[c]pyrimido[4,5-e]azepin-2-ylamino]-N-(2-morpholin-4-yl-ethyl)-benzamide |
| IV-31 | 4-(9-Chloro-7-o-tolyl-5H-benzo[c]pyrimido[4,5-e]azepin-2-ylamino)-N-(2-morpholin-4-yl-ethyl)-benzamide |
| IV-32 | 4-[9-Chloro-7-(2-methoxy-phenyl)-5H-benzo[c]pyrimido[4,5-e]azepin-2-ylamino]-N-(3-morpholin-4-yl-propyl)-benzamide |
| IV-33 | 4-[9-Chloro-7-(4-fluoro-phenyl)-5H-benzo[c]pyrimido[4,5-e]azepin-2-ylamino]-N-(2-morpholin-4-yl-ethyl)-benzamide |
| IV-34 | 4-[9-Chloro-7-(2-chloro-phenyl)-5H-benzo[c]pyrimido[4,5-e]azepin-2-ylamino]-2-hydroxy-N-(2-morpholin-4-yl-ethyl)-benzamide |
| IV-35 | [9-Chloro-7-(2-chloro-phenyl)-5H-benzo[c]pyrimido[4,5-e]azepin-2-yl]-pyridin-2-yl-amine |
| IV-36 | [9-Chloro-7-(2-fluoro-phenyl)-5H-benzo[c]pyrimido[4,5-e]azepin-2-yl]-(3,5-dichloro-phenyl)-amine |
| IV-37 | [9-Chloro-7-(2-fluoro-phenyl)-5H-benzo[c]pyrimido[4,5-e]azepin-2-yl]-(4-methoxy-phenyl)-amine |
| IV-38 | [9-Chloro-7-(2-fluoro-phenyl)-5H-benzo[c]pyrimido[4,5-e]azepin-2-yl]-(4-ethoxy-phenyl)-amine |
| IV-39 | [9-Chloro-7-(2-fluoro-phenyl)-5H-benzo[c]pyrimido[4,5-e]azepin-2-yl]-(3-methoxy-phenyl)-amine |
| IV-40 | [9-Chloro-7-(2-fluoro-phenyl)-5H-benzo[c]pyrimido[4,5-e]azepin-2-yl]-(2-methoxy-phenyl)-amine |
| IV-41 | [9-Chloro-7-(2-fluoro-phenyl)-5H-benzo[c]pyrimido[4,5-e]azepin-2-yl]-(4-chloro-phenyl)-amine |
| IV-42 | [9-Chloro-7-(2-chloro-phenyl)-5H-benzo[c]pyrimido[4,5-e]azepin-2-yl]-(4-chloro-phenyl)-amine |
| IV-43 | [9-Chloro-7-(2-fluoro-phenyl)-5H-benzo[c]pyrimido[4,5-e]azepin-2-yl]-(3-chloro-phenyl)-amine |
| IV-44 | [9-Chloro-7-(2-fluoro-phenyl)-5H-benzo[c]pyrimido[4,5-e]azepin-2-yl]-(2-chloro-phenyl)-amine |
| IV-45 | 4-[9-Chloro-7-(2-chloro-phenyl)-5H-benzo[c]pyrimido[4,5-e]azepin-2-ylamino]-phenol |
| IV-46 | [9-Chloro-7-(2-fluoro-phenyl)-5H-benzo[c]pyrimido[4,5-e]azepin-2-yl]-(4-morpholin-4-yl-phenyl)-amine |
| IV-47 | [9-Chloro-7-(2-fluoro-phenyl)-5H-benzo[c]pyrimido[4,5-e]azepin-2-yl]-[4-(4-methyl-piperazin-1-yl)-phenyl]-amine |
| IV-48 | [9-Chloro-7-(2-fluoro-phenyl)-5H-benzo[c]pyrimido[4,5-e]azepin-2-yl]-(4-pyridin-4-ylmethyl-phenyl)-amine |
| IV-49 | 4-[9-Chloro-7-(2-fluoro-phenyl)-5H-benzo[c]pyrimido[4,5-e]azepin-2-ylamino]-benzonitrile |
| IV-50 | [9-Chloro-7-(2-fluoro-phenyl)-5H-benzo[c]pyrimido[4,5-e]azepin-2-yl]-(4-nitro-phenyl)-amine |
| IV-51 | 4-[7-(2-Fluoro-phenyl)-5H-benzo[c]pyrimido[4,5-e]azepin-2-ylamino]-benzoic acid |
| IV-52 | 4-[9-Chloro-7-(2-fluoro-phenyl)-5H-benzo[c]pyrimido[4,5-e]azepin-2-ylamino]-benzoic acid |
| IV-53 | 4-[9-Chloro-7-(2-chloro-phenyl)-5H-benzo[c]pyrimido[4,5-e]azepin-2-ylamino]-benzoic acid |
| IV-54 | 4-(9-Chloro-7-o-tolyl-5H-benzo[c]pyrimido[4,5-e]azepin-2-ylamino)-benzoic acid |
| IV-55 | 4-[9-Chloro-7-(2-methoxy-phenyl)-5H-benzo[c]pyrimido[4,5-e]azepin-2-ylamino]-benzoic acid |
| IV-56 | 4-[9-Chloro-7-(4-fluoro-phenyl)-5H-benzo[c]pyrimido[4,5-e]azepin-2-ylamino]-benzoic acid |
| IV-57 | 4-[9-Fluoro-7-(2-fluoro-phenyl)-5H-benzo[c]pyrimido[4,5-e]azepin-2-ylamino]-benzoic acid |
| IV-58 | 4-[7-(2-Fluoro-phenyl)-9-methyl-5H-benzo[c]pyrimido[4,5-e]azepin-2-ylamino]-benzoic acid |
| IV-59 | 4-[10-Fluoro-7-(2-fluoro-phenyl)-5H-benzo[c]pyrimido[4,5-e]azepin-2-ylamino]-benzoic acid |

TABLE 3-continued

Examples of Compounds of Formula (IV)

| | |
|---|---|
| IV-60 | 4-[10-Chloro-7-(2-fluoro-phenyl)-5H-benzo[c]pyrimido[4,5-e]azepin-2-ylamino]-benzoic acid |
| IV-61 | 4-[10-Bromo-7-(2-fluoro-phenyl)-5H-benzo[c]pyrimido[4,5-e]azepin-2-ylamino]-benzoic acid |
| IV-62 | 4-[7-(2-Fluoro-phenyl)-10-methoxy-5H-benzo[c]pyrimido[4,5-e]azepin-2-ylamino]-benzoic acid |
| IV-63 | 4-[9-Chloro-7-(2-chloro-phenyl)-5H-benzo[c]pyrimido[4,5-e]azepin-2-ylamino]-benzamide |
| IV-64 | 3-[9-Chloro-7-(2-chloro-phenyl)-5H-benzo[c]pyrimido[4,5-e]azepin-2-ylamino]-benzamide |
| IV-65 | {3-[9-Chloro-7-(2-chloro-phenyl)-5H-benzo[c]pyrimido[4,5-e]azepin-2-ylamino]-phenyl}-acetic acid |
| IV-66 | 2-{3-[9-Chloro-7-(2-chloro-phenyl)-5H-benzo[c]pyrimido[4,5-e]azepin-2-ylamino]-phenyl}-acetamide |
| IV-67 | 4-[9-Chloro-7-(2-fluoro-phenyl)-5H-benzo[c]pyrimido[4,5-e]azepin-2-ylamino]-benzenesulfonic acid |
| IV-68 | 4-[9-Chloro-7-(2-fluoro-phenyl)-5H-benzo[c]pyrimido[4,5-e]azepin-2-ylamino]-benzenesulfonamide |
| IV-69 | 4-[9-Chloro-7-(2-chloro-phenyl)-5H-benzo[c]pyrimido[4,5-e]azepin-2-ylamino]-N-(5-methyl-isoxazol-3-yl)-benzenesulfonamide |
| IV-70 | [9-Chloro-7-(2-fluoro-phenyl)-5H-benzo[c]pyrimido[4,5-e]azepin-2-yl]-(4-trifluoromethanesulfonyl-phenyl)-amine |
| IV-71 | [9-Chloro-7-(2-fluoro-phenyl)-5H-benzo[c]pyrimido[4,5-e]azepin-2-yl]-(3,4-dimethoxy-phenyl)-amine |
| IV-72 | [9-Chloro-7-(2-fluoro-phenyl)-6,7-dihydro-5H-benzo[c]pyrimido[4,5-e]azepin-2-yl]-(3,4-dimethoxy-phenyl)-amine |
| IV-73 | [9-Chloro-7-(2-chloro-phenyl)-5H-benzo[c]pyrimido[4,5-e]azepin-2-yl]-(3,4-dimethoxy-phenyl)-amine |
| IV-74 | (9-Chloro-7-o-tolyl-5H-benzo[c]pyrimido[4,5-e]azepin-2-yl)-(3,4-dimethoxy-phenyl)-amine |
| IV-75 | (3,4-Dimethoxy-phenyl)-[7-(2-fluoro-phenyl)-9-methyl-5H-benzo[c]pyrimido-[4,5-e]azepin-2-yl]-amine |
| IV-76 | (3,4-Dimethoxy-phenyl)-[7-(2-fluoro-phenyl)-9-isopropyl-5H-benzo[c]pyrimido[4,5-e]azepin-2-yl]-amine |
| IV-77 | (3,4-Dimethoxy-phenyl)-[10-fluoro-7-(2-fluoro-phenyl)-5H-benzo[c]pyrimido[4,5-e]azepin-2-yl]-amine |
| IV-78 | [10-Bromo-7-(2-fluoro-phenyl)-5H-benzo[c]pyrimido[4,5-e]azepin-2-yl]-(3,4-dimethoxy-phenyl)-amine |
| IV-79 | (3,4-Dimethoxy-phenyl)-4[7-(2-fluoro-phenyl)-10-trifluoromethyl-5H-benzo[c]pyrimido[4,5-e]azepin-2-yl]-amine |
| IV-80 | (3,4-Dimethoxy-phenyl)-[7-(2-fluoro-phenyl)-10-methyl-5H-benzo[c]pyrimido-[4,5-e]azepin-2-yl]-amine |
| IV-81 | (3,4-Dimethoxy-phenyl)-[7-(2-fluoro-phenyl)-10-methoxy-5H-benzo[c]pyrimido[4,5-e]azepin-2-yl]-amine |
| IV-82 | (3,4-Dimethoxy-phenyl)-[7-(2-fluoro-phenyl)-11-methyl-5H-benzo[c]pyrimido-[4,5-e]azepin-2-yl]-amine |
| IV-83 | [9-Chloro-7-(2-fluoro-phenyl)-5H-benzo[c]pyrimido[4,5-e]azepin-2-yl]-(2,3-dihydro-benzo[1,4]dioxin-6-yl)-amine |
| IV-84 | [9-Chloro-7-(2-fluoro-phenyl)-5H-benzo[c]pyrimido[4,5-e]azepin-2-yl]-(4-fluoro-3-methoxy-phenyl)-amine |
| IV-85 | 4-[9-Chloro-7-(2-fluoro-phenyl)-5H-benzo[c]pyrimido[4,5-e]azepin-2-ylamino]-2-hydroxy-benzoic acid |
| IV-86 | 4-[9-Chloro-7-(2-chloro-phenyl)-5H-benzo[c]pyrimido[4,5-e]azepin-2-ylamino]-2-hydroxy-benzoic acid |
| IV-87 | [9-Chloro-7-(2-fluoro-phenyl)-5H-benzo[c]pyrimido[4,5-e]azepin-2-yl]-(3,4-dichloro-phenyl)-amine |
| IV-88 | [9-Chloro-7-(2-chloro-phenyl)-5H-benzo[c]pyrimido[4,5-e]azepin-2-yl]-(3,5-dimethoxy-phenyl)-amine |
| IV-89 | [9-Chloro-7-(2-fluoro-phenyl)-5H-benzo[c]pyrimido[4,5-e]azepin-2-yl]-(3,5-dimethyl-phenyl)-amine |
| IV-90 | [9-Chloro-7-(2-fluoro-phenyl)-5H-benzo[c]pyrimido[4,5-e]azepin-2-yl]-phenyl-amine |
| IV-91 | 4-[9-Chloro-7-(2,5-difluoro-phenyl)-5H-benzo[c]pyrimido[4,5-e]azepin-2-ylamino]-benzoic acid |
| IV-92 | 4-[9-Chloro-7-(2,3-difluoro-phenyl)-5H-benzo[c]pyrimido[4,5-e]azepin-2-ylamino]-benzoic acid |
| IV-93 | (3-Dimethylamino-pyrrolidin-1-yl)-{4-[7-(2-fluoro-phenyl)-9-methoxy-5H-benzo[c]pyrimido[4,5-e]azepin-2-ylamino]-phenyl}-methanone |
| IV-94 | 4-[9-Chloro-7-(2,5-dimethoxy-phenyl)-5H-benzo[c]pyrimido[4,5-e]azepin-2-ylamino]-benzoic acid |
| IV-95 | 4-[7-(2-Fluoro-phenyl)-9-methoxy-5H-benzo[c]pyrimido[4,5-e]azepin-2-ylamino]-N,N-bis-(2-hydroxy-ethyl)-benzamide |
| IV-96 | 4-[9-Chloro-7-(2,4-difluoro-phenyl)-5H-benzo[c]pyrimido[4,5-e]azepin-2-ylamino]-benzoic acid |
| IV-97 | 4-[9-Chloro-7-(2,4-difluoro-phenyl)-7H-benzo[c]pyrimido[4,5-e]azepin-2-ylamino]-benzoic acid |
| IV-98 | {4-[9-Chloro-7-(2-fluoro-phenyl)-5H-benzo[c]pyrimido[4,5-e]azepin-2-ylamino]-phenyl}-(3-dimethylamino-azetidin-1-yl)-methanone |
| IV-99 | 4-[9-Chloro-7-(2-fluoro-phenyl)-5H-benzo[c]pyrimido[4,5-e]azepin-2-ylamino]-N-methyl-N-(1-methyl-pyrrolidin-3-yl)-benzamide |
| IV-100 | {4-[9-Chloro-7-(2-fluoro-phenyl)-5H-benzo[c]pyrimido[4,5-e]azepin-2-ylamino]-phenyl}-(3-dimethylamino-pyrrolidin-1-yl)-methanone |
| IV-101 | 4-[9-Chloro-7-(2,4-dimethoxy-phenyl)-5H-benzo[c]pyrimido[4,5-e]azepin-2-ylamino]-benzoic acid |
| IV-102 | {4-[9-Chloro-7-(2-fluoro-phenyl)-5H-benzo[c]pyrimido[4,5-e]azepin-2-ylamino]-phenyl}-(3-methylamino-pyrrolidin-1-yl)-methanone |
| IV-103 | (3-Amino-pyrrolidin-1-yl)-{4-[9-chloro-7-(2-fluoro-phenyl)-5H-benzo[c]pyrimido[4,5-e]azepin-2-ylamino]-phenyl}-methanone |
| IV-104 | 4-[9-Chloro-7-(2,3-difluoro-phenyl)-5H-benzo[c]pyrimido[4,5-e]azepin-2-ylamino]-benzoic acid methyl ester |
| IV-105 | 4-[9-Chloro-7-(2,5-difluoro-phenyl)-5H-benzo[c]pyrimido[4,5-e]azepin-2-ylamino]-benzoic acid methyl ester |
| IV-106 | {4-[9-Chloro-7-(2-fluoro-phenyl)-5H-benzo[c]pyrimido[4,5-e]azepirt-2-ylamino]-phenyl}-phosphonic acid |
| IV-107 | N-{4-[9-Chloro-7-(2-fluoro-phenyl)-5H-benzo[c]pyrimido[4,5-e]azepin-2-ylamino]-phenyl}-methanesulfonamide |
| IV-108 | N-{4-[9-Chloro-7-(2-fluoro-phenyl)-5H-benzo[c]pyrimido[4,5-e]azepin-2-ylamino]-phenyl}-N-methyl-acetamide |
| IV-109 | 2-{4-[9-Chloro-7-(2-fluoro-phenyl)-5H-benzo[c]pyrimido[4,5-e]azepin-2-ylamino]-benzoylamino}-succinic acid |
| IV-110 | [9-Chloro-7-(2-fluoro-phenyl)-4-methyl-5H-benzo[c]pyrimido[4,5-e]azepin-2-yl]-(3,4-dimethoxy-phenyl)-amine |
| IV-111 | {4-[9-Chloro-7-(2-fluoro-phenyl)-5H-benzo[c]pyrimido[4,5-e]azepin-2-ylamino]-phenyl}-(3,5-dimethyl-piperazin-1-yl)-methanone |
| IV-112 | 1-{4-[9-Chloro-7-(2-fluoro-phenyl)-5H-benzo[c]pyrimido[4,5-e]azepin-2-ylamino]-benzoyl}-pyrrolidine-2-carboxylic acid |
| IV-113 | {4-[9-Chloro-7-(2-fluoro-phenyl)-5H-benzo[c]pyrimido[4,5-e]azepin-2-ylamino]-phenyl}-(3-methyl-piperazin-1-yl)-methanone |
| IV-114 | [9-Chloro-7-(2-fluoro-phenyl)-5H-benzo[c]pyrimido[4,5-e]azepin-2-yl]4-[-(2H-tetrazol-5-yl)-phenyl]-amine |
| IV-115 | N-{4-[9-Chloro-7-(2-fluoro-phenyl)-5H-benzo[c]pyrimido[4,5-e]azepin-2-ylamino]-phenyl}-acetamide |
| IV-116 | 5-[9-Chloro-7-(2-fluoro-phenyl)-5H-benzo[c]pyrimido[4,5-e]azepin-2-ylamino]-2-fluoro-benzoic acid |
| IV-117 | N-(3-Amino-propyl)-4-[9-chloro-7-(2-fluoro-phenyl)-5H-benzo[c]pyrimido-[4,5-e]azepin-2-ylamino]-N-methyl-benzamide |
| IV-118 | 2-{4-[9-Chloro-7-(2-fluoro-phenyl)-5H-benzo[c]pyrimido[4,5-e]azepin-2-ylamino]-benzoylamino}-propionic acid |
| IV-119 | 5-[9-Chloro-7-(2-fluoro-phenyl)-5H-benzo[c]pyrimido[4,5-e]azepin-2-ylamino]-pyridine-2-carboxylic acid |
| IV-120 | 2-{4-[9-Chloro-7-(2-fluoro-phenyl)-5H-benzo[c]pyrimido[4,5-e]azepin-2-ylamino]-phenyl}-N-(2-morpholin-4-yl-ethyl)-acetamide |
| IV-121 | 5-[9-Chloro-7-(2-fluoro-phenyl)-5H-benzo[c]pyrimido[4,5-e]azepin-2-ylamino]-2-methoxy-benzoic acid |
| IV-122 | 5-[9-Chloro-7-(2-fluoro-phenyl)-5H-benzo[c]pyrimido[4,5-e]azepin-2-ylamino]-2-methyl-benzoic acid |
| IV-123 | 6-[9-Chloro-7-(2-fluoro-phenyl)-5H-benzo[c]pyrimido[4,5-e]azepin-2-ylamino]-nicotinic acid |
| IV-124 | 4-[9-Chloro-7-(2-fluoro-phenyl)-5H-benzo[c]pyrimido[4,5-e]azepin-2-ylamino]-N-(2-morpholin-4-yl-ethyl)-benzenesulfonamide |
| IV-125 | 2-Chloro-5-[9-chloro-7-(2-fluoro-phenyl)-5H-benzo[c]pyrimido[4,5-e]azepin-2-ylamino]-benzoic acid |

TABLE 3-continued

Examples of Compounds of Formula (IV)

| | |
|---|---|
| IV-126 | {4-[9-Chloro-7-(2-fluoro-phenyl)-5H-benzo[c]pyrimido[4,5-e]azepin-2-ylamino]-phenyl}-acetic acid |
| IV-127 | 4-[9-Chloro-7-(2-fluoro-phenyl)-5H-benzo[c]pyrimido[4,5-e]azepin-2-ylamino]-2-trifluoromethyl-benzoic acid |
| IV-128 | 4-[9-Chloro-7-(2-fluoro-phenyl)-5H-benzo[c]pyrimido[4,5-e]azepin-2-ylamino]-N-methyl-N-(1-methyl-piperidin-4-yl)-benzamide |
| IV-129 | N-(3-Amino-propyl)-4-[9-chloro-7-(2-fluoro-phenyl)-5H-benzo[c]pyrimido-[4,5-e]azepin-2-ylamino]-benzamide |
| IV-130 | 4-[9-Chloro-7-(2-fluoro-phenyl)-5H-benzo[c]pyrimido[4,5-e]azepin-2-ylamino]-N-(3-methylamino-propyl)-benzamide |
| IV-131 | N-(2-Amino-2-methyl-propyl)-4-[9-chloro-7-(2-fluoro-phenyl)-5H-benzo[c]pyrimido[4,5-e]azepin-2-ylamino]-benzamide |
| IV-132 | 2-(3,4-Dimethoxy-phenylamino)-7-(2-fluoro-phenyl)-5H-benzo[c]pyrimido-[4,5-e]azepine-10-carboxylic acid |
| IV-133 | 4-[9-Chloro-7-(2-fluoro-phenyl)-5H-benzo[c]pyrimido[4,5-e]azepin-2-ylamino]-2-methyl-benzoic acid |
| IV-134 | 2-Chloro-4-[9-chloro-7-(2-fluoro-phenyl)-5H-benzo[c]pyrimido[4,5-e]azepin-2-ylamino]-benzoic acid |
| IV-135 | 4-[9-Chloro-7-(2,6-difluoro-phenyl)-5H-benzo[c]pyrimido[4,5-e]azepin-2-ylamino]-benzoic acid |
| IV-136 | 4-[9-Chloro-7-(2-fluoro-phenyl)-5H-benzo[c]pyrimido[4,5-e]azepin-2-ylamino]-2-fluoro-benzoic acid |
| IV-137 | 4-[7-(2-Fluoro-phenyl)-9-methoxy-5H-benzo[c]pyrimido[4,5-e]azepin-2-ylamino]-benzoic acid |
| IV-138 | (3,4-Dimethoxy-phenyl)-[7-(2-fluoro-phenyl)-9-methoxy-5H-benzo[c]pyrimido-[4,5-e]azepin-2-yl]-amine |
| IV-139 | [9,10-Dichloro-7-(2-fluoro-phenyl)-5H-benzo[c]pyrimido[4,5-e]azepin-2-yl]-(3,4-dimethoxy-phenyl)-amine |
| IV-140 | 4-[9,10-Dichloro-7-(2-fluoro-phenyl)-5H-benzo[c]pyrimido[4,5-e]azepin-2-ylamino]-benzoic acid |
| IV-141 | 4-[9-Chloro-7-(2-fluoro-phenyl)-5H-benzo[c]pyrimido[4,5-e]azepin-2-ylamino]-2-methoxy-benzoic acid |
| IV-142 | N-(2-Amino-ethyl)-4-[9-chloro-7-(2-fluoro-phenyl)-5H-benzo[c]pyrimido-[4,5-e]azepin-2-ylamino]-benzamide |
| IV-143 | 4-(9-Chloro-7-phenyl-5H-benzo[c]pyrimido[4,5-e]azepin-2-ylamino)-benzoic acid |
| IV-144 | [7-(2-Bromo-phenyl)-9-chloro-5H-benzo[c]pyrimido[4,5-e]azepin-2-yl]-(3,4-dimethoxy-phenyl)-amine |
| IV-145 | 2-{4-[9-Chloro-7-(2-fluoro-phenyl)-5H-benzo[c]pyrimido[4,5-e]azepin-2-ylamino]-phenyl}-1-(4-methyl-piperazin-1-yl)-ethanone |
| IV-146 | 3-[9-Chloro-7-(2-fluoro-phenyl)-5H-benzo[c]pyrimido[4,5-e]azepin-2-ylamino]-benzoic acid |
| IV-147 | 4-[9-Chloro-7-(2-fluoro-phenyl)-5H-benzo[c]pyrimido[4,5-e]azepin-2-ylamino]-N-[2-(1H-imidazol-4-yl)-ethyl]-benzamide |
| IV-148 | 4-[7-(2-Fluoro-phenyl)-9-methyl-5H-benzo[c]pyrimido[4,5-e]azepin-2-ylamino]-N-(2-morpholin-4-yl-ethyl)-benzamide |
| IV-149 | {3-[9-Chloro-7-(2-fluoro-phenyl)-5H-benzo[c]pyrimido[4,5-e]azepin-2-ylamino]-phenyl}-acetic acid |
| IV-150 | 4-[9-Chloro-7-(2-fluoro-phenyl)-5H-benzo[c]pyrimido[4,5-e]azepin-2-ylamino]-N-(2-pyridin-4-yl-ethyl)-benzamide |
| IV-151 | 4-[9-Chloro-7-(2-fluoro-phenyl)-5H-benzo[c]pyrimido[4,5-e]azepin-2-ylamino]-N-(2-pyridin-3-yl-ethyl)-benzamide |
| IV-152 | (9-Chloro-7-phenyl-5H-benzo[c]pyrimido[4,5-e]azepin-2-yl)-(3,4-dimethoxy-phenyl)-amine |
| IV-153 | 4-[7-(2-Fluoro-phenyl)-10-methyl-5H-benzo[c]pyrimido[4,5-e]azepin-2-ylamino]-benzoic acid |
| IV-154 | (3,4-Dimethoxy-phenyl)-[7-(2-fluoro-phenyl)-5H-benzo[c]pyrimido-[4,5-e]azepin-2-yl]-amine |
| IV-155 | 4-[9-Chloro-7-(4-methoxy-phenyl)-5H-benzo[c]pyrimido[4,5-e]azepin-2-ylamino]-benzoic acid |
| IV-156 | 4-[9-Chloro-7-(3-methoxy-phenyl)-5H-benzo[c]pyrimido[4,5-e]azepin-2-ylamino]-benzoic acid |
| IV-157 | 4-[9-Chloro-7-(3-fluoro-phenyl)-5H-benzo[c]pyrimido[4,5-e]azepin-2-ylamino]-N-[3-(4-methyl-piperazin-1-yl)-propyl]-benzamide |
| IV-158 | 4-[9-Chloro-7-(3-fluoro-phenyl)-5H-benzo[c]pyrimido[4,5-e]azepin-2-ylamino]-N-(2-morpholin-4-yl-ethyl)-benzamide |
| IV-159 | {4-[9-Chloro-7-(3-fluoro-phenyl)-5H-benzo[c]pyrimido[4,5-e]azepin-2-ylamino]-phenyl}-(4-methyl-piperazin-1-yl)-methanone |
| IV-160 | 4-[9-Chloro-7-(2-fluoro-phenyl)-5H-benzo[c]pyrimido[4,5-e]azepin-2-ylamino]-N-methyl-N-(2-pyridin-2-yl-ethyl)-benzamide |
| IV-161 | 4-[9-Chloro-7-(2-fluoro-phenyl)-5H-benzo[c]pyrimido[4,5-e]azepin-2-ylamino]-N-(2-pyridin-2-yl-ethyl)-benzamide |
| IV-162 | 4-[9-Chloro-7-(3-fluoro-phenyl)-5H-benzo[c]pyrimido[4,5-e]azepin-2-ylamino]-benzoic acid |
| IV-163 | {3-[9-Chloro-7-(2-fluoro-phenyl)-5H-benzo[c]pyrimido[4,5-e]azepin-2-ylamino]-phenyl}-(4-methyl-piperazin-1-yl)-methanone |
| IV-164 | 9-Chloro-7-(2-fluorophenyl)-N-{4-[(4-pyridin-2-ylpiperazin-1-yl)carbonyl]phenyl}-5H-pyrimido[5,4-d][2]benzazepin-2-amine |
| IV-165 | 9-Chloro-7-(2-fluorophenyl)-N-(4-{[4-(2-morpholin-4-yl-2-oxoethyl)piperazin-1-yl]carbonyl}phenyl)-5H-pyrimido[5,4-d][2]benzazepin-2-amine |
| IV-166 | 9-Chloro-7-(2-fluorophenyl-N-(4-{[4-(2-furoyl)piperazin-1-yl]carbonyl}phenyl)-5H-pyrimido[5,4-d][2]benzazepin-2-amine |
| IV-167 | Benzyl-4-(4-{[9-chloro-7-(2-fluorophenyl)-5H-pyrimido[5,4-d][2]benzazepin-2-yl]amino}benzoyl)piperazine-1-carboxylate |
| IV-168 | Ethyl-4-(4-{[9-chloro-7-(2-fluorophenyl)-5H-pyrimido[5,4-d][2]benzazepin-2-yl]amino}benzoyl)piperazine-1-carboxylate |
| IV-169 | 2-[4-(4-{[9-Chloro-7-(2-fluorophenyl)-5H-pyrimido[5,4-d][2]benzazepin-2-yl]amino}benzoyl)piperazin-1-yl]benzoic acid |
| IV-170 | 2-[4-(4-{[9-Chloro-7-(2-fluorophenyl)-5H-pyrimido[5,4-d][2]benzazepin-2-yl]amino}benzoyl)piperazin-1-yl]-N-isopropylacetamide |
| IV-171 | 9-Chloro-7-(2-fluorophenyl)-N-(4-{[4-(2-pyrrolidin-1-ylethyl)piperazin-1-yl]carbonyl}phenyl)-5H-pyrimido[5,4-d][2]benzazepin-2-amine |
| IV-172 | N-[2-(aminocarbonyl)phenyl]-4-{[9-chloro-7-(2-fluorophenyl)-5H-pyrimido-[5,4-d][2]benzazepin-2-yl]amino}benzamide |
| IV-173 | 9-Chloro-7-(2-fluorophenyl)-N-{4-[(4-pyrimidin-2-ylpiperazin-1-yl)carbonyl]phenyl}-5H-pyrimido[5,4-d][2]benzazepin-2-amine |
| IV-174 | 4-{[9-Chloro-7-(2-chloro-6-fluorophenyl)-5H-pyrimido[5,4-d][2]benzazepin-2-yl]amino}benzoic acid |
| IV-175 | 9-Chloro-7-(2,6-difluorophenyl)-N-{4-[3,5-dimethylpiperazin-1-yl)carbonyl]phenyl}-5H-pyrimido[5,4-d][2]benzazepin-2-amine |
| IV-176 | 9-Chloro-7-(2,6-difluorophenyl)-N-(4-{[3-(dimethylamino)pyrrolidin-1-yl]carbonyl}phenyl)-5H-pyrimido[5,4-d][2]benzazepin-2-amine |
| IV-177 | 9-Chloro-N-{4-[(3,5-dimethylpiperazin-1-yl)carbonyl]phenyl}-7-(2-fluoro-6-methoxyphenyl)-5H-pyrimido[5,4-d][2]benzazepin-2-amine |
| IV-178 | 9-Chloro-N-(4-{[3-(dimethylamino)pyrrolidin-1-yl]carbonyl}phenyl)-7-(2-fluoro-6-methoxyphenyl)-5H-pyrimido[5,4-d][2]benzazepin-2-amine |
| IV-179 | 9-Chloro-N-(4-{[3-(dimethylamino)azetidin-1-yl]carbonyl}phenyl)-7-(2-fluoro-6-methoxyphenyl)-5H-pyrimido[5,4-d][2]benzazepin-2-amine |
| IV-180 | 9-Chloro-7-(2,6-difluorophenyl)-N-(4-{[3-(dimethylamino)azetidin-1-yl]carbonyl}phenyl)-5H-pyrimido[5,4-d][2]benzazepin-2-amine |
| IV-181 | {4-[9-Chloro-7-(2-fluoro-phenyl)-5H-benzo[c]pyrimido[4,5-e]azepin-2-ylamino]-phenyl}-[4-(3-piperidin-1-yl-propyl)-piperazin-1-yl]-methanone |
| IV-182 | {4-[9-Chloro-7-(2-fluoro-phenyl)-5H-benzo[c]pyrimido[4,5-e]azepin-2-ylamino]-phenyl}-[4-(2-piperidin-1-yl-ethyl)-piperazin-1-yl]-methanone |
| IV-183 | {4-[9-Chloro-7-(2,6-difluoro-phenyl)-5H-benzo[c]pyrimido[4,5-e]azepin-2-ylamino]-phenyl}-(4-dimethylamino-piperidin-1-yl)-methanone |
| IV-184 | {4-[9-Chloro-7-(2,6-difluoro-phenyl)-5H-benzo[c]pyrimido[4,5-e]azepin-2-ylamino]-phenyl}-(4-methyl-piperazin-1-yl)-methanone |
| IV-185 | 4-[9-Chloro-7-(2,6-difluoro-phenyl)-5H-benzo[c]pyrimido[4,5-e]azepin-2-ylamino]-N-(3-dimethylamino-propyl)-N-methyl-benzamide |
| IV-186 | {4-[9-Chloro-7-(2-fluoro-6-methoxy-phenyl)-5H-benzo[c]pyrimido-[4,5-e]azepin-2-ylamino]-phenyl}-(4-dimethylamino-piperidin-1-yl)-methanone |
| IV-187 | {4-[9-Chloro-7-(2-fluoro-phenyl)-5H-benzo[c]pyrimido[4,5-e]azepin-2-ylamino]-phenyl}-[4-(2-dipropylamino-ethyl)-piperazin-1-yl]-methanone |
| IV-188 | {4-[9-Chloro-7-(2-fluoro-phenyl)-5H-benzo[c]pyrimido[4,5-e]azepin-2-ylamino]-phenyl}-[4-(3-pyrrolidin-1-yl-propyl)-piperazin-1-yl]-methanone |
| IV-189 | {4-[9-Chloro-7-(2-fluoro-phenyl)-5H-benzo[c]pyrimido[4,5-e]azepin-2-ylamino]-phenyl}-[4-(2-morpholin-4-yl-ethyl)-piperazin-1-yl]-methanone |

TABLE 3-continued

Examples of Compounds of Formula (IV)

| | |
|---|---|
| IV-190 | 4-[9-Chloro-7-(2-fluoro-6-methoxy-phenyl)-5H-benzo[c]pyrimido[4,5-e]azepin-2-ylamino]-benzoic acid |
| IV-191 | {4-[9-Chloro-7-(2,6-difluoro-phenyl)-5H-benzo[c]pyrimido[4,5-e]azepin-2-ylamino]-phenyl}-(3(S)-methyl-piperazin-1-yl)-methanone |
| IV-192 | (3-Amino-azetidin-1-yl)-{4-[9-chloro-7-(2-fluoro-phenyl)-5H-benzo[c]pyrimido[4,5-e]azepin-2-ylamino]-phenyl}-methanone |
| IV-193 | {4-[9-Chloro-7-(2-fluoro-phenyl)-5H-benzo[c]pyrimido[4,5-e]azepin-2-ylamino]-phenyl}-(3-dimethylaminomethyl-azetidin-1-yl)-methanone |
| IV-194 | {4-[9-Chloro-7-(2,6-difluoro-phenyl)-5H-benzo[c]pyrimido[4,5-e]azepin-2-ylamino]-phenyl}-(3(R)-methyl-piperazin-1-yl)-methanone |
| IV-195 | {4-[9-Chloro-7-(2,6-difluoro-phenyl)-5H-benzo[c]pyrimido[4,5-e]azepin-2-ylamino]-phenyl}-piperazin-1-yl-methanone |
| IV-196 | (3-Amino-pyrrolidin-1-yl)-{4-[9-chloro-7-(2,6-difluoro-phenyl)-5H-benzo[c]pyrimido[4,5-e]azepin-2-ylamino]-phenyl}-methanone |
| IV-197 | {4-[9-Chloro-7-(2,6-difluoro-phenyl)-5H-benzo[c]pyrimido[4,5-e]azepin-2-ylamino]-phenyl}-(3-methylamino-pyrrolidin-1-yl)-methanone |
| IV-198 | 4-[9-Chloro-7-(2,6-difluoro-phenyl)-5H-benzo[c]pyrimido[4,5-e]azepin-2-ylamino]-N-methyl-N-(3-methylamino-propyl)-benzamide |
| IV-199 | {4-[9-Chloro-7-(2-fluoro-6-methoxy-phenyl)-5H-benzo[c]pyrimido[4,5-e]azepin-2-ylamino]-phenyl}-(3-methylamino-pyrrolidin-1-yl)-methanone |
| IV-200 | 4-[9-Chloro-7-(2-fluoro-phenyl)-5H-benzo[c]pyrimido[4,5-e]azepin-2-ylamino]-cyclohexanecarboxylic acid |
| IV-201 | 9-chloro-N-(4-{[4-(2-ethoxyphenyl)piperazin-1-yl]carbonyl}phenyl)-7-(2-fluorophenyl)-5H-pyrimido[5,4-d][2]benzazepin-2-amine |
| IV-202 | N-[amino(imino)methyl]-4-{[9-chloro-7-(2,6-difluorophenyl)-5H-pyrimido[5,4-d][2]benzazepin-2-yl]amino}benzamide |
| IV-203 | 3-{[9-chloro-7-(2,6-difluorophenyl)-5H-pyrimido[5,4-d][2]benzazepin-2-yl]amino}benzoic acid |
| IV-204 | 9-chloro-7-(2,6-difluorophenyl)-N-(3-{[3-(dimethylamino)azetidin-1-yl]carbonyl}phenyl)-5H-pyrimido[5,4-d][2]benzazepin-2-amine |
| IV-205 | 9-chloro-7-(2,6-difluorophenyl)-N-(3-{[4-(dimethylamino)piperidin-1-yl]carbonyl}phenyl)-5H-pyrimido[5,4-d][2]benzazepin-2-amine |
| IV-206 | 9-chloro-7-(2,6-difluorophenyl)-N-(3-{[3-(dimethylamino)pyrrolidin-1-yl]carbonyl}phenyl)-5H-pyrimido[5,4-d][2]benzazepin-2-amine |
| IV-207 | N-[2-(aminomethyl)-1,3-benzoxazol-5-yl]-9-chloro-7-(2,6-difluorophenyl)-5H-pyrimido[5,4-d][2]benzazepin-2-amine |
| IV-208 | 9-chloro-N-[4-({4-[3-(diethylamino)propyl]piperazin-1-yl}carbonyl)phenyl]-7-(2-fluorophenyl)-5H-pyrimido[5,4-d][2]benzazepin-2-amine |
| IV-209 | 9-chloro-N-[4-({4-[2-(diethylamino)ethyl]piperazin-1-yl}carbonyl)phenyl]-7-(2-fluorophenyl)-5H-pyrimido[5,4-d][2]benzazepin-2-amine |
| IV-210 | 9-chloro-N-[4-({4-[3-(dimethylamino)propyl]piperazin-1-yl}carbonyl)phenyl]-7-(2-fluorophenyl)-5H-pyrimido[5,4-d][2]benzazepin-2-amine |
| IV-211 | 9-chloro-7-(2-fluorophenyl)-N-[4-({4-[(1-methylpiperidin-3-yl)methyl]piperazin-1-yl}carbonyl)phenyl]-5H-pyrimido[5,4-d][2]benzazepin-2-amine |
| IV-212 | 9-chloro-7-(2,6-difluorophenyl)-N-(4-nitrophenyl)-5H-pyrimido[5,4-d][2]benzazepin-2-amine |
| IV-213 | 9-chloro-N-(3-chloro-4-{[4-(2-pyrrolidin-1-ylethyl)piperazin-1-yl]carbonyl}phenyl)-7-(2-fluorophenyl)-5H-pyrimido[5,4-d][2]benzazepin-2-amine |
| IV-214 | 9-chloro-N-{3-chloro-4-[(3-methylpiperazin-1-yl)carbonyl]phenyl}-7-(2-fluorophenyl)-5H-pyrimido[5,4-d][2]benzazepin-2-amine |
| IV-215 | 9-chloro-N-(3-chloro-4-{[3-(dimethylamino)pyrrolidin-1-yl]carbonyl}phenyl)-7-(2,6-difluorophenyl)-5H-pyrimido[5,4-d][2]benzazepin-2-amine |
| IV-216 | 9-chloro-N-{3-chloro-4-[(3-methylpiperazin-1-yl)carbonyl]phenyl}-7-(2,6-difluorophenyl)-5H-pyrimido[5,4-d][2]benzazepin-2-amine |
| IV-217 | N-[9-chloro-7-(2,6-difluorophenyl)-5H-pyrimido[5,4-d][2]benzazepin-2-yl]benzene-1,4-diamine |
| IV-218 | methyl 2-chloro-4-{[9-chloro-7-(2,6-difluorophenyl)-5H-pyrimido[5,4-d][2]benzazepin-2-yl]amino}benzoate |
| IV-219 | 1-(4-{[9-chloro-7-(2,6-difluorophenyl)-5H-pyrimido[5,4-d][2]benzazepin-2-yl]amino}benzoyl)piperazine-2-carboxylic acid |
| IV-220 | 9-chloro-7-(2,6-difluorophenyl)-N-(4-{[4-(methylamino)piperidin-1-yl]carbonyl}phenyl)-5H-pyrimido[5,4-d][2]benzazepin-2-amine |
| IV-221 | N-{4-[(3-aminopiperidin-1-yl)carbonyl]phenyl}-9-chloro-7-(2,6-difluorophenyl)-5H-pyrimido[5,4-d][2]benzazepin-2-amine |
| IV-222 | 9-chloro-7-(2,6-difluorophenyl)-N-{3-[(3,5-dimethylpiperazin-1-yl)carbonyl]phenyl}-5H-pyrimido[5,4-d][2]benzazepin-2-amine |
| IV-223 | 4-{[9-chloro-7-(2,6-difluorophenyl)-5H-pyrimido[5,4-d][2]benzazepin-2-yl]amino}-N-[[4-(dimethylamino)piperidin-1-yl](imino)methyl]benzamide |
| IV-224 | 4-{[9-chloro-7-(2,6-difluorophenyl)-5H-pyrimido[5,4-d][2]benzazepin-2-yl]amino}-N-[imino(piperazin-1-yl)methyl]benzamide |
| IV-225 | 4-{[9-chloro-7-(2-fluoro-6-methoxyphenyl)-5H-pyrimido[5,4-d][2]benzazepin-2-yl]amino}-N-[3-(dimethylamino)propyl]-N-methylbenzamide |
| IV-226 | 3-{[9-chloro-7-(2-fluoro-6-methoxyphenyl)-5H-pyrimido[5,4-d][2]benzazepin-2-yl]amino}-N-[3-(dimethylamino)propyl]-N-methylbenzamide |
| IV-227 | 9-chloro-N-(3-{[3-(dimethylamino)azetidin-1-yl]carbonyl}phenyl)-7-(2-fluoro-6-methoxyphenyl)-5H-pyrimido[5,4-d][2]benzazepin-2-amine |
| IV-228 | 9-chloro-N-{3-[(3,5-dimethylpiperazin-1-yl)carbonyl]phenyl}-7-(2-fluoro-6-methoxyphenyl)-5H-pyrimido[5,4-d][2]benzazepin-2-amine |
| IV-229 | 9-chloro-N-(3-{[4-(dimethylamino)piperidin-1-yl]carbonyl}phenyl)-7-(2-fluoro-6-methoxyphenyl)-5H-pyrimido[5,4-d][2]benzazepin-2-amine |
| IV-230 | N-(4-{[3-(aminomethyl)azetidin-1-yl]carbonyl}phenyl)-9-chloro-7-(2-fluorophenyl)-5H-pyrimido[5,4-d][2]benzazepin-2-amine |
| IV-231 | 9-chloro-N-(3-{[3-(dimethylamino)pyrrolidin-1-yl]carbonyl}phenyl)-7-(2-fluoro-6-methoxyphenyl)-5H-pyrimido[5,4-d][2]benzazepin-2-amine |
| IV-232 | 9-chloro-7-(2-fluoro-6-methoxyphenyl)-N-{4-[(3-methylpiperazin-1-yl)carbonyl]phenyl}-5H-pyrimido[5,4-d][2]benzazepin-2-amine |
| IV-233 | 9-chloro-7-(2-fluoro-6-methoxyphenyl)-N-{4-[(4-methylpiperazin-1-yl)carbonyl]phenyl}-5H-pyrimido[5,4-d][2]benzazepin-2-amine |
| IV-234 | 9-chloro-7-(2,6-difluorophenyl)-N-(4-{[3-(methylamino)azetidin-1-yl]carbonyl}phenyl)-5H-pyrimido[5,4-d][2]benzazepin-2-amine |
| IV-235 | 9-chloro-7-(2-fluoro-6-methoxyphenyl)-N-(4-{[3-(methylamino)azetidin-1-yl]carbonyl}phenyl)-5H-pyrimido[5,4-d][2]benzazepin-2-amine |
| IV-236 | 4-{[9-chloro-7-(2,6-difluorophenyl)-5H-pyrimido[5,4-d][2]benzazepin-2-yl]amino}benzonitrile |
| IV-237 | 4-{[9-chloro-7-(2,6-difluorophenyl)-5H-pyrimido[5,4-d][2]benzazepin-2-yl]amino}-N-[[3-(dimethylamino)pyrrolidin-1-yl](imino)methyl]benzamide |
| IV-238 | 4-{[9-chloro-7-(2,6-difluorophenyl)-5H-pyrimido[5,4-d][2]benzazepin-2-yl]amino}-N-[(3,5-dimethylpiperazin-1-yl)(imino)methyl]benzamide |
| IV-239 | N-{4-[(4-aminopiperidin-1-yl)carbonyl]phenyl}-9-chloro-7-(2,6-difluorophenyl)-5H-pyrimido[5,4-d][2]benzazepin-2-amine |
| IV-240 | N-{4-[3-aminopyrrolidin-1-yl)carbonyl]phenyl}-9-chloro-7-(2-fluoro-6-methoxyphenyl)-5H-pyrimido[5,4-d][2]benzazepin-2-amine |
| IV-241 | N-{4-[(4-aminopiperidin-1-yl)carbonyl]phenyl}-9-chloro-7-(2-fluoro-6-methoxyphenyl)-5H-pyrimido[5,4-d][2]benzazepin-2-amine |
| IV-242 | 9-chloro-7-(2-fluoro-6-methoxyphenyl)-N-(4-{[4-(methylamino)piperidin-1-yl]carbonyl}phenyl)-5H-pyrimido[5,4-d][2]benzazepin-2-amine |
| IV-243 | 9-chloro-7-(2-fluoro-6-methoxyphenyl)-N-[4-(piperazin-1-ylcarbonyl)phenyl]-5H-pyrimido[5,4-d][2]benzazepin-2-amine |
| IV-244 | 9-chloro-7-(2,6-difluorophenyl)-N-{4-[[4-(dimethylamino)piperidin-1-yl](imino)methyl]phenyl}-5H-pyrimido[5,4-d][2]benzazepin-2-amine |
| IV-245 | N-(4-{[9-chloro-7-(2,6-difluorophenyl)-5H-pyrimido[5,4-d][2]benzazepin-2-yl]amino}phenyl)guanidine |
| IV-246 | 4-{[9-chloro-7-(2,6-difluorophenyl)-5H-pyrimido[5,4-d][2]benzazepin-2-yl]amino}-N-methyl-N-[2-(methylamino)ethyl]benzamide |

TABLE 3-continued

Examples of Compounds of Formula (IV)

| | |
|---|---|
| IV-247 | 4-{[9-chloro-7-(2,6-difluorophenyl)-5H-pyrimido[5,4-d][2]benzazepin-2-yl]amino}-N-[2-(dimethylamino)ethyl]-N-methylbenzamide |
| IV-248 | methyl 4-(4-{[9-chloro-7-(2,6-difluorophenyl)-5H-pyrimido[5,4-d][2]benzazepin-2-yl]amino}benzoyl)piperazine-2-carboxylate |
| IV-249 | 2-[(4-carboxyphenyl)amino]-7-(2-fluorophenyl)-5H-pyrimido[5,4-d][2]benzazepine-9-carboxylic acid |
| IV-250 | 9-chloro-7-(2,6-difluorophenyl)-N-{4-[[3-(dimethylamino)pyrrolidin-1-yl](imino)methyl]phenyl}-5H-pyrimido[5,4-d][2]benzazepin-2-amine |
| IV-251 | 9-chloro-7-(2,6-difluorophenyl)-N-{4-[(3,5-dimethylpiperazin-1-yl)(imino)methyl]phenyl}-5H-pyrimido[5,4-d][2]benzazepin-2-amine |
| IV-252 | N-(2-aminoethyl)-4-{[9-chloro-7-(2,6-difluorophenyl)-5H-pyrimido[5,4-d][2]benzazepin-2-yl]amino}-N-methylbenzamide |
| IV-253 | 9-chloro-7-(2,6-difluorophenyl)-N-(4-{[3-(methylamino)piperidin-1-yl]carbonyl}phenyl)-5H-pyrimido[5,4-d][2]benzazepin-2-amine |
| IV-254 | 4-{[9-chloro-7-(2-fluoro-6-methoxyphenyl)-5H-pyrimido[5,4-d][2]benzazepin-2-yl]amino}-N-methyl-N-[2-(methylamino)ethyl]benzamide |
| IV-255 | 4-{[9-chloro-7-(2-fluoro-6-methoxyphenyl)-5H-pyrimido[5,4-d][2]benzazepin-2-yl]amino}-N-[2-(dimethylamino)ethyl]-N-methylbenzamide |
| IV-256 | 7-(2-fluorophenyl)-2-[(3-methoxyphenyl)amino]-5H-pyrimido[5,4-d][2]benzazepine-9-carboxylic acid |
| IV-257 | N-(3-aminopropyl)-4-{[9-chloro-7-(2,6-difluorophenyl)-5H-pyrimido[5,4-d][2]benzazepin-2-yl]amino}-N-methylbenzamide |
| IV-258 | 2-chloro-5-{[9-chloro-7-(2,6-difluorophenyl)-5H-pyrimido[5,4-d][2]benzazepin-2-yl]amino}benzoic acid |
| IV-259 | 4-{[9-chloro-7-(2,6-difluorophenyl)-5H-pyrimido[5,4-d][2]benzazepin-2-yl]amino}-N-[[3-(dimethylamino)azetidin-1-yl](imino)methyl]benzamide |
| IV-260 | N-(2-amino-2-methylpropyl)-4-{[9-chloro-7-(2,6-difluorophenyl)-5H-pyrimido[5,4-d][2]benzazepin-2-yl]amino}benzamide |
| IV-261 | 4-{[9-chloro-7-(2-fluoro-6-methoxyphenyl)-5H-pyrimido[5,4-d][2]benzazepin-2-yl]amino}-N-methyl-N-[3-(methylamino)propyl]benzamide |
| IV-262 | N-{4-[3-aminopiperidin-1-yl)carbonyl]phenyl}-9-chloro-7-(2-fluoro-6-methoxyphenyl)-5H-pyrimido[5,4-d][2]benzazepin-2-amine |
| IV-263 | 9-chloro-7-(2-fluoro-6-methoxyphenyl)-N-(4-{[3-(methylamino)piperidin-1-yl]carbonyl}phenyl)-5H-pyrimido[5,4-d][2]benzazepin-2-amine |
| IV-264 | N-(3-aminopropyl)-4-{[9-chloro-7-(2-fluoro-6-methoxyphenyl)-5H-pyrimido[5,4-d][2]benzazepin-2-yl]amino}-N-methylbenzamide |
| IV-265 | N-(2-aminoethyl)-4-{[9-chloro-7-(2-fluoro-6-methoxyphenyl)-5H-pyrimido[5,4-d][2]benzazepin-2-yl]amino}-N-methylbenzamide |
| IV-266 | 4-(4-{[9-chloro-7-(2,6-difluorophenyl)-5H-pyrimido[5,4-d][2]benzazepin-2-yl]amino}benzoyl)piperazine-2-carboxylic acid |
| IV-267 | 9-chloro-7-(2,6-difluorophenyl)-N-{4-[[3-(dimethylamino)azetidin-1-yl](imino)methyl]phenyl}-5H-pyrimido[5,4-d][2]benzazepin-2-amine |
| IV-268 | 9-chloro-7-(2,6-difluorophenyl)-N-(4-{imino[3-(methylamino)pyrrolidin-1-yl]methyl}phenyl)-5H-pyrimido[5,4-d][2]benzazepin-2-amine |
| IV-269 | 9-chloro-N-(4-chloro-3-{[4-(dimethylamino)piperidin-1-yl]carbonyl}phenyl)-7-(2,6-difluorophenyl)-5H-pyrimido[5,4-d][2]benzazepin-2-amine |
| IV-270 | 9-chloro-7-(2,6-difluorophenyl)-N-[4-(5,5-dimethyl-4,5-dihydro-1H-imidazol-2-yl)phenyl]-5H-pyrimido[5,4-d][2]benzazepin-2-amine |
| IV-271 | N-[9-chloro-7-(2,6-difluorophenyl)-5H-pyrimido[5,4-d][2]benzazepin-2-yl]-N'-pyrimidin-2-ylbenzene-1,4-diamine |
| IV-272 | 4-{[9-(3-aminoprop-1-yn-1-yl)-7-(2,6-difluorophenyl)-5H-pyrimido[5,4-d][2]benzazepin-2-yl]amino}benzoic acid |
| IV-273 | 9-bromo-7-(2,6-difluorophenyl)-N-(3-methoxyphenyl)-5H-pyrimido[5,4-d][2]benzazepin-2-amine |
| IV-274 | 4-{[9-bromo-7-(2,6-difluorophenyl)-5H-pyrimido[5,4-d][2]benzazepin-2-yl]amino}benzoic acid |
| IV-275 | 7-(2,6-difluorophenyl)-N-(3-methoxyphenyl)-9-(3-pyrrolidin-1-ylprop-1-yn-1-yl)-5H-pyrimido[5,4-d][2]benzazepin-2-amine |
| IV-276 | 9-(3-aminoprop-1-yn-1-yl)-7-(2,6-difluorophenyl)-N-(3-methoxyphenyl)-5H-pyrimido[5,4-d][2]benzazepin-2-amine |
| IV-277 | 4-({9-chloro-7-(2-(trifluoromethyl)phenyl]-5H-pyrimido[5,4-d][2]benzazepin-2-yl}amino)benzoic acid |
| IV-278 | N-{4-[(3-aminoazetidin-1-yl)carbonyl]phenyl}-9-chloro-7-(2,6-difluorophenyl)-5H-pyrimido[5,4-d][2]benzazepin-2-amine |
| IV-279 | 4-[(9-chloro-7-pyridin-2-yl-5H-pyrimido[5,4-d][2]benzazepin-2-yl)amino]benzoic acid |
| IV-280 | N-(4-{[9-chloro-7-(2,6-difluorophenyl)-5H-pyrimido[5,4-d][2]benzazepin-2-yl]amino}phenyl)-4-methylpiperazine-1-carboxamide |
| IV-281 | 9-chloro-N-(4-chloro-3-{[3-(methylamino)pyrrolidin-1-yl]carbonyl}phenyl)-7-(2,6-difluorophenyl)-5H-pyrimido[5,4-d][2]benzazepin-2-amine |
| IV-282 | 9-chloro-N-(4-chloro-3-{[4-(methylamino)piperidin-1-yl]carbonyl}phenyl)-7-(2,6-difluorophenyl)-5H-pyrimido[5,4-d][2]benzazepin-2-amine |
| IV-283 | 2-chloro-5-{[9-chloro-7-(2,6-difluorophenyl)-5H-pyrimido[5,4-d][2]benzazepin-2-yl]amino}-N-methyl-N-(2-(methylamino)ethyl]benzamide |
| IV-284 | N-{4-[(3-aminopyrrolidin-1-yl)(imino)methyl]phenyl}-9-chloro-7-(2,6-difluorophenyl)-5H-pyrimido[5,4-d][2]benzazepin-2-amine |
| IV-285 | 2-(4-{[9-chloro-7-(2,6-difluorophenyl)-5H-pyrimido[5,4-d][2]benzazepin-2-yl]amino}phenyl)-1,4,5,6-tetrahydropyrimidin-5-ol |
| IV-286 | N-{4-[(3-aminoazetidin-1-yl)carbonyl]phenyl}-9-chloro-7-(2-fluoro-6-methoxyphenyl)-5H-pyrimido[5,4-d][2]benzazepin-2-amine |
| IV-287 | N-{4-[(4-aminopiperidin-1-yl)carbonyl]phenyl}-9-chloro-7-[2-(trifluoromethyl)phenyl]-5H-pyrimido[5,4-d][2]benzazepin-2-amine |
| IV-288 | 9-chloro-N-(4-{[4-(methylamino)piperidin-1-yl]carbonyl}phenyl)-7-[2-(trifluoromethyl)phenyl]-5H-pyrimido[5,4-d][2]benzazepin-2-amine |
| IV-289 | N-{4-[(3-aminopyrrolidin-1-yl)carbonyl]phenyl}-9-chloro-7-[2-(trifluoromethyl)phenyl]-5H-pyrimido[5,4-d][2]benzazepin-2-amine |
| IV-290 | 9-chloro-N-(4-{[3-(methylamino)pyrrolidin-1-yl]carbonyl}phenyl)-7-[2-(trifluoromethyl)phenyl]-5H-pyrimido[5,4-d][2]benzazepin-2-amine |
| IV-291 | 9-chloro-N-(4-chloro-3-{[3-(methylamino)azetidin-1-yl]carbonyl}phenyl)-7-(2,6-difluorophenyl)-5H-pyrimido[5,4-d][2]benzazepin-2-amine |
| IV-292 | N-{3-[(4-aminopiperidin-1-yl)carbonyl]-4-chlorophenyl}-9-chloro-7-(2,6-difluorophenyl)-5H-pyrimido[5,4-d][2]benzazepin-2-amine |
| IV-293 | 9-chloro-7-(2,6-difluorophenyl)-N-(4-{[3-(dimethylamino)piperidin-1-yl]carbonyl}phenyl)-5H-pyrimido[5,4-d][2]benzazepin-2-amine |
| IV-294 | methyl 4-amino-1-(4-{[9-chloro-7-(2,6-difluorophenyl)-5H-pyrimido[5,4-d][2]benzazepin-2-yl]amino}benzoyl)piperidine-4-carboxylate |
| IV-295 | 4-amino-1-(4-{[9-chloro-7-(2,6-difluorophenyl)-5H-pyrimido[5,4-d][2]benzazepin-2-yl]amino}benzoyl)piperidine-4-carboxylic acid |
| IV-296 | N-{4-[(3-aminoazetidin-1-yl)carbonyl]phenyl}-9-chloro-7-[2-(trifluoromethyl)phenyl]-5H-pyrimido[5,4-d][2]benzazepin-2-amine |
| IV-297 | 9-chloro-N-(4-{[3-(methylamino)azetidin-1-yl]carbonyl}phenyl)-7-[2-(trifluoromethyl)phenyl]-5H-pyrimido[5,4-d][2]benzazepin-2-amine |
| IV-298 | N-{4-[(4-aminopiperidin-1-yl)carbonyl]phenyl}-9-chloro-7-pyridin-2-yl-5H-pyrimido[5,4-d][2]benzazepin-2-amine |
| IV-299 | N-{4-[(3-aminopyrrolidin-1-yl)carbonyl]phenyl}-9-chloro-7-pyridin-2-yl-5H-pyrimido[5,4-d][2]benzazepin-2-amine |
| IV-300 | ethyl 2-amino-4-[(4-{[9-chloro-7-(2,6-difluorophenyl)-5H-pyrimido[5,4-d][2]benzazepin-2-yl]amino}benzoyl)amino]butanoate |
| IV-301 | 4-{[9-chloro-7-(3-fluoropyridin-2-yl)-5H-pyrimido[5,4-d][2]benzazepin-2-yl]amino}benzoic acid |
| IV-302 | 9-{[3-(dimethylamino)azetidin-1-yl]carbonyl}-7-(2-fluorophenyl)-N-(3-methoxyphenyl)-5H-pyrimido[5,4-d][2]benzazepin-2-amine |

TABLE 3-continued

Examples of Compounds of Formula (IV)

| | |
|---|---|
| IV-303 | 7-(2-fluorophenyl)-2-[(3-methoxyphenyl)amino]-N-methyl-N-[3-(methylamino)propyl]-5H-pyrimido[5,4-d][2]benzazepine-9-carboxamide |
| IV-304 | N-{4-[4-aminopiperidin-1-yl]carbonyl]phenyl}-9-chloro-7-(3-fluoropyridin-2-yl)-5H-pyrimido[5,4-d][2]benzazepin-2-amine |
| IV-305 | N-{4-[(3-aminopyrrolidin-1-yl)carbonyl]phenyl}-9-chloro-7-(3-fluoropyridin-2-yl)-5H-pyrimido[5,4-d][2]benzazepin-2-amine |
| IV-306 | 2-(4-{[9-chloro-7-(2,6-difluorophenyl)-5H-pyrimido[5,4-d][2]benzazepin-2-yl]amino}phenyl)-4,5-dihydro-1H-imidazole-5-carboxylic acid |
| IV-307 | N-(4-{[9-chloro-7-(2,6-difluorophenyl)-5H-pyrimido[5,4-d][2]benzazepin-2-yl]amino}phenyl)-2-(dimethylamino)acetamide |
| IV-308 | 2-amino-N-(4-{[9-chloro-7-(2,6-difluorophenyl)-5H-pyrimido[5,4-d][2]benzazepin-2-yl]amino}phenyl)-2-methylpropanamide |
| IV-309 | ethyl (2R)-4-amino-2-[(4-{[9-chloro-7-(2,6-difluorophenyl)-5H-pyrimido[5,4-d][2]benzazepin-2-yl]amino}benzoyl)amino]butanoate |
| IV-310 | 4-(4-{[9-chloro-7-(2,6-difluorophenyl)-5H-pyrimido[5,4-d][2]benzazepin-2-yl]amino}benzoyl)-N-methylpiperazine-2-carboxamide |
| IV-311 | 7-(2-fluorophenyl)-2-[(3-methoxyphenyl)amino]-N-(3-morpholin-4-ylpropyl)-5H-pyrimido[5,4-d][2]benzazepine-9-carboxamide |
| IV-312 | 9-[(3,5-dimethylpiperazin-1-yl)carbonyl]-7-(2-fluorophenyl)-N-(3-methoxyphenyl)-5H-pyrimido[5,4-d][2]benzazepin-2-amine |
| IV-313 | 9-chloro-N-(3-chloro-4-{[4-(dimethylamino)piperidin-1-yl]carbonyl}phenyl)-7-(2,6-difluorophenyl)-5H-pyrimido[5,4-d][2]benzazepin-2-amine |
| IV-314 | ethyl 2-(4-{[9-chloro-7-(2,6-difluorophenyl)-5H-pyrimido[5,4-d][2]benzazepin-2-yl]amino}phenyl)-4,5-dihydro-1H-imidazole-5-carboxylate |
| IV-315 | 9-chloro-N-(4-{[3-(methylamino)pyrrolidin-1-yl]carbonyl}phenyl)-7-pyridin-2-yl-5H-pyrimido[5,4-d][2]benzazepin-2-amine |
| IV-316 | 9-chloro-N-(4-{[4-(methylamino)piperidin-1-yl]carbonyl}phenyl)-7-pyridin-2-yl-5H-pyrimido[5,4-d][2]benzazepin-2-amine |
| IV-317 | 4-(4-{[9-chloro-7-(2,6-difluorophenyl)-5H-pyrimido[5,4-d][2]benzazepin-2-yl]amino}benzoyl)piperazine-2-carboxamide |
| IV-318 | N-{4-[(3-aminopyrrolidin-1-yl)carbonyl]-3-chlorophenyl}-9-chloro-7-(2,6-difluorophenyl)-5H-pyrimido[5,4-d][2]benzazepin-2-amine |
| IV-319 | N-(4-{[9-chloro-7-(2,6-difluorophenyl)-5H-pyrimido[5,4-d][2]benzazepin-2-yl]amino}phenyl)piperidine-4-carboxamide |
| IV-320 | 4-{[9-chloro-7-(2-fluoro-6-{methyl[2-(methylamino)ethyl]amino}phenyl)-5H-pyrimido[5,4-d][2]benzazepin-2-yl]amino}benzoic acid |
| IV-321 | 9-chloro-7-(2,4-difluorophenyl)-N-{4-[(3,5-dimethylpiperazin-1-yl)carbonyl]phenyl}-5H-pyrimido[5,4-d][2]benzazepin-2-amine |
| IV-322 | 9-chloro-7-(2,4-dimethoxyphenyl)-N-{4-[(3,5-dimethylpiperazin-1-yl)carbonyl]phenyl}-5H-pyrimido[5,4-d][2]benzazepin-2-amine |
| IV-323 | 9-chloro-7-(2-chloro-6-fluorophenyl)-N-{4-[(3-methylpiperazin-1-yl)carbonyl]phenyl}-5H-pyrimido[5,4-d][2]benzazepin-2-amine |
| IV-324 | 9-chloro-7-(2-chloro-6-fluorophenyl)-N-{4-[(3,5-dimethylpiperazin-1-yl)carbonyl]phenyl}-5H-pyrimido[5,4-d][2]benzazepin-2-amine |
| IV-325 | 9-chloro-7-(2-chloro-6-fluorophenyl)-N-(4-{[4-(methylamino)piperidin-1-yl]carbonyl}phenyl)-5H-pyrimido[5,4-d][2]benzazepin-2-amine |
| IV-326 | 9-chloro-7-(2-chloro-6-fluorophenyl)-N-(4-{[3-(methylamino)piperidin-1-yl]carbonyl}phenyl)-5H-pyrimido[5,4-d][2]benzazepin-2-amine |
| IV-327 | 9-chloro-7-(2-chloro-6-fluorophenyl)-N-(4-{[3-(methylamino)pyrrolidin-1-yl]carbonyl}phenyl)-5H-pyrimido[5,4-d][2]benzazepin-2-amine |
| IV-328 | 9-chloro-N-(3,4-dimethoxyphenyl)-7-{2-[(dimethylamino)methyl]phenyl}-5H-pyrimido[5,4-d][2]benzazepin-2-amine |
| IV-329 | 9-chloro-7-(2-methoxyphenyl)-N-{4-[(3-methylpiperazin-1-yl)carbonyl]phenyl}-5H-pyrimido[5,4-d][2]benzazepin-2-amine |
| IV-330 | 9-chloro-N-{4-[(3,5-dimethylpiperazin-1-yl)carbonyl]phenyl}-7-(2-methoxyphenyl)-5H-pyrimido[5,4-d][2]benzazepin-2-amine |
| IV-331 | 9-chloro-7-(2-methoxyphenyl)-N-(4-{[4-(methylamino)piperidin-1-yl]carbonyl}phenyl)-5H-pyrimido[5,4-d][2]benzazepin-2-amine |
| IV-332 | 9-chloro-7-(2-methoxyphenyl)-N-(4-{[3-(methylamino)pyrrolidin-1-yl]carbonyl}phenyl)-5H-pyrimido[5,4-d][2]benzazepin-2-amine |
| IV-333 | 9-chloro-7-(2-methoxyphenyl)-N-(4-{[3-(methylamino)piperidin-1-yl]carbonyl}phenyl)-5H-pyrimido[5,4-d][2]benzazepin-2-amine |
| IV-334 | 4-{[9-chloro-7-(2,6-difluorophenyl)-5H-pyrimido[5,4-d][2]benzazepin-2-yl]amino}-N-methylbenzamide |
| IV-335 | 4-{[9-chloro-7-(2-fluoro-6-{methyl[3-(methylamino)propyl]amino}phenyl)-5H-pyrimido[5,4-d][2]benzazepin-2-yl]amino}benzoic acid |
| IV-336 | 4-{[9-chloro-7-(2-fluoro-6-{methyl[3-(methylamino)propyl]amino}phenyl)-5H-pyrimido[5,4-d][2]benzazepin-2-yl]amino}-N-methylbenzamide |
| IV-337 | 1-(4-{[9-chloro-7-(2,6-difluorophenyl)-5H-pyrimido[5,4-d][2]benzazepin-2-yl]amino}phenyl)ethanone |
| IV-338 | N-[3-(3-aminoprop-1-yn-1-yl)phenyl]-9-chloro-7-(2,6-difluorophenyl)-5H-pyrimido[5,4-d][2]benzazepin-2-amine |
| IV-339 | 4-[(9-chloro-7-{2-fluoro-6-[(2-hydroxyethyl)amino]phenyl}-5H-pyrimido[5,4-d][2]benzazepin-2-yl)amino]-N-methylbenzamide |
| IV-340 | 4-[(7-{2-[(2-aminoethyl)amino]-6-fluorophenyl}-9-chloro-5H-pyrimido[5,4-d][2]benzazepin-2-yl)amino]-N-methylbenzamide |
| IV-341 | 4-amino-1-(4-{[9-chloro-7-(2,6-difluorophenyl)-5H-pyrimido[5,4-d][2]benzazepin-2-yl]amino}benzoyl)-N-methylpiperidine-4-carboxamide |
| IV-342 | 4-[(9-chloro-7-{24-[-(dimethylamino)piperidin-1-yl]-6-fluorophenyl}-5H-pyrimido[5,4-d][2]benzazepin-2-yl)amino]-N-methylbenzamide |
| IV-343 | 9-chloro-7-(2,6-difluorophenyl)-N-{3-[3-(dimethylamino)prop-1-yn-1-yl]phenyl}-5H-pyrimido[5,4-d][2]benzazepin-2-amine |
| IV-344 | 9-chloro-7-(2,6-difluorophenyl)-N-(3-iodophenyl)-5H-pyrimido[5,4-d][2]benzazepin-2-amine |
| IV-345 | 4-{[9-chloro-7-(2-{[2-(dimethylamino)ethyl]amino}-6-fluorophenyl)-5H-pyrimido[5,4-d][2]benzazepin-2-yl]amino}-N-methylbenzamide |
| IV-346 | 4-[(9-chloro-7-{2-[[2-(dimethylamino)ethyl](methyl)amino]-6-fluorophenyl}-5H-pyrimido[5,4-d][2]benzazepin-2-yl)amino]-N-methylbenzamide |
| IV-347 | 4-{[9-chloro-7-(2-fluoro-6-{methyl[2-(methylamino)ethyl]amino}phenyl)-5H-pyrimido[5,4-d][2]benzazepin-2-yl]amino}-N-methylbenzamide |
| IV-348 | 4-({7-[2-(4-aminopiperidin-1-yl)-6-fluorophenyl]-9-chloro-5H-pyrimido[5,4-d][2]benzazepin-2-yl}amino)-N-methylbenzamide |
| IV-349 | 7-(2-fluorophenyl)-2-[(3-methoxyphenyl)amino]-N-methyl-N-[2-(methylamino)ethyl]-5H-pyrimido[5,4-d][2]benzazepine-9-carboxamide |
| IV-350 | 4-amino-1-(4-{[9-chloro-7-(2,6-difluorophenyl)-5H-pyrimido[5,4-d][2]benzazepin-2-yl]amino}benzoyl)piperidine-4-carboxamide |
| IV-351 | 9-chloro-7-(2-chloro-6-fluorophenyl)-N-(4-{[3-(methylamino)azetidin-1-yl]carbonyl}phenyl)-5H-pyrimido[5,4-d][2]benzazepin-2-amine |
| IV-352 | 9-chloro-7-(2,6-difluorophenyl)-N-(4-methyl-1,3-thiazol-2-yl)-5H-pyrimido[5,4-d][2]benzazepin-2-amine |
| IV-353 | 7-(2,6-difluorophenyl)-2-[(3-methoxyphenyl)amino]-5H-pyrimido[5,4-d][2]benzazepine-9-carboxylic acid |
| IV-354 | 4-({9-chloro-7-(2-fluoro-6-(methylamino)phenyl]-5H-pyrimido[5,4-d][2]benzazepin-2-yl}amino)-N-methylbenzamide |
| IV-355 | 2-{[9-chloro-7-(2,6-difluorophenyl)-5H-pyrimido[5,4-d][2]benzazepin-2-yl]amino}-N-methyl-1,3-thiazole-4-carboxamide |
| IV-356 | N-1H-benzimidazol-2-yl-9-chloro-7-(2,6-difluorophenyl)-5H-pyrimido[5,4-d][2]benzazepin-2-amine |

TABLE 3-continued

Examples of Compounds of Formula (IV)

| | |
|---|---|
| IV-357 | 7-(2,6-difluorophenyl)-2-[(4-methyl-1,3-thiazol-2-yl)amino]-5H-pyrimido[5,4-d][2]benzazepine-9-carboxylic acid |
| IV-358 | 3-amino-1-(3-{[9-chloro-7-(2,6-difluorophenyl)-5H-pyrimido[5,4-d][2]benzazepin-2-yl]amino}phenyl)propan-1-one |
| IV-359 | 1-(3-{[9-chloro-7-(2,6-difluorophenyl)-5H-pyrimido[5,4-d][2]benzazepin-2-yl]amino}phenyl)-3-(dimethylamino)propan-1-one |
| IV-360 | 2-{[9-chloro-7-(2,6-difluorophenyl)-5H-pyrimido[5,4-d][2]benzazepin-2-yl]amino}-1,3-thiazole-4-carboxylic acid |
| IV-361 | ethyl 2-{[9-chloro-7-(2,6-difluorophenyl)-5H-pyrimido[5,4-d][2]benzazepin-2-yl]amino}-1,3-thiazole-4-carboxylate |
| IV-362 | 9-chloro-7-(2,6-difluorophenyl)-N-{4-[(3,5-dimethylpiperazin-1-yl)carbonyl]-1,3-thiazol-2-yl}-5H-pyrimido[5,4-d][2]benzazepin-2-amine |
| IV-363 | ethyl 2-{[9-chloro-7-(2,6-difluorophenyl)-5H-pyrimido[5,4-d][2]benzazepin-2-yl]amino}-1,3-oxazole-5-carboxylate |
| IV-364 | 2-{[9-chloro-7-(2,6-difluorophenyl)-5H-pyrimido[5,4-d][2]benzazepin-2-yl]amino}-1,3-oxazole-5-carboxylic acid |
| IV-365 | 9-chloro-7-(2,6-difluorophenyl)-N-(4-{[(3R)-3-methylpiperazin-1-yl]carbonyl}-1,3-thiazol-2-yl)-5H-pyrimido[5,4-d][2]benzazepin-2-amine |
| IV-366 | 9-chloro-7-(2,6-difluorophenyl)-N-(4-{[(2R)-2-methylpiperazin-1-yl]carbonyl}phenyl)-5H-pyrimido[5,4-d][2]benzazepin-2-amine |
| IV-367 | 9-chloro-7-(2,6-difluorophenyl)-N-(4-{[3-(methylamino)pyrrolidin-1-yl]carbonyl}-1,3-thiazol-2-yl)-5H-pyrimido[5,4-d][2]benzazepin-2-amine |
| IV-368 | 2-{[9-chloro-7-(2,6-difluorophenyl)-5H-pyrimido[5,4-d][2]benzazepin-2-yl]amino}-1,3-oxazole-4-carboxylic acid |
| IV-369 | 9-chloro-7-(2,6-difluorophenyl)-N-{5-[(3,5-dimethylpiperazin-1-yl)carbonyl]-1,3-oxazol-2-yl}-5H-pyrimido[5,4-d][2]benzazepin-2-amine |
| IV-370 | 9-chloro-7-(2,6-difluorophenyl)-N-(5-{[3-(methylamino)pyrrolidin-1-yl]carbonyl}-1,3-oxazol-2-yl)-5H-pyrimido[5,4-d][2]benzazepin-2-amine |
| IV-371 | 4-{[9-chloro-7-(2,6-difluorophenyl)-5-methyl-5H-pyrimido[5,4-d][2]benzazepin-2-yl]amino}benzoic acid |
| IV-372 | 9-chloro-7-(2,6-difluorophenyl)-N-{3-[3-(dimethylamino)propyl]phenyl}-5H-pyrimido[5,4-d][2]benzazepin-2-amine |
| IV-373 | N-[3-(3-aminopropyl)phenyl]-9-chloro-7-(2,6-difluorophenyl)-5H-pyrimido[5,4-d][2]benzazepin-2-amine |
| IV-374 | 9-chloro-7-(2,6-difluorophenyl)-N-{4-[3,5-dimethylpiperazin-1-yl)carbonyl]-1,3-oxazol-2-yl}-5H-pyrimido[5,4-d][2]benzazepin-2-amine |
| IV-375 | 9-chloro-7-(2,6-difluorophenyl)-N-(4-{[3-(methylamino)pyrrolidin-1-yl]carbonyl}-1,3-oxazol-2-yl)-5H-pyrimido[5,4-d][2]benzazepin-2-amine |
| IV-376 | 7-(2,6-difluorophenyl)-2-({4-[(3,5-dimethylpiperazin-1-yl)carbonyl]phenyl}amino)-N-methyl-5H-pyrimido[5,4-d][2]benzazepine-9-carboxamide |
| IV-377 | 2-{[4-(aminocarbonyl)phenyl]amino}-7-(2,6-difluorophenyl)-5H-pyrimido[5,4-d][2]benzazepine-9-carboxylic acid |
| IV-378 | 1-(4-{[9-chloro-7-(2,6-difluorophenyl)-5H-pyrimido[5,4d][2]benzazepin-2-yl]amino}benzoyl)-N-methyl-4-(methylamino)piperidine-4-carboxamide |
| IV-379 | N-{4-[(3-amino-3-methylpyrrolidin-1-yl)carbonyl]phenyl}-9-chloro-7-(2,6-difluorophenyl)-5H-pyrimido[5,4-d][2]benzazepin-2-amine |
| IV-380 | 9-chloro-7-(2,6-difluorophenyl)-N-(4-{[3-methyl-3-(methylamino)pyrrolidin-1-yl]carbonyl}phenyl)-5H-pyrimido[5,4-d][2]benzazepin-2-amine |
| IV-381 | 1-(4-{[9-chloro-7-(2,6-difluorophenyl)-5H-pyrimido[5,4-d][2]benzazepin-2-yl]amino}benzoyl)-4-(methylamino)piperidine-4-carboxamide |
| IV-382 | 9-chloro-7-(2,6-difluorophenyl)-N-{4-[(3,3,5-trimethylpiperazin-1-yl)carbonyl]phenyl}-5H-pyrimido[5,4-d][2]benzazepin-2-amine |
| IV-383 | N-1-azabicyclo[2.2.2]oct-3-yl-4-{[9-chloro-7-(2,6-difluorophenyl)-5H-pyrimido[5,4-d][2]benzazepin-2-yl]amino}-N-methylbenzamide |
| IV-384 | N-1-azabicyclo[2.2.2]oct-3-yl-4-{[9-chloro-7-(2,6-difluorophenyl)-5H-pyrimido[5,4-d][2]benzazepin-2-yl]amino}benzamide |
| IV-385 | 4-{[9-chloro-7-(2,6-difluorophenyl)-5H-pyrimido[5,4-d][2]benzazepin-2-yl]amino}-N-hydroxybenzamide |
| IV-386 | N-{4-[(aminooxy)carbonyl]phenyl}-9-chloro-7-(2,6-difluorophenyl)-5H-pyrimido[5,4-d][2]benzazepin-2-amine |
| IV-387 | 4-{[9-chloro-7-(2,6-difluorophenyl)-7H-pyrimido[5,4-d][2]benzazepin-2-yl]amino}benzoic acid |
| IV-388 | 4-{[9-chloro-7-(2,3-difluorophenyl)-7H-pyrimido[5,4-d][2]benzazepin-2-yl]amino}benzoic acid |
| IV-389 | 3-amino-1-(4-{[9-chloro-7-(2,6-difluorophenyl)-5H-pyrimido[5,4-d][2]benzazepin-2-yl]amino}benzoyl)-N-methylpyrrolidine-3-lcarboxamide |
| IV-390 | 3-amino-1-(2-chloro-4-{[9-chloro-7-(2,6-difluorophenyl)-5H-pyrimido[5,4-d][2]benzazepin-2-yl]amino}benzoyl)pyrrolidine-3-carboxamide |
| IV-391 | 9-chloro-7-(2,6-difluorophenyl)-N-{4-[(3,3-dimethylpiperazin-1-yl)carbonyl]phenyl}-5H-pyrimido[5,4-d][2]benzazepin-2-amine |
| IV-392 | 4-{[9-chloro-7-(2,6-difluorophenyl)-5H-pyrimido[5,4-d][2]benzazepin-2-yl]amino}-N-(8-methyl-8-azabicyclo[3.2.1]oct-3-yl)benzamide |
| IV-393 | 9-chloro-7-(2,6-difluorophenyl)-N-(4-{[3-(dimethylamino)-3-methylpyrrolidin-1-yl]carbonyl}phenyl)-5H-pyrimido[5,4-d][2]benzazepin-2-amine |
| IV-394 | 9-chloro-7-(2,6-difluorophenyl)-N-(3-methyl-1H-pyrazol-5-yl)-5H-pyrimido[5,4-d][2]benzazepin-2-amine |
| IV-395 | 2-chloro-4-{[9-chloro-7-(2,6-difluorophenyl)-5H-pyrimido[5,4-d][2]benzazepin-2-yl]amino}benzoic acid |
| IV-396 | 4-amino-1-(2-chloro-4-{[9-chloro-7-(2,6-difluorophenyl)-5H-pyrimido[5,4-d][2]benzazepin-2-yl]amino}benzoyl)-N-methylpiperidine-4-carboxamide |
| IV-397 | 4-amino-1-(2-chloro-4-{[9-chloro-7-(2,6-difluorophenyl)-5H-pyrimido[5,4-d][2]benzazepin-2-yl]amino}benzoyl)-N,N-dimethylpiperidine-4-carboxamide |
| IV-398 | 4-[(9-methoxy-7-oxo-6,7-dihydro-5H-pyrimido[5,4-d][2]benzazepin-2-yl)amino}benzoic acid |
| IV-399 | 2-({4-[(3,5-dimethylpiperazin-1-yl)carbonyl]phenyl}amino)-9-methoxy-5,6-dihydro-7H-pyrimido[5,4-d][2]benzazepin-7-one |
| IV-400 | 9-methoxy-2-[(4-{[3-(methylamino)pyrrolidin-1-yl]carbonyl}phenyl)amino]-5,6-dihydro-7H-pyrimido[5,4-d][2]benzazepin-7-one |
| IV-401 | 4-[(8-methyl-7-oxo-5,6,7,8-tetrahydropyrimido[5,4-c]pyrrolo[3,2-e]azepin-2-yl)amino]benzoic acid |
| IV-402 | 2-({4-[(3,5-dimethylpiperazin-1-yl)carbonyl]phenyl}amino)-8-methyl-5,8-dihydropyrimido[5,4-c]pyrrolo[3,2-e]azepin-7(6H)-one |
| IV-403 | 2-[(3-methoxyphenyl)amino]-8-methyl-5,8-dihydropyrimido[5,4-c]pyrrolo[3,2-e]azepin-7(6H)-one |
| IV-404 | 9-chloro-2-[(3,4-dimethoxyphenyl)amino]-5,6-dihydro-7H-pyrimido[5,4-d][2]benzazepin-7-one |
| IV-405 | 4-{[4-amino-9-chloro-7-(2,6-difluorophenyl)-5H-pyrimido[5,4-d][2]benzazepin-2-yl]amino}benzoic acid |
| IV-406 | 9-chloro-N-(3-chloro-4-{[4-(methylamino)piperidin-1-yl]carbonyl}phenyl)-7-(2,6-difluorophenyl)-5H-pyrimido[5,4-d][2]benzazepin-2-amine |
| IV-407 | 9-chloro-N-(3-chloro-4-{[4-(methylamino)piperidin-1-yl]carbonyl}phenyl)-7-(2-fluoro-6-methoxyphenyl)-5H-pyrimido[5,4-d][2]benzazepin-2-amine |
| IV-408 | 4-{[9-chloro-7-(2-fluoro-6-hydroxyphenyl)-5H-pyrimido[5,4-d][2]benzazepin-2-yl]amino}benzoic acid |
| IV-409 | 9-chloro-N-[4-(1,7-diazaspiro[4.4]non-7-ylcarbonyl)phenyl]-7-(2,6-difluorophenyl)-5H-pyrimido[5,4-d][2]benzazepin-2-amine |
| IV-410 | 9-chloro-7-(2,6-difluorophenyl)-N-(4-{[2-(methylamino)-7-azabicyclo[2.2.1]hept-7-yl]carbonyl}phenyl)-5H-pyrimido[5,4-d][2]benzazepin-2-amine |
| IV-411 | 1-(4-{[9-chloro-7-(2,6-difluorophenyl)-5H-pyrimido[5,4-d][2]benzazepin-2-yl]amino}benzoyl)-N-methyl-3-(methylamino)pyrrolidine-3-carboxamide |
| IV-412 | 1-(4-{[9-chloro-7-(2,6-difluorophenyl)-5H-pyrimido[5,4-d][2]benzazepin-2-yl]amino}benzoyl)-3-(methylamino)pyrrolidine-3-carboxamide |
| IV-413 | 1-(2-chloro-4-{[9-chloro-7-(2,6-difluorophenyl)-5H-pyrimido[5,4-d][2]benzazepin-2-yl]amino}benzoyl)-N-methyl-3-(methylamino)piperidine-3-carboxamide |
| IV-414 | 9-chloro-7-(2,6-difluorophenyl)-N-(4-{[3-methyl-3-(methylamino)piperidin-1-yl]carbonyl}phenyl)-5H-pyrimido[5,4-d][2]benzazepin-2-amine |

TABLE 3-continued

Examples of Compounds of Formula (IV)

| | |
|---|---|
| IV-415 | 9-chloro-7-(2-fluoro-6-methoxyphenyl)-N-(4-{[3-methyl-3-(methylamino)piperidin-1-yl]carbonyl}phenyl)-5H-pyrimido[5,4-d][2]benzazepin-2-amine |
| IV-416 | {2-Chloro-4-[9-chloro-7-(2-fluoro-6-methoxy-phenyl)-5H-benzo[c]pyrimido[4,5-e]azepin-2-ylamino]-phenyl}-(3-methyl-3-methylamino-piperidin-1-yl)-methanone |
| IV-417 | 9-chloro-7-(2,6-difluorophenyl)-N-(4-{[4-methyl-4-(methylamino)piperidin-1-yl]carbonyl}phenyl)-5H-pyrimido[5,4-d][2]benzazepin-2-amine |
| IV-418 | 9-chloro-7-(2,6-difluorophenyl)-N-(4-{[4-(dimethylamino)-4-methylpiperidin-1-yl]carbonyl}phenyl)-5H-pyrimido[5,4-d][2]benzazepin-2-amine |
| IV-419 | N-{4-[(4-amino-4-methylpiperidin-1-yl)carbonyl]phenyl}-9-chloro-7-(2,6-difluorophenyl)-5H-pyrimido[5,4-d][2]benzazepin-2-amine |
| IV-420 | 9-chloro-N-(3-chloro-4-{[4-methyl-4-(methylamino)piperidin-1-yl]carbonyl}phenyl)-7-(2,6-difluorophenyl)-5H-pyrimido[5,4-d][2]benzazepin-2-amine |
| IV-421 | 9-chloro-7-(2-fluoro-6-methoxyphenyl)-N-(4-{[4-methyl-4-(methylamino)piperidin-1-yl]carbonyl}phenyl)-5H-pyrimido[5,4-d][2]benzazepin-2-amine |
| IV-422 | 2-Chloro-4-[9-chloro-7-(2-fluoro-6-methoxy-phenyl)-5H-benzo[c]pyrimido[4,5-e]azepin-2-ylamino]-phenyl}-(4-methyl-4-methylamino-piperidin-1-yl)-methanone |
| IV-423 | 9-chloro-7-(2-fluoro-6-methoxyphenyl)-N-(3-fluoro-4-{[4-methyl-4-(methylamino)piperidin-1-yl]carbonyl}phenyl)-5H-pyrimido[5,4-d][2]benzazepin-2-amine |
| IV-424 | 9-chloro-N-{3-chloro-4-[(3,3,5,5-tetramethylpiperazin-1-yl)carbonyl]phenyl}-7-(2-fluoro-6-methoxyphenyl)-5H-pyrimido[5,4-d][2]benzazepin-2-amine |
| IV-425 | N-1-azabicyclo[2.2.2]oct-3-yl-4-{[9-chloro-7-(2,6-difluorophenyl)-5H-pyrimido[5,4-d][2]benzazepin-2-yl]amino}-2-fluoro-N-methylbenzamide |
| IV-426 | N-1-azabicyclo[2.2.2]oct-3-yl-4-{[9-chloro-7-(2-fluoro-6-methoxyphenyl)-5H-pyrimido[5,4-d][2]benzazepin-2-yl]amino}-N-methylbenzamide |
| IV-427 | N-8-azabicyclo[3.2.1]oct-3-yl-4-{[9-chloro-7-(2,6-difluorophenyl)-5H-pyrimido[5,4-d][2]benzazepin-2-yl]amino}-N-methylbenzamide |
| IV-428 | 9-chloro-7-(2,6-difluorophenyl)-N-(4-{[3-(methylamino)-8-azabicyclo[3.2.1]oct-8-yl]carbonyl}phenyl)-5H-pyrimido[5,4-d][2]benzazepin-2-amine |
| IV-429 | 9-chloro-7-(2-fluoro-6-methoxyphenyl)-N-(4-{[3-(methylamino)-8-azabicyclo[3.2.1]oct-8-yl]carbonyl}phenyl)-5H-pyrimido[5,4-d][2]benzazepin-2-amine |
| IV-430 | 4-{[7-(2,6-difluorophenyl)-9-methyl-5H-pyrimido[5,4-c]thieno[2,3-e]azepin-2-yl]amino}benzoic acid |
| IV-431 | 7-(2,6-difluorophenyl)-N-{4-[(3,3,5,5-tetramethylpiperazin-1-yl)carbonyl]phenyl}-5H-pyrimido[5,4-c]thieno[2,3-e]azepin-2-amine |
| IV-432 | N-{4-[(3-amino-3-methylpyrrolidin-1-yl)carbonyl]phenyl}-7-(2,6-difluorophenyl)-10-methyl-5,10-dihydropyrimido[5,4-c]pyrrolo[2,3-e]azepin-2-amine |
| IV-433 | 7-(2,6-difluorophenyl)-9-methyl-N-(4-{[3-(methylamino)pyrrolidin-1-yl]carbonyl}phenyl)-5H-furo[2,3-c]pyrimido[4,5-e]azepin-2-amine |
| IV-434 | 4-(2,6-difluorophenyl)-2-methyl-N-(4-{[3-methyl-3-(methylamino)pyrrolidin-1-yl]carbonyl}phenyl)-6H-pyrimido[5,4-c][1,3]thiazolo[4,5-e]azepin-9-amine |
| IV-435 | N-{4-[(3-amino-3-methylpyrrolidin-1-yl)carbonyl]phenyl}-7-(2-fluoro-6-methoxyphenyl)-5,9-dihydropyrimido[5,4-c]pyrrolo[3,4-e]azepin-2-amine |
| IV-436 | 4-{[4-(2,6-difluorophenyl)-1-methyl-1,6-dihydropyrazolo[4,3-c]pyrimido[4,5-e]azepin-9-yl]amino}benzoic acid |
| IV-437 | 1-{4-[4-(2,6-Difluoro-phenyl)-2-methyl-6H-3-thia-5,8,10-triaza-benzo[e]azulen-9-ylamino]-benzoyl}-4-dimethylamino-piperidine-4-carboxylic acid methylamide |
| IV-438 | 4-(4-{[7-(2,6-difluorophenyl)-5H-furo[3,2-c]pyrimido[4,5-e]azepin-2-yl]amino}benzoyl)-N-methylpiperazine-2-carboxamide |
| IV-439 | 4-(4-{[4-(2,6-difluorophenyl)-6H-isoxazolo[4,5-c]pyrimido[4,5-e]azepin-9-yl]amino}benzoyl)-N-methylpiperazine-2-carboxamide |
| IV-440 | 4-(2,6-difluorophenyl)-9-[(4-{[3-methyl-3-(methylamino)pyrrolidin-1-yl]carbonyl}phenyl)amino]-3,6-dihydroimidazo[4,5-c]pyrimido[4,5-e]azepin-2(1H)-one |
| IV-441 | 2-amino-N-(3-{[7-(2,6-difluorophenyl)-8,10-dimethyl-5H-pyrimido[5,4-c]thieno[3,4-e]azepin-2-yl]amino}phenyl)-N,2-dimethylpropanamide |
| IV-442 | 9-chloro-7-(2,6-difluorophenyl)-N-{3-[(2,2,6,6-tetramethylpiperidin-4-yl)oxy]phenyl}-5H-pyrimido[5,4-d][2]benzazepin-2-amine |
| IV-443 | 4-(4-{[9-chloro-7-(2,6-difluorophenyl)-5H-pyrimido[5,4-d][2]benzazepin-2-yl]amino}phenyl)-N-methyl-1-(methylamino)cyclohexanecarboxamide |
| IV-444 | 7-(3-{[7-(2-fluoro-6-methoxyphenyl)-9-methoxy-5H-pyrimido[5,4-d][2]benzazepin-2-yl]amino}phenyl)-1,7-diazaspiro[4.4]nonan-6-one |
| IV-445 | 9-chloro-N-[4-(3,8-diazabicyclo[3.2.1]oct-3-ylcarbonyl)phenyl]-7-(2,6-difluorophenyl)-5H-pyrimido[5,4-d][2]benzazepin-2-amine |
| IV-446 | 1-(3-{[9-chloro-7-(2,6-difluorophenyl)-5H-pyrimido[5,4-d][2]benzazepin-2-yl]amino}phenyl)-3,5,5-trimethylpiperazin-2-one |
| IV-447 | 9-chloro-N-[4-(2,6-dimethylpiperidin-4-yl)phenyl]-7-(2-fluoro-6-methoxyphenyl)-5H-pyrimido[5,4-d][2]benzazepin-2-amine |
| IV-448 | N-[4-(1-amino-1-methylethyl)phenyl]-9-chloro-7-(2,6-difluorophenyl)-5H-pyrimido[5,4-d][2]benzazepin-2-amine |
| IV-449 | N-[4-(2,5-diazaspiro[3.4]oct-2-ylcarbonyl)phenyl]-7-(2,6-difluorophenyl)-10-methyl-5H-isothiazolo[5,4-c]pyrimido[4,5-e]azepin-2-amine |
| IV-450 | 4-(2,6-difluorophenyl)-1-methyl-9-[(4-{[4-methyl-4-(methylamino)piperidin-1-yl]carbonyl}phenyl)amino]-1,6-dihydro-2H-pyrimido[5,4-c][1,3]thiazolo[4,5-e]azepin-2-one |
| IV-451 | 4-(2,6-difluorophenyl)-N-[4-(1H-imidazol-2-yl)phenyl]-1-methyl-1,6-dihydroimidazo[4,5-c]pyrimido[4,5-dazepin-9-amine |
| IV-452 | 4-{[7-(2,6-difluorophenyl)-5H-[1]benzofuro[2,3-c]pyrimido[4,5-e]azepin-2-yl]amino}benzoic acid |
| IV-453 | 7-(2-fluorophenyl)-N-{4-[3,3,5,5-tetramethylpiperazin-1-yl)carbonyl]phenyl}-8,9,10,11-tetrahydro-5H-pyrido[4',3':4,5]thieno[3,2-c]pyrimido[4,5-e]azepin-2-amine |
| IV-454 | 9-bromo-7-(2-fluorophenyl)-N-(4-{[3-(methylamino)pyrrolidin-1-yl]carbonyl}phenyl)-5,8-dihydropyrimido[5,4-c]pyrrolo[3,2-e]azepin-2-amine |
| IV-455 | 7-(2-fluorophenyl)-N-(3-methyl-1H-indazol-6-yl)-5,12-dihydropyrimido[4',5':5,6]azepino[4,3-b]indol-2-amine |
| IV-456 | 1-(4-{[7-(2,6-difluorophenyl)-9,10-dimethyl-5,8-dihydropyrimido[5,4-c]pyrrolo[3,2-e]azepin-2-yl]amino}benzoyl)-3-(methylamino)pyrrolidine-3-carboxamide |
| IV-457 | {3-[9-Chloro-7-(2-fluoro-6-methoxy-phenyl)-5H-benzo[c]pyrimido-[4,5-e]azepin-2-ylamino]-phenyl}-(4-methyl-piperazin-1-yl)-methanone |
| IV-458 | [9-Chloro-7-(2,6-difluoro-phenyl)-5H-benzo[c]pyrimido[4,5-e]azepin-2-yl]-(2-methylaminomethyl-benzothiazol-6-yl)-amine |
| IV-459 | 4-[9-Chloro-7-(2-isopropoxy-phenyl)-5H-benzo[c]pyrimido[4,5-e]azepin-2-ylamino]-benzoic acid |
| IV-460 | 4-[9-Chloro-7-(2-fluoro-6-isopropoxy-phenyl)-5H-benzo[c]pyrimido-[4,5-e]azepin-2-ylamino]-benzoic acid |
| IV-461 | 4-[9-Chloro-7-(2-ethoxy-phenyl)-5H-benzo[c]pyrimido[4,5-e]azepin-2-ylamino]-benzoic acid |
| IV-462 | 4-[9-Chloro-7-(2-ethoxy-6-fluoro-phenyl)-5H-benzo[c]pyrimido[4,5-e]azepin-2-ylamino]-benzoic acid |
| IV-463 | 4-[9-Chloro-7-(2-fluoro-6-methyl-phenyl)-5H-benzo[c]pyrimido[4,5-e]azepin-2-ylamino]-benzoic acid |
| IV-464 | 4-[9-Chloro-7-(2-trifluoromethoxy-phenyl)-5H-benzo[c]pyrimido[4,5-e]azepin-2-ylamino]-benzoic acid |
| IV-465 | 4-[9-Chloro-7-(2-fluoro-6-trifluoromethoxy-phenyl)-5H-benzo[c]pyrimido-[4,5-e]azepin-2-ylamino]-benzoic acid |
| IV-466 | 4-[9-Chloro-7-(3-fluoro-2-trifluoromethoxy-phenyl)-5H-benzo[c]pyrimido-[4,5-e]azepin-2-ylamino]-benzoic acid |
| IV-467 | 4-[9-Chloro-7-(2,3-dimethoxy-phenyl)-5H-benzo[c]pyrimido[4,5-e]azepin-2-ylamino]-benzoic acid |
| IV-468 | 4-[9-Chloro-7-(2-isobutyl-phenyl)-5H-benzo[c]pyrimido[4,5-e]azepin-2-ylamino]-benzoic acid |
| IV-469 | 4-(7-Benzofuran-2-yl-9-chloro-5H-benzo[c]pyrimido[4,5-e]azepin-2-ylamino)-benzoic acid |
| IV-470 | 4-[9-Chloro-7-(1-methyl-1H-pyrrol-2-yl)-5H-benzo[c]pyrimido[4,5-e]azepin-2-ylamino]-benzoic acid |

TABLE 3-continued

Examples of Compounds of Formula (IV)

| | |
|---|---|
| IV-471 | 4-[9-Chloro-7-(1-methyl-1H-imidazol-2-yl)-5H-benzo[c]pyrimido[4,5-e]azepin-2-ylamino]-benzoic acid |
| IV-472 | 4-(9-Chloro-7-thiophen-2-yl-5H-benzo[c]pyrimido[4,5-e]azepin-2-ylamino)-benzoic acid |
| IV-473 | 4-[9-Chloro-7-(2H-pyrazol-3-yl)-5H-benzo[c]pyrimido[4,5-e]azepin-2-ylamino]-benzoic acid |
| IV-474 | 4-[9-Chloro-7-(2-ethynyl-phenyl)-5H-benzo[c]pyrimido[4,5-e]azepin-2-ylamino]-benzoic acid |
| IV-475 | 4-[7-(2-Aminomethyl-phenyl)-9-chloro-5H-benzo[c]pyrimido[4,5-e]azepin-2-ylamino]-benzoic acid |
| IV-476 | 4-[9-Chloro-7-(5-fluoro-2-methoxy-phenyl)-5H-benzo[c]pyrimido[4,5-e]azepin-2-ylamino]-benzoic acid |
| IV-477 | 4-[9-Chloro-7-(3-methoxy-pyridin-2-yl)-5H-benzo[c]pyrimido[4,5-e]azepin-2-ylamino]-benzoic acid |
| IV-478 | 4-[8-Fluoro-7-(2-fluoro-phenyl)-5H-benzo[c]pyrimido[4,5-e]azepin-2-ylamino]-benzoic acid |
| IV-479 | 4-[8-Chloro-7-(2-fluoro-phenyl)-5H-benzo[c]pyrimido[4,5-e]azepin-2-ylamino]-benzoic acid |
| IV-480 | 4-[11-Fluoro-7-(2-fluoro-phenyl)-5H-benzo[c]pyrimido[4,5-e]azepin-2-ylamino]-benzoic acid |
| IV-481 | 4-[11-Chloro-7-(2-fluoro-phenyl)-5H-benzo[c]pyrimido[4,5-e]azepin-2-ylamino]-benzoic acid |
| IV-482 | 6-[9-Chloro-7-(2-fluoro-phenyl)-5H-benzo[c]pyrimido[4,5-e]azepin-2-ylamino]-pyridazine-3-carboxylic acid |
| IV-483 | 2-[9-Chloro-7-(2-fluoro-phenyl)-5H-benzo[c]pyrimido[4,5-e]azepin-2-ylamino]-1H-imidazole-4-carboxylic acid |
| IV-484 | 4-[9-Chloro-7-(2-fluoro-phenyl)-4-methyl-5H-benzo[c]pyrimido[4,5-e]azepin-2-ylamino]-benzoic acid |
| IV-485 | 4-[4-Aminomethyl-9-chloro-7-(2-fluoro-phenyl)-5H-benzo[c]pyrimido-[4,5-e]azepin-2-ylamino]-benzoic acid |
| IV-486 | 4-(9-Aminomethyl-7-phenyl-5H-benzo[c]pyrimido[4,5-e]azepin-2-ylamino)-benzoic acid |
| IV-487 | 9-Chloro-7-(2-fluorophenyl)-N-{4-[(2-methylpiperazin-1-yl)carbonyl]phenyl}-5H-pyrimido[5,4-d][2]benzazepin-2-amine |
| IV-488 | 4-{[9-Chloro-7-(2-fluorophenyl)-5H-pyrimido[5,4-d][2]benzazepin-2-yl]amino}-N-{[3-[(dimethylamino)methyl]azetidin-1-yl}(imino)methyl]benzamide |
| IV-489 | 4-{[9-Chloro-7-(2-fluorophenyl)-5H-pyrimido[5,4-d][2]benzazepin-2-yl]amino}-N-[imino(piperazin-1-yl)methyl]benzamide |
| IV-490 | 4-{[9-Chloro-7-(2-fluorophenyl)-5H-pyrirnido[5,4-d][2]benzazepin-2-yl]amino}-N-[imino(3-methylpiperazin-1-yl)methyl]benzamide |
| IV-491 | 4-{[9-Chloro-7-(2-fluorophenyl)-5H-pyrimido[5,4-d][2]benzazepin-2-yl]amino}-N-[[3-(dimethylamino)pyrrolidin-1-yl](imino)methyl]benzamide |
| IV-492 | 4-{[9-Chloro-7-(2-fluorophenyl)-5H-pyrimido[5,4-d][2]benzazepin-2-yl]amino}-N-[imino(4-methylpiperazin-1-yl)methyl]benzamide |
| IV-493 | 4-{[9-Chloro-7-(2-fluorophenyl)-5H-pyrimido[5,4-d][2]benzazepin-2-yl]amino}-N-[(3,5-dimethylpiperazin-1-yl)(imino)methyl]benzamide |
| IV-494 | 1-[[(4-{[9-Chloro-7-(2-fluorophenyl)-5H-pyrimido[5,4-d][2]benzazepin-2-yl]amino}benzoyl)amino](imino)methyl]pyrrolidine-3-carboxamide |
| IV-495 | 1-[[(4-{[9-Chloro-7-(2-fluorophenyl)-5H-pyrimido[5,4-d][2]benzazepin-2-yl]amino}benzoyl)amino](imino)methyl]piperidine-3-carboxamide |
| IV-496 | 4-{[9-Chloro-7-(2-fluorophenyl)-5H-pyrimido[5,4-d][2]benzazepin-2-yl]amino}-N-[{4-[(cyclopropylcarbonyl)amino]piperidin-1-yl}(imino)methyl]benzamide |
| IV-497 | 4-{[9-Chloro-7-(2-fluorophenyl)-5H-pyrimido[5,4-d][2]benzazepin-2-yl]amino}-N-[(dimethylamino)(imino)methyl]benzamide |
| IV-498 | N-[[(4-{[9-Chloro-7-(2-fluorophenyl)-5H-pyrimido[5,4-d][2]benzazepin-2-yl]amino}phenyl)amino](imino)methyl]cyclopropanecarboxamide |
| IV-499 | N-[[(4-{[9-Chloro-7-(2-fluorophenyl)-5H-pyrimido[5,4-d][2]benzazepin-2-yl]amino}phenyl)amino](imino)methyl]-3-(dimethylamino)cyclopentanecarboxamide |
| IV-500 | 4-({9-Chloro-7-(2-fluoro-6-(trifluoromethyl)phenyl]-5H-pyrimido-[5,4-d][2]benzazepin-2-yl}amino)benzoic acid |
| IV-501 | 4-{[9-Chloro-7-(2,6-dichlorophenyl)-5H>-pyrimido[5,4-d][2]benzazepin-2-yl]amino}benzoic acid |
| IV-502 | 4-{[9-Chloro-7-(2-fluoro-6-methylphenyl)-5H-pyrimido[5,4-d][2]benzazepin-2-yl]amino}benzoic acid |
| IV-503 | 4-{[7-(2-Bromo-6-chlorophenyl)-9-chloro-5H-pyrimido[5,4-d][2]benzazepin-2-yl]amino}benzoic acid |
| IV-504 | 9-Chloro-7-(2,6-difluorophenyl)-N-{4-[(3,5-dimethylpiperazin-1-yl)carbonyl]-3-fluorophenyl}-5H-pyrimido[5,4-d][2]benzazepin-2-amine |
| IV-505 | 4-{[9-Chloro-7-(2,6-difluorophenyl)-5H-pyrimido[5,4-d][2]benzazepin-2-yl]amino}-N-[(3,5-dimethylpiperazin-1-yl)(imino)methyl]-N-methylbenzamide |
| IV-506 | 4-{[9-Chloro-7-(2,6-difluorophenyl)-5H-pyrimido[5,4-d][2]benzazepin-2-yl]amino}-N-[[3-(dimethylamino)azetidin-1-yl](imino)methyl]-N-methylbenzamide |
| IV-507 | 3-{[9-Chloro-7-(2,6-difluorophenyl)-5H-pyrimido[5,4-d][2]benzazepin-2-yl]amino}-N-[(3,5-dimethylpiperazin-1-yl)(imino)methyl]benzamide |
| IV-508 | 3-{[9-Chloro-7-(2,6-difluorophenyl)-5H-pyrimido[5,4-d][2]benzazepin-2-yl]amino}-N-[[3-(dimethylamino)pyrrolidin-1-yl](imino)methyl]benzamide |
| IV-509 | 9-Chloro-7-(2,6-difluorophenyl)-N-{3-[(3,5-dimethylpiperazin-1-yl)carbonyl]-4-fluorophenyl}-5H-pyrimido[5,4-d][2]benzazepin-2-amine |
| IV-510 | N-[[(4-{[9-Chloro-7-(2,6-difluorophenyl)-5H-pyrimido[5,4-d][2]benzazepin-2-yl]amino}phenyl)amino](imino)methyl]-3-(dimethylamino)cyclopentanecarboxamide |
| IV-511 | N-[[(4-{[9-Chloro-7-(2,6-difluorophenyl)-5H-pyrimido[5,4-d][2]benzazepin-2-yl]amino}-2-fluorophenyl)amino](imino)methyl]-3-(dimethylamino)cyclopentanecarboxamide |
| IV-512 | N-[[(5-{[9-Chloro-7-(2,6-difluorophenyl)-5H-pyrimido[5,4-d][2]benzazepin-2-yl]amino}-2-fluorophenyl)amino](imino)methyl]-3-(dimethylamino)cyclopentanecarboxamide |
| IV-513 | N-(4-{[9-Chloro-7-(2,6-difluorophenyl)-5H-pyrimido[5,4-d][2]benzazepin-2-yl]amino}phenyl)-3,5-dimethylpiperazine-1-carboximidamide |
| IV-514 | 4-{[9-Chloro-7-(2,6-difluorophenyl)-5H-pyrimido[5,4-d][2]benzazepin-2-yl]amino}-N-[[3-(dimethylamino)pyrrolidin-1-yl](imino)methyl]-N-methylbenzamide |
| IV-515 | N-(3-{[9-Chloro-7-(2,6-difluorophenyl)-5H-pyrimido[5,4-d][2]benzazepin-2-yl]amino}phenyl)-3,5-dimethylpiperazine-1-carboximidamide |
| IV-516 | N-(3-{[9-Chloro-7-(2,6-difluorophenyl)-5H-pyrimido[5,4-d][2]benzazepin-2-yl]amino}phenyl)-N,3,5-trimethylpiperazine-1-carboximidamide |
| IV-517 | 3-{[9-Chloro-7-(2,6-difluorophenyl)-5H-pyrimido[5,4-d][2]benzazepin-2-yl]amino}-N-[[3-(dimethylamino)azetidin-1-yl](imino)methyl]benzamide |
| IV-518 | N-(5-{[9-Chloro-7-(2,6-difluorophenyl)-5H-pyrimido[5,4-d][2]benzazepin-2-yl]amino}-2-fluorophenyl)-N,3,5-trimethylpiperazine-1-carboximidamide |
| IV-519 | N-[[(3-{[9-Chloro-7-(2,6-difluorophenyl)-5H-pyrimido[5,4-d][2]benzazepin-2-yl]amino}phenyl)amino](imino)methyl]-3-(dimethylamino)cyclopentanecarboxamide |
| IV-520 | 9-Chloro-7-(2,6-difluorophenyl)-N-{3-[(3,5-dimethylpiperazin-1-yl)(imino)methyl]phenyl}-5H-pyrimido[5,4-d][2]benzazepin-2-amine |
| IV-521 | N-(4-{[9-Chloro-7-(2,6-difluorophenyl)-5H-pyrimido[5,4-d][2]benzazepin-2-yl]amino}phenyl)-N,3,5-trimethylpiperazine-1-carboximidamide |
| IV-522 | N-(4-{[9-Chloro-7-(2,6-difluorophenyl)-5H-pyrimido[5,4-d][2]benzazepin-2-yl]amino}-2-fluorophenyl)-3,5-dimethylpiperazine-1-carboximidamide |
| IV-523 | 9-Chloro-7-(2,6-difluorophenyl)-N-{4-[(3,5-dimethylpiperazin-1-yl)(imino)methyl]-3-fluorophenyl}-5H-pyrimido[5,4-d][2]benzazepin-2-amine |
| IV-524 | 5-{[9-Chloro-7-(2,6-difluorophenyl)-5H-pyrimido[5,4-d][2]benzazepin-2-yl]amino}-2-(2,6-dimethylpiperidin-4-yl)-1H-isoindole-1,3(2H)-dione |
| IV-525 | N-[2-(Aminomethyl)-1H-benzimidazol-6-yl]-9-chloro-7-(2-fluorophenyl)-5H-pyrimido[5,4-d][2]benzazepin-2-amine |

TABLE 3-continued

Examples of Compounds of Formula (IV)

| | |
|---|---|
| IV-526 | 9-Chloro-7-(2-fluorophenyl)-N-{2-[(methylamino)methyl]-1H-benzimidazol-6-yl}-5H-pyrimido[5,4-d][2]benzazepin-2-amine |
| IV-527 | 9-Chloro-N-{2-[(dimethylamino)methyl]-1H-benzimidazol-6-yl}-7-(2-fluorophenyl)-5H-pyrimido[5,4-d][2]benzazepin-2-amine |
| IV-528 | 9-Chloro-7-(2-fluorophenyl)-N-{2-[(methylamino)methyl]-1,3-benzothiazol-6-yl}-5H-pyrimido[5,4-d][2]benzazepin-2-amine |
| IV-529 | 9-Chloro-7-(2,6-difluorophenyl)-N-{2-[(methylamino)methyl]-1H-benzimidazol-6-yl)-5H-pyrimido[5,4-d][2]benzazepin-2-amine |
| IV-530 | 9-Chloro-7-(2,6-difluorophenyl)-N-{2-[(methylamino)methyl]-1,3-benzoxazol-6-yl}-5H-pyrimido[5,4-d][2]benzazepin-2-amine |
| IV-531 | 9-Chloro-7-(2-fluorophenyl)-N-{2-[(methylamino)methyl]-1,3-benzoxazol-6-yl}-5H-pyrimido[5,4-d][2]benzazepin-2-amine |
| IV-532 | 9-Chloro-7-(2,6-difluorophenyl)-N-{3-[(3,5-dimethylpiperazin-1-yl)(imino)methyl]-4-fluorophenyl}-5H-pyrimido[5,4-d][2]benzazepin-2-amine |
| IV-533 | 9-Chloro-7-(2,6-difluorophenyl)-N-{2-[(methylamino)methyl]-1,3-benzothiazol-6-yl}-5H-pyrimido[5,4-d][2]benzazepin-2-amine |
| IV-534 | {3-[9-Chloro-7-(2,6-difluorophenyl)-5H-benzo[c]pyrimido[4,5-e]azepin-2-ylamino]-phenyl}-(4-methyl-piperazin-1-yl)-methanone |
| IV-535 | 3-[9-Chloro-7-(2,6-difluoro-phenyl)-5H-benzo[c]pyrimido[4,5-e]azepin-2-ylamino]-N-methyl-N-(4-methyl-pentyl)-benzamide |

In some embodiments, the selective Aurora A kinase inhibitor is represented by formula (V):

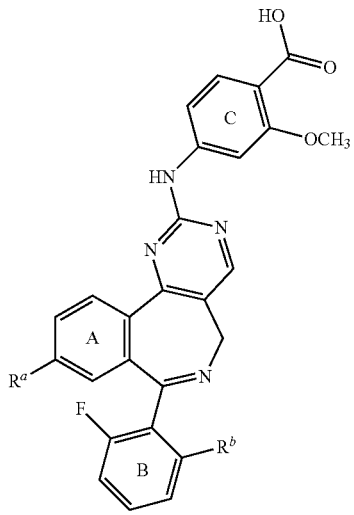

(V)

or a pharmaceutically acceptable salt thereof; wherein:

$R^a$ is selected from the group consisting of $C_{1-3}$ aliphatic, $C_{1-3}$ fluoroaliphatic, —$R^1$, -T-$R^1$, —$R^2$, and -T-$R^2$;

T is a $C_{1-3}$ alkylene chain optionally substituted with fluoro;

$R^1$ is an optionally substituted aryl, heteroaryl, or heterocyclyl group;

$R^2$ is selected from the group consisting of halo, —C≡C—$R^3$, —CH═CH—$R^3$, —N($R^4$)$_2$, and —O$R^5$;

$R^3$ is hydrogen or an optionally substituted aliphatic, aryl, heteroaryl, or heterocyclyl group;

each $R^4$ independently is hydrogen or an optionally substituted aliphatic, aryl, heteroaryl, or heterocyclyl group; or two $R^4$ on the same nitrogen atom, taken together with the nitrogen atom form an optionally substituted 5- to 6-membered heteroaryl or 4- to 8-membered heterocyclyl ring having, in addition to the nitrogen atom, 0-2 ring heteroatoms selected from N, O, and S;

$R^5$ is hydrogen or an optionally substituted aliphatic, aryl, heteroaryl, or heterocyclyl group; and $R^b$ is selected from the group consisting of fluoro, chloro, —$CH_3$, —$CF_3$, —OH, —$OCH_3$, —$OCF_3$, —$OCH_2CH_3$, and —$OCH_2CF_3$.

In some embodiments, $R^1$ is a 5- or 6-membered aryl, heteroaryl, or heterocyclyl ring optionally substituted with one or two substituents independently selected from the group consisting of halo, $C_{1-3}$ aliphatic, and $C_{1-3}$ fluoroaliphatic. In certain embodiments, $R^1$ is a phenyl, furyl, pyrrolidinyl, or thienyl ring optionally substituted with one or two substituents independently selected from the group consisting of halo, $C_{1-3}$ aliphatic, and $C_{1-3}$ fluoroaliphatic.

In some embodiments, $R^3$ is hydrogen, $C_{1-3}$ aliphatic, $C_{1-3}$ fluoroaliphatic, or —$CH_2$—$OCH_3$.

In some embodiments, $R^5$ is hydrogen, $C_{1-3}$ aliphatic, or $C_{1-3}$ fluoroaliphatic.

In certain embodiments, $R^a$ is halo, $C_{1-3}$ aliphatic, $C_{1-3}$ fluoroaliphatic, —OH, —O($C_{1-3}$ aliphatic), —O($C_{1-3}$ fluoroaliphatic), —C≡C—$R^3$, —CH═CH—$R^3$, or an optionally substituted pyrrolidinyl, thienyl, furyl, or phenyl ring, wherein $R^3$ is hydrogen, $C_{1-3}$ aliphatic, $C_{1-3}$ fluoroaliphatic, or —$CH_2$—$OCH_3$. In certain particular embodiments, $R^a$ is selected from the group consisting of chloro, fluoro, $C_{1-3}$ aliphatic, $C_{1-3}$ fluoroaliphatic, —$OCH_3$, —$OCF_3$, —C≡C—H, —C≡C—$CH_3$, —C≡C—$CH_2OCH_3$, —CH═$CH_2$, —CH═CHC$H_3$, N-methylpyrrolidinyl, thienyl, methylthienyl, furyl, methylfuryl, phenyl, fluorophenyl, and tolyl. In certain embodiments, $R^a$ is a phenyl, furyl, pyrrolidinyl, or thienyl ring optionally substituted with one or two substituents independently selected from the group consisting of halo, $C_{1-3}$ aliphatic, and $C_{1-3}$ fluoroaliphatic.

Table 4 provides the chemical names for specific examples of compounds of formula (V).

TABLE 4

Examples of Compounds of Formula (V)

| | Chemical Name |
|---|---|
| V-1 | 4-{[9-chloro-7-(2-fluoro-6-methoxyphenyl)-5H-pyrimido[5,4-d][2]benzazepin-2-yl]amino}-2-methoxybenzoic acid |
| V-2 | 4-{[9-ethynyl-7-(2-fluoro-6-methoxyphenyl)-5H-pyrimido[5,4-d][2]benzazepin-2-yl]amino}-2-methoxybenzoic acid |
| V-3 | 4-({9-chloro-7-[2-fluoro-6-(trifluoromethoxy)phenyl]-5H-pyrimido[5,4-d][2]benzazepin-2-yl}amino)-2-methoxybenzoic acid |
| V-4 | 4-{[7-(2-fluoro-6-methoxyphenyl)-9-(1-methyl-1H-pyrrol-2-yl)-5H-pyrimido[5,4-d][2]benzazepin-2-yl]amino}-2-methoxybenzoic acid |

TABLE 4-continued

Examples of Compounds of Formula (V)

| | Chemical Name |
|---|---|
| V-5 | 4-{[7-(2-fluoro-6-methoxyphenyl)-9-(4-methyl-3-thienyl)-5H-pyrimido[5,4-d][2]benzazepin-2-yl]amino}-2-methoxybenzoic acid |
| V-6 | 4-{[7-(2-fluoro-6-methoxyphenyl)-9-(3-methyl-2-furyl)-5H-pyrimido[5,4-d][2]benzazepin-2-yl]amino}-2-methoxybenzoic acid |
| V-7 | 4-({9-ethynyl-7-[2-fluoro-6-(2,2,2-trifluoroethoxy)phenyl]-5H-pyrimido[5,4-d][2]benzazepin-2-yl}amino)-2-methoxybenzoic acid |
| V-8 | 4-{[9-chloro-7-(2,6-difluorophenyl)-5H-pyrimido[5,4-d][2]benzazepin-2-yl]amino}-2-methoxybenzoic acid |
| V-9 | 4-{[7-(2-fluoro-6-methoxyphenyl)-9-(2-methylphenyl)-5H-pyrimido[5,4-d][2]benzazepin-2-yl]amino}-2-methoxybenzoic acid |
| V-10 | 4-{[7-(2-fluoro-6-methoxyphenyl)-9-prop-1-yn-1-yl-5H-pyrimido[5,4-d][2]benzazepin-2-yl]amino}-2-methoxybenzoic acid |
| V-11 | 4-{[7-(2-fluoro-6-methoxyphenyl)-9-vinyl-5H-pyrimido[5,4-d][2]benzazepin-2-yl]amino}-2-methoxybenzoic acid |
| V-12 | 4-{[7-(2-fluoro-6-methoxyphenyl)-9-(2-fluorophenyl)-5H-pyrimido[5,4-d][2]benzazepin-2-yl]amino}-2-methoxybenzoic acid |
| V-13 | 4-{[7-(2-fluoro-6-methoxyphenyl)-9-(3-methoxyprop-1-yn-1-yl)-5H-pyrimido[5,4-d][2]benzazepin-2-yl]amino}-2-methoxybenzoic acid |
| V-14 | 4-({7-(2-fluoro-6-methoxyphenyl)-9-[(1E)-prop-1-en-1-yl]-5H-pyrimido[5,4-d][2]benzazepin-2-yl}amino)-2-methoxybenzoic acid |
| V-15 | 4-({9-chloro-7-[2-fluoro-6-(2,2,2-trifluoroethoxy)phenyl]-5H-pyrimido[5,4-d][2]benzazepin-2-yl}amino)-2-methoxybenzoic acid |
| V-16 | 4-{[7-(2-fluoro-6-methoxyphenyl)-9-(2-furyl)-5H-pyrimido[5,4-d][2]benzazepin-2-yl]amino}-2-methoxybenzoic acid |
| V-17 | 4-{[9-chloro-7-(2-fluoro-6-hydroxyphenyl)-5H-pyrimido[5,4-d][2]benzazepin-2-yl]amino}-2-methoxybenzoic acid |
| V-18 | 4-{[7-(2-fluoro-6-methoxyphenyl)-9-phenyl-5H-pyrimido[5,4-d][2]benzazepin-2-yl]amino}-2-methoxybenzoic acid |

In one embodiment, the compound of formula (III), (IV), or (V) is 4-{[9-chloro-7-(2-fluoro-6-methoxyphenyl)-5H-pyrimido[5,4-d][2]benzazepin-2-yl]amino}-2-methoxybenzoic acid (alisertib (MLN8237)), or a pharmaceutically acceptable salt thereof. In a particular embodiment, the compound of formula (III), (IV), or (V) is sodium 4-{[9-chloro-7-(2-fluoro-6-methoxyphenyl)-5H-pyrimido[5,4-d][2]benzazepin-2-yl]amino}-2-methoxybenzoate (alisertib sodium). In another embodiment, the compound of formula (III), (IV), or (V) is sodium 4-{[9-chloro-7-(2-fluoro-6-methoxyphenyl)-5H-pyrimido[5,4-d][2]benzazepin-2-yl]amino}-2-methoxybenzoate monohydrate. In another embodiment, the compound of formula (III), (IV), or (V) is sodium 4-{[9-chloro-7-(2-fluoro-6-methoxyphenyl)-5H-pyrimido[5,4-d][2]benzazepin-2-yl]amino}-2-methoxybenzoate polymorph Form 2, as described in US Publication No. 2008/0167292, U.S. Pat. No. 8,026,246, and US Publication No. 2011/0245234, hereby incorporated by reference in their entirety.

Compounds of formula (III), (IV), or (V) are known in the art and can be prepared by the methods of US Publication No. 2008/0045501, U.S. Pat. No. 7,572,784, WO 05/111039, WO 08/021038, U.S. Pat. No. 7,718,648, WO 08/063525, US Publication No. 2008/0167292, U.S. Pat. No. 8,026,246, WO 10/134965, US Publication No. 2010/0310651, WO 11/014248, US Publication No. 2011/0039826, and US Publication No. 2011/0245234, which are hereby incorporated by reference in their entirety.

In another aspect, the invention provides a method for inhibiting cellular growth/cellular proliferation comprising contacting a cell with an mTORC1/2 inhibitor (as described herein) in combination with a selective inhibitor of Aurora A kinase (as described herein). In one embodiment, the invention provides a method for inhibiting cellular growth/cellular proliferation comprising contacting a cell with an mTORC1/2 inhibitor in combination with a selective inhibitor of Aurora A kinase, e.g., sodium 4-{[9-chloro-7-(2-fluoro-6-methoxyphenyl)-5H-pyrimido[5,4-d][2]benzazepin-2-yl]amino}-2-methoxybenzoate. In an another embodiment, the invention provides a method for inhibiting cellular growth/cellular proliferation comprising contacting a cell with an mTORC1/2 inhibitor, e.g., 3-(2-amino-1,3-benzoxazol-5-yl)-1-(propan-2-yl)-1H-pyrazolo [3,4-d] pyrimidin-4-amine, or a pharmaceutically acceptable salt thereof, in combination with a selective inhibitor of Aurora A kinase.

Preferably, the method according to the invention causes an inhibition of cell proliferation of the contacted cells. The phrase "inhibiting cell proliferation" is used to denote the ability of an mTORC1/2 inhibitor in combination with a selective inhibitor of Aurora A kinase to inhibit cell number or cell growth in contacted cells as compared to cells not contacted with the inhibitors. An assessment of cell proliferation can be made by counting cells using a cell counter or by an assay of cell viability, e.g., a BrdU, MTT, XTT, or WST assay. Where the cells are in a solid growth (e.g., a solid tumor or organ), such an assessment of cell proliferation can be made by measuring the growth, e.g., with calipers, and comparing the size of the growth of contacted cells with non-contacted cells.

Preferably, the growth of cells contacted with an mTORC1/2 inhibitor in combination with a selective inhibitor of Aurora A kinase is retarded by at least about 50% as compared to growth of non-contacted cells. In various embodiments, cell proliferation of contacted cells is inhibited by at least about 75%, at least about 90%, or at least about 95% as compared to non-contacted cells. In some embodiments, the phrase "inhibiting cell proliferation" includes a reduction in the number of contacted cells, as compare to non-contacted cells. Thus, an mTORC1/2 inhibitor in combination with a selective inhibitor of Aurora A kinase that inhibits cell proliferation in a contacted cell may induce the contacted cell to undergo growth retardation, to undergo growth arrest, to undergo programmed cell death (i.e., apoptosis), or to undergo necrotic cell death.

In another aspect, the invention provides a pharmaceutical composition comprising i) an mTORC1/2 inhibitor (as described herein); and ii) a selective inhibitor of Aurora A kinase (as described herein). In some embodiments, the mTORC1/2 inhibitor is selected from the group consisting of a) the compounds of formulas I, I-A, I-B, I-B1, I-B2, I-C, I-D, I-C1, I-C2, I-D1, I-D2, I-E, I-E1, I-E2, I-C1a; b) the compounds as described in, for example, U.S. Pat. No. 7,651,687 or 7,585,868; or International Patent Applications WO 2007/079164, WO 2007/061737, WO 2007/106503, WO 2007/134828 or WO2011/025889, hereby incorporated by reference in their entirety; c) the compounds 3-(2-amino-1,3-benzoxazol-5-yl)-1-(propan-2-yl)-1H-pyrazolo [3, 4-d] pyrimidin-4-amine, CC223 (Celgene), OSI027 (OSI Pharmaceuticals), DS3078 (Daiichi), AZD8055 (Astra Zeneca), or AZD2014 (Astra Zeneca); and d) pharmaceutically acceptable salts thereof. In some embodiments the selective inhibitor of Aurora A kinase is selected from the group consisting of a) the compounds of formulas (III), (IV), and (V); b) the compounds disclosed in, for example, US Publication No. 2008/0045501, U.S. Pat. No. 7,572,784, WO 05/111039, WO 08/021038, U.S. Pat. No. 7,718,648, WO 08/063525, US Publication No. 2008/0167292, U.S. Pat. No. 8,026,246, WO 10/134965, US Publication No. 2010/0310651, WO 11/014248, US Publication No. 2011/0039826, and US Publication No. 2011/0245234; c) sodium 4-{[9-chloro-7-(2-fluoro-6-methoxyphenyl)-5H-pyrimido [5,4-d][2]benzazepin-2-yl]amino}-2-methoxybenzoate, ENMD-2076 (EntreMed), and MK-5108 (Vertex/Merck); and d) pharmaceutically acceptable salts of any of the foregoing.

If a pharmaceutically acceptable salt of the mTORC1/2 inhibitor or selective inhibitor of Aurora A kinase is utilized in these compositions, the salt preferably is derived from an inorganic or organic acid or base. For reviews of suitable salts, see, e.g., Berge et al, *J. Pharm. Sci.* 66:1-19 (1977) and *Remington: The Science and Practice of Pharmacy*, 20th Ed., ed. A. Gennaro, Lippincott Williams & Wilkins, 2000.

Nonlimiting examples of suitable acid addition salts include the following: acetate, adipate, alginate, aspartate, benzoate, benzene sulfonate, bisulfate, butyrate, citrate, camphorate, camphor sulfonate, cyclopentanepropionate, digluconate, dodecylsulfate, ethanesulfonate, fumarate, lucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenyl-propionate, picrate, pivalate, propionate, succinate, tartrate, thiocyanate, tosylate and undecanoate.

Suitable base addition salts include, without limitation, ammonium salts, alkali metal salts, such as sodium and potassium salts, alkaline earth metal salts, such as calcium and magnesium salts, salts with organic bases, such as dicyclohexylamine, N-methyl-D-glucamine, t-butylamine, ethylene diamine, ethanolamine, and choline, and salts with amino acids such as arginine, lysine, and so forth.

Also, basic nitrogen-containing groups may be quaternized with such agents as lower alkyl halides, such as methyl, ethyl, propyl, and butyl chlorides, bromides and iodides; dialkyl sulfates, such as dimethyl, diethyl, dibutyl and diamyl sulfates, long chain halides such as decyl, lauryl, myristyl and stearyl chlorides, bromides and iodides, aralkyl halides, such as benzyl and phenethyl bromides and others. Water or oil-soluble or dispersible products are thereby obtained.

The term "pharmaceutically acceptable carrier" is used herein to refer to a material that is compatible with a recipient subject, preferably a mammal, more preferably a human, and is suitable for delivering an active agent to the target site without terminating the activity of the agent. The toxicity or adverse effects, if any, associated with the carrier preferably are commensurate with a reasonable risk/benefit ratio for the intended use of the active agent.

The terms "carrier", "adjuvant", or "vehicle" are used interchangeably herein, and include any and all solvents, diluents, and other liquid vehicles, dispersion or suspension aids, surface active agents, isotonic agents, thickening or emulsifying agents, preservatives, solid binders, lubricants and the like, as suited to the particular dosage form desired. *Remington: The Science and Practice of Pharmacy, 20th Ed.*, ed. A. Gennaro, Lippincott Williams & Wilkins, 2000 discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as disodium hydrogen phosphate, potassium hydrogen phosphate, sodium carbonate, sodium bicarbonate, potassium carbonate, potassium bicarbonate, magnesium hydroxide and aluminum hydroxide, glycine, sorbic acid, or potassium sorbate, partial glyceride mixtures of saturated vegetable fatty acids, water, pyrogen-free water, salts or electrolytes such as protamine sulfate, disodium hydrogen phosphate, potassium hydrogen phosphate, sodium chloride, and zinc salts, colloidal silica, magnesium trisilicate, polyvinyl pyrrolidone, polyacrylates, waxes, polyethylene-polyoxypropylene-block polymers, wool fat, sugars such as lactose, glucose, sucrose, starches such as corn starch and potato starch, cellulose and its derivatives such as sodium carboxymethyl cellulose, ethyl cellulose and cellulose acetate, powdered tragacanth; malt, gelatin, talc, excipients such as cocoa butter and suppository waxes, oils such as peanut oil, cottonseed oil, safflower oil, sesame oil, olive oil, corn oil and soybean oil, glycols such as propylene glycol and polyethylene glycol, esters such as ethyl oleate and ethyl laurate, agar, alginic acid, isotonic saline, Ringer's solution, alcohols such as ethanol, isopropyl alcohol, hexadecyl alcohol, and glycerol, cyclodextrins, lubricants such as sodium lauryl sulfate and magnesium stearate, petroleum hydrocarbons such as mineral oil and petrolatum. Coloring agents, releasing agents, coating agents, sweetening, flavoring and perfuming agents, preservatives and antioxidants can also be present in the composition, according to the judgment of the formulator.

The pharmaceutical compositions of the invention can be manufactured by methods well known in the art such as conventional granulating, mixing, dissolving, encapsulating, lyophilizing, or emulsifying processes, among others. Compositions may be produced in various forms, including granules, precipitates, or particulates, powders, including freeze dried, rotary dried or spray dried powders, amorphous powders, tablets, capsules, syrup, suppositories, injections, emulsions, elixirs, suspensions or solutions. Formulations may optionally contain solvents, diluents, and other liquid vehicles, dispersion or suspension aids, surface active agents, pH modifiers, isotonic agents, thickening or emulsifying agents, stabilizers and preservatives, solid binders, lubricants and the like, as suited to the particular dosage form desired.

According to a preferred embodiment, the compositions of this invention are formulated for pharmaceutical administration to a mammal, preferably a human being. Such pharmaceutical compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intravenously, or subcutaneously. The formulations of the invention may be designed to be short-acting, fast-releasing, or long-acting. Still further, compounds can be administered in a local rather than systemic means, such as administration (e.g., by injection) at a tumor site.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, cyclodextrins, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use. Compositions formulated for parenteral administration may be injected by bolus injection or by timed push, or may be administered by continuous infusion.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents such as phosphates or carbonates.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

In another aspect, the present invention provides new combination therapies for the treatment of disease conditions including proliferative disorders, autoimmune diseases, inflammatory diseases, fibrotic diseases and kidney diseases.

As used herein, the terms "proliferative disorders" or "proliferative diseases" includes, but is not limited to, Acanthoma, Accelerated myelogenous leukemia, Acinic cell carcinoma, Acoustic neuroma, Acral lentiginous melanoma, Acrospiroma, Acute eosinophilic leukemia, Acute lymphoblastic leukemia (ALL), Acute megakaryoblastic leukemia, Acute monocytic leukemia, Acute myeloblastic leukemia with maturation, Acute myeloid dendritic cell leukemia, Acute myeloid leukemia (AML), Acute promyelocytic leukemia, Adamantinoma, Adenocarcinoma, Adenocarcinoma of the lung, Adenoid cystic carcinoma, Adenoma, Adenomatoid odontogenic tumor, Adrenocortical carcinoma, Adult T-cell leukemia, Aggressive NK-cell leukemia, AIDS-Related Cancers, AIDS-related lymphoma, Alveolar soft part sarcoma, Ameloblastic fibroma, Anal cancer, Anaplastic large cell lymphoma, Anaplastic thyroid cancer, Androgen-dependent prostate cancer, Androgen-independent prostate cancer Angioimmunoblastic T-cell lymphoma, Angiomyolipoma, Angiosarcoma, Appendix cancer, Astrocytoma, Atypical teratoid rhabdoid tumor, Basal cell carcinoma, Basal-like carcinoma, B-cell leukemia, B-cell lymphoma, Bellini duct carcinoma, Biliary tract cancer, Bladder cancer, Blastoma, Bone Cancer, Bone tumor, Brain Stem Glioma, Brain Tumor, Breast Cancer, Brenner tumor, Bronchial Tumor, Bronchioloalveolar carcinoma, Brown tumor, Burkitt's lymphoma, Cancer of Unknown Primary Site, Carcinoid Tumor, Carcinoma, Carcinoma in situ, Carcinoma of the penis, Carcinoma of Unknown Primary Site, Carcinosarcoma, Castleman's Disease, Central Nervous System Embryonal Tumor, Cerebellar Astrocytoma, Cerebral Astrocytoma, Cervical Cancer, Cholangiocarcinoma, Chondroma, Chondrosarcoma, Chordoma, Choriocarcinoma, Choroid plexus papilloma, Chronic Lymphocytic Leukemia (CLL), Chronic monocytic leukemia, Chronic myelogenous leukemia (CML), Chronic myelogenous leukemia blast phase, Chronic Myeloproliferative Disorder, Chronic neutrophilic leukemia, Clear-cell tumor, Colon Cancer, Colorectal cancer, Craniopharyngioma, Cutaneous T-cell lymphoma, Degos disease, Dermatofibrosarcoma protuberans, Dermoid cyst, Desmoplastic small round cell tumor, Diffuse large B cell lymphoma, Dysembryoplastic neuroepithelial tumor, Embryonal carcinoma, Endodermal sinus tumor, Endometrial cancer, Endometrial Uterine Cancer, Endometrioid tumor, Enteropathy-associated T-cell lymphoma, Ependymoblastoma, Ependymoma, Epidermoid cancer, Epithelioid sarcoma, Erythroleukemia, Esophageal cancer, Esthesioneuroblastoma, Ewing Family of Tumor, Ewing Family Sarcoma, Ewing's sarcoma, Extracranial Germ Cell Tumor, Extragonadal Germ Cell Tumor, Extrahepatic Bile Duct Cancer, Extramammary Paget's disease, Fallopian tube cancer, Fetus in fetu, Fibroma, Fibrosarcoma, Follicular lymphoma, Follicular thyroid cancer, Gallbladder Cancer, Gallbladder cancer, Ganglioglioma, Ganglioneuroma, Gastric Cancer, Gastric lymphoma, Gastrointestinal cancer, Gastrointestinal Carcinoid Tumor, Gastrointestinal Stromal Tumor, Gastrointestinal stromal tumor, Germ cell tumor, Germinoma, Gestational choriocarcinoma, Gestational Trophoblastic Tumor, Giant cell tumor of bone, Glioblastoma multiforme, Glioma, Gliomatosis cerebri, Glomus tumor, Glucagonoma, Gonadoblastoma, Granulosa cell tumor, Gynecological cancer, Hairy Cell Leukemia, Hairy cell leukemia, Head and Neck Cancer, Head and neck cancer, Heart cancer, Hemangioblastoma, Hemangioma, Hemangiopericytoma, Hemangiosarcoma, Hematological malignancy, Hepatocellular carcinoma, Hepatosplenic T-cell lymphoma, Hereditary breast-ovarian cancer syndrome, Hodgkin disease, Hodgkin's disease, Hodgkin Lymphoma, Hodgkin's lymphoma, Hypopharyngeal Cancer, Hypothalamic Glioma, Inflammatory breast cancer, Intraocular Melanoma, Islet cell carcinoma, Islet Cell Tumor, Juvenile myelomonocytic leukemia, Kaposi Sarcoma, Kaposi's sarcoma, Kidney Cancer, Klatskin tumor, Krukenberg tumor, Laryngeal Cancer, Laryngeal cancer, Lentigo maligna melanoma, Leukemia, Lip and Oral Cavity Cancer, Liposarcoma, Lung cancer, Luteoma, Lymphangioma, Lymphangiosarcoma, Lymphoepithelioma, Lymphoid leukemia, Lymphoma, Macroglobulinemia, Malignant Fibrous Histiocytoma, Malignant fibrous histiocytoma, Malignant Fibrous Histiocytoma of Bone, Malignant Glioma, Malignant Mesothelioma, Malignant peripheral nerve sheath tumor, Malignant rhabdoid tumor, Malignant triton tumor, MALT lymphoma, Mantle cell lymphoma, Mast cell leukemia, Mediastinal germ cell tumor, Mediastinal tumor, Medullary thyroid cancer, Medulloblastoma, Medulloblastoma, Medulloepithelioma, Melanoma, Meningioma, Merkel Cell Carcinoma, Mesothelioma, Metastatic Squamous Neck Cancer with Occult Primary, Metastatic urothelial carcinoma, Mixed Mullerian tumor, Monocytic leukemia, Mouth Cancer, Mucinous tumor, Multiple Endocrine Neoplasia Syndrome, Multiple Myeloma (MM), Mycosis Fungoides, Mycosis fungoides, Myelodysplastic Disease, Myelodysplastic Syndromes (MDS), Myeloid leukemia, Myeloid sarcoma, Myeloproliferative Disease, Myeloproliferative Syndromes, Myxoma, Nasal Cavity Cancer, Nasopharyngeal Cancer, Nasopharyngeal carcinoma, Neoplasm, Neurinoma, Neuroblastoma, Neuroblastoma, Neuroendocrine cancer, Neurofibroma, Neuroma, Nodular melanoma, Non-Hodgkin Lymphoma, Non-Hodgkin's lymphoma, Nonmelanoma Skin Cancer, Non-Small Cell Lung Cancer (NSCLC), Ocular oncology, Oligoastrocytoma, Oligodendroglioma, Oncocytoma, Optic nerve sheath meningioma, Oral Cancer, Oropharyngeal Cancer, Osteosarcoma, Osteosarcoma, Ovarian cancer, Ovarian Epithelial Cancer, Ovarian Germ Cell Tumor, Ovarian Low Malignant Potential Tumor, Paget's disease of the breast, Pancoast tumor, Pancreatic Cancer, Pancreatic cancer, Papillary thyroid cancer, Papillomatosis, Paraganglioma, Paranasal Sinus Cancer, Parathyroid Cancer, Pediatric Sarcomas, Penile Cancer, Perivascular epithelioid cell tumor, Pharyngeal Cancer, Pheochromocytoma, Pineal Parenchymal Tumor of Intermediate Differentiation, Pineoblastoma, Pituicytoma, Pituitary adenoma, Pituitary tumor, Plasma Cell Neoplasm, Pleuropulmonary blastoma, Polyembryoma, Precursor T-lymphoblastic lymphoma, Primary central nervous system lymphoma, Primary effusion lymphoma, Primary Hepatocellular Cancer, Primary Liver Cancer, Primary peritoneal cancer, Primitive neuroectodermal tumor, Progressive epithelial ovarian cancer, Prostate cancer, Pseudomyxoma peritonei, Rectal Cancer, Renal cell carcinoma, Respiratory Tract Carcinoma Involving the NUT Gene on Chromosome 15, Retinoblastoma, Refractory anemia, Refractory anemia with ringed sideroblasts, Refractory anemia with excess blasts (RAEB), and RAEB in transformation, Rhabdomyoma, Rhabdomyosarcoma, Richter's transformation, Sacrococcygeal teratoma, Salivary Gland Cancer, Sarcoma, Schwannomatosis, Sebaceous gland carcinoma, Secondary neoplasm, Seminoma, Serous tumor, Sertoli-Leydig cell tumor, Sex cord-stromal tumor, Sezary Syndrome, Signet ring cell carcinoma, Skin Cancer, Small blue round cell tumor, Small cell carcinoma, Small Cell Lung Cancer (SCLC), Small cell lymphoma, Small intestine cancer, Soft tissue sarcoma, Somatostatinoma, Soot wart, Spinal Cord Tumor, Spinal tumor, Splenic marginal zone lymphoma, Squamous cell carcinoma, Squamous cell carcinoma of the head and neck, Stomach cancer, Superficial spreading melanoma, Supratentorial Primitive Neuroectodermal Tumor, Surface epithelial-stromal tumor, Synovial sarcoma, T-cell acute lymphoblastic leukemia, T-cell large granular lymphocyte leukemia, T-cell leukemia, T-cell lymphoma, T-cell prolymphocytic leukemia, Teratoma, Terminal lymphatic cancer, Testicular cancer, Thecoma, Throat Cancer, Thymic Carcinoma, Thymoma, Thyroid cancer, Transitional Cell Cancer of Renal Pelvis and Ureter, Transitional cell carcinoma, Tumor angiogenesis, Urachal cancer, Urethral cancer, Urogenital neoplasm, Uterine sarcoma, Uveal melanoma, Vaginal Cancer, Verner Morrison syndrome, Verrucous carcinoma, Visual Pathway Glioma, Vulvar Cancer, Waldenstrom's macroglobulinemia, Warthin's tumor, Wilms' tumor, or any combination thereof. These "proliferative disorders" and "proliferative diseases" encompass both primary and metastatic or advanced cancers, including intransient metasteses. In one embodiment, the cancer is metastatic. In one embodiment the cancer is a solid tissue cancer or a heme-lymphatic cancer.

In some embodiments, the disease condition treatable by the combination of an mTORC1/2 inhibitor and an Aurora A kinase selective inhibitor include bladder cancer, colon cancer, breast cancer, ovarian cancer, lung cancer, SCLC, NSCLC, head and neck cancer, gastrointestinal cancer, brain tumor, melanoma, renal cell carcinoma, prostate cancer, neuroendocrine cancer, endometrial cancer, glioblastoma, leukemia, non-Hodgkin's lymphoma, Diffuse large B cell lymphoma, mantle cell lymphoma, glioma, sarcoma, and neuroblastoma. In some other embodiments, the disease condition treatable by the combination of an mTORC1/2 inhibitor and an Aurora A kinase selective inhibitor include colon cancer, breast cancer, ovarian cancer, renal cell carcinoma, melanoma, SCLC, Diffuse large B cell lymphoma, mantle cell lymphoma, and neuroblastoma. In some other embodiments, the disease condition treatable by the combination of an mTORC1/2 inhibitor and an Aurora A kinase selective inhibitor include breast cancer, ovarian cancer, renal cell carcinoma, SCLC, Diffuse large B cell lymphoma, mantle cell lymphoma, and neuroblastoma. In some other embodiments the disease condition is a PIK3CA/PTEN mutant tumor.

In some other embodiments, the disease condition treatable by the combination of an mTORC1/2 inhibitor and an Aurora A kinase selective inhibitor include heart conditions including atherosclerosis, heart hypertrophy, cardiac myocyte dysfunction, elevated blood pressure and vasoconstriction. In some other embodiments, the disease condition is related to vasculogenesis or angiogenesis.

In some other embodiments, the disease condition treatable by the combination of an mTORC1/2 inhibitor and an Aurora A kinase selective inhibitor include tumor angiogenesis, chronic inflammatory disease such as rheumatoid arthritis, atherosclerosis, inflammatory bowel disease, skin diseases such as psoriasis, eczema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer.

In some other embodiments, the disease condition treatable by the combination of an mTORC1/2 inhibitor and an Aurora A kinase selective inhibitor include conditions related to an undesirable, over-active, harmful or deleterious immune response in a mammal, collectively termed "autoimmune disease." Autoimmune disorders include, but are not limited to, Crohn's disease, ulcerative colitis, psoriasis, psoriatic arthritis, juvenile arthritis and ankylosing spondylitis, Other non-limiting examples of autoimmune disorders include autoimmune diabetes, multiple sclerosis, systemic lupus erythematosus (SLE), rheumatoid spondylitis, gouty arthritis, allergy, autoimmune uveitis, nephrotic syndrome, multisystem autoimmune diseases, autoimmune hearing loss, adult respiratory distress syndrome, shock lung, chronic pulmonary inflammatory disease, pulmonary sarcoidosis, pulmonary fibrosis, idiopathic pulmonary fibrosis, silicosis, idiopathic interstitial lung disease, chronic obstructive pulmonary disease, asthma, restenosis, spondyloarthropathies, Reiter's syndrome, autoimmune hepatitis, inflammatory skin disorders, vasculitis of large vessels, medium vessels or small vessels, endometriosis, prostatitis and Sjogren's syndrome. Undesirable immune response can also be associated with or result in, e.g., asthma, emphysema, bronchitis, psoriasis, allergy, anaphylaxsis, auto-immune diseases, rhuematoid arthritis, graft versus host disease, transplantation rejection, lung injuries, and lupus erythematosus. The pharmaceutical compositions of the present invention can be used to treat other respiratory diseases including but not limited to diseases affecting the lobes of lung, pleural cavity, bronchial tubes, trachea, upper respiratory tract, or the nerves and muscle for breathing.

In some other embodiments, the disease condition treatable by the combination of an mTORC1/2 inhibitor and an Aurora A kinase selective inhibitor include liver diseases (including diabetes), pancreatitis or kidney disease (including proliferative glomerulonephritis and diabetes-induced renal disease).

In some other embodiments, the disease condition treatable by the combination of an mTORC1/2 inhibitor and an Aurora A kinase selective inhibitor include vasculogenesis or angiogenesis in a mammal which can manifest as tumor angiogenesis, chronic inflammatory disease such as rheumatoid arthritis, inflammatory bowel disease, atherosclerosis, skin diseases such as psoriasis, eczema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer.

In some other embodiments, the disease condition treatable by the combination of an mTORC1/2 inhibitor and an Aurora A kinase selective inhibitor include disorders involving platelet aggregation or platelet adhesion, including but not limited to Bernard-Soulier syndrome, Glanzmann's thrombasthenia, Scott's syndrome, von Willebrand disease, Hermansky-Pudlak Syndrome, and Gray platelet syndrome.

In some other embodiments, the disease condition treatable by the combination of an mTORC1/2 inhibitor and an Aurora A kinase selective inhibitor include skeletal muscle atrophy, skeletal muscle hypertrophy, leukocyte recruitment in cancer tissue, invasion metastasis, melanoma, Kaposi's sarcoma, acute and chronic bacterial and viral infections, sepsis, glomerulo sclerosis, glomerulo, nephritis, or progressive renal fibrosis.

The term "patient", as used herein, means an animal, preferably a mammal, more preferably a human. In some embodiments, the patient has been treated with an agent, e.g., an Aurora A kinase selective inhibitor or an mTORC1/2 inhibitor, prior to initiation of treatment according to the method of the invention. In some embodiments, the patient is a patient at risk of developing or experiencing a recurrence of a proliferative disorder.

The expressions "therapeutically effective" and "therapeutic effect" refer to a benefit including, but not limited to, the treatment or amelioration of symptoms of a proliferative disorder discussed herein. It will be appreciated that the therapeutically effective amount or the amount of agent required to provide a therapeutic effect will vary depending upon the intended application (in vitro or in vivo), or the subject and disease condition being treated (e.g., nature of the severity of the condition to be treated, the particular inhibitor, the route of administration and the age, weight, general health, and response of the individual patient), which can be readily determined by a person of skill in the art. For example, an amount of a selective inhibitor of Aurora A kinase in combination with an amount of an mTORC1/2 inhibitor is therapeutically effective if it is sufficient to effect the treatment or amelioration of symptoms of a proliferative disorder discussed herein.

The expressions "prophylactically effective" and "prophylactic effect" refer to a benefit including, but not limited to, the prophylaxis of symptoms of a proliferative disorder discussed herein. It will be appreciated that the prophylactically effective amount or the amount of agent required to provide a prophylactic effect will vary depending upon the intended application (in vitro or in vivo), or the subject and disease condition being prevented (e.g., nature of the severity of the condition to be prevented, the particular inhibitor, the route of administration and the age, weight, general health, and response of the individual patient), which can be readily determined by a person of skill in the art. For example, an amount of an mTORC1/2 inhibitor in combination with an amount of a selective inhibitor of Aurora A kinase is prophylactically effective if it is sufficient to effect the prophylaxis of symptoms of a proliferative disorder discussed herein.

Compositions for use in the method of the invention may be formulated in unit dosage form for ease of administration and uniformity of dosage. The expression "unit dosage form" as used herein refers to a physically discrete unit of agent appropriate for the patient to be treated. It will be understood, however, that the total daily usage of the compounds and compositions of the present invention will be decided by the attending physician within the scope of sound medical judgment. A unit dosage form for parenteral administration may be in ampoules or in multi-dose containers.

The mTORC1/2 inhibitor may be administered with the selective inhibitor of Aurora A kinase in a single dosage form or as a separate dosage form. In one embodiment, when administered as a separate dosage form, the mTORC1/2 inhibitor may be administered prior to, at the same time as, or following administration of the selective inhibitor of Aurora A kinase of the invention. In another embodiment, when administered as a separate dosage form, one or more doses of the mTORC1/2 inhibitor may be administered prior to the selective inhibitor of Aurora A kinase of the invention. In another embodiment, when administered as a separate dosage form, one or more doses of the selective inhibitor of Aurora A kinase may be administered prior to the mTORC1/2 inhibitor of the invention.

In some particular embodiments, the method of the invention comprises administering to a patient suffering from a proliferative disorder an mTORC1/2 inhibitor of Formula I, I-A, I-B, I-B1, I-B2, I-C, I-D, I-C1, I-C2, I-D1, I-D2, I-E, I-E1, I-E2, or I-C1a, as defined herein, in combination with a selective inhibitor of Aurora A kinase of Formula (III), (IV) or (V), as defined herein, wherein the amounts of each inhibitor are therapeutically effective when used in combination.

In another embodiment, the method of the invention comprises administering to a patient suffering from a proliferative disorder 3-(2-amino-1,3-benzoxazol-5-yl)-1-(propan-2-yl)-1H-pyrazolo [3, 4-d] pyrimidin-4-amine, in combination with a selective inhibitor of Aurora A kinase of Formula (III), (IV) or (V), as defined herein, wherein the amounts of each inhibitor are therapeutically effective when used in combination.

In another embodiment, the method of the invention comprises administering to a patient suffering from a proliferative disorder an mTORC1/2 inhibitor of Formula I, I-A, I-B, I-B1, I-B2, I-C, I-D, I-C1, I-C2, I-D1, I-D2, I-E, I-E1, I-E2, or I-C1a, as defined herein, in combination with sodium 4-{[9-chloro-7-(2-fluoro-6-methoxyphenyl)-5H-pyrimido[5,4-d][2]benzazepin-2-yl]amino}-2-methoxybenzoate, wherein the amounts of each inhibitor are therapeutically effective when used in combination.

In another embodiment, the method of the invention comprises administering to a patient suffering from a proliferative disorder 3-(2-amino-1,3-benzoxazol-5-yl)-1-(propan-2-yl)-1H-pyrazolo [3, 4-d] pyrimidin-4-amine, in combination with sodium 4-({[9-chloro-7-(2-fluoro-6-methoxyphenyl)-5H-pyrimido[5,4-d][2]benzazepin-2-yl] amino}-2-methoxybenzoate, wherein the amounts of each inhibitor are therapeutically effective when used in combination.

Additionally, the invention relates to use of an mTORC1/2 inhibitor in the manufacture of a medicament for use in combination therapy with a selective inhibitor of Aurora A kinase for the treatment of a proliferative disorder. In other particular embodiments, the invention relates to the use of an mTORC1/2 inhibitor of Formula I, I-A, I-B, I-B1, I-B2, I-C, I-D, I-C1, I-C2, I-D1, I-D2, I-E, I-E1, I-E2, or I-C1a, (as defined herein), in the manufacture of a medicament for use in combination therapy with a selective inhibitor of Aurora A kinase of Formula (II), (IV) or (V) (as defined herein), for the treatment of a proliferative disorder.

In another embodiment, the invention relates to the use of 3-(2-amino-1,3-benzoxazol-5-yl)-1-(propan-2-yl)-1H-pyrazolo [3, 4-d] pyrimidin-4-amine, in the manufacture of a medicament for use in combination therapy with a selective inhibitor of Aurora A kinase of Formula (III), (IV) or (V) (as defined herein), for the treatment of a proliferative disorder.

In another embodiment, the invention relates to the use of an mTORC1/2 inhibitor of Formula I, I-A, I-B, I-B1, I-B2, I-C, I-D, I-C1, I-C2, I-D1, I-D2, I-E, I-E1, I-E2, or I-C1a, in the manufacture of a medicament for use in combination therapy with sodium 4-{[9-chloro-7-(2-fluoro-6-methoxyphenyl)-5H-pyrimido[5,4-d][2]benzazepin-2-yl]amino}-2-methoxybenzoate, as defined herein, for the treatment of a proliferative disorder.

In another embodiment, the invention relates to the use of 3-(2-amino-1,3-benzoxazol-5-yl)-1-(propan-2-yl)-1H-pyrazolo [3, 4-d] pyrimidin-4-amine, in the manufacture of a medicament for use in combination therapy with sodium 4-{[9-chloro-7-(2-fluoro-6-methoxyphenyl)-5H-pyrimido [5,4-d][2]benzazepin-2-yl]amino}-2-methoxybenzoate for the treatment of a proliferative disorder.

As specifically contemplated herein, the instant invention includes the following methods:

a. A method to treat a patient suffering from a proliferative disorder comprising administering to said patient an mTORC1/2 inhibitor, as defined herein, in combination with a selective inhibitor of Aurora A kinase, as defined herein, wherein the amounts of each inhibitor are therapeutically effective when used in combination. In some embodiments, the proliferative disorder is selected from the group consisting of breast cancer, ovarian cancer, renal cell carcinoma, SCLC, Diffuse large B cell lymphoma, mantle cell lymphoma, and neuroblastoma. In one embodiment, the proliferative disorder is breast cancer. In another embodiment, the proliferative disorder is ovarian cancer. In another embodiment, the proliferative disorder is renal cell carcinoma. In another embodiment, the proliferative disorder is SCLC. In another embodiment, the proliferative disorder is neuroblastoma.

b. A method to treat a patient suffering from a proliferative disorder comprising administering to said patient 3-(2-amino-1,3-benzoxazol-5-yl)-1-(propan-2-yl)-1H-pyrazolo [3, 4-d] pyrimidin-4-amine, or a pharmaceutically acceptable salt thereof, in combination with a selective inhibitor of Aurora A kinase, as defined herein, wherein the amounts of each inhibitor are therapeutically effective when used in combination. In some embodiments, the proliferative disorder is selected from the group consisting of breast cancer, ovarian cancer, renal cell carcinoma, SCLC, Diffuse large B cell lymphoma, mantle cell lymphoma, and neuroblastoma. In one embodiment, the proliferative disorder is breast cancer. In another embodiment, the proliferative disorder is ovarian cancer. In another embodiment, the proliferative disorder is renal cell carcinoma. In another embodiment, the proliferative disorder is SCLC. In another embodiment, the proliferative disorder is neuroblastoma.

c. A method to treat a patient suffering from a proliferative disorder comprising administering to said patient an mTORC1/2 inhibitor, as defined herein, in combination with sodium 4-{[9-chloro-7-(2-fluoro-6-methoxyphenyl)-5H-pyrimido[5,4-d][2]benzazepin-2-yl]amino}-2-methoxybenzoate, wherein the amounts of each inhibitor are therapeutically effective when used in combination. In some embodiments, the proliferative disorder is selected from the group consisting of breast cancer, ovarian cancer, renal cell carcinoma, SCLC, Diffuse large B cell lymphoma, mantle cell lymphoma, and neuroblastoma. In one embodiment, the proliferative disorder is breast cancer. In another embodiment, the proliferative disorder is ovarian cancer. In another embodiment, the proliferative disorder is renal cell carcinoma. In another embodiment, the proliferative disorder is SCLC. In another embodiment, the proliferative disorder is neuroblastoma.

d. A method to treat a patient suffering from a proliferative disorder comprising administering to said patient 3-(2-amino-1,3-benzoxazol-5-yl)-1-(propan-2-yl)-1H-pyrazolo [3, 4-d] pyrimidin-4-amine in combination with sodium 4-{[9-chloro-7-(2-fluoro-6-methoxyphenyl)-5H-pyrimido[5,4-d][2]benzazepin-2-yl]amino}-2-methoxybenzoate, or a pharmaceutically acceptable salt thereof, wherein the amounts of each inhibitor are therapeutically effective when used in combination. In some embodiments, the proliferative disorder is selected from the group consisting of breast cancer, ovarian cancer, renal cell carcinoma, SCLC, Diffuse large B cell lymphoma, mantle cell lymphoma, and neuroblastoma. In one embodiment, the proliferative disorder is breast cancer. In another embodiment, the proliferative disorder is ovarian cancer. In another embodiment, the proliferative disorder is renal cell carcinoma. In another embodiment, the proliferative disorder is SCLC. In another embodiment, the proliferative disorder is neuroblastoma.

In the methods of the invention, the mTORC1/2 inhibitor can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a selective Aurora A kinase inhibitor to a patient with a cell proliferative disorder. In some embodiments, the mTORC1/2 inhibitor and the selective Aurora A kinase inhibitor are administered within the same patient visit. In some embodiments, the mTORC1/2 inhibitor and the selective Aurora A kinase inhibitor are administered by the patient at home over a period of time that is approximately the same duration as a patient visit.

In some embodiments, the mTORC1/2 inhibitor and selective Aurora A kinase inhibitor are administered to a patient, for example, a mammal, such as a human, in a sequence and within a time interval such that the inhibitor that is administered first acts together with the inhibitor that is administered second to provide greater benefit than if each inhibitor were administered otherwise. For example, the mTORC1/2 inhibitor and selective Aurora A kinase inhibitor can be administered at the same time or sequentially in any order at different points in time; however, if not administered at the same time, the mTORC1/2 inhibitor and selective Aurora A kinase inhibitor are administered sufficiently close in time so as to provide the desired therapeutic or prophylactic effect of the combination of the two inhibitors. In one embodiment, the mTORC1/2 inhibitor and selective Aurora A kinase inhibitor exert their effect at times which overlap. In some embodiments, the mTORC1/2 inhibitor and Aurora A kinase inhibitor each are administered as separate dosage forms, in any appropriate form and by any suitable route. In other embodiments, the mTORC1/2 inhibitor and selective Aurora A kinase inhibitor are administered simultaneously in a single dosage form.

It will be appreciated that the frequency with which any of these therapeutic agents can be administered can be once or more than once over a period of about 2 days, about 3 days, about 4 days, about 5 days, about 6 days, about 7 days, about 8 days, about 9 days, about 10 days, about 11 days, about 12 days, about 13 days, about 14 days, about 20 days, about 28 days, about a week, about 2 weeks, about 3 weeks, about 4 weeks, about a month, about every 2 months, about every 3 months, about every 4 months, about every 5 months, about every 6 months, about every 7 months, about every 8 months, about every 9 months, about every 10 months, about every 11 months, about every year, about every 2 years, about every 3 years, about every 4 years, or about every 5 years.

In some embodiments of the invention, an agent may be administered daily, weekly, biweekly, or monthly for a particular period of time. For example, an agent may be dosed daily over a 28 day time period, daily over a 21 day time period, daily over a 14 day time period, or daily over a seven day time period. In another example, an agent may be dosed twice daily over a 28 day time period, twice daily over a 21 day time period, twice daily over a 14 day time period, or twice daily over a seven day time period. In another example, an agent may be dosed weekly over a one week time period, weekly over a two week time period, weekly over a three week time period, or weekly over a four week time period. Alternatively, an agent may be administered daily, weekly, biweekly, or monthly for a particular period of time followed by a particular period of non-treatment. In some embodiments, a certain amount of the mTORC1/2 inhibitor can be administered daily for five days followed by two days of non-treatment, and repeated for one or more cycles of daily administration for five days followed by two days of non-treatment. In some embodiments, a certain amount of the mTORC1/2 inhibitor can be administered daily for three days followed by four days of non-treatment, and repeated for one or more cycles of daily administration for three days followed by four days of non-treatment. In some embodiments, a certain amount of the selective Aurora A kinase inhibitor can be administered twice daily for seven days followed by 14 days of non-treatment, which may be repeated for one or more cycles of twice daily administration for seven days followed by 14 days of non-treatment.

In some embodiments, courses of treatment are administered concomitantly to a patient, i.e., individual doses of the mTORC1/2 inhibitor and the selective Aurora A kinase inhibitor are administered as separate dosage forms yet within a time interval such that the two inhibitors can work together (e.g., within 1 hour, 2 hours, 4 hours, 6 hours, 12 hours, 24 hours, 48 hours, 72 hours, 96 hours, 5 days, 6 days, 1 week, or 2 weeks). In other words, the dosing regimens are carried out concomitantly because day one of each cycle begins on the same day even if the therapeutic agents are not administered simultaneously or during the same day during every day of the cycle.

In some embodiments, the treatment period during which the therapeutic agents are administered is then followed by a non-treatment period of a particular time duration, during which the therapeutic agents are not administered to the patient. This non-treatment period can then be followed by a series of subsequent treatment and non-treatment periods of the same or different frequencies for the same or different lengths of time. In some embodiments, the treatment and non-treatment periods are alternated. It will be understood that the period of treatment in cycling therapy may continue until the patient has achieved a complete response or a partial response, at which point the treatment may be stopped. Alternatively, the period of treatment in cycling therapy may continue until the patient has achieved a complete response or a partial response, at which point the period of treatment may continue for a particular number of cycles. In some embodiments, the length of the period of treatment may be a particular number of cycles, regardless of patient response. In some other embodiments, the length of the period of treatment may continue until the patient relapses.

In some embodiments, the mTORC1/2 inhibitor and the selective Aurora A kinase inhibitor are cyclically administered to a patient. Cycling therapy involves the administration of a first agent (e.g., a first prophylactic or therapeutic agents) for a period of time, followed by the administration of a second agent and/or third agent (e.g., a second and/or third prophylactic or therapeutic agents) for a period of time and repeating this sequential administration. Cycling therapy can reduce the development of resistance to one or more of the therapies, avoid or reduce the side effects of one of the therapies, and/or improve the efficacy of the treatment.

In some embodiments, the mTORC1/2 inhibitor and selective Aurora A kinase inhibitor each are administered at a dose and schedule typically used for that agent when used as a single agent. In some other embodiments, when the mTORC1/2 inhibitor and selective Aurora A kinase inhibitor are administered concomitantly, one or both of the agents can advantageously be administered at a lower dose than typically administered when the agent is used as a single agent, such that the dose falls below the threshold that an adverse side effect is elicited.

The therapeutically effective amounts or suitable dosages of the mTORC1/2 inhibitor and the selective inhibitor of Aurora A kinase in combination depends upon a number of factors, including the nature of the severity of the condition to be treated, the particular inhibitor, the route of administration and the age, weight, general health, and response of the individual patient. In certain embodiments, the suitable dose level is one that achieves an effective exposure as measured by increased skin mitotic index, or decreased chromosome alignment and spindle bipolarity in tumor mitotic cells, or other standard measures of effective exposure in patients with cell proliferative disorders. In certain embodiments, the suitable dose level is one that achieves a therapeutic response as measured by tumor regression or other standard measures of disease progression, progression free survival, or overall survival. In other embodiments, the suitable dose level is one that achieves this therapeutic response and also minimizes any side effects associated with the administration of the therapeutic agent.

Suitable daily dosages of mTORC1/2 inhibitors kinase can generally range, in single or divided or multiple doses, from about 10% to about 120% of the maximum tolerated dose as a single agent. In certain embodiments, the suitable dosages are from about 20% to about 100% of the maximum tolerated dose as a single agent. In some other embodiments, the suitable dosages are from about 25% to about 90% of the maximum tolerated dose as a single agent. In some other embodiments, the suitable dosages are from about 30% to about 80% of the maximum tolerated dose as a single agent. In some other embodiments, the suitable dosages are from about 40% to about 75% of the maximum tolerated dose as a single agent. In some other embodiments, the suitable dosages are from about 45% to about 60% of the maximum tolerated dose as a single agent. In other embodiments, suitable dosages are about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 105%, about 110%, about 115%, or about 120% of the maximum tolerated dose as a single agent.

Suitable daily dosages of an mTORC1/2 inhibitor can generally range, in single or divided or multiple doses, from about 1 mg to about 20 mg per day. Other suitable daily dosages of an mTORC1/2 inhibitor can generally range, in single or divided or multiple doses, from about 2.5 mg to about 10 mg per day. Other suitable daily dosages of an mTORC1/2 inhibitor can generally range, in single or divided or multiple doses, from about 5 mg to about 10 mg per day. In other embodiments, suitable daily dosages are about 0.5 mg, about 1 mg, about 1.5 mg, about 2 mg, about 4.5 mg, about 5 mg, about 10 mg, about 15 mg, or about 20 mg per day. In some embodiments, the mTORC1/2 inhibitor is administered once daily in an amount of about 4.5 mg, about 5 mg, about 10 mg, about 15 mg, or about 20 mg. In some other embodiments, the mTORC1/2 inhibitor is administered twice daily in an amount of about 0.25 mg, about 0.5 mg, about 0.75 mg, or about 1 mg.

Suitable weekly dosages of an mTORC1/2 inhibitor can generally range, in single or divided or multiple doses, from about 5 mg to about 25 mg per day. Other suitable weekly dosages of an mTORC1/2 inhibitor can generally range, in single or divided or multiple doses, from about 10 mg to about 20 mg per day. In other embodiments, suitable weekly dosages are about 5 mg, about 10 mg, about 15 mg, about 20 mg, or about 25 mg per day.

Suitable daily dosages of MLN0128 can generally range, in single or divided or multiple doses, from about 1 mg to about 20 mg per day. Other suitable daily dosages of MLN0128 can generally range, in single or divided or multiple doses, from about 4 mg to about 16 mg per day. Other suitable daily dosages of MLN0128 can generally range, in single or divided or multiple doses, from about 6 mg to about 10 mg per day. In other embodiments, suitable daily dosages are about 2 mg, about 3 mg, about 4 mg, about 5 mg, about 6 mg, about 7 mg, 8 mg, about 9 mg, about 10 mg, about 11 mg, about 12 mg, about 13 mg, or about 14 mg per day. In another embodiment, a suitable daily dosage is about 5 mg per day.

Suitable weekly dosages of MLN0128 can generally range, in single or divided or multiple doses, from about 20 mg to about 50 mg per day. Other suitable weekly dosages of MLN0128 can generally range, in single or divided or multiple doses, from about 30 mg to about 40 mg per day. Other suitable weekly dosages of MLN0128 can generally range, in single or divided or multiple doses, from about 35 mg to about 40 mg per day. In other embodiments, suitable weekly dosages are about 30 mg, about 31 mg, about 32 mg, about 33 mg, about 34 mg, about 35 mg, 36 mg, about 37 mg, about 38 mg, about 39 mg, about 40 mg, about 41 mg, about 42 mg, about 43 mg, about 44 mg, or about 45 mg per day. In another embodiment, a suitable weekly dosage is about 30 mg per week. In another embodiment, a suitable weekly dosage is about 40 mg per week.

It will be understood that a suitable dosage of an mTORC1/2 inhibitor may be taken at any time of the day or night. In some embodiments, a suitable dosage of mTORC1/2 inhibitor is taken in the morning. In some other embodiments, a suitable dosage of mTORC1/2 inhibitor is taken in the evening. It will be understood that a suitable dosage of mTORC1/2 inhibitor may be taken with or without food. In some embodiments a suitable dosage of mTORC1/2 inhibitor is taken with a meal. In some embodiments a suitable dosage of mTORC1/2 inhibitor is taken while fasting.

Suitable daily dosages of selective inhibitors of Aurora A kinase can generally range, in single or divided or multiple doses, from about 10% to about 120% of the maximum tolerated dose as a single agent. In certain embodiments, the suitable dosages are from about 20% to about 100% of the maximum tolerated dose as a single agent. In some other embodiments, the suitable dosages are from about 25% to about 90% of the maximum tolerated dose as a single agent. In some other embodiments, the suitable dosages are from about 30% to about 80% of the maximum tolerated dose as a single agent. In some other embodiments, the suitable dosages are from about 40% to about 75% of the maximum tolerated dose as a single agent. In some other embodiments, the suitable dosages are from about 45% to about 60% of the maximum tolerated dose as a single agent. In other embodiments, suitable dosages are about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 105%, about 110%, about 115%, or about 120% of the maximum tolerated dose as a single agent.

Suitable daily dosages of alisertib can generally range, in single or divided or multiple doses, from about 20 mg to about 100 mg per day. Other suitable daily dosages of alisertib can generally range, in single or divided or multiple doses, from about 30 mg to about 90 mg per day. Other suitable daily dosages of alisertib can generally range, in single or divided or multiple doses, from about 40 mg to about 80 mg per day. In certain embodiments, the suitable dosages are from about 10 mg twice daily to about 50 mg twice daily. In some other embodiments, the suitable dosages are from about 15 mg twice daily to about 45 mg twice daily. In some other embodiments, the suitable dosages are from about 20 mg twice daily to about 40 mg twice daily. In some other embodiments, the suitable dosages are from about 25 mg twice daily to about 40 mg twice daily. In some other embodiments, the suitable dosages are from about 30 mg twice daily to about 40 mg twice daily. In other embodiments, suitable dosages are about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, or about 100 mg per day. In certain other embodiments, suitable dosages are about 10 mg, about 15 mg, about 20 mg, about 25 mg, about 30 mg, about 35 mg, about 40 mg, about 45 mg, or about 50 mg twice daily. In another embodiment, a suitable daily dosage is about 30 mg twice daily. In another embodiment, a suitable daily dosage is about 40 mg twice daily. In another embodiment, a suitable daily dosage is about 50 mg twice daily.

It will be understood that a suitable dosage of a selective inhibitor of Aurora A kinase may be taken at any time of the day or night. In some embodiments, a suitable dosage of a selective inhibitor of Aurora A kinase is taken in the morning. In some other embodiments, a suitable dosage of a selective inhibitor of Aurora A kinase is taken in the evening. In some other embodiments, a suitable dosage of a selective inhibitor of Aurora A kinase is taken both in the morning and the evening. It will be understood that a suitable dosage of a selective inhibitor of Aurora A kinase may be taken with or without food. In some embodiments a suitable dosage of a selective inhibitor of Aurora A kinase is taken with a meal.

In some embodiments a suitable dosage of a selective inhibitor of Aurora A kinase is taken while fasting.

In some embodiments, a first treatment period in which a first amount of the selective inhibitor of Aurora A kinase is administered can be followed by another treatment period in which a same or different amount of the same or a different selective inhibitor of Aurora A kinase is administered. A wide variety of therapeutic agents may have a therapeutically relevant added benefit in combination with the combination of mTORC1/2 inhibitors and selective inhibitors of Aurora A kinase of the present invention. Combination therapies that comprise the mTORC1/2 inhibitors and selective inhibitors of Aurora A kinase of the present invention with one or more other therapeutic agents can be used, for example, to: 1) enhance the therapeutic effect(s) of the methods of the present invention and/or the one or more other therapeutic agents; 2) reduce the side effects exhibited by the methods of the present invention and/or the one or more other therapeutic agents; and/or 3) reduce the effective dose of the mTORC1/2 inhibitors and selective inhibitors of Aurora A kinase of the present invention and/or the one or more other therapeutic agents. For example, such therapeutic agents may combine with the mTORC1/2 inhibitors and selective inhibitors of Aurora A kinase of the present invention to inhibit undesirable cell growth, such as inappropriate cell growth resulting in undesirable benign conditions or tumor growth.

Examples of therapeutic agents that may be used in combination with the combination of mTORC1/2 inhibitors and selective inhibitors of Aurora A kinase of the present invention include, but are not limited to, anti-proliferative agents, anticancer agents, alkylating agents, antibiotic agents, antimetabolic agents, hormonal agents, plant-derived agents, and biologic agents.

The present invention is also directed to kits and other articles of manufacture for treating proliferative diseases. In one embodiment, a kit is provided that comprises an mTORC1/2 inhibitor, or a pharmaceutically acceptable salt thereof, as described herein; a selective inhibitor of Aurora A kinase, or a pharmaceutically acceptable salt thereof, as described herein; and instructions. The kit may optionally further include the one or more additional therapeutic agents. The instructions may indicate the disease state for which the kit is to be used, storage information, dosing information and/or instructions regarding how to administer the mTORC1/2 inhibitor, the selective inhibitor of Aurora A kinase, and/or additional therapeutic agent or agents. The kit may also comprise packaging materials. The packaging material may comprise a container for housing the contents of the kit. The kit may also optionally comprise additional components, such as syringes for administration of the contents of the kit. The kit may comprise the mTORC1/2 inhibitor, the selective inhibitor Aurora A kinase, and/or additional therapeutic agent or agents in single or multiple dose forms.

In another embodiment, an article of manufacture is provided that comprises the mTORC1/2 inhibitor, or a pharmaceutically acceptable salt thereof; the selective inhibitor of Aurora A kinase, or a pharmaceutically acceptable salt thereof; and packaging materials. The article of manufacture may optionally further include the one or more additional therapeutic agents. The packaging material may comprise a container for housing the contents of the article of manufacture. The container may optionally comprise a label indicating the disease state for which the article is to be used, storage information, dosing information and/or instructions regarding how to administer the mTORC1/2 inhibitor, selective inhibitor of Aurora A kinase, and/or additional therapeutic agent or agents. The article of manufacture may also optionally comprise additional components, such as syringes for administration of the composition. The article may comprise the mTORC1/2 inhibitor, selective inhibitor of Aurora A kinase, and/or additional therapeutic agent or agents in single or multiple dose forms.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices and materials are herein described. All publications mentioned herein are hereby incorporated by reference in their entirety for the purpose of describing and disclosing the materials and methodologies that are reported in the publication which might be used in connection with the invention.

EXAMPLES

In the Examples described below, MLN8237 refers to the sodium salt, sodium 4-{[9-chloro-7-(2-fluoro-6-methoxyphenyl)-5H-pyrimido[5,4-d][2]benzazepin-2-yl]amino}-2-methoxybenzoate monohydrate, and MLN0128 refers to 3-(2-amino-1,3-benzoxazol-5-yl)-1-(propan-2-yl)-1H-pyrazolo [3, 4-d] pyrimidin-4-amine. MLN8237 and MLN0128 were prepared by the methods described in the above referenced patents and patent applications.

Example 1

In Vitro Cell Viability Assays

Cell Culture and Compound Treatment

A375, CALU6, HCC70, HCT116, HL-60, PA-1, SK-MEL-2, SW620, THP-1, U87-MG, and WM266.4 human tumor cell lines were obtained from the American Type Culture Collection (ATCC [Manassas, Va., USA]) and maintained according to the ATCC's recommendations. A2780 human tumor cell line was obtained from the European Collection of Cell Cultures (ECACC, distributed by Sigma Aldrich [St. Louis, Mo., USA]), and maintained following the ECACC's recommendations. SW48, G12V-SW48-KRAS, and G13D-SW48-KRAS human tumor cell lines were obtained from Horizon Discovery (Cambridge, UK) and maintained according to their recommendations. NB4 and SK-MEL-30 human tumor cell lines were obtained from the German Collection of Microorganisms and Cell Cultures (DSMZ [Braunschweig, Germany]) and maintained according to their recommendations. (A2780: Behrens B C, et al. *Cancer Res.* (1987) 47: 414-418; G13D-SW48-KRAS: Chen T R, et al. *Cancer Genet. Cytogenet.* (1983) 10: 351-362; HCT116: Brattain M G, et al. *J. Natl. Cancer Inst.* (1982) 69: 767-771; SW620: Leibovitz A, et al. *Cancer Res.* (1976) 36: 4562-4569; CALU-6: Fogh J, et al. J. Natl. Cancer Inst. (1977) 59: 221-226; NB4: Lanotte, M., et al. *Blood* (1991) 77: 1080-1086; A375: Giard D J, et al. *J. Natl. Cancer Inst.* (1973) 51: 1417-1423; G12V-SW48-KRAS: Chen T R, et al. *Cancer Genet. Cytogenet.* (1983) 10: 351-362; SW48: Chen T R, et al. *Cancer Genet. Cytogenet.* (1983) 10: 351-362; PA-1: Zeuthen J, et al. *Int. J. Cancer* (1980) 25: 19-32; HCC70: Gazdar A F, et al. *Int. J. Cancer* (1998) 78: 766-774; U-87 MG: Ponten J, Macintyre E H. *Microbiol. Scand.* (1968) 74: 465-486; SK-MEL-30: Carey, T. E., et al. *PNAS* (1976) 73: 3278-3282; SK-MEL-2: Fogh J, et al. *J. Natl. Cancer Inst.* (1977) 59: 221-226; WM266-4: Lee K H, et al. *J Invest Dermatol.* (1992) 98:79-85).

MLN8237 and MLN0128 were dissolved in DMSO at 10 mM concentration and aliquoted into small vials to reduce the number of freeze-thaw cycles. Aliquots were stored at −20° C. DMSO was used as vehicle. All compounds were diluted within the growth media for each particular cell line before addition to the cells.

The combination of MLN8237 and MLN0128 was evaluated in 15 cell lines in individual 384-well plates, which contained variable doses of both compounds as single agents, as well as two 10×10 matrices that contained mixtures of the two test compounds. Cells were seeded and incubated at 37° C. 5% $CO_2$, 24 hours prior to compound treatment. After 72 hours, ATP levels were measured to assess cell viability. The compound dilution plates were used for compound transfer into assay plates according to a combination matrix plate map. All wells were back-filled to give a constant percentage DMSO.

Final DMSO concentration was held constant in all wells across the plate and was maintained at less than 0.5%. Dose concentrations of each targeted agent ranged from inactive to maximally effective (defined as causing maximum growth inhibition). The top concentration of MLN8237 ranged from 65 to 25,000 nM and the top concentration of MLN0128 ranged from 1,400 to 25,000 nM. These cell viability datasets were used to calculate single agent concentration producing 50% efficacy ($EC_{50}$) values and classify the inhibitor combination response. Cells treated with vehicle (DMSO) served as the untreated control. After compound addition, assay plates were mixed and incubated at 37° C. and 5% $CO_2$ for 72 hours in a humidified cell culture chamber.

Compound activity in the 17 cell lines was assessed using the ATP detection reagent, ATPLite™ 1 Step (Perkin Elmer [Boston, Mass., USA]). After 72 hours incubation, the plates were treated as per package insert protocol for the Perkin Elmer ATPLite 1 Step Luminescence ATP Detection System. Briefly, 25 µL of substrate solution (provided in kit form) was added to each well and the plate was mixed at room temperature on an orbital shaker for 5 minutes. Luminescence was measured using a PHERAstar multi-label counter (BMG Labtech [Ortenberg, Germany]) following the ATP luminometry 384-well protocol. Luminescence values were analyzed using the Double-Agent software, a program developed in-house to generate $EC_{50}$ curves and evaluate synergy.

Statistical Analysis for In Vitro Data

The data were analyzed using a software program developed in-house to generate $EC_{50}$ curves and evaluate synergy. Each plate representing a single drug combination was analyzed separately. First, the viability measurements (luminescence values) were normalized by scaling the data so that the median of the negative controls was 0 and the median of the positive controls was 100. Some of the wells on the plate contained only one drug, and the software program used this data to compute the single drug $EC_{50}$'s by fitting this data to the Hill equation (Hill, 1910).

Normalization.

The viability data was normalized separately for each plate by scaling the data so that the median of the negative controls was 0 and the median of the positive controls was 100. More formally, $$V_i = 100 \frac{U_i - \text{median}(U_-)}{\text{median}(U_+) - \text{median}(U_-)}$$

where $V_i$ is the normalized viability of the $i^{th}$ well, $U_i$ is the raw viability measurement, median($U_-$) is the median of the negative controls, and median($U_+$) is the median of the positive controls. After normalization, the controls were discarded.

Response Surface Model and Fitting.

A response surface model similar to that of Minto et al. (C. F. Minto, et al., *Anesthesiology*, 2000, 92, 1603-1616) was used to describe the relationship between the normalized viability and the drug concentrations. For a given plate, let $$C = (C_A/I_1) + (C_B/I_2)$$

$$x = (C_A/I_1)/C$$

$$E_{max} = E_1 + E_2 x + E_3 x^2 + E_4 x^3$$

$$I = 1 + I_3 x(1-x)$$

$$S = S_1 + S_2 x + S_3 x^2 + S_4 x^3$$

$$V = 100 - E_{max}(1 + (I/C)^S)^{-1} + \text{error}$$

where $E_1$, $E_2$, $E_3$, $E_4$, $I_1$, $I_2$, $I_3$, $S_1$, $S_2$, $S_3$, and $S_4$ are parameters, $C_A$ and $C_B$ are the respective concentrations of drugs A and B, and V is the normalized viability measurement. It was assumed that the error values were independent and identically distributed normal random variables. This model is an extension of the Hill equation (A. V. Hill, *J. Physiol.*, 1910, 40, iv-vii), which is commonly used to model the effect of a single drug. The data were fitted to this model using the maximum likelihood method with the statistical software program R (R Development Core Team, 2008, ISBN 3-900051-07-0, URL http://www.R-project.org).

From each set of replicates, two plates were selected at random. The data was fit to the model by minimizing the residual sum of squares. If some of the data points had large residuals, these points were marked as outliers and removed from the analysis. The remaining data was then fit a second time. Based on the fitted response surface, plots of constant viability, called isobolograms, were produced. The contours within the isobolograms ranged from 90% to 10% Viability, with a separation of 10% in viability.

Quality Checks.

Three types of quality checks were applied to the plates. First, it was checked that the variation of the positive controls and the mean of the negative controls were small. Next, it was checked that the new data agreed with data from previous single drug experiments. Finally, the residuals from the response surface fit were analyzed to ensure that the residual sum of squares was sufficiently small. All of these quality checks were based on numerical thresholds to make pass/fail decisions, and the same thresholds were used for all of the plates in the experiment. If a plate failed any one of the quality checks, it was removed from the analysis.

Measuring Synergy.

The Combination Index (M. C. Berenbaum, *J. Theor. Biol.*, 1985, 114, 413-431) and Nonlinear Blending (J. J Peterson and S. J. Novik, *Journal of Receptors and Signal Transduction*, 2007, 27:125-146) were used as measures of drug synergy. The Combination Index is computed based on an isobologram, which is a slice of the dose response surface with constant viability. For the present analysis, the 50% isobologram, which is the dose contour that has 50% viability, was used. The $EC50_A$ and $EC50_B$ are defined be the respective doses of drugs A and B alone that have a viability of 50%. For a point ($D_A$, $D_B$) along the 50% isobologram, the Combination Index is defined as $(D_A/EC50_A)+(D_B/EC50_B)$. Since the choice of $(D_A, D_B)$ can be arbitrary, the constraint $D_A/D_B=EC50_A/EC50_B$ was used.

In some cases, the Combination Index cannot be computed because the $EC50_A$ or $EC50_B$ does not exist. In such cases, Nonlinear Blending could be used as an alternative measure of synergy. Nonlinear Blending is found by considering a slice of the dose response surface that intersects both concentration axes and runs parallel to the viability axis. Let $V_A$ and $V_B$ be the viability where the slice intersects the drug A and B axes, respectively. Let $V_{max}$ and $V_{min}$ be the maximum and minimum viabilities along the slice. Let $$NLB_S = \min(V_A, V_B) - V_{min}$$

$$NLB_A = V_{max} - \max(V_A, V_B)$$

Define the Nonlinear Blending value to be $NLB_S$ if $NLB_S > NLB_A$ and $-NLB_A$ otherwise. Since the choice of the slice is arbitrary, the slice between the EC50 values (or the highest dose values, if the EC50s did not exist) of each drug alone was chosen. The standard error for both the Combination Index and the Nonlinear Blending were found using the Cramer-Rao lower bound (H Cramer, 1946. Mathematical Methods of Statistics; C. R. Rao, *Bulletin of the Calcutta Mathematical Society*, 1945, 37: 81-89).

Summarizing Replicates.

After completing the analysis of individual plates, the results were combined across the replicates. For a given synergy measure and a set of replicates, the overall mean and standard error were computed using weighted averaging. A null mean, which corresponded to an additive effect, was then compared with the overall mean. The null mean was 1 for the Combination Index and 0 for Nonlinear Blending. Next, a two sized Z-test was performed based on the estimated mean and standard error. This produced a p-value for each synergy measure and each cell line.

After computing the mean, standard error, and p-value for each set of replicates, these values required interpretation. Thus, a standard procedure was created to produce a call (synergy, additivity, subadditivity, antagonism, or inconclusive) in each case. If the Combination Index existed for more than half of the replicates, then these measures were used to make the call. If the Combination Index did not exist for a majority of the replicates, then a similar procedure based on Nonlinear Blending was used to make the call. When the p-value is greater than 0.05, the estimate for the Combination Index is not statistically different from 1. However, if the standard error is also very large, then the estimate is too uncertain to be informative. Hence, the call is "Inconclusive". Otherwise, the call is "Additivity". When the p-value is less than 0.05, the estimate for the Combination Index is statistically different from 1. However, if the mean is still close to 1, then the difference is not of practical significance. Thus, the result is classified based on the mean. Tables 5 and 6 describe how these calls were made.

When the p-value is greater than 0.05, the estimate for the Combination Index is not statistically different from 1. However, if the standard error is also very large, then the estimate is too uncertain to be informative. Hence, the call is "Inconclusive". Otherwise, the call is "Additivity". When the p-value is less than 0.05, the estimate for the Combination Index is statistically different from 1. However, if the mean is still close to 1, then the difference is not of practical significance. Thus, the result is classified based on the mean.

TABLE 5

Interpreting Combination Index

| P-value | Standard error | Mean | Call |
|---|---|---|---|
| >0.05 | >0.25 | Any | Inconclusive |
| >0.05 | <0.25 | Any | Additivity |
| <0.05 | Any | 0.7 to 1.3 | Additivity |
| <0.05 | Any | 0 to 0.7 | Synergy |
| <0.05 | Any | 1.3 to 2 | Subadditivity |
| <0.05 | Any | >2 | Antagonism |

The Nonlinear Blending result is classified in a manner similar to the Combination Index.

TABLE 6

Interpreting Nonlinear Blending

| P-value | Standard error | Mean | Call |
|---|---|---|---|
| >0.05 | >15 | Any | Inconclusive |
| >0.05 | <15 | Any | Additivity |
| <0.05 | Any | −15 to 15 | Additivity |
| <0.05 | Any | >15 | Synergy |
| <0.05 | Any | <−15 | Antagonism |

Figure 2:
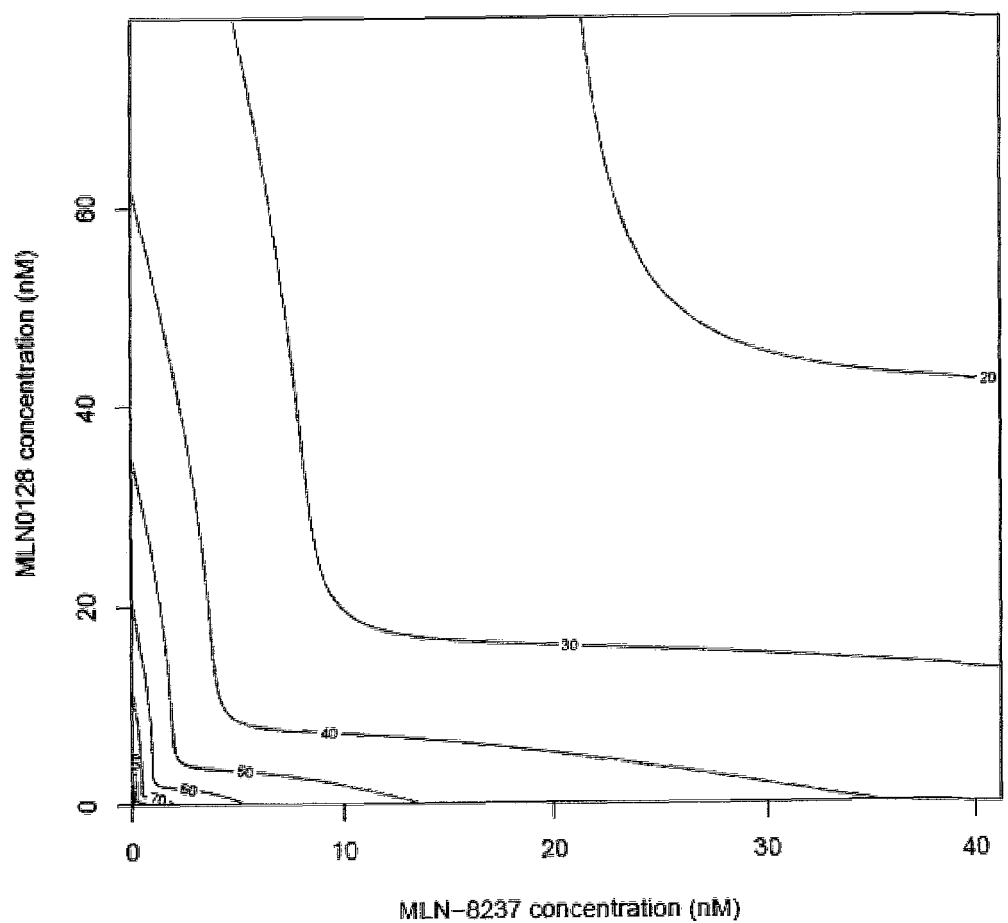
FIG. 2 shows a fitted isobologram for MLN0128 in combination with MLN8237 in the A2780 ovarian cancer cell line. The contours range from 90% to 10% viability, with a separation of 10% in viability.

Results:

FIGS. 1 and 2 show representative isobolograms. The results of the synergy analysis are summarized in Table 7. MLN8237 and MLN0128 demonstrated synergistic effects in 5 of the 17 human tumor cell lines tested. The combination exhibited an additive effect in the 12 other cell lines tested. These data demonstrate that relative to each single agent the combination of MLN8237 and MLN0128 demonstrated greater inhibition than either single agent alone, and that this increased inhibition can be considered synergistic in some settings.

TABLE 7

Summary of the In Vitro Synergy Analysis

| Cell line | Replicate experiments | Combination Index | Nonlinear Blending | Call |
|---|---|---|---|---|
| A2780 | 2 | 0.58 ± 0.2 | 11 ± 4 | Additivity |
| WM266.4 | 1 | NA | 9 ± 1 | Additivity |
| HCC70 | 2 | NA | 5 ± 3 | Additivity |
| U87 | 2 | NA | 12 ± 4 | Additivity |
| THP1 | 2 | NA | 6 ± 5 | Additivity |
| HCT116 | 1 | 0.44 ± 0.1 | 10 ± 2 | Synergy |
| SW620 | 1 | 0.52 ± 0.06 | 9 ± 1 | Synergy |
| HL60 | 2 | 1.03 ± 0.1 | 0 ± 3 | Additivity |
| PA-1 | 1 | 1.21 ± 0.05 | −9 ± 2 | Additivity |
| SW48 | 1 | 1.02 ± 0.08 | 8 ± 2 | Additivity |
| SKMEL2 | 1 | NA | 15 ± 3 | Synergy |
| NB4 | 2 | 0.77 ± 0.05 | 9 ± 2 | Additivity |
| SKMEL30 | 1 | NA | 8 ± 1 | Additivity |
| CALU6 | 1 | 0.61 ± 0.06 | 9 ± 1 | Synergy |
| G13D-SW48-KRAS | 1 | 0.34 ± 0.03 | 19 ± 2 | Synergy |
| G12V-SW48-KRAS | 1 | 0.92 ± 0.06 | 9 ± 1 | Additivity |
| A375 | 1 | 0.8 ± 0.04 | 8 ± 1 | Additivity |

Example 2

In Vivo Tumor Efficacy Models

Tumor Models

The PHTX-14B breast xenograft model was established from a patient-derived tumor collected during surgery from a 43 year Caucasian female with ductal carcinoma classified as triple negative breast cancer (ER−/PR−/Her2−) by IHC. PHTX-14B tumor fragments (approximately 2×2×3 mm$^3$) at passage 7 are implanted into the subcutaneous space in the right dorsal flank of female Balb/c nude mice (age 4-6 weeks, Shanghai SINO-British SIPPR/BK Lab Animal Ltd) using a 13-gauge trocar tumor implantation needle.

The PHTX-147B breast xenograft model was established from a patient-derived tumor collected during surgery from a 62 year Caucasian female with ductal carcinoma classified as triple negative breast cancer (ER−/PR−/Her2−) by IHC. PHTX-147B tumor fragments (approximately 2×2×3 mm$^3$) at passage 7 are implanted into the subcutaneous space in the right dorsal flank of female Balb/c nude mice (age 4-6 weeks, Shanghai SINO-British SIPPR/BK Lab Animal Ltd.).

SUM-149PT (5×10$^6$) is a tumor cell line grown in Ham's F12 (BD Biosciences) media with 5% FBS, supplemented with 5 µg/ml insulin and 1 µg/ml hydrocortisone media mixed with an equal volume of Matrigel (BD Biosciences). Cell suspension at passage 84 was aseptically injected into the subcutaneous space in the right dorsal flank of Balb/c Nude mice (age 8 weeks, Shanghai SINO-British SIPPR/BK Lab Animal Ltd.) using a 25-gauge needle.

Test Agents:

MLN8237 was formulated in 10% HPbCD+1% NaHCO$_3$ and administered by oral injection (1 cc syringe, 20-22 gauge, oral gavages needle) on QD schedule at 3 mg/kg and 20 mg/kg for 21 days. MLN8237 as used in the experimental section refers to sodium 4-{[9-chloro-7-(2-fluoro-6-methoxyphenyl)-5H-pyrimido[5,4-d][2]benzazepin-2-yl]amino}-2-methoxybenzoate monohydrate and the amount referenced is the amount of alisertib dosed. MLN8237 is dosed 24 hours prior to MLN0128 in all three models.

MLN0128 is formulated in 100% PEG400 and administered by oral injection (1 cc syringe, 20-22 gauge, oral gavages needle) on QD schedule at 0.3 mg/kg for 21 days. 1 mg/kg QD×3/weeks for 3 weeks. MLN0128 is dosed 24 hours after MLN8237 dosing.

Figure 3:
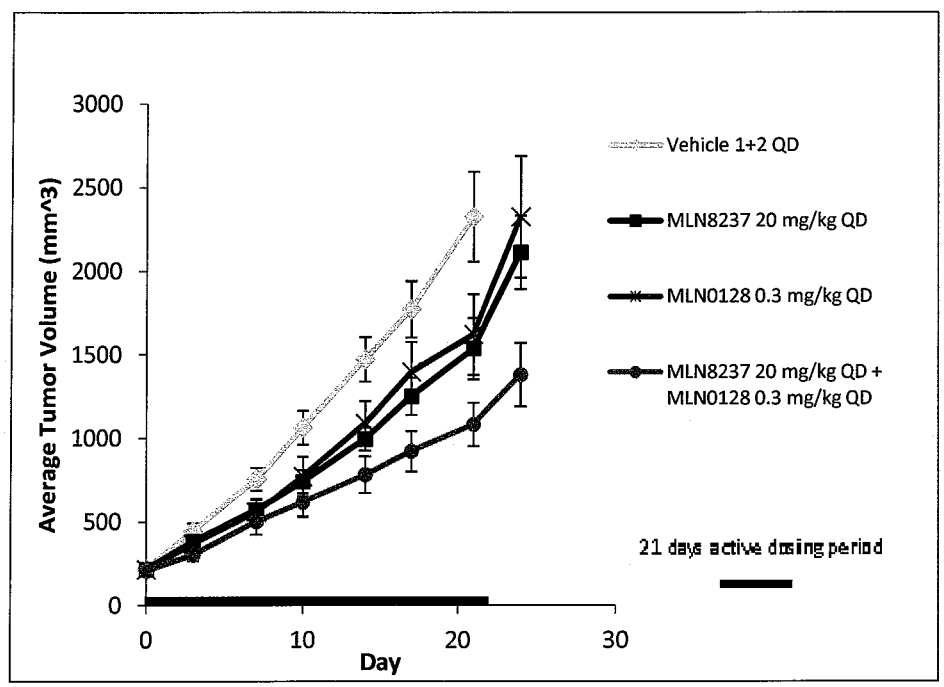
FIG. 3 shows the antitumor activity (average tumor volume as a function of time) of MLN0128 in combination with MLN8237 in a PHTX-14B breast cancer xenograft tumor model.
Figure 4:
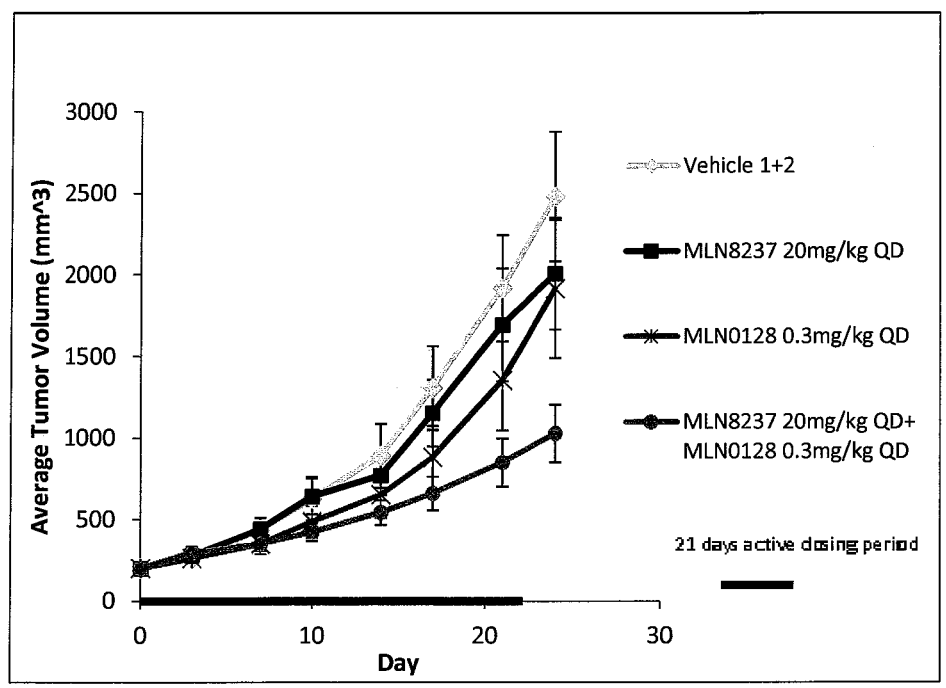
FIG. 4 shows the antitumor activity (average tumor volume as a function of time) of MLN0128 in combination with MLN8237 in a PHTX-147B breast cancer xenograft tumor model.
Figure 5:
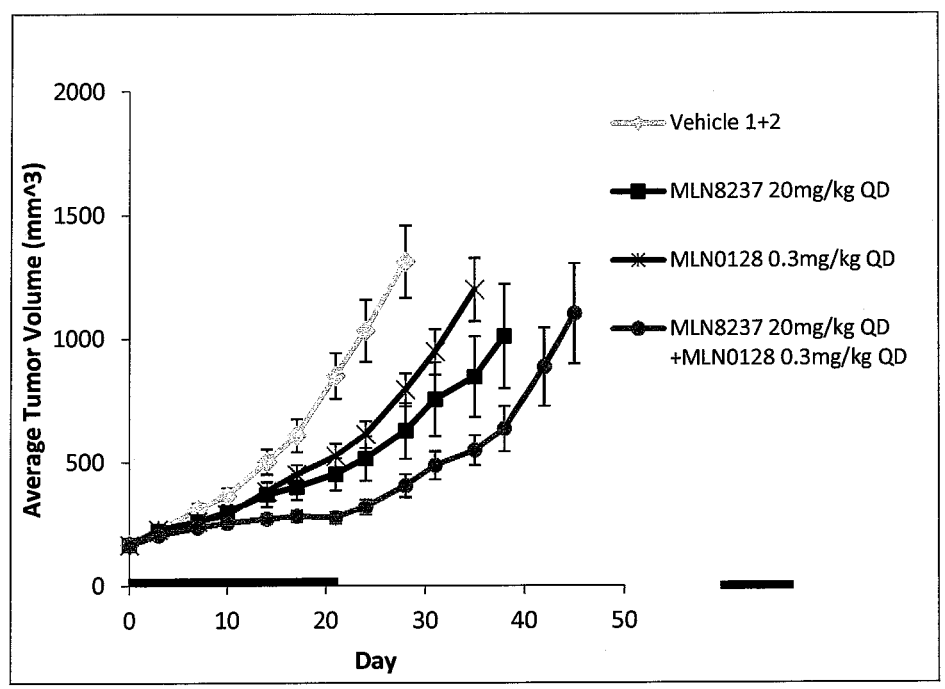
FIG. 5 shows the antitumor activity (average tumor volume as a function of time) of MLN0128 in combination with MLN8237 in a SUM-149PT breast cancer xenograft tumor model.

Tumor Measurements:

Tumors are measured twice weekly using a vernier caliper. Tumor volumes are calculated using standard procedures (0.5×(length×width$^2$)). When the tumors reached a volume of approximately 200 mm$^3$ (PHTX-14B, PHTX-147B) or 167 mm$^3$ (SUM-149PT), mice are randomized into groups of 8 as described in the tables below, and dosed with vehicle, MLN8237 or MLN0128 or the combination of MLN8237 with MLN0128, at various doses as described below in Tables 8a-10a. Tumor size and body weight are measured approximately twice a week for the duration of the study. Mice are euthanized when their tumor volume reached 10% of their body weight, or when the average tumor volume of a treatment or control group reached approximately 2000 mm$^3$. Tumor growth continued to be monitored after the dosing period in some studies. Tumor volume on study day 21 for all groups of all studies is shown in Tables 8a-10a. Average tumor volume is reported as a function of time for selected groups of selected studies in FIGS. 3, 4 and 5.

Statistical Analyses of Combination Effect for Tumor Growth in Subcutaneous Xenograft Models.

Measurements from day 0 to 21 are analyzed as specified in Tables 8a-10a. All tumor volumes have a value of 1 added to them before log$_{10}$ transformation. For each animal, the log tumor volume at day 0 is subtracted from the log tumor volume on the subsequent days. This difference vs. time is used to calculate an area under the curve (AUC) for each animal using the trapezoid rule. In instances when an animal in a treatment group is removed early from the study, the last observed tumor value is carried forward through all subsequent time points. The synergy score for the combination of agents A and B is defined as:

$$100*(\text{mean}(AUC_{AB}) - \text{mean}(AUC_A) - \text{mean}(AUC_B) + \text{mean}(AUC_{ctl}))/\text{mean}(AUC_{ctl}):$$

where $AUC_{AB}$, $AUC_A$, $AUC_B$, and $AUC_{ctl}$ are the AUC values for animals in the combination group, the A group, the B group, and the control group, respectively. The standard error of the synergy score is computed based on the variation in the AUC values among the animals. A two sided t-test is used to determine if the synergy score is significantly different from zero. If the P-value is above 0.05, then the combination is considered to be additive. If the P-value is below 0.05, and the synergy score is less than zero, then the combination is considered to be synergistic. If the P-value is below 0.05, the synergy score is greater than zero, and the combination is more effective than either agent alone, then the combination is considered to be subadditive. Otherwise, the combination is classified as antagonistic.

Results:

Three mouse tumor xenograft models including two primary breast carcinoma models (PHTX-14B and PHTX-147B); and a single human breast cancer call line model (SUM-149PT), were assessed for their response to the combination of MLN8237 and MLN0128. The details for each study are as shown below in Tables 8a-10a. The results were analyzed using the statistical analysis described above and the classification of the combination is shown below in Tables 8b-10b.

PHTX-14B Breast Xenograft Model

In the PHTX-14B breast xenograft model (shown in FIG. 3), dosing of administration of MLN8237 (at 20 mg/kg) or MLN0128 (at 1.0 or 0.3 mg/kg) alone (QD×21) significantly delayed growth of PHTX-14B xenografts in female Balb/c nude mice. Antitumor activity of MLN8237 at 3 mg/kg alone (QD×21) was limited and not significant. Significant delays in PHTX 14B xenograft growth were observed in animals treated with MLN8237 and MLN0128 in combination. All treatment groups from the study are shown in Table 8a. The combination benefit for this combination in this study was scored as additive at all doses and schedules assessed (Table 8b).

TABLE 8a

Combination of MLN8237 and MLN0128 in PHTX-14B xenograft model

| Group | Treatment groups | Dosing Regimen | Administration route | Average tumor volume at day 21 | SEM tumor volume at day 21 | Number of the mice in group at day 21 |
|---|---|---|---|---|---|---|
| 1 | *10% HPbCD + 100% PEG400 | QD + QD | PO | 749 | 108.2 | 8 |
| 2 | *20 mg/kg MLN8237 | QD | PO | 533.9 | 89.7 | 8 |
| 3 | *3 mg/kg MLN8237 | QD | PO | 795.1 | 120.6 | 8 |

TABLE 8a-continued

Combination of MLN8237 and MLN0128 in PHTX-14B xenograft model

| Group | Treatment groups | Dosing Regimen | Administration route | Average tumor volume at day 21 | SEM tumor volume at day 21 | Number of the mice in group at day 21 |
|---|---|---|---|---|---|---|
| 4 | 1 mg/kg MLN0128 | QD × 3/week | PO | 475.6 | 85.1 | 8 |
| 5 | 0.3 mg/kg MLN0128 | QD | PO | 539.1 | 80.3 | 8 |
| 6 | *20 mg/kg MLN8237 + 1 mg/kg MLN0128 | QD + QD × 3/week | PO | 334.1 | 35.9 | 8 |
| 7 | *20 mg/kg MLN8237 + 0.3 mg/kg MLN0128 | QD + QD | PO | 396.3 | 59.9 | 8 |
| 8 | *3 mg/kg MLN8237 + 1 mg/kg MLN0128 | QD + QD × 3/week | PO | 353.7 | 43.7 | 8 |
| 9 | *3 mg/kg MLN8237 + 0.3 mg/kg MLN0128 | QD + QD | PO | 537.5 | 80.3 | 8 |

*MLN8237 dosed as 24 hours prior to MLN0128

TABLE 8b

Classification for in vivo combination of MLN8237 and MLN0128 in PHTX-14B xenograft model

| Treatment groups | Synergy score day 21 | Synergy score SEM | P-Value | Combination Outcome |
|---|---|---|---|---|
| 20 mg/kg MLN8237 + 1 mg/kg MLN0128 | 18.5 | 10.8 | 0.104 | Additive |
| 20 mg/kg MLN8237 + 0.3 mg/kg MLN0128 | 12.8 | 11 | 0.260 | Additive |
| 3 mg/kg MLN8237 + 1 mg/kg MLN0128 | −10.1 | 11.1 | 0.372 | Additive |
| 3 mg/kg MLN8237 + 0.3 mg/kg MLN0128 | 10.5 | 11.1 | 0.355 | Additive |

PHTX-147B Breast Xenograft Model

In the PHTX-147B breast xenograft model (shown in FIG. 4), dosing of MLN0128 alone at 1.0 mg/kg (PO, QD×3/wk×3) significantly delayed the growth of PHTX-147B xenografts in female Balb/c nude mice. The growth of PHTX-147B also responded moderately to MLN0128 alone at 0.3 mg/kg (PO, QD×21). But MLN8237 alone at 20 or 3 mg/kg (PO, QD×21) had only slight or no effect on PHTX-147B xenograft growth. Strong and significant delays in PHTX-147B xenograft growth were observed in animals treated with MLN8237 and MLN0128 in combination. All treatment groups from the study are shown in Table 9a. The combination benefit for this combination in this study was scored as additive (Table 9b).

TABLE 9a

Combination of MLN8237 and MLN0128 in PHTX-147B xenograft model

| Group | Treatment groups | Dosing Regimen | Administration route | Average tumor volume at day 21 | SEM tumor volume at day 21 | Number of the mice in group at day 21 |
|---|---|---|---|---|---|---|
| 1 | *10% HPbCD + 100% PEG400 | QD QD | PO | 1919.7 | 326.2 | 8 |
| 2 | *20 mg/kg MLN8237 | QD | PO | 1694.9 | 346.4 | 8 |
| 3 | *3 mg/kg MLN8237 | QD | PO | 1951.9 | 323.8 | 8 |
| 4 | 1 mg/kg MLN0128 | QD × 3/week | PO | 974.8 | 147.1 | 8 |
| 5 | 0.3 mg/kg MLN0128 | QD | PO | 1354.1 | 306 | 8 |
| 6 | *20 mg/kg MLN8237 + 1 mg/kg MLN0128 | QD + QD × 3/week | PO | 744.3 | 107.6 | 8 |
| 7 | *20 mg/kg MLN8237 + 0.3 mg/kg MLN0128 | QD + QD | PO | 850.9 | 147.6 | 8 |
| 8 | *3 mg/kg MLN8237 + 1 mg/kg MLN0128 | QD + QD × 3/week | PO | 873.4 | 95.8 | 8 |

TABLE 9a-continued

Combination of MLN8237 and MLN0128 in PHTX-147B xenograft model

| Group | Treatment groups | Dosing Regimen | Administration route | Average tumor volume at day 21 | SEM tumor volume at day 21 | Number of the mice in group at day 21 |
|---|---|---|---|---|---|---|
| 9 | *3 mg/kg MLN8237 + 0.3 mg/kg MLN0128 | QD + QD | PO | 925.6 | 103.1 | 8 |

*MLN8237 dosed as 24 hours prior to MLN0128

TABLE 9b

Classification for in vivo combination of MLN8237 and MLN0128 in PHTX-147B xenograft model

| Treatment groups | Synergy score day 21 | Synergy score SEM | P-Value | Combination Outcome |
|---|---|---|---|---|
| 20 mg/kg MLN8237 + 1 mg/kg MLN0128 | −9.3 | 12 | 0.559 | Additive |
| 20 mg/kg MLN8237 + 0.3 mg/kg MLN0128 | −8.1 | 13.9 | 0.565 | Additive |
| 3 mg/kg MLN8237 + 1 mg/kg MLN0128 | −5.4 | 11.6 | 0.648 | Additive |
| 3 mg/kg MLN8237 + 0.3 mg/kg MLN0128 | −10.8 | 12.9 | 0.411 | Additive |

SUM-149PT Breast Xenograft Model

In the SUM-149PT breast xenograft model (shown in FIG. 5), dosing of MLN8237 alone at 20 or 3 mg/kg (PO, QD×21) or MLN0128 alone at 0.3 mg/kg (PO, QD×21) significantly delayed the growth of SUM149PT human breast cancer xenografts in female Balb/c nude mice. The growth of SUM149PT only responded lightly to treatment with MLN0128 alone at 1.0 mg/kg (PO, QD×3/wk×3 weeks). Strong and significant delays in SUM149PT xenograft growth were observed in animals treated with MLN8237 and MLN0128 in combination. All treatment groups from the study are shown in Table 10a. The combination benefit for this combination in this study was scored as additive (Table 10b).

TABLE 10a

Combination of MLN8237 and MLN0128 in SUM-149PT xenograft model

| Group | Treatment groups | Dosing Regimen | Administration route | Average tumor volume at day 21 | SEM tumor volume at day 21 | Number of the mice in group at day 21 |
|---|---|---|---|---|---|---|
| 1 | *10% HPbCD + 100% PEG400 | QD QD | PO | 848.9 | 92.3 | 8 |
| 2 | *20 mg/kg MLN8237 | QD | PO | 451.6 | 64.8 | 8 |
| 3 | *3 mg/kg MLN8237 | QD | PO | 613.4 | 92.9 | 8 |
| 4 | 1 mg/kg MLN0128 | QD × 3/week | PO | 696.8 | 77.2 | 8 |
| 5 | 0.3 mg/kg MLN0128 | QD | PO | 524.5 | 51.3 | 8 |
| 6 | *20 mg/kg MLN8237 + 1 mg/kg MLN0128 | QD + QD × 3/week | PO | 231.6 | 19 | 8 |
| 7 | *20 mg/kg MLN8237 + 0.3 mg/kg MLN0128 | QD + QD | PO | 276.4 | 23.2 | 8 |
| 8 | *3 mg/kg MLN8237 + 1 mg/kg MLN0128 | QD + QD × 3/ week | PO | 510.3 | 48.8 | 8 |
| 9 | *3 mg/kg MLN8237 + 0.3 mg/kg MLN0128 | QD + QD | PO | 442.6 | 35.8 | 8 |

*MLN8237 dosed as 24 hours prior to MLN0128

TABLE 10b

Classification for in vivo combination of MLN8237 and MLN0128 in SUM-149PT xenograft model

| Treatment groups | Synergy score day 21 | Synergy score SEM | P-Value | Combination Outcome |
|---|---|---|---|---|
| 20 mg/kg MLN8237 + 1 mg/kg MLN0128 | −22.7 | 14.3 | 0.128 | Additive |
| 20 mg/kg MLN8237 + 0.3 mg/kg MLN0128 | 0.6 | 10.5 | 0.954 | Additive |
| 3 mg/kg MLN8237 + 1 mg/kg MLN0128 | 7.1 | 13.2 | 0.599 | Additive |
| 3 mg/kg MLN8237 + 0.3 mg/kg MLN0128 | 11.9 | 9.8 | 0.242 | Additive |

What is claimed is:

1. A method of treating a patient suffering from breast cancer, comprising administering to the patient an mTORC1/2 inhibitor in combination with a selective inhibitor of Aurora A kinase, wherein the mTORC1/2 inhibitor is 3-(2-amino-1,3-benzoxazol-5-yl)-1-(propan-2-yl)-1H-pyrazolo [3, 4-d] pyrimidin-4-amine, or a pharmaceutically acceptable salt thereof, and the selective inhibitor of Aurora A kinase is 4-{[9-chloro-7-(2-fluoro-6-methoxyphenyl)-5H-pyrimido[5,4-d][2]benzazepin-2-yl]amino}-2-methoxybenzoic acid, or a pharmaceutically acceptable salt thereof.

2. The method of claim 1, wherein the pharmaceutically acceptable salt is sodium 4-{[9-chloro-7-(2-fluoro-6-methoxyphenyl)-5H-pyrimido[5,4-d][2]benzazepin-2-yl]amino}-2-methoxybenzoate.

* * * * *